US012774319B2

(12) United States Patent
Maghodia et al.

(10) Patent No.: US 12,774,319 B2
(45) Date of Patent: Oct. 27, 2026

(54) OPTIMIZED FACTOR VIII GENES

(71) Applicant: BIOVERATIV THERAPEUTICS INC., Waltham, MA (US)

(72) Inventors: Ajay Maghodia, Waltham, MA (US); Tongyao Liu, Waltham, MA (US); Philip Zakas, Waltham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 0 days.

(21) Appl. No.: 17/821,359

(22) Filed: Aug. 22, 2022

(65) Prior Publication Data

US 2023/0084036 A1 Mar. 16, 2023

Related U.S. Application Data

(60) Provisional application No. 63/236,225, filed on Aug. 23, 2021.

(51) Int. Cl.
*C07K 14/755* (2006.01)
*A61K 48/00* (2006.01)
*C12N 15/86* (2006.01)

(52) U.S. Cl.
CPC ........ *C07K 14/755* (2013.01); *A61K 48/0058* (2013.01); *C12N 15/86* (2013.01); *C12N 2750/14143* (2013.01); *C12N 2830/48* (2013.01); *C12N 2830/50* (2013.01)

(58) Field of Classification Search
CPC .... A61P 7/04; A61P 7/00; A61P 19/00; A61P 25/00; A61P 1/00; A61P 1/02; A61P 17/02; A61P 19/02; A61P 21/00; A61P 11/00; A61P 37/06; A61P 43/00; A61P 7/02; A61P 19/08; A61P 1/16; C07K 14/755; C07K 2319/31; C07K 2319/30; C07K 2319/00; C07K 16/00; C07K 2319/50; C07K 2319/35; C07K 19/00; C07K 2319/02; C07K 14/745; C07K 2317/94; C07K 14/00; C07K 2319/70; C07K 2319/90; C07K 14/005; C07K 14/775; C07K 14/47; C07K 14/001; C07K 2319/21; C07K 2319/41; C07K 2319/95; C07K 14/475; C07K 14/575; C07K 14/75; A61K 38/00; A61K 38/37; A61K 47/6811; A61K 9/0019; A61K 48/005; A61K 48/0058; A61K 48/0066; A61K 48/0016; A61K 2039/6031; A61K 2039/6056; A61K 38/21; A61K 38/36; A61K 39/0008; A61K 47/55; A61K 47/6815; A61K 47/62; A61K 48/00; A61K 2300/00; A61K 31/713; A61K 39/395; A61K 31/7105; A61K 47/68; A61K 48/0033; A61K 48/0075; A61K 47/50; A61K 48/0091; A61K 39/12; A61K 48/0041; C07H 21/00

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Kary |
| 4,770,999 | A | 9/1988 | Kaufman et al. |
| 4,800,159 | A | 1/1989 | Mullis et al. |
| 4,868,112 | A | 9/1989 | Toole, Jr. |
| 4,965,188 | A | 10/1990 | Mullis et al. |
| 5,112,950 | A | 5/1992 | Meulien et al. |
| 5,171,844 | A | 12/1992 | van Ooyen et al. |
| 5,304,489 | A | 4/1994 | Rosen |
| 5,348,886 | A | 9/1994 | Lee et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,648,260 | A | 7/1997 | Winter et al. |
| 5,658,570 | A | 8/1997 | Newman et al. |
| 5,712,122 | A | 1/1998 | Boime et al. |
| 5,736,137 | A | 4/1998 | Anderson et al. |
| 5,739,277 | A | 4/1998 | Presta et al. |
| 5,741,957 | A | 4/1998 | Deboer et al. |
| 5,789,203 | A | 8/1998 | Chapman et al. |
| 5,834,250 | A | 11/1998 | Wells et al. |
| 5,849,992 | A | 12/1998 | Meade et al. |
| 5,869,046 | A | 2/1999 | Presta et al. |
| 5,972,885 | A | 10/1999 | Spira et al. |
| 6,030,613 | A | 2/2000 | Blumberg et al. |

(Continued)

FOREIGN PATENT DOCUMENTS

| | | | |
|---|---|---|---|
| CN | 101124328 | A | 2/2008 |
| CN | 103215308 | A | 7/2013 |

(Continued)

OTHER PUBLICATIONS

Saranov, A.G. et al. "Identification of coagulation Factor VIII A2 domain residues forming the binding epitope for low-density lipoprotein receptor-related protein." Biochemistry, vol. 45 (2006), pp. 1829-1840 (Year: 2006).*

Radcliffe, P.A. et al."Analysis of factor VIII mediated suppression of lentiviral vector titres". Gene Therapy, vol. 15 (2008), pp. 289-297. (Year: 2008).*

Pdf-1 (Synthetic construct coagulation factor VIII gene, complete cds; GenBank Accession No. EU159409.1, submitted Sep. 17, 2007, published Jul. 23, 2009). (Year: 2009).*

(Continued)

*Primary Examiner* — Nancy J Leith
*Assistant Examiner* — Alexandra Geraldine Dace Denito
(74) *Attorney, Agent, or Firm* — LATHROP GPM LLP; James H. Velema, Esq.; James V. DeGiulio, Esq.

(57) ABSTRACT

The present disclosure provides codon optimized Factor VIII sequences, vectors, and host cells comprising codon optimized Factor VIII sequences, polypeptides encoded by codon optimized Factor VIII sequences, and methods of producing such polypeptides.

11 Claims, 8 Drawing Sheets

Specification includes a Sequence Listing.

(56) References Cited

U.S. PATENT DOCUMENTS

| | | | |
|---|---|---|---|
| 6,033,885 | A | 3/2000 | Latta et al. |
| 6,048,720 | A | 4/2000 | Dalborg et al. |
| 6,060,447 | A | 5/2000 | Chapman et al. |
| 6,086,875 | A | 7/2000 | Blumberg et al. |
| 6,096,871 | A | 8/2000 | Presta et al. |
| 6,121,022 | A | 9/2000 | Presta et al. |
| 6,159,730 | A | 12/2000 | Reff |
| 6,193,980 | B1 | 2/2001 | Efstathiou et al. |
| 6,194,551 | B1 | 2/2001 | Idusogie et al. |
| 6,228,620 | B1 | 5/2001 | Chapman et al. |
| 6,242,195 | B1 | 6/2001 | Idusogie et al. |
| 6,251,632 | B1 | 6/2001 | Lillicrap et al. |
| 6,277,375 | B1 | 8/2001 | Ward |
| 6,291,214 | B1 | 9/2001 | Richards et al. |
| 6,316,226 | B1 | 11/2001 | Van Ooyen et al. |
| 6,346,513 | B1 | 2/2002 | Van Ooyen et al. |
| 6,413,777 | B1 | 7/2002 | Reff et al. |
| 6,458,563 | B1 | 10/2002 | Lollar |
| 6,485,726 | B1 | 11/2002 | Blumberg et al. |
| 6,491,907 | B1 | 12/2002 | Rabinowitz |
| 6,528,624 | B1 | 3/2003 | Idusogie et al. |
| 6,538,124 | B1 | 3/2003 | Idusogie et al. |
| 6,696,245 | B2 | 2/2004 | Winter et al. |
| 6,723,551 | B2 | 4/2004 | Kotin et al. |
| 6,737,056 | B1 | 5/2004 | Presta |
| 6,808,905 | B2 | 10/2004 | McArthur et al. |
| 6,821,505 | B2 | 11/2004 | Ward |
| 6,998,253 | B1 | 2/2006 | Presta et al. |
| 7,041,635 | B2 | 5/2006 | Kim et al. |
| 7,083,784 | B2 | 8/2006 | Dall'Acqua et al. |
| 7,179,903 | B2 | 2/2007 | McArthur et al. |
| 7,271,002 | B2 | 9/2007 | Kotin et al. |
| 7,317,091 | B2 | 1/2008 | Lazar et al. |
| 7,404,956 | B2 | 7/2008 | Peters et al. |
| 7,598,071 | B2 | 10/2009 | Brown et al. |
| 7,700,734 | B2 | 4/2010 | Lin et al. |
| 7,745,179 | B2 | 6/2010 | McArthur et al. |
| 7,939,632 | B2 | 5/2011 | Metzner et al. |
| 8,071,751 | B2 | 12/2011 | Delwart et al. |
| 8,110,350 | B2 | 2/2012 | Allander et al. |
| 8,945,918 | B2 | 2/2015 | Chen et al. |
| 9,062,098 | B2 | 6/2015 | Allander et al. |
| 9,115,373 | B2 | 8/2015 | Hermens et al. |
| 9,186,381 | B2 | 11/2015 | Zender et al. |
| 9,212,374 | B2 | 12/2015 | Roy et al. |
| 9,828,587 | B2 | 11/2017 | Yan et al. |
| 9,856,468 | B2 | 1/2018 | Salas et al. |
| 9,879,279 | B2 | 1/2018 | Chen |
| 9,890,365 | B2 | 2/2018 | Wang et al. |
| 9,943,611 | B2 | 4/2018 | Balazs et al. |
| 10,793,835 | B2 | 10/2020 | Yan et al. |
| 11,066,679 | B2 | 7/2021 | Kotin et al. |
| 11,103,597 | B2 | 8/2021 | Gray et al. |
| 11,142,775 | B2 | 10/2021 | Yan et al. |
| 11,634,742 | B2 | 4/2023 | De Beer et al. |
| 12,168,776 | B2 | 12/2024 | Liu et al. |
| 2003/0069395 | A1 | 4/2003 | Sato et al. |
| 2003/0235536 | A1 | 12/2003 | Blumberg et al. |
| 2006/0008469 | A1 | 1/2006 | Brown et al. |
| 2007/0231329 | A1 | 10/2007 | Lazar et al. |
| 2007/0237765 | A1 | 10/2007 | Lazar et al. |
| 2007/0237766 | A1 | 10/2007 | Lazar et al. |
| 2007/0237767 | A1 | 10/2007 | Lazar et al. |
| 2007/0243188 | A1 | 10/2007 | Lazar et al. |
| 2007/0248603 | A1 | 10/2007 | Lazar et al. |
| 2007/0253936 | A1 | 11/2007 | Kay et al. |
| 2007/0286859 | A1 | 12/2007 | Lazar et al. |
| 2008/0004206 | A1 | 1/2008 | Rosen et al. |
| 2008/0057056 | A1 | 3/2008 | Lazar et al. |
| 2008/0153751 | A1 | 6/2008 | Rosen et al. |
| 2008/0161243 | A1 | 7/2008 | Rosen et al. |
| 2008/0194481 | A1 | 8/2008 | Rosen et al. |
| 2008/0213233 | A1 | 9/2008 | Wang et al. |
| 2008/0260738 | A1 | 10/2008 | Moore et al. |
| 2008/0261877 | A1 | 10/2008 | Ballance et al. |
| 2009/0087411 | A1 | 4/2009 | Fares et al. |
| 2010/0136514 | A1 | 6/2010 | Brown et al. |
| 2010/0239554 | A1 | 9/2010 | Schellenberger et al. |
| 2010/0292130 | A1 | 11/2010 | Skerra et al. |
| 2010/0323956 | A1 | 12/2010 | Schellenberger et al. |
| 2011/0046060 | A1 | 2/2011 | Schellenberger et al. |
| 2011/0046061 | A1 | 2/2011 | Schellenberger et al. |
| 2011/0077199 | A1 | 3/2011 | Schellenberger et al. |
| 2011/0172146 | A1 | 7/2011 | Schellenberger et al. |
| 2011/0190166 | A1 | 8/2011 | Wong et al. |
| 2013/0109742 | A1 | 5/2013 | Hewitt et al. |
| 2014/0107186 | A1 | 4/2014 | Garcia et al. |
| 2014/0271551 | A1 | 9/2014 | Hirsch et al. |
| 2014/0308280 | A1 | 10/2014 | Maloney et al. |
| 2014/0349374 | A1 | 11/2014 | Galibert et al. |
| 2014/0370035 | A1 | 12/2014 | Jiang et al. |
| 2015/0023959 | A1 | 1/2015 | Chhabra et al. |
| 2015/0111955 | A1 | 4/2015 | High et al. |
| 2015/0158929 | A1 | 6/2015 | Schellenberger et al. |
| 2016/0102297 | A1 | 4/2016 | Hewitt et al. |
| 2016/0229904 | A1 | 8/2016 | Xiao et al. |
| 2016/0296607 | A1 | 10/2016 | Jiang |
| 2016/0311885 | A1 | 10/2016 | Peters et al. |
| 2017/0021037 | A1 | 1/2017 | Wang et al. |
| 2017/0081392 | A1 | 3/2017 | Wilson et al. |
| 2017/0130245 | A1 | 5/2017 | Kotin et al. |
| 2017/0356009 | A1 | 12/2017 | Lu et al. |
| 2017/0362608 | A1 | 12/2017 | Mclaughlin et al. |
| 2019/0048362 | A1 | 2/2019 | Kyostio-Moore et al. |
| 2019/0185543 | A1 | 6/2019 | Tan et al. |
| 2019/0203229 | A1 | 7/2019 | Engelhardt et al. |
| 2019/0231901 | A1 | 8/2019 | Seymour et al. |
| 2020/0069817 | A1* | 3/2020 | Liu ...................... A61K 48/005 |
| 2020/0224220 | A1 | 7/2020 | Finer et al. |
| 2020/0283794 | A1 | 9/2020 | Kotin et al. |
| 2021/0010028 | A1 | 1/2021 | Horowitz et al. |
| 2021/0163986 | A1 | 6/2021 | Seregin et al. |
| 2022/0042040 | A1 | 2/2022 | Grabherr et al. |
| 2022/0090130 | A1* | 3/2022 | Maghodia ............ C07K 14/755 |
| 2022/0098633 | A1* | 3/2022 | de Beer ................... C12N 9/22 |
| 2022/0175970 | A1 | 6/2022 | Kerr et al. |
| 2022/0243201 | A1 | 8/2022 | Maghodia et al. |
| 2022/0356490 | A1 | 11/2022 | Liu et al. |
| 2023/0063208 | A1 | 3/2023 | Ceruti et al. |
| 2023/0091932 | A1 | 3/2023 | Maghodia et al. |
| 2024/0294940 | A1 | 9/2024 | Maghodia et al. |
| 2024/0350671 | A1 | 10/2024 | Maghodia et al. |
| 2025/0171805 | A1 | 5/2025 | Liu et al. |

FOREIGN PATENT DOCUMENTS

| | | | |
|---|---|---|---|
| CN | 107531774 | A | 1/2018 |
| CN | 111247251 | A | 6/2020 |
| EP | 0295597 | A2 | 12/1988 |
| EP | 1395293 | A1 | 3/2004 |
| EP | 1572893 | B1 | 1/2009 |
| EP | 2061891 | B1 | 4/2012 |
| EP | 2508607 | A1 | 10/2012 |
| EP | 2195439 | B1 | 6/2013 |
| EP | 2644698 | A1 | 10/2013 |
| EP | 2698163 | A1 | 2/2014 |
| EP | 2524037 | B1 | 5/2018 |
| EP | 3230441 | A4 | 10/2018 |
| EP | 3294309 | A4 | 1/2019 |
| EP | 3476860 | A1 | 5/2019 |
| EP | 2914731 | B1 | 9/2019 |
| EP | 3665289 | A1 | 6/2020 |
| EP | 3722434 | A1 | 10/2020 |
| EP | 3678710 | A4 | 6/2021 |
| EP | 3423110 | B1 | 8/2021 |
| EP | 3877528 | A1 | 9/2021 |
| EP | 3914717 | A1 | 12/2021 |
| JP | 2002-527493 | A | 8/2002 |
| JP | 2011-067212 | A | 4/2011 |
| JP | 2014-511180 | A | 5/2014 |
| JP | 2014-511690 | A | 5/2014 |
| RU | 2569183 | C2 | 11/2015 |
| RU | 2653444 | C2 | 5/2018 |
| TW | 201629225 | A | 8/2016 |

(56) References Cited

FOREIGN PATENT DOCUMENTS

WO WO 1987/004187 A1 7/1987
WO WO 1988/000831 A1 2/1988
WO WO 1988/007089 A1 9/1988
WO WO 1991/009122 A1 6/1991
WO WO 1994/028157 A1 12/1994
WO WO 1995/009923 A1 4/1995
WO WO 1995/023867 A1 9/1995
WO WO 1996/014339 A1 5/1996
WO WO 1998/005787 A1 2/1998
WO WO 1998/023289 A1 6/1998
WO WO 1999/051642 A1 10/1999
WO WO 1999/058572 A1 11/1999
WO WO 2000/005355 A1 2/2000
WO WO 2000/009560 A2 2/2000
WO WO 2000/023116 A1 4/2000
WO WO 2000/028004 A1 5/2000
WO WO 2000/032767 A1 6/2000
WO WO 2000/042072 A2 7/2000
WO WO 2001/075092 A2 10/2001
WO WO 2002/044215 A2 6/2002
WO WO 2002/060919 A2 8/2002
WO WO 2002/040544 A3 10/2002
WO WO 2002/092134 A1 11/2002
WO WO 2003/020764 A2 3/2003
WO WO 2003/042361 A2 5/2003
WO WO 2003/074569 A2 9/2003
WO WO 2003/077834 A2 9/2003
WO WO 2003/104392 A2 12/2003
WO WO 2004/016750 A2 2/2004
WO WO 2004/029207 A2 4/2004
WO WO 2004/035752 A2 4/2004
WO WO 2004/044859 A1 5/2004
WO WO 2004/063351 A2 7/2004
WO WO 2004/074455 A2 9/2004
WO WO 2004/094642 A2 11/2004
WO WO 2004/099249 A2 11/2004
WO WO 2005/040217 A2 5/2005
WO WO 2005/070963 A1 8/2005
WO WO 2005/077981 A2 8/2005
WO WO 2005/085456 A1 9/2005
WO WO 2005/092925 A2 10/2005
WO WO 2007/057062 A1 11/2005
WO WO 2005/123780 A2 12/2005
WO WO 2006/019447 A1 2/2006
WO WO 2006/033756 A 3/2006
WO WO 2006/047350 A2 5/2006
WO WO 2006/085967 A2 8/2006
WO WO 2007/000668 A2 1/2007
WO WO 2007/021494 A2 2/2007
WO WO 2007/149406 A2 12/2007
WO WO 2008/012543 A1 1/2008
WO WO 2008/016391 A2 2/2008
WO WO 2008/024998 A2 2/2008
WO WO 2008/033413 A2 3/2008
WO WO 2008/118507 A2 10/2008
WO WO 2008/141400 A1 11/2008
WO WO 2008/143954 A2 11/2008
WO WO 2008/155134 A1 12/2008
WO WO 2009/038462 A1 3/2009
WO WO 2009/051717 A2 4/2009
WO WO 2009/058322 A1 5/2009
WO WO 2009/130198 A2 10/2009
WO WO 2009/137254 A2 11/2009
WO WO 2009/140015 A2 11/2009
WO WO 2009/146210 A2 12/2009
WO WO 2010/055413 A1 5/2010
WO WO 2010/091122 A1 8/2010
WO WO 2010/125471 A2 11/2010
WO WO 2010/140148 A1 12/2010
WO WO 2010/144502 A2 12/2010
WO WO 2010/144508 A1 12/2010
WO WO 2011/020710 A2 2/2011
WO WO 2011/028228 A1 3/2011
WO WO 2011/028229 A1 3/2011
WO WO 2011/028344 A2 3/2011
WO WO 2011/088081 A1 7/2011
WO WO 2011/100330 A2 8/2011
WO WO 2011/112090 A2 9/2011
WO WO 2012/006624 A2 1/2012
WO WO 2012/006635 A1 1/2012
WO WO 2012/115980 A1 8/2012
WO WO 2012/136859 A1 10/2012
WO WO 2013/123457 A1 8/2013
WO WO 2014/011819 A2 1/2014
WO WO 2014/070949 A1 5/2014
WO WO 2014/127215 A1 8/2014
WO WO 2014/143932 A1 9/2014
WO WO 2014/168953 A1 10/2014
WO WO 2015/023891 A2 2/2015
WO WO 2015/038625 A1 3/2015
WO WO 2015/106052 A1 7/2015
WO WO 2015/191508 A1 12/2015
WO WO 2016/004113 A1 1/2016
WO WO 2016/081927 A2 5/2016
WO WO 2016/094783 A1 6/2016
WO WO 2016/127057 A1 8/2016
WO WO 2016/134338 A1 8/2016
WO WO 2016/183422 A1 11/2016
WO WO 2017/075619 A1 5/2017
WO WO 2017/136358 A1 8/2017
WO WO 2017/152149 A1 9/2017
WO WO 2017/205739 A1 11/2017
WO WO 2018/024998 A1 2/2018
WO WO 2018/132747 A1 7/2018
WO WO 2019/014623 A1 1/2019
WO WO 2019/032102 A1 2/2019
WO WO 2019/032898 A1 2/2019
WO WO 2019/051255 A1 3/2019
WO WO 2019/067766 A1 4/2019
WO WO 2019/051289 A1 6/2019
WO WO 2019/113310 A1 6/2019
WO WO 2019/143885 A1 7/2019
WO WO 2019/161059 A1 8/2019
WO WO 2019/165050 A1 8/2019
WO WO 2019/169232 A1 9/2019
WO WO 2019/169233 A1 9/2019
WO WO 2019/173434 A1 9/2019
WO WO 2019/246544 A3 12/2019
WO WO 2020/033863 A1 2/2020
WO WO 2020/069429 A1 4/2020
WO WO-2020077250 A1 * 4/2020 ..... C12Y 114/16001
WO WO 2020/097417 A1 5/2020
WO WO 2020/154645 A1 7/2020
WO WO 2020/161168 A1 8/2020
WO WO 2020/168222 A1 8/2020
WO WO 2020/181182 A1 9/2020
WO WO 2020/186207 A2 9/2020
WO WO 2020/208379 A1 10/2020
WO WO 2020/225405 A1 11/2020
WO WO 2020/257590 A1 12/2020
WO WO 2021/011840 A1 1/2021
WO WO 2021/216975 A1 10/2021
WO WO 2022/046665 A1 3/2022
WO WO 2023/028440 A2 3/2023
WO WO 2023/028441 A1 3/2023
WO WO 2023/028455 A1 3/2023

OTHER PUBLICATIONS

Pdf-2 (Synthetic construct B domain-deleted coagulation factor VIII gene, complete cds; GenBank Accession No. EU159410.1, submitted Sep. 17, 2007, published Jul. 23, 2009. (Year: 2009).*

Shestopal, S.A. et al. "Expression and characterization of a codon-optimized blood coagulation factor VIII". Journal of Thrombosis and Haemostasis, vol. 15 (2017), pp. 709-720. (Year: 2017).*

Pdf-3 (Synthetic construct coagulation factor VIII gene, complete cds; GenBank Accession No. MT568995.1, submitted Jun. 4, 2020, published Aug. 3, 2021). (Year: 2021).*

U.S. Appl. No. 16/636,583 2021/0163986, filed Aug. 9, 2018 Jun. 3, 2021, Tongyao Liu.

U.S. Appl. No. 16/537,192 2020/0069817, filed Aug. 9, 2019 Mar. 5, 2020, Tongyao Liu.

(56) References Cited

OTHER PUBLICATIONS

U.S. Appl. No. 17/576,561, filed Jan. 14, 2022, Tongyao Liu.
U.S. Appl. No. 17/409,774 2022/0090130, filed Aug. 23, 2021 Mar. 24, 2022, Ajay Maghodia.
U.S. Appl. No. 17/409,776, filed Aug. 23, 2021, Ajay Maghodia.
U.S. Appl. No. 17/576,562, filed Jan. 14, 2022, Ajay Maghodia.
U.S. Appl. No. 17/821,356, filed Aug. 22, 2022, Ajay Maghodia.
U.S. Appl. No. 17/821,359, filed Aug. 22, 2022, Ajay Maghodia.
Armour et al., "Recombinant Human IgG Molecules Lacking Fc Gamma Receptor I Binding and Monocyte Triggering Activities", European Journal of Immunology, vol. 29, No. 8, pp. 2613-2624, Aug. 1999.
Babkin et al., "A study of the human bocavirus replicative genome structures", Virus Research, Oct. 31, 2014, 195: 196-202.
Baldassarre et al., "Production of Transgenic Goats by Pronuclear Microinjection of In Vitro Produced Zygotes Derived From Oocytes Recovered by Laparoscopy", Theriogenology, vol. 59, Issues 3-4, pp. 831-839, Feb. 2003.
Beerli et al. (2002) "Engineering polydactyl zinc-finger transcription factors", Nature Biotechnol., 20: 135-141.
Behrman et al., "A CHOP-Regulated MicroRNA Controls Rhodopsin Expression", Journal of Cell Biology, 2011, vol. 192, No. 6, pp. 919-927.
Benhar et al., "Cloning, Expression and Characterization of the Fv Fragments of the Anti-Carbohydrate mAbs BI and B5 as Single-Chain Immunotoxins", Protein Engineering, Design and Selection, vol. 7, No. 12, pp. 1509-1515, Dec. 1994.
Bril et al. (2006) "Tolerance to factor VIII in a transgenic mouse expressing human factor VIII cDNA carrying an $Arg^{593}$ to Cys substitution", Thromb. Haemost. 95(2): 341-347.
Brinster et al., "Expression of a Microinjected Immunoglobulin Gene in the Spleen of Transgenic Mice", Nature, vol. 306, No. 5941, pp. 332-336, 1983.
Brinster et al., "Factors Affecting the Efficiency of Introducing Foreign DNA Into Mice by Microinjecting Eggs", Proceedings of the National Academy of Sciences of the United States of America, vol. 82, No. 13, pp. 4438-4442, Jul. 1, 1985.
Brown et al., "Production of Recombinant H1 Parvovirus Stocks Devoid of Replication-Competent Viruses", Human Gene Therapy, vol. 13, No. 18, pp. 2135-2145, Dec. 10, 2002.
Burmeister et al., "Crystal Structure of the Complex of Rat Neonatal Fc Receptor with Fc", Nature, Nov. 24, 1994, vol. 372, No. 6504, pp. 379-383.
Bzymek et al., "Evidence for Two Mechanisms of Palindrome-Stimulated Deletion in *Escherichia coli*: Single-Strand Annealing and Replication Slipped Mispairing", Genetics, vol. 158, Jun. 2001, pp. 527-540.
Cameron et al., "The Canine Factor VIII cDNA and 5' Flanking Sequence", Journal of Thrombosis and Haemostasis, Feb. 1998, vol. 79, No. 2, pp. 317-322.
Capon et al. (1989) "Designing CD4 immunoadhesins for AIDS therapy," Nature, 337, 525-531.
Chen et al. (2005) "MicroRNAs as regulators of mammalian hematopoiesis," Seminars in Immunology, 17:155-165.
Chen et al., "Vector-based siRNA Delivery Strategies for High-throughput Screening of Novel Target Genes", Journal of RNAi and Gene Silencing: An International Journal of RNA and Gene Targeting Research, Jul. 27, 2005, 1(1): 5-11.
Chiorini et al. (1997) "Cloning of adeno-associated virus type 4 (AAV4) and generation of recombinant AAV4 particles", J. Vir., 71: 6823-6833.
Chiorini et al. (1999) "Cloning and Characterization of Adeno-Associated Virus Type 5", J. Vir. 73: 1309-1319.
Cho et al., (2015) "DNA repair: ends with alternative endings", Nature 518, 174-176.
Choo et al. (2000) "Advances in zinc finger engineering", Curr. Opin. Struct. Biol. 10(4): 411-416.
Choo et al., "Molecular Cloning of The Gene for Human Anti-Haemophilic Factor IX", Nature, 1982, vol. 299, No. 5879, pp. 178-180.
Connelly et al., "The sbcC and sbcD genes of *Escherichia coli* encode a nuclease involved in palindrome inviability and genetic recombination", Mar. 1996, p. 285-291.
Costa et al. (1986) "Transcriptional Control of the Mouse Prealbumin (Transthyretin) Gene: Both Promoter Sequences and a Distinct Enhancer Are Cell Specific," Molecular and Cellular Biology, 6(12):4697-4708.
Cotter et al., "The induction of Inflammation by Adenovirus Vectors used for Gene Therapy", Frontiers in Bioscience vol. 10, May 1, 2005, pp. 1098-1105.
Cutler et al., "The Identification and Classification of 41 Novel Mutations in the Factor VIII Gene (F8c)", Human Mutation, Mar. 2002, vol. 19, No. 3, pp. 274-278.
Dalkara et al. (2013) "In Vivo-Directed Evolution of a New Adeno-Associated Virus for Therapeutic Outer Retinal Gene Delivery from the Vitreous", Sci. Transl. Med. 5(189): 189ra76.
Deng et al., "Site-Directed Mutagenesis of Virtually any Plasmid by Eliminating a Unique Site", Analytical Biochemistry, Jan. 1, 1992, vol. 200, Issue 1, pp. 81-88.
Dennis et al. (2002) "Albumin binding as a general strategy for improving the pharmacokinetics of proteins," The Journal of Biological Chemistry, 277(38):35035-35043.
Dirren et al., "SOD1 Silencing in Motoneurons or Glia Rescues Neuromuscular Function in ALS Mice", Annals of Clinical and Translational Neurology, Feb. 2015, vol. 2, No. 2, pp. 167-184.
Doherty et al., "*Escherichia coli* host strains SURE™ and SRB fail to preserve a palindrome cloned in lambda phage: improved alternate host strains", Gene, vol. 124 pp. 29-35, 1993.
Dong et al., "Quantitative Analysis of the Packaging Capacity of Recombinant Adeno-Associated Virus", Human Gene Therapy vol. 7, pp. 2101-2112, Nov. 10, 1996.
Eaton et al., "Construction and Characterization of an Active Factor VIII Variant Lacking the Central One-Third of the Molecule", Biochemistry, Dec. 1986, vol. 25, No. 26, pp. 8343-8347.
Ellman et al. (1991) "Biosynthetic Method for Introducing Unnatural Amino Acids Site-Specifically into Proteins," Methods in Enzymology, 202 (15): 301-336.
Esvelt et al. (Nov. 2013) "Orthogonal Cas9 proteins for RNA-guided gene regulation and editing", Nat Methods., 10(11): 1116-1121.
Evers et al., "AAV5-miHTT Gene Therapy Demonstrates Broad Distribution and Strong Human Mutant Huntingtin Lowering in a Huntington's Disease Minipig Model", Molecular Therapy, Sept. 5, 2018, vol. 26, Issue 9, pp. 2163-2177.
Fair et al., "Human Hepatoma Cells Secrete Single Chain Factor X, Prothrombin, and Antithrombin III", Blood, 1984, vol. 64, No. 1, pp. 194-204.
Fallaux et al. (1996) "The Human Clotting Factor VIII cDNA Contains an Autonomously Replicating Sequence Consensus- and Matrix Attachment Region-Like Sequence That Binds a Nuclear Factor, Represses Heterologous Gene Expression, and Mediates the Transcriptional Effects of Sodium Butyrate," Molecular and Cellular Biology, 16 (8): 4264-4272.
Figueiredo et al., "Cis-Acting Elements and Transcription Factors Involved in the Promoter Activity of the Human Factor VIII Gene", Journal of Biological Chemistry, May 19, 1995, vol. 270, No. 20, pp. 11828-11838.
Friend et al. (1999) "Phase I Study of an Engineered Aglycosylated Humanized CD3 Antibody in Renal Transplant Rejection," Transplantation, 68 (11): 1632-1637.
Gao et al., "Clades of Adeno-Associated Viruses are Widely Disseminated in Human Tissues", Journal of Virology, Jun. 15, 2004, vol. 78, No. 12, pp. 6381-6388.
GenBank, "", GenBank Accession No. U25749.1, Dec. 12, 1995, Retrieved From: https://www.ncbi.nlm.nih.gov/nuccore/U25749.1.
GenBank, "Adeno-associated virus-2, complete genome", GenBank Accession No. NC_001401.2, Aug. 13, 2019, Retrieved From: https://www.ncbi.nlm.nih.gov/nuccore/NC_001401.2.
GenBank, "Adeno-associated virus 2, complete genome", GenBank Accession No. AF043303.1, May 20, 2010, Retrieved From: <<http://www.ncbi.nlm.nih.gov/nuccore/AF043303>>.
GenBank, "Adeno-associated virus 5 DNA binding trs helicase (Rep22) and capsid protein (VP1) genes, complete cds", GenBank

(56) References Cited

OTHER PUBLICATIONS

Accession No. AF085716.1, Feb. 9, 1999, Retrieved From: <<http://www.ncbi.nlm.nih.gov/nuccore/AF085716>>.

GenBank, "Goose parvovirus, complete genome", GenBank Accession No. NC001701.1, Aug. 13, 2018, Retrieved From: <<http://www.ncbi.nlm.nih.gov/nuccore/NC001701>>.

GenBank, "*Homo sapiens* transferrin (TF), mRNA", GenBank Accession No. XM_039845.1, Jul. 16, 2001, Retrieved From: https://www.ncbi.nlm.nih.gov/nuccore/XM_039845.1?report=genbank.

GenBank, "*Homo sapiens* Transferrin (TF), mRNA", GenBank Accession No. XM002793, May 13, 2002, 2 pages, Retrieved from: <<https://www.ncbi.nlm.nih.gov/nuccore/XM_002793.7?report=genbank>>.

GenBank, "*Homo sapiens* Transferrin (TF), mRNA", GenBank Accession No. XM039847, Jul. 16, 2001, 2 pages, Retrieved From <<https://www.ncbi.nlm.nih.gov/nuccore/XM_039847.1?report=genbank>>.

GenBank, "*Homo sapiens* Transferrin (TF), Transcript Variant 1, mRNA", GenBank Accession No. NM001063, Sep. 3, 2009, 5 pages, Retrieved from: <<http://www.ncbi.nlm.nih.gov/nuccore/NM_001063>>.

GenBank, "*Homo sapiens* Von Willebrand Factor (VWF), mRNA", NCBI Reference Sequence: NM_000552.3, Mar. 29, 2016, 10 pages, Retrieved from: <<https://www.ncbi.nlm.nih.gov/nuccore/NM_000552.3>>.

GenBank, "Human parvovirus B19, complete genome", GenBank Accession No. NC000883.2, Aug. 13, 2018, Retrieved From: <<http://www.ncbi.nlm.nih.gov/nuccore/NC000883>>.

GenBank, "Human Transferrin mRNA, Complete cds", GenBank Accession No. M12530, Jan. 14, 1995, 2 pages, Retrieved From: <<http://www.ncbi.nlm.nih.gov/nuccore/M12530>>.

GenBank, "Minute virus of mice, complete genome", GenBank Accession No. NC001510.1, Aug. 13, 2018, Retrieved From: <<http://www.ncbi.nlm.nih.gov/nuccore/NC001510>>.

GenBank, "Snake parvovirus 1, complete genome", GenBank Accession No. NC 0096148.1, Aug. 13, 2018, Retrieved From: <<http://www.ncbi.nlm.nih.gov/nuccore/NC006148>>.

GenBank, "Synthetic construct hepatocyte-restricted expression cassette", GenBank Accession No. AY661265, Sep. 29, 2009, Retrieved From: https://www.ncbi.nlm.nih.gov/nuccore/AY661265.

GenBank, "Synthetic parvovirus B19, complete genome", GenBank Accession No. KY940273.1, May 29, 2017, Retrieved From: https://www.ncbi.nlm.nih.gov/nuccore/KY940273.1.

GenBank, "Transferrin [Human, Liver, mRNA, 2347 nt]", GenBank Accession No. S95936, May 7, 1993, 2 pages, Retrieved From: <<http://www.ncbi.nlm.nih.gov/nuccore/S95936>>.

GenBank, "Transferrin Precursor [*Homo sapiens*]", GenBank Accession No. AAA61140.1, Jan. 14, 1995, 1 page, Retrieved from: <<http://www.ncbi.nlm.nih.gov/protein/AAA61140.1>>.

GenBank, "Von Willebrand Factor Preproprotein [*Homo sapiens*]". NCBI Reference Sequence: NP_000543.2, Mar. 29, 2016, 8 pages, Retrieved from: <<http://www.ncbi.nlm.nih.gov/protein/NP_000543.2>>.

Gonçalves, M.A. (2005) "Adeno-associated virus: from defective virus to effective vector", Virol Journal, 2(43).

Gottleib et al., "In vitro excision of adeno-associated virus DNA from recombinant plasmids: isolation of an enzyme fraction from HeLa cells that cleaves DNA at poly(G) sequences", Mol Cell Biol., Jun. 1988, 8(6): 2513-2522.

Grimm et al. (1999) "Progress in Adeno-Associated Virus Type 2 Vector Production: Promises and Prospects for Clinical Use", Hum. Gene Ther., 10(15): 2445-2450.

Groth et al. (2000) "A phage integrase directs efficient site-specific integration in human cells", Proc. Natl. Acad. Sci. USA, 97(11): 5995-6000.

Ho et al. (1989) "Site-directed mutagenesis by overlap extension using the polymerase chain reaction," Elsevier Science Pub. B.V. (Biomed. Div.), Gene, 77: 51-59.

Hoeben et al. (1995) "Expression of the blood-clotting factor-VIII cDNA is repressed by a transcriptional silencer located in its coding region", Blood, 85(9): 2447-2454.

Hoeben et al., "Expression of Functional Factor VIII in Primary Human Skin Fibroblasts After Retrovirus-Mediated Gene Transfer", Journal of Biological Chemistry, May 1990, vol. 265, No. 13, pp. 7318-7323.

Holt et al. (2008) "Anti-serum albumin domain antibodies for extending the half-lives of short lived drugs," Protein Engineering, Design and Selection, 21(5):283-288.

Horton et al. (1993) "Gene Splicing by Overlap Extension," Methods in Enzymology, 217 (17): 270-279.

Ill et al., (1997) "Optimization of the Human Factor VIII Complementary DNA Expression Plasmid for Gene Therapy of Hemophilia A", Blood Coagulation & Fibrinolysis: An International Journal in Haemostasis and Thrombosis, vol. 8, pp. S23-S30.

International Search Report & Written Opinion Received for PCT Application No. PCT/US2018/046110, mailed on Nov. 15, 2018, 13 Pages.

International Search Report and Written Opinion for PCT International Patent Application No. PCT/US2019/045957, mailed Jan. 17, 2020.

International Search Report and Written Opinion for PCT International Patent Application No. PCT/US2021/047207, mailed Jan. 12, 2022.

Isalan et al. (2001) "A rapid, generally applicable method to engineer zinc fingers illustrated by targeting the HIV-1 promoter", Nature Biotechnol., 19(7): 656-660.

Israel et al. (1997) "Expression of the neonatal Fc receptor, FcRn, on human intestinal epithelial cells," Immunology 92: 69-74.

Kasuda et al., "Establishment of Embryonic Stem Cells Secreting Human Factor VIII for Cell-Based Treatment of Hemophilia A", Journal of Thrombosis and Haemostasis, Aug. 2008, vol. 6, No. 8, pp. 1352-1359.

Klinman et al. (1996) "CpG motifs present in bacteria DNA rapidly induce lymphocytes to secrete interleukin 6, interleukin 12, and interferon gamma", PNAS, 93(7): 2879-2883.

Kobayashi et al. (2002) "FcRn-mediated transcytosis of immunoglobulin G in human renal proximal tubular epithelial cells," Am J Physiol Renal Physiol 282: F358-F365.

Koeberl et al., (1995) "Sequences Within the Coding Regions of Clotting Factor VIII and CFTR Block Transcriptional Elongation", Hum. Gene. Ther., 6(4): 469-479.

Konig et al. (1998) "Use of an albumin-binding domain for the selective immobilisation of recombinant capture antibody fragments on ELISA plates," Journal of Immunological Methods, 218:73-83.

Kotterman et al. (2014) "Engineering adeno-associated viruses for clinical gene therapy", Nat. Rev. Genet., 15(7): 455-451.

Kraulis et al. (1996) "The serum albumin-binding domain of streptococcal protein G is a three-helical bundle: a heteronuclear NMR study," FEBS Letters, 378:190-194.

Kudla et al. (2006) "High Guanine and Cytosine Content Increases mRNA Levels in Mammalian Cells," PloS Biol, e180.

Kulkarni et al., "Interaction Between the sbcC Gene of *Escherichia coli* and the gam Gene of Phage λ" Genetics, vol. 123, Oct. 1989, pp. 249-253.

Kurachi et al., "Isolation and Characterization of a cDNA Coding for Human Factor IX", Proceedings of the National Academy of Sciences, 1982, pp. 6461-6464.

Langner et al., "Synthesis of Biologically Active Deletion Mutants of Human Factor VIII:C", Behring Institute Mitteilungen, Apr. 1988, No. 82, pp. 16-25.

Larrick et al. (1989) "Rapid Cloning of Rearranged Immunoglobulin Genes From Human Hybridoma Cells Using Mixed Primers and the Polymerase Chain Reaction," Biochem. and Biophys. Res. Comm. 160 (3): 1250-1256.

Leach, "Long DNA Palindromes, Cruciform Structures, Genetic Instability and Secondary Structure Repair", BioEssays, vol. 16, No. 12, Dec. 1994, pp. 893-900.

Lenting et al., "Clearance Mechanisms of von Willebrand Factor and Factor VIII", Journal of Thrombosis and Haemostasis, Jul. 2007, vol. 5, No. 7, pp. 1353-1360.

(56) References Cited

OTHER PUBLICATIONS

Lenting et al., "The Life Cycle of Coagulation Factor VIII in View of its Structure and Function", Blood, Dec. 1, 1998, vol. 92, No. 11, pp. 3983-3996.
Li et al., "Production and characterization of Novel Recombinant Adeno-Associated Virus Replicative-Form Genomes: A Eukaryotic Source of DNA for Gene Transfer", PLoS ONE vol. 8, Issue 8, e69879, Aug. 2013.
Lilley, David M.J., "In vivo consequences of Plasmid Topology", Nature, vol. 292, Jul. 23, 1981, pp. 380-382.
Linhult et al. (2002) "Mutational analysis of the interaction between albumin-binding domain from streptococcal protein G and human serum albumin," Protein Science, 11:206-213.
Loeb et al. (1999) "Enhanced expression of transgenes from adeno-associated virus vectors with the woodchuck hepatitis virus post-transcriptional regulatory element: implications for gene therapy", Hum Gene Ther., 10(14): 2295-2305.
Luo et al., "Human parvovirus B19: a mechanistic overview of infection and DNA replication", Future Virology, vol. 10, No. 2, Feb. 2015, p. 155-167.
Lynch et al. (1993) "Sequences in the Coding Region of Clotting Factor VIII Act as Dominant Inhibitors of RNA Accumulation and Protein Production," Human Gene Therapy 4: 259-272.
Malassagne et al. (Apr. 14, 2003) "Hypodermin A, A New Inhibitor of Human Complement for the Prevention of Xenogeneic Hyper-acute Rejection", Xenotransplantation, vol. 10, Issue 3, pp. 267-277.
Manaresi et al., "A Parvovirus B19 synthetic genome: sequence features and functional competence", Virology, vol. 508, May 2017, p. 54-62.
Manco-Johnson et al. (2007) "Prophylaxis versus Episodic Treatment to Prevent Joint Disease in Boys with Severe Hemophilia," N. Engl. J. Med. 357 (6): 535-44.
Maxwell et al.m "Autonomous Parvovirus Vectors", Methods, 2002, vol. 28, Issue 2, pp. 168-181.
McKnight et al. (Sep. 1983) "Expression of the Chicken Transferrin Gene in Transgenic Mice", Cell, vol. 34, Issue 2, pp. 335-341.
McLaughlin et al., "Adeno-Associated Virus General Transduction Vectors: Analysis of Proviral Structures", Journal of Virology, vol. 62, No. 6, Jun. 1988, pp. 1963-1973.
Meulien et al., "A New Recombinant Procoagulant Protein Derived From the Cdna Encoding Human Factor VIII", Protein Engineering, Design and Selection, Oct. 1, 1988, vol. 2, No. 4, pp. 301-306.
Miao et al., "Bioengineering of Coagulation Factor VIII for Improved Secretion", Blood, May 1, 2004, vol. 103, No. 9, pp. 3412-3419.
Morfini et al. (2003) "Pharmacokinetics of factor VIII and factor IX," Haemophilia, 9 (Suppl. 1): 94-100.
Mori et al., "Two novel adeno-associated viruses from cynomolgus monkey: pseudotyping characterization of capsid protein", Virology, Dec. 2004, 330(2): 375-383.
Muller et al. (Aug. 2007) "Recombinant Bispecific Antibodies for Cellular Cancer Immunotherapy", Current opinion in molecular therapeutics, vol. 9, No. 4, pp. 319-326.
Nakamura et al. (2000) "Codon usage tabulated from international DNA sequence databases: status for the year 2000," Nucleic Acids Research, 28 (1): 292.
Narita et al. (1998) "The low-density lipoprotein receptor-related protein (LRP) mediates clearance of coagulation factor Xa in Vivo," Blood, 91(2):555-560.
Naso et al., "Adeno-Associated Virus (AAV) as a Bector for Gene Therapy", BioDrugs, vol. 31, 2017, pp. 317-334.
NCBI, "Codon Usage Database", Retrieved from <<http://www.kazusa.or.jp/codon/>>, 2013, pp. 1-2.
Neumann et al., (1982) "Gene transfer into mouse lyoma cells by electroporation in high electric fields", EMBO J., 1(7): 841-845.
Ni et al., "Virus-Inspired Nucleic Acid Delivery System: Linking Virus and Viral Mimicry", Advanced Drug Delivery Reviews vol. 106(Part A), 2016, pp. 3-26.
Noren et al. (1989) "A General Method for Site-Specific Incorporation of Unnatural Amino Acids into Proteins," Science, 244: 182-188.
O'Gorman et al. (1991) "Recombinase-Mediated Gene Activation and Site-Specific Integration in Mammalian Cells", Science, 251(4999): 1351-1355.
Pabo et al. (2001) "Design and selection of novel Cys2His2 zinc finger proteins", Ann. Rev. Biochem., 70: 313-340.
Pipe et al., "Functional Factor VIII Made With Von Willebrand Factor at High Levels in Transgenic Milk", Journal of Thrombosis and Haemostasis, Nov. 2011, vol. 9, No. 11, pp. 2235-2242.
Rennie et al., "STarMirDB: A Database of MicroRNA Binding Sites", RNA Biology, May 4, 2016, vol. 13, No. 6, pp. 554-560.
Ridgway, (1988) "Introduction of Vector into Host Cells", Mammalian Expression Vectors, Chapter 24.2, pp. 470-472.
Ritchie et al. (Dec. 6, 1984) "Allelic Exclusion and Control of Endogenous Immunoglobulin Gene Rearrangement in κ Transgenic Mice", Nature, vol. 312, No. 5994, pp. 517-520.
Robl et al. (Jan. 1, 2003) "Artificial Chromosome Vectors and Expression of Complex Proteins in Transgenic Animals", Theriogenology, vol. 59, Issue 1, pp. 107-113.
Rodriguez-Merchan (2003) "Management of musculoskeletal complications of hemophilia", Thromb. Hemost., 29(1): 87-96.
Roovers et al. (2007) "Efficient inhibition of EGFR signalling and of tumour growth by antagonistic anti-EGFR Nanobodies," Cacer Immunol Immunother, 56:303-317.
Rouet et al. (1992) "A potent enhancer made of clustered liver-specific elements in the transcription control sequences of human α1-Microglobulin/bikunin," The Journal of Biological Chemistry, 267(29):20765-20773.
Rouet et al. (1995) "Hierarchy and positive/negative interplays of the hepatocyte nuclear factors HNF-1,-3 and -4 in the liver-specific enhancer for the human α-1-microglobulin/bikunin precursor," Nucleic Acids Research, 23(3):395-404.
Rouet et al. (1998) "An array of binding sites for hepatocyte nuclear factor of 4 of high and low affinities modulates the liver-specific enhancer for the human α1-microglobulin/bikunin precursor," Biochem. J., 334:577-584.
Routledge et al. (1995) "The Effect of Aglycosylation on the Immunogenicity of a Humanized Therapeutic CD3 Monoclonal Antibody," Transplantation, 60 (8): 847-853.
Ruberti et al. (1994) "The use of the RACE method to clone hybridoma cDNA when V region primers fail," Journal of Immunological Methods, 173: 33-39.
Ruther et al. (1983) "Easy identification of cDNA clones", EMBO J., 2(10): 1791-1794.
Rutledge et al. (1998) "Infectious clones and vectors derived from adeno-associated virus (AAV) serotypes other than AAV type 2", J. Vir., 72(1): 309-319.
Samulski et al., "A Recombinant Plasmid from Which an Infectious Adeno-Associated Virus Genome Can Be Excised In Vitro and Its Use to Study Viral Replication", Journal of Virology, vol. 61, No. 10, Oct. 1987, pp. 3096-3101.
Samulski et al., "Helper-Free Stocks of Recombinant Adeno-Associated Viruses: Normal Integration Does Not Require Viral Gene Expression", Journal of Virology, vol. 63, No. 9, Sep. 1989, pp. 3822-3828.
Samulski et al., "Rescue of adeno-associated virus from recombinant plasmids: gene correction within the terminal repeats of AAV", Cell, May 1983, 33(1): 135-143.
Sarver et al., "Stable Expression of Recombinant Factor VIII Molecules Using a Bovine Papillomavirus Vector", DNA, Dec. 1987, vol. 6, No. 6, pp. 553-564.
Sauer et al. (1988) "Site-specific DNA recombination in mammalian cells by the Cre recombinase of bacteriophage P1", Proc. Natl. Acad. Sci., 85(14): 5166-5170.
Schmidt et al., "Structure-Function Relationships in Factor IX and Factor IXa", Trends in Cardiovascular Medicine, 2003, vol. 13, No. 1, pp. 39-45.
Segal et al. (2001) "Custom DNA-binding proteins come of age: polydactyl zinc-finger proteins", Curr. Opin. Biotechnol. 12: 632-637.

(56) References Cited

OTHER PUBLICATIONS

Senapathy et al., "Molecular Cloning of Adeno-Associated Virus Variant Genomes and Generation of Infectious Virus by Recombination in Mammalian Cells", Journal of Biological Chemistry, vol. 259, No. 7, Apr. 10, 1984, pp. 4661-4666.

Senapathy et al., "Replication of adeno-associated virus DNA. Complementation of naturally occurring rep-mutants by a wild-type genome or an ori-mutant and correction of terminal palindrome deletions", Journ Mol Biol., Oct. 15, 1984, 179(1): 1-20.

Shields et al. (2001) "High Resolution Mapping of the Binding Site on Human IgG1 for FcyRI, FcyRII, FcyRIII, and FcRn and Design of IgG1 Variants with Improved Binding to the FcyR," J. Biol. Chem., 276 (9) 6591-6604.

Srivastava et al. (1983) "Nucleotide sequence and organization of the adeno-associated virus 2 genome", J. Vir., 45(2): 555-564.

Story et al. (1994) "A Major Histocompatibility Complex Class I-like Fc Receptor Cloned from Human Placenta: Possible Role in Transfer of Immunoglobulin G from Mother to Fetus," J. Exp. Med., Brief Definitive Report, 180: 2377-2381.

Toole, et al., "A Large Region (Approximately Equal to 95 kDa) of Human Factor VIII Is Dispensable for In Vitro Procoagulant Activity", Proceedings of the National Academy of Sciences, Aug. 1986, vol. 83, No. 16, pp. 5939-5942.

Tratschin et al. (1985) "Adeno-associated virus vector for high-frequency integration, expression, and rescue of genes in mammalian cells", Mol. Cell Biol., 5(11): 3251-3260.

Trüssel et al. (2009) "New Strategy for the Extension of the Serum Half-Life of Antibody Fragments," Bioconjugate Chem., 20:2286-2292.

Vigna et al. (2004) "Efficient Tet-Dependent Expression of Human Factor IX in Vivo by a New Self-Regulating Lentiviral Vector," Molecular Therapy, 11(5):763-775.

Wagner et al., "Microinjection of a Rabbit Beta-Globin Gene Into Zygotes and Its Subsequent Expression in Adult Mice and Their Offspring", Proceedings of the National Academy of Sciences of the United States of America, Oct. 1, 1981, vol. 78, No. 10 , pp. 6376-6380.

Wang et al., "Sequencing and generation of an infectious clone of the pathogenic goose parvovirus strain LH", Jan. 2015, vol. 160, No. 3, p. 711-718.

Wang et al., "Analysis of the genome sequence of the pathogenic Muscovy duck parvovirus strain YY reveals a 14-nucleotide-pair deletion in the invertied terminal repeats", Arch Virol., 2016, 161: 2589-2594.

Ward et al., "The Effector Functions of Immunoglobulins: Implications for Therapy", Therapeutic immunology, vol. 2, No. 2, pp. 77-94. (Apr. 1995).

White et al. (1997) "A multicenter study of recombinant factor VIII (Recombinate) in previously treated patients with haemophilia," Thrombosis and Heamostasis, 4:660-667.

Wigler et al. (1978) "Biochemical transfer of single-copy eucaryotic genes using total cellular DNA as donor", Cell, 14(3): 725-731.

Wold et al. (2013) "Adenovirus vectors for gene therapy, vaccination and cancer gene therapy", Curr Gene Ther., 13(6): 421-433.

Woychik et al. (1984) "Requirement for the 3'flanking region of the bovine growth hormone gene for accurate polyadenylylation", PNAS, 81: 3944-3948.

Wu et al. (2000) "Mutational analysis of the adeno-associated virus type 2 (AAV2) capsid gene and construction of AAV2 vectors with altered tropism", J. Vir., 74(18): 8635-8647.

Yew et al. (2002). "CpG-Depleted Plasmid DNA Vectors with Enhanced Safety and Long-Term Gene Expression in Vivo", Mol Ther., 5(6): 731-738.

Zhang et al. (2014) "Comparison of non-canonical PAMs for CRISPR/Cas9-mediated DNA cleavage in human cells", Sci Rep., 2014, 4(5405).

Zhou, et al., "Deletion of the B—B' and C—C' Regions of Inverted Terminal Repeats Reduces rAAV Productivity but Increases Transgene Expression", Scientific Reports, Jul. 14, 2017, vol. 7, Article No. 5432, pp. 1-13.

Chambers et al., "Overview of the Baculovirus Expression System", Unit 5.4.1, Production of Recombinant Proteins, Current Protocols in Protein Science, Feb. 2018, Suppl. 91: 5.4.1-5.4.6.

Dongmei et al., "Isolation, Identification and Complete Genomic Sequence Analysis of Goose Parvovirus HN Strain", Progress in Veterinary Medicine, Dec. 31, 2016, 37(12): 13-18.

Generation Bio, "Generation Bio Announces Two Non-Viral Gene Therapy Milestone Achievements: Target Levels of Factor VIII Expression in Hemophilia A Mice and Translation of Expression from Mice to Non-Human Primates", Jan. 4, 2021, obtained from url: <https://www.globenewswire.com/en/news-release/2021/01/04/2152472/0/en/Generation-Bio-Announces-Two-Non-Viral-Gene-Therapy-Milestone-Achievements-Target-Levels-of-Factor-VIII-Expression-in-Hemophilia-A-Mice-and-Translation-of-Expression-from-Mice-to-N.html>.

Hu et al., "Enhancement and Prolongation of Baculovirus-Mediated Expression in Mammalian Cells: Focuses on Strategic Infection and Feeding", Biotechnology Progress, 2003, 19: 373-379.

International Search Report and Written Opinion for PCT International Patent Application No. PCT/US2022/075186, mailed Apr. 5, 2023.

International Search Report and Written Opinion for PCT International Patent Application No. PCT/US2022/075187, mailed Dec. 13, 2022.

International Search Report and Written Opinion for PCT International Patent Application No. PCT/US2022/075280, mailed Nov. 24, 2022.

International Search Report and Written Opinion for PCT International Patent Application No. PCT/US2022/075282, mailed Nov. 17, 2022.

Li et al., "A Novel Recombinant AAV Production System with Low Side-Toxicity Pollution", Science Engine, Jan. 15, 2003, 48(1).

Meyer, "Development of an Integrated Expression Platform for Protein Production in Eukaryotic Hosts", Thesis, 2012.

Nguyen, et al., "Evaluation of Gene Promoters for Liver Expression by Hydrodynamic Gene transfer", J Surg res., Jul. 2008, 148(1): 60-66.

Rohrmann et al., "Chapter 10: Baculovirus expression technology: Theory and application", Baculovirus Molecular Biology [internet], 4th Edition, 2019.

Rohrmann et al., "Chapter 2: Structural proteins of baculovirus occlusion bodies and virions", Baculovirus Molecular Biology [internet], 4th Edition, 2019.

Sarafanov et al., "Identification of Coagulation Factor VIII A2 Domain Residues Forming the Binding Epitope for Low-Density Lipoprotein Receptor-Related Protein", Biochemistry, 2006, 45: 1829-1840.

Ward et al., "Codon Optimization of Human Factor VIII cDNAs Leads to High-Level Expression", Blood, Jan. 20, 2011, 117(3): 798-807.

Wickham et al., "Comparison of Different Cell Lines for the Production of Recombinant Baculovirus Proteins", Methods in Molecular Biology, 1995, Chapter 22, vol. 39: 385-395.

Zakas, "Evolutionary approaches to coagulation factor VIII biopharmaceutical engineering", Dissertation, Emory University, 2016.

U.S. Appl. No. 16/636,583 2021/0163986, filed Aug. 9, 2018 Jun. 3, 2021, Tongyao Liu, Nucleic Acid Molecules and Uses Thereof.

U.S. Appl. No. 18/440,712, filed Feb. 13, 2024, Ajay Maghodia, Engineered ITR Sequences and Methods of Use.

U.S. Appl. No. 16/636,583 2021/0163986 U.S. Pat. No. 12,168,776, filed Aug. 9, 2018 Jun. 3, 2021 Dec. 17, 2024, Tongyao Liu, Nucleic Acid Molecules and Uses Thereof.

U.S. Appl. No. 18/937,874, filed Nov. 5, 2024, Tongyao Liu, Nucleic Acid Molecules and Uses Thereof.

U.S. Appl. No. 16/537,192 2020/0069817, filed Aug. 9, 2019 Mar. 5, 2020, Tongyao Liu, Nucleic Acid Molecules and Uses Thereof for Non-Viral Gene Therapy.

U.S. Appl. No. 19/025,334, filed Jan. 16, 2025, Tongyao Liu, Nucleic Acid Molecules and Uses Thereof for Non-Viral Gene Therapy.

U.S. Appl. No. 17/409,773, filed Aug. 23, 2021, Tongyao Liu, Baculovirus Expression System.

(56) References Cited

OTHER PUBLICATIONS

U.S. Appl. No. 17/576,561 2022/0356490, filed Jan. 14, 2022 Nov. 10, 2022, Tongyao Liu, Baculovirus Expression System.
U.S. Appl. No. 18/440,711 2024/0294940, filed Feb. 13, 2024 Sep. 5, 2024, Tongyao Liu, Baculovirus Expression System
U.S. Appl. No. 17/409,774 2022/0090130, filed Aug. 23, 2021 Mar. 24, 2022, Ajay Maghodia, Modified Baculovirus System for Improved Production of Closed-Ended DNA (ceDNA).
U.S. Appl. No. 17/409,776, filed Aug. 23, 2021, Ajay Maghodia, Engineered ITR Sequences and Methods of Use.
U.S. Appl. No. 17/576,562 2022/0243201, filed Jan. 14, 2022 Aug. 2022, Ajay Maghodia, Engineered ITR Sequences and Methods of Use.
U.S. Appl. No. 18/440,712 2024/0350671, filed Feb. 13, 2024 Oct. 24, 2024, Ajay Maghodia, Engineered ITR Sequences and Methods of Use.
U.S. Appl. No. 17/821,356 2023/0091932, filed Aug. 22, 2022 Mar. 23, 2023, Ajay Maghodia, Closed-End DNA Production with Inverted Terminal Repeat Sequences.
U.S. Appl. No. 17/821,359 2023/0084036, filed Aug. 22, 2022 Mar. 16, 2023, Ajay Maghodia, Optimized Factor VIII Genes.
Gray et al., "Design and construction of functional AAV vectors", Methods Mol Biol., Jan. 1, 2011, Chapter 2, 807: 25-46.
Bieniossek et al., "MultiBac: Multigene Baculovirus-Based Eukaryotic Protein Complex Production", Current Protocols in Protein Science, 2008, 51: 5.20.1-5.20.26.
Deboy et al., "Target site selection by Tn7: attTn7 transcription and target activity", Journal of bacteriology, 2000, 182(11), 3310-3313.
Invitrogen, "Bac-to-Bac TOPO Expression System: An efficient cloning and site-specific transposition system to generate recombinant baculovirus for high-level protein expression", Catalog No. A11101 and A11100 Version A User Manual; Dec. 15, 2008.
Lin et al., "Utility of temporally distinct baculovirus promoters for constitutive and baculovirus-inducible transgene expression in transformed insect cells", Journal of Biotechnology, May 10, 2013, 165(1): 11-17.
Sari et al., "The MultiBac Baculovirus/Insect Cell Expression Vector System for Producing Complex Protein Biologics", Adv Exp Med Biol., May 11, 2016, 896: 199-215.
Yu et al., "Functional Assembly of Protein Fragments Induced by Spatial Confinement", PLoS ONE, 2015, 10(4): e0122101.
Burns et al., "A high molecular weight melanoma-associated antigen-specific chimeric antigen receptor redirects lymphocytes to target human melanomas", Cancer Research, Apr. 15, 2010, 70(8): 3027-3033.
Eyler et al., "Pseudouridinylation of mRNA coding sequences alters translation", Pnas USA, Oct. 31, 2019, 116(46): 23068-23074.
Kaufman, "Overview of vector design for mammalian gene expression", Mol Biotechnol, Oct. 2000, 16(2): 151-160.
Khan et al., "Gene expression in Mammalian cells and its applications", Advanced Pharmaceutical Bulletin, Aug. 20, 2013, 3(2): 257-263.
Pakula et al., "Genetic analysis of protein stability and function", Anna. Rev. Genet., 1989, 23: 289-310.
Palillo, "Transforming DH10Bac E. coli, continued", Oct. 11, 2017, Retrieved from url: < https://lab.rockefeller.edu/chen/assets/file/BacmidTransformation.pdf>.
Raup et al., "Promoter, transgene, and cell line effects in the transfection of mammalian cells using PDMAEMA-based nano-stars", Biotechnology Reports, Sep. 2016, 11: 53-61.
Richman et al., High-affinity GD2-specific Car T cells induce fatal encephalitis in a preclinical neuroblastoma model, Cancer Immunology Research, Jan. 2018, 6(1): 36-46.
Tokuriki et al., "Stability effects of mutations and protein evolvability", Curr. Opin. Struct. Biol., Oct. 2009, 19(5): 596-604, Epublished Sep. 16, 2009.
Viola et al., "Non-viral nanovectors for gene delivery: factors that govern successful therapeutics", Expert Opin. Drug Deliv., Apr. 5, 2010, 7(6): 721-735.
Dong et al., "Construction and characterization of a synthetic Baculovirus-inducible 39K promoter", Journal of Biological Engineering, Dec 4, 2018, 12: 30.
Wang et al., "Human Bocavirus 1 Is a Novel Helper for Adeno-associated Virus Replication", J. Virol., Aug. 24, 2017, 91(18):e00710-e00717.

* cited by examiner

SEQUENCE LISTING

```
Sequence total quantity: 36
SEQ ID NO: 1            moltype = DNA  length = 140
FEATURE                 Location/Qualifiers
misc_feature            1..140
                        note = Human Bocavirus 1
source                  1..140
                        mol_type = other DNA
                        organism = synthetic construct
SEQUENCE: 1
gtggttgtac agacgccatc ttggaatcca atatgtctgc cggctcagtc atgcctgcgc  60
tgcgcgcagc gcgctgcgcg cgcgcatgat ctaatcgccg gcagacatat tggattccaa  120
gatggcgtct gtacaaccac                                             140

SEQ ID NO: 2            moltype = DNA  length = 200
FEATURE                 Location/Qualifiers
misc_feature            1..200
                        note = Human Bocavirus 1
source                  1..200
                        mol_type = other DNA
                        organism = synthetic construct
SEQUENCE: 2
ttgcttatgc aatcgcgaaa ctctatatct tttaatgtgt tgttgttgta catgcgccat  60
cttagtttta tatcagctgg cgccttagtt atataacatg catgttatat aactaaggcg  120
ccagctgata taaaactaag atggcgcatg tacaacaaca acacattaaa agatatagag  180
tttcgcgatt gcataagcaa                                             200

SEQ ID NO: 3            moltype = DNA  length = 8257
FEATURE                 Location/Qualifiers
misc_feature            1..8257
                        note = Expression construct
source                  1..8257
                        mol_type = other DNA
                        organism = synthetic construct
SEQUENCE: 3
gtatacctgc aggctagcca cgtgttgttg ttgtacatgc gccatcttag ttttatatca  60
gctggcgcct tagttatata acatgcatgt tatataacta aggcgccagc tgatataaaa  120
ctaagatggc gcatgtacaa caacaacaca ttaaaagata tagagtttcg cgattgcaag  180
cttggcccca ggttaatttt taaaaagcag tcaaaggtca aagtggccct tggcagcatt  240
tactctctct attgactttg gttaataatc tcaggagcac aaacattcct ggaggcagga  300
gaagaaatca acatcctgga cttatcctct gggcctctcc ccaccttcga tggccccagg  360
ttaattttta aaaagcagtc aaaggtcaaa gtggcccttg gcagcattta ctctctctat  420
tgactttggt taataatctc aggagcacaa acattcctgg aggcaggaga agaaatcaac  480
atcctggact tatcctctgg gcctctcccc accgatatct acctgctgat cgcccggccc  540
ctgttcaaac atgtcctaat actctgtcgg ggcaaaggtc ggcagtagtt ttccatctta  600
ctcaacatcc tcccagtgta cgtaggatcc tgtctgtctg cacatttcgt agagcgagtg  660
ttccgatact ctaatctccc ggggcaaagg tcgtattgac ttaggttact tattctcctt  720
```

-continued

```
ttgttgacta agtcaataat cagaatcagc aggtttggag tcagcttggc agggatcagc  780
agcctgggtt ggaaggaggg ggtataaaag ccccttcacc aggagaagcc gtcacacaga  840
tccacaagct cctgctagga attctcagga gcacaaacat tcctggaggc aggagaagaa  900
atcaacatcc tggacttatc ctctgggcct ctccccaccg atatctacct gctgatcgcc  960
cggcccctgt tcaaacatgt cctaatactc tgtcggggca aaggtcggca gtagttttcc  1020
atcttactca acatcctccc agtgtacgta ggatcctgtc tgtctgcaca tttcgtagag  1080
cgagtgttcc gatactctaa tctcccgggg caaaggtcgt attgacttag gttacttatt  1140
ctcctttttgt tgactaagtc aataatcaga atcagcaggt ttggagtcag cttggcaggg  1200
atcagcagcc tgggttggaa ggaggggggta taaaagcccc ttcaccagga gaagccgtca  1260
cacagatcca caagctcctg ctagagtcgc tgcgcgctgc cttcgccccg tgccccgctc  1320
cgccgccgcc tcgcgccgcc cgccccggct ctgactgacc gcgttactcc cacaggtgag  1380
cgggcgggac ggcccttctc ctccgggctg taattagcgc ttggtttatt gacggcttgt  1440
ttcttttctg tggctgcgtg aaagccttga ggggctccgg gaaggccctt tgtgcggggg  1500
gagcggctcg gggggtgcgt gcgtgtgtgt gtgcgtgggg agcgccgcgt gcggctccgc  1560
gctgcccggc ggctgtgagc gctgcgggcg cggcgcgggg ctttgtgcgc tccgcagtgt  1620
gcgcgagggg agcgcggccg ggggcggtgc cccgcggtgc ggggggggct gcgaggggaa  1680
caaaggctgc gtgcggggtg tgtgcgtggg ggggtgagca gggggtgtgg gcgcgtcggt  1740
cgggctgcaa ccccccctgc acccccctcc ccgagttgct gagcacggcc cggcttcggg  1800
tgcggggctc cgtacggggc gtggcgcggg gctcgccgtg ccgggcgggg ggtggcggca  1860
ggtgggggtg ccgggcgggg cggggccgcc tcgggccggg gagggctcgg gggaggggcg  1920
cggcggcccc cggagcgccg gcggctgtcg aggcgcggcg agccgcagcc attgcctttt  1980
atggtaatcg tgcgagaggg cgcagggact tcctttgtcc caaatctgtg cggagccgaa  2040
atctgggagg cgccgccgca ccccctctag cgggcgcggg gcgaagcggt gcggcgccgg  2100
caggaaggaa atgggcgggg agggccttcg tgcgtcgccg cgccgccgtc cccttctccc  2160
tctccagcct cggggctgtc cgcgggggga cggctgcctt cgggggggac ggggcagggc  2220
ggggttcggc ttctggcgtg tgaccggcgg ctctagagcc tctgctaacc ttgttcttgc  2280
cttcttcttt ttcctacagc tcctgggcaa cgtgctggtt attgtgctgt ctcatcattt  2340
tggcaaagaa ttactcgagg ccaccatgca gattgaactg tccacttgct tcttcctgtg  2400
cctcctgcgg ttttgcttct cggccacccg ccggtattac ttaggtgctg tggaactgag  2460
ctgggactac atgcagtccg acctgggaga actgccggtg gacgcgagat tcccacctag  2520
agtcccgaag tccttcccat tcaacacctc cgtggtctac aaaaagaccc tgttcgtgga  2580
gttcactgac caccttttca atattgccaa gccgcgcccc ccctggatgg gcctgcttgg  2640
tcctacgatc caagcagagg tctacgacac cgtggtcatc acactgaaga acatggcctc  2700
acaccccgtg tcgctgcatg ctgtgggagt gtcctactgg aaggcctcag agggtgccga  2760
atatgatgac cagaccagcc agagggaaaa ggaggatgac aaagtgttcc cgggtggcag  2820
ccacacttac gtgtggcaag tgctgaagga aaacgggcct atggcgtcgg acccccctatg  2880
cctgacctac tcctacctgt cccatgtgga ccttgtgaag gatctcaact cgggactgat  2940
cggcgccctc ttggtgtgca gagaaggcag cctggcgaag gaaaagactc agaccctgca  3000
caagttcatt ctgttgtttg ctgtgttcga tgaaggaaag tcctggcact cagaaaccaa  3060
gaactcgctg atgcaggata gagatgcggc ctcggccaga gcctggccta aaatgcacac  3120
cgtcaacgga tatgtgaaca ggtcgctccc tggcctcatc ggctgccaca gaaagtccgt  3180
gtattggcat gtgatcggca tgggtactac tccggaagtg catagtatct ttctggaggg  3240
ccataccttc ttggtgcgca accacagaca ggcctcgctg gaaatctcgc ctatcacttt  3300
cttgactgcg cagaccctcc ttatggacct tggacagttc ctgctgttct gtcacatcag  3360
ctcccatcag catgatggga tggaggccta tgtcaaagtg gactcctgcc ctgaggagcc  3420
acagctccgg atgaagaaca atgaggaagc ggaggattac gacgacgacc tgactgacag  3480
cgaaatggac gtcgtgcgat tcgatgacga caacagcccg tccttcatcc aaattagatc  3540
agtggcgaag aagcacccca agacctgggt gcactacatt gccgccgagg aagaggactg  3600
ggactacgcg ccgctggtgc tggcgccaga cgacaggagc tacaagtccc agtacctcaa  3660
caacgggccg cagcgcattg gcaggaagta caagaaagtc cgcttcatgg cctacactga  3720
tgaaaccttc aagacgaggg aagccatcca gcacgagtca ggcatcctgg gaccgctcct  3780
ttacggcgaa gtcggggata ccctgctcat cattttcaag aaccaggcat cgcggcccta  3840
caacatctac cctcacggga tcacagacgt gcgcccgctc tactcccgcc ggctgcccaa  3900
gggagtgaag cacctgaagg attttcccat cctgccggga gaaatcttca agtacaagtg  3960
gaccgtgact gtggaagatg gccctaccaa gtcggaccct cgctgtctga cccggtacta  4020
ttcctcgttt gtgaacatgg agcgcgacct ggcctcgggg ctgattggtc cgctgctgat  4080
ctgctacaag gagtccgtgg accagcgcgg gaaccagatc atgtccgaca agcgcaacgt  4140
gatcctgttc tctgtctttg atgaaaacag atcgtggtac ttgactgaga atatccagcg  4200
gttcctgccc aacccagcgg gagtgcaact ggaggacccg gagttccagg cctcaaacat  4260
tatgcactct atcaacggct atgtgttcga ctcgctccaa ctgagcgtgt gcctgcatga  4320
agtggcatac tggtacattc tgtccatcgg agcccagacc gacttcctgt ccgtgttctt  4380
ctccggatac accttcaagc ataagatggt gtacgaggac actctgaccc tcttcccatt  4440
ttccggagaa actgtgttca tgtcaatgga aaacccgggc ttgtggattc tgggttgcca  4500
taactcggac ttccggaata gagggatgac cgccctgctg aaagtgtcca gctgtgacaa  4560
gaataccggc gattactacg aggacagcta tgaggacatc tccgcttatc tgctgtccaa  4620
gaacaacgcc attgaaccca ggtccttctc ccaaaacggt gcaccgacct ccgaaagcgc  4680
caccccagag tcaggacctg gctcggaacc ggctacctcg ggctcagaga caccggggac  4740
ttccgagtcc gcaacccccg agagtggacc cggatccgaa ccagcaacct caggatcaga  4800
aaccccggga acttcggaat ccgccactcc cgagtcggga ccaggcacct ccactgagcc  4860
ttccgaggga agcgcccccg gatcccctgc tggatcccct accagcactg aagaaggcac  4920
ctcagaatcc gcgacccctg agtccggccc tggaagcgaa cccgccacct ccggttccga  4980
aacccctggg actagcgaga gcgccactcc ggaatcgggc ccaggaagcc ctgccggatc  5040
cccgaccagc accgaggagg gaagccccgc cgggtcaccg acttccactg aggagggagc  5100
ctcatccccc cccgtgctga agcggcatca aagagagatc accaggacca ctctccagtc  5160
cgatcaggaa gaaattgact acgacgatac tatcagcgtg gagatgaaga aggaggactt  5220
cgacatctac gatgaggatg agaaccagtc ccctcggagc tttcagaaga aaacccgcca  5280
ctacttcatc gctgccgtgg agcggctgtg ggattacggg atgtccagct caccgcatgt  5340
gctgcggaat agagcgcagt caggatcggt gccccagttc aagaaggtcg tgttccaaga  5400
gttcaccgac gggtccttca ctcaacccct gtaccggggc gaactcaacg aacacctggg  5460
```

```
actgcttggg ccgtatatca gggcagaagt ggaagataac atcatggtca ccttccgcaa  5520
ccaggcctcc cggccgtaca gcttctactc ttcactgatc tcctacgagg aagatcagcg  5580
gcagggagcc gagccccgga agaacttcgt caagcctaac gaaactaaga cctacttttg  5640
gaaggtccag catcacatgg ccccgaccaa agacgagttc gactgtaaag cctgggccta  5700
cttctccgat gtggacctgg agaaggacgt gcactcggga ctcattggcc cgctccttgt  5760
gtgccatact aataccctga accctgctca cggtcgccaa gtcacagtgc aggagttcgc  5820
cctcttcttc accatcttcg atgaaacaaa gtcctggtac tttactgaga acatggaacg  5880
caattgcagg gcaccctgca acatccagat ggaagatccc accttcaagg aaaactaccg  5940
gtttcatgcc attaacggct acataatgga cacgttgcca ggactggtca tggcccagga  6000
ccagagaatc cggtggtatc tgctctccat gggctccaac gaaaacattc acagcattca  6060
tttttccggc catgtgttca ccgtccggaa gaaggaagag tacaagatgg ctctgtacaa  6120
cctctaccct ggagtgttcg agactgtgga aatgctgcct agcaaggccg gcatttggag  6180
agtggaatgc ctgatcggag agcatttgca cgccggaatg tccaccctgt ttcttgtgta  6240
ctccaacaag tgccagaccc cgctgggaat ggcctcaggt catattaggg atttccagat  6300
cactgcttcg gggcagtacg ggcagtgggc acctaagttg gcccggctgc actactctgg  6360
ctccatcaat gcctggtcca ccaaggaacc cttctcctgg attaaggtgg acctcctggc  6420
cccaatgatt attcacggta ttaagaccca gggtgcccga cagaagttct cctcactcta  6480
catctcgcaa ttcatcataa tgtacagcct ggatgggaag aagtggcaga cctaccgggg  6540
aaactccact ggaacgctca tggtgttttt cggcaacgtg gactcctccg gcattaagca  6600
caacatcttc aaccctccga tcattgctcg gtacatccgg ctgcacccaa ctcactacag  6660
catccggtcc accctgcgga tggaactgat gggttgtgac ctgaactcct gctccatgcc  6720
ccttgggatg gaatccaagg ccattagcga tgcacagatc accgcctctt catacttcac  6780
caacatgttc gcgacctggt ccccgtcgaa ggcccgcctg cacctccaag gtcgctccaa  6840
tgcgtggcgg cctcaagtga acaaccccaa ggagtggctc caggtcgact tccaaaagac  6900
catgaaggtc accggagtga ccacccaggg cgtgaagtcc ctgctgacct ctatgtacgt  6960
taaggagttc ctcatctcct caagccaaga cggacatcag tggaccctgt tcttccaaaa  7020
cggaaaagtc aaagtattcc agggcaacca ggactccttc acccctgtgg tcaacagcct  7080
ggaccccccca ttgctgaccc gctacctccg catccacccc caaagctggg tccaccagat  7140
cgcactgcgc atggaggtcc ttggatgcga agcccaagat ctgtactaag cggccgctca  7200
taatcaacct ctggattaca aaatttgtga aagattgact ggtattctta actatgttgc  7260
tccttttacg ctatgtggat acgctgcttt aatgcctttg tatcatgcta ttgcttcccg  7320
tatggctttc attttctcct ccttgtataa atcctggttg ctgtctcttt atgaggagtt  7380
gtggcccgtt gtcaggcaac gtggcgtggt gtgcactgtg tttgctgacg caacccccac  7440
tggttggggc attgccacca cctgtcagct cctttccggg actttcgctt tccccctccc  7500
tattgccacg gcggaactca tcgccgcctg ccttgcccgc tgctggacag gggctcggct  7560
gttgggcact gacaattccg tggtgttgtc ggggaaatca tcgtcctttc cttggctgct  7620
cgcctgtgtt gccacctgga ttctgcgcgg gacgtccttc tgctacgtcc cttcggccct  7680
caatccagcg gaccttcctt cccgcggcct gctgccggct ctgcggcctc ttccgcgtct  7740
tcgccttcgc cctcagacga gtcggatctc cctttgggcc gcctccccgc tgcctaggcg  7800
actgtgcctt ctagttgcca gccatctgtt gtttgcccct cccccgtgcc ttccttgacc  7860
ctggaaggtg ccactcccac tgtcctttcc taataaaatg aggaaattgc atcgcattgt  7920
ctgagtaggt gtcattctat tctggggggt ggggtggggc aggacagcaa gggggaggat  7980
tgggaagaca atagcaggca tgctggggaa gaccatgggc gcgccaggcc tgtcgacgcc  8040
cgggcggtac cgcgatcgct cgcgacgcat aaagtatatg tgacgtggtt gtacagacgc  8100
catcttggaa tccaatatgt ctgccggcga ttagatcatg cgcgcgcgca gcgcgctgcg  8160
cgcagcgcag gcatgactga gccggcagac atattggatt ccaagatggc gtctgtacaa  8220
ccacgtgctt aagctgcaga ctagtgagct cgttaac                           8257

SEQ ID NO: 4            moltype = DNA  length = 1979
FEATURE                 Location/Qualifiers
misc_feature            1..1979
                        note = Expression construct
source                  1..1979
                        mol_type = other DNA
                        organism = synthetic construct
SEQUENCE: 4
gcggccgcgg atccgccacc atggcattca atccgcccgt aatacgcgca ttttcacaac  60
ccgcctttac gtatgtcttt aagtttccgt accctcaatg gaaagagaaa gagtggctac  120
tgcacgcgtt gcttgcccac ggcaccgagc agtccatgat tcaattacgt aactgtgccc  180
cacacccgga cgaggatatt atccgggacg atcttctaat aagtttggaa gataggcatt  240
tcggggcggt cctgtgtaaa gcggtataca tggctactac cacgttgatg tctcacaagc  300
aacgcaatat gttcccaagg tgcgacataa tcgttcagtc agagttaggt gaaaaaaatt  360
tacattgtca tattatcgtt ggaggcgaag gcctatcaaa gagaaacgct aagagctctt  420
gcgctcagtt ttacggactt atattagcag aaattatcca gcgctgtaag agtttactag  480
ccacccgtcc gtttgagccg gaagaagcgg atatatttca tacgttgaag aaagcggagc  540
gcgaggcctg ggtggagtt actggcggta acatgcaaat cttacaatac agggaccgtc  600
ggggtgacct gcatgcacag actgttgatc ccctcagatt cttcaaaaat tatttgttac  660
cgaagaaccg atgcataagt agttacagca aacctgatgt ctgtactagc cctgataact  720
ggttcattct ggccgaaaaa acgtactcgc atacacttat caatggattg ccgcttcccg  780
agcactatcg aaaaaactat catgccaccc tggataatga agttatacct ggaccacaga  840
ctatggcgta tggagggaga ggcccttggg aacatttacc cgaggtgggt gaccagaggc  900
ttgccgcaag ttccgtgagc actacgtata agccaaacaa gaaggagaag ctaatgctca  960
acctcctcga caagtgtaag gagttgaatc ttctagttta tgaggatctt gtagcgaact  1020
gcccagagct gctgctcatg ctagaaggcc aacctggagg tgctcgactc atcgagcaag  1080
tactaggaat gcatcacatc aatgtatgct cgaatttcac cgcgctaacg tacctcttcc  1140
atctgcatcc ggtgacatcg ctggatagtg acaacaaagc gttacagctt ttactaattc  1200
aagggtacaa ccccctggca gtggggcatg ctctctgttg tgtgttaaac aaacaatttg  1260
gtaaacagaa cacagtctgt ttttacgggc cagcatctac tgggaaaaca aatatggcaa  1320
aagcgattgt gcagggaatc cggctatatg gctgcgtcaa ccatcttaac aagggttttg  1380
```

```
ttttcaatga ttgtcgacaa cgcctcgtag tctggtggga ggaatgccta atgcaccagg  1440
actgggtgga gccagcaaag tgtattcttg gcgggaccga atgtcgtatc gacgtcaagc  1500
acagagattc tgtcctattg acacaaacgc ctgtaataat ttcgactaat cacgacattt  1560
acgccgtcgt gggagggaat tcggtgtctc acgttcacgc tgcgcctctc aaagaacggg  1620
ttattcagct gaattttatg aaacaactcc cccaaacttt tggtgagata accgccacag  1680
aaatcgctgc tctgctacag tggtgcttta atgaatatga ctgcaccctg acaggtttca  1740
aacagaagtg gaatttggac aagataccta actcattccc gttgggggta ttgtgcccaa  1800
cacattccca agatttcaca cttcacgaaa atgggtattg cacggactgc gggggctacc  1860
ttccccactc cgctgataat tcaatgtata ccgatcgggc tagcgaaaca tccaccggcg  1920
acataacgcc ctccaaatga ttcgaatcta gagcctgcag tctcgaggca tgcggtacc   1979

SEQ ID NO: 5           moltype = DNA  length = 18
FEATURE                Location/Qualifiers
misc_feature           1..18
                       note = primer
source                 1..18
                       mol_type = other DNA
                       organism = synthetic construct
SEQUENCE: 5
gtggacgtga aagaaacc                                                18

SEQ ID NO: 6           moltype = DNA  length = 20
FEATURE                Location/Qualifiers
misc_feature           1..20
                       note = primer
source                 1..20
                       mol_type = other DNA
                       organism = synthetic construct
SEQUENCE: 6
ggtcatagct gtttcctgtg                                              20

SEQ ID NO: 7           moltype = DNA  length = 2033
FEATURE                Location/Qualifiers
misc_feature           1..2033
                       note = expression construct
source                 1..2033
                       mol_type = other DNA
                       organism = synthetic construct
SEQUENCE: 7
attaagcttc cgcgtaaaac acaatcaagt atgagtcata agctgatgtc atgttttgca  60
cacggctcat aaccgaactg gctttacgag tagaattcta cttgtaacgc acgatcagtg  120
gatgatgtca tttgttttc aaatcgagat gatgtcatgt tttgcacacg gctcataaac  180
tcgctttacg ggtagaattc tacgtgtaac gcacgatcga ttgatgagtc atttgttttg  240
caatatgata tcatacaata tgactcattt gtttttcaaa accgaacttg atttacgggt  300
agaattctac ttgtaaagca caatcaaaaa gatgatgtca tttgttttc aaaactgaac  360
tcgctttacg agtagaattc tacgtgtaaa acacaatcaa gaaatgatgt catttgttat  420
aaaaataaaa gctgatgtca tgttttgcac atggctcata actaaactcg ctttacgggt  480
agaattctac gcgcgtcgat gtctttgtga tgcgcgcgac atttttgtag gttattgata  540
aaatgaacgg atacgttgcc cgacattatc attaaatcct tggcgtagaa tttgtcgggt  600
ccattgtccg tgtgcgctag catgcccgta acggacctcg tacttttggc ttcaaaggtt  660
ttgcgcacag acaaaatgtg ccacacttgc agctctgcat gtgtgcgcgt taccacaaat  720
cccaacggcg cagtgtactt gttgtatgca aataaatctc gataaaggcg cggcgcgcga  780
atgcagctga tcacgtacgc tcctcgtgtt ccgttcaagg acggtgttat cgacctcaga  840
ttaatgttta tcggccgact gttttcgtat ccgctcacca aacgcgtttt tgcattaaca  900
ttgtatgtcg gcggatgttc tatatctaat ttgaataaat aaacgataac cgcgttggtt  960
ttagagggca taataaaaga aatattgtta tcgtgttcgc cattagggca gtataaattg  1020
acgttcatgt tggatattgt ttcagttgca agttgacact ggcggcgaca agatcgtgaa  1080
caaccaagtg acgcggccgc atttgtaaaa aaaaaataaa taaaaatgat cgagcaggac  1140
ggcctgcacg ctggttctcc agctgcttgg gtcgagcgtc tgttcggtta cgactgggct  1200
cagcagacca tcggttgctc cgacgctgct gtgttccgtc tgtccgctca gggtcgtccc  1260
gtgctgttcg tcaagaccga cctgtccggt gctctgaacg agctgcagga cgaggctgct  1320
cgtctgtcct ggctggctac cactggtgtc ccttgcgctg ctgtcctgga cgtggtcact  1380
gaggctggtc gtgactggct gctgctggga gaagtgcctg gacaggacct gctgtccagc  1440
cacctggctc cagctgagaa ggtgtccatc atggctgacg ctatgcgtcg tctgcacacc  1500
ctggaccctg ctacctgccc cttcgaccac caagctaagc accgtatcga gcgtgctcgt  1560
acccgtatgg aagctggcct ggtggaccag gacgacctgg acgaagaaca ccagggactg  1620
gcccctgctg agctgttcgc tcgtctgaag gctcgtatgc ccgacggcga ggacctggtg  1680
gttactcacg gcgacgcttg cctgcccaac atcatggtcg agaacggtcg tttctccggt  1740
ttcatcgact gcggtcgtct gggtgtcgct gaccgttacc aggatatcgc tctggctacc  1800
cgtgatatcg ctgaggaact gggtggcgag tgggctgaca gattcctggt gctgtacggt  1860
atcgctgctc ccgactccca gcgtatcgct ttctaccgtc tgctggacga gttcttctaa  1920
gccccttgta aacgccacaa ttgtgtttgt tgcaaataaa cccatgatta tttgattaaa  1980
attgttgttt tctttgttca tagacaatag tgtgttttgc ctaaacgggt acc         2033

SEQ ID NO: 8           moltype = DNA  length = 1958
FEATURE                Location/Qualifiers
misc_feature           1..1958
                       note = Expression construct
source                 1..1958
```

```
                        mol_type = other DNA
                        organism = synthetic construct
SEQUENCE: 8
attaagcttc cgcgtaaaac acaatcaagt atgagtcata agctgatgtc atgttttgca  60
cacggctcat aaccgaactg gctttacgag tagaattcta cttgtaacgc acgatcagtg  120
gatgatgtca tttgtttttc aaatcgagat gatgtcatgt tttgcacacg gctcataaac  180
tcgctttacg ggtagaattc tacgtgtaac gcacgatcga ttgatgagtc atttgttttg  240
caatatgata tcatacaata tgactcattt gtttttcaaa accgaacttg atttacgggt  300
agaattctac ttgtaaagca caatcaaaaa gatgatgtca tttgtttttc aaaactgaac  360
tcgctttacg agtagaattc tacgtgtaaa acacaatcaa gaaatgatgt catttgttat  420
aaaaataaaa gctgatgtca tgttttgcac atggctcata actaaactcg ctttacgggt  480
agaattctac gcgcgtcgat gtctttgtga tgcgcgcgac atttttgtag gttattgata  540
aaatgaacgg atacgttgcc cgacattatc attaaatcct tggcgtagaa tttgtcgggt  600
ccattgtccg tgtgcgctag catgcccgta acggacctcg tacttttggc ttcaaaggtt  660
ttgcgcacag acaaaatgtg ccacacttgc agctctgcat gtgtgcgcgt taccacaaat  720
cccaacggcg cagtgtactt gttgtatgca aataaatctc gataaaggcg cggcgcgcga  780
atgcagctga tcacgtacgc tcctcgtgtt ccgttcaagg acggtgttat cgacctcaga  840
ttaatgttta tcggccgact gttttcgtat ccgctcacca aacgcgtttt tgcattaaca  900
ttgtatgtcg gcggatgttc tatatctaat ttgaataaat aaacgataac cgcgttggtt  960
ttagagggca taataaaaga aatattgtta tcgtgttcgc cattagggca gtataaattg  1020
acgttcatgt tggatattgt ttcagttgca agttgacact ggcggcgaca agatcgtgaa  1080
caaccaagtg acgcggccgc atttgtaaaa aaaaaataaa taaaaatggt gtccaagggc  1140
gaggaactgt tcaccggtgt cgtgcccatc ctggtcgaac tggacggcga cgtgaacggt  1200
cacaagttct ccgtgtctgg cgaaggcgag ggcgacgcta cctacggaaa gctgaccctg  1260
aagttcatct gcaccaccgg caagctgccc gtgccttggc ctaccctggt caccactctg  1320
acctacggtg tccagtgctt ctcccgttac cccgaccaca tgaagcagca cgatttcttc  1380
aagtccgcta tgcccgaggg ttacgtgcaa gagcgtacca tcttcttcaa ggacgacggc  1440
aactacaaga cccgtgctga agtgaagttc gaaggcgaca ccctcgtgaa ccgtatcgag  1500
ctgaagggta tcgacttcaa ggaagatgga aacatcctgg gccacaagct cgagtacaac  1560
tacaactccc acaacgtgta catcatggcc gacaagcaaa agaacggcat caaagtgaac  1620
ttcaagatcc gccacaacat cgaggacggt tccgtgcagc tggctgacca ctaccagcag  1680
aacaccccca tcggcgacgg tcctgtgctg ctgcctgaca accactacct gtccacccag  1740
tccgctctgt ccaaggaccc caacgagaag cgtgaccaca tggtgctgct cgagttcgtg  1800
accgctgctg gtatcaccct gggcatggac gagctgtaca agtaagcccc ttgtaaacgc  1860
cacaattgtg tttgttgcaa ataaacccat gattatttga ttaaaattgt tgttttcttt  1920
gttcatagac aatagtgtgt tttgcctaaa cgggtacc                        1958

SEQ ID NO: 9            moltype = DNA  length = 4824
FEATURE                 Location/Qualifiers
misc_feature            1..4824
                        note = expression construct
source                  1..4824
                        mol_type = other DNA
                        organism = synthetic construct
SEQUENCE: 9
atgcagattg aactgtccac ttgcttcttc ctgtgcctcc tgcggttttg cttctcggcc  60
acccgccggt attacttagg tgctgtggaa ctgagctggg actacatgca gtccgacctg  120
ggagaactgc cggtggacgc gagattccca cctagagtcc cgaagtcctt cccattcaac  180
acctccgtgg tctacaaaaa gaccctgttc gtggagttca ctgaccacct tttcaatatt  240
gccaagccgc gcccccccctg gatgggcctg cttggtccta cgatccaagc agaggtctac  300
gacaccgtgg tcatcacact gaagaacatg gcctcacacc ccgtgtcgct gcatgctgtg  360
ggagtgtcct actggaaggc ctcagagggt gccgaatatg atgaccagac cagccagagg  420
gaaaaggagg atgacaaagt gttcccgggt ggcagccaca cttacgtgtg gcaagtgctg  480
aaggaaaacg ggcctatggc gtcggacccc ctatgcctga cctactccta cctgtcccat  540
gtggaccttg tgaaggatct caactcggga ctgatcggcg ccctcttggt gtgcagagaa  600
ggcagcctgg cgaaggaaaa gactcagacc ctgcacaagt tcattctgtt gtttgctgtg  660
ttcgatgaag gaaagtcctg gcactcagaa accaagaact cgctgatgca ggatagagat  720
gcggcctcgg ccagagcctg gcctaaaatg cacaccgtca acggatatgt gaacaggtcg  780
ctccctggcc tcatcggctg ccacagaaag tccgtgtatt ggcatgtgat cggcatgggt  840
actactccgg aagtgcatag tatctttctg gagggccata ccttcttggt gcgcaaccac  900
agacaggcct cgctggaaat ctcgcctatc actttcttga ctgcgcagac cctccttatg  960
gaccttggac agttcctgct gttctgtcac atcagctccc atcagcatga tgggatggag  1020
gcctatgtca aagtggactc ctgccctgag gagccacagc tccggatgaa gaacaatgag  1080
gaagcggagg attacgacga cgacctgact gacagcgaaa tggacgtcgt gcgattcgat  1140
gacgacaaca gcccgtcctt catccaaatt agatcagtgg cgaagaagca ccccaagacc  1200
tgggtgcact acattgccgc cgaggaagag gactgggact acgcgccgct ggtgctggcg  1260
ccagacgaca ggagctacaa gtcccagtac ctcaacaacg ggccgcagcg cattggcagg  1320
aagtacaaga aagtccgctt catggcctac actgatgaaa ccttcaagac gagggaagcc  1380
atccagcacg agtcaggcat cctgggaccg ctcctttacg gcgaagtcgg ggataccctg  1440
ctcatcattt tcaagaacca ggcatcgcgg ccctacaaca tctaccctca cgggatcaca  1500
gacgtgcgcc cgctctactc ccgccggctg cccaagggag tgaagcacct gaaggatttt  1560
cccatcctgc cgggagaaat cttcaagtac aagtggaccg tgactgtgga agatggccct  1620
accaagtcgg accctcgctg tctgacccgg tactattcct cgtttgtgaa catggagcgc  1680
gacctggcct cggggctgat tggtccgctg ctgatctgct acaaggagtc cgtggaccag  1740
cgcgggaacc agatcatgtc cgacaagcgc aacgtgatcc tgttctctgt ctttgatgaa  1800
aacagatcgt ggtacttgac tgagaatatc cagcggttcc tgcccaaccc agcgggagtg  1860
caactggagg acccggagtt ccaggcctca aacattatgc actctatcaa cggctatgtg  1920
ttcgactcgc tccaactgag cgtgtgcctg catgaagtgg catactggta cattctgtcc  1980
atcggagccc agaccgactt cctgtccgtg ttcttctccg gatacacctt caagcataag  2040
```

```
atggtgtacg aggacactct gaccctcttc ccattttccg gagaaactgt gttcatgtca  2100
atggaaaacc cgggcttgtg gattctgggt tgccataact cggacttccg gaatagaggg  2160
atgaccgccc tgctgaaagt gtccagctgt gacaagaata ccggcgatta ctacgaggac  2220
agctatgagg acatctccgc ttatctgctg tccaagaaca acgccattga acccaggtcc  2280
ttctcccaaa acggtgcacc gacctccgaa agcgccaccc cagagtcagg acctggctcg  2340
gaaccggcta cctcgggctc agagacaccg gggacttccg agtccgcaac ccccgagagt  2400
ggacccggat ccgaaccagc aacctcagga tcagaaaccc cgggaacttc ggaatccgcc  2460
actcccgagt cgggaccagg cacctccact gagccttccg agggaagcgc ccccggatcc  2520
cctgctggat cccctaccag cactgaagaa ggcacctcag aatccgcgac ccctgagtcc  2580
ggccctggaa gcgaacccgc cacctccggt tccgaaaccc ctgggactag cgagagcgcc  2640
actccggaat cgggcccagg aagccctgcc ggatccccga ccagcaccga ggagggaagc  2700
cccgccgggt caccgacttc cactgaggag ggagcctcat cccccccgt gctgaagcgg  2760
catcaaagag agatcaccag gaccactctc cagtccgatc aggaagaaat tgactacgac  2820
gatactatca gcgtggagat gaagaaggag gacttcgaca tctacgatga ggatgagaac  2880
cagtcccctc ggagctttca gaagaaaacc cgccactact tcatcgctgc cgtggagcgg  2940
ctgtgggatt acgggatgtc cagctcaccg catgtgctgc ggaatagagc gcagtcagga  3000
tcggtgcccc agttcaagaa ggtcgtgttc caagagttca ccgacgggtc cttcactcaa  3060
cccctgtacc ggggcgaact caacgaacac ctgggactgc ttgggccgta tatcagggca  3120
gaagtggaag ataacatcat ggtcaccttc cgcaaccagg cctcccggcc gtacagcttc  3180
tactcttcac tgatctccta cgaggaagat cagcggcagg gagccgagcc ccggaagaac  3240
ttcgtcaagc ctaacgaaac taagacctac ttttggaagg tccagcatca catggccccg  3300
accaaagacg agttcgactg taaagcctgg gcctacttct ccgatgtgga cctggagaag  3360
gacgtgcact cgggactcat tggcccgctc cttgtgtgcc atactaatac cctgaaccct  3420
gctcacggtc gccaagtcac agtgcaggag ttcgccctct tcttcaccat cttcgatgaa  3480
acaaagtcct ggtactttac tgagaacatg gaacgcaatt gcagggcacc ctgcaacatc  3540
cagatggaag atcccacctt caaggaaaac taccggtttc atgccattaa cggctacata  3600
atggacacgt tgccaggact ggtcatggcc caggaccaga gaatccggtg gtatctgctc  3660
tccatgggct ccaacgaaaa cattcacagc attcattttt ccggccatgt gttcaccgtc  3720
cggaagaagg aagagtacaa gatggctctg tacaacctct accctggagt gttcgagact  3780
gtggaaatgc tgcctagcaa ggccggcatt tggagagtgg aatgcctgat cggagagcat  3840
ttgcacgccg gaatgtccac cctgtttctt gtgtactcca acaagtgcca gaccccgctg  3900
ggaatggcct caggtcatat tagggatttc cagatcactg cttcggggca gtacgggcag  3960
tgggcaccta agttggcccg gctgcactac tctggctcca tcaatgcctg gtccaccaag  4020
gaacccttct cctggattaa ggtggacctc ctggccccaa tgattattca cggtattaag  4080
acccagggtg cccgacagaa gttctcctca ctctacatct cgcaattcat cataatgtac  4140
agcctggatg ggaagaagtg gcagacctac cggggaaact ccactggaac gctcatggtg  4200
tttttcggca acgtggactc ctccggcatt aagcacaaca tcttcaaccc tccgatcatt  4260
gctcggtaca tccggctgca cccaactcac tacagcatcc ggtccaccct gcggatggaa  4320
ctgatgggtt gtgacctgaa ctcctgctcc atgccccttg ggatggaatc caaggccatt  4380
agcgatgcac agatcaccgc ctcttcatac ttcaccaaca tgttcgcgac ctggtccccg  4440
tcgaaggccc gcctgcacct ccaaggtcgc tccaatgcgt ggcggcctca agtgaacaac  4500
cccaaggagt ggctccaggt cgacttccaa aagaccatga aggtcaccgg agtgaccacc  4560
cagggcgtga agtccctgct gacctctatg tacgttaagg agttcctcat ctcctcaagc  4620
caagacggac atcagtggac cctgttcttc caaaacggaa aagtcaaagt attccagggc  4680
aaccaggact ccttcacccc tgtggtcaac agcctggacc ccccattgct gacccgctac  4740
ctccgcatcc acccccaaag ctgggtccac cagatcgcac tgcgcatgga ggtccttgga  4800
tgcgaagccc aagatctgta ctaa                                         4824

SEQ ID NO: 10          moltype = AA  length = 1588
FEATURE                Location/Qualifiers
REGION                 1..1588
                       note = expression construct
source                 1..1588
                       mol_type = protein
                       organism = synthetic construct
SEQUENCE: 10
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNGAPTS ESATPESGPG SEPATSGSET PGTSESATPE  780
SGPGSEPATS GSETPGTSES ATPESGPGTS TEPSEGSAPG SPAGSPTSTE EGTSESATPE  840
SGPGSEPATS GSETPGTSES ATPESGPGSP AGSPTSTEEG SPAGSPTSTE EGASSPPVLK  900
RHQREITRTT LQSDQEEIDY DDTISVEMKK EDFDIYDEDE NQSPRSFQKK TRHYFIAAVE  960
RLWDYGMSSS PHVLRNRAQS GSVPQFKKVV FQEFTDGSFT QPLYRGELNE HLGLLGPYIR  1020
AEVEDNIMVT FRNQASRPYS FYSSLISYEE DQRQGAEPRK NFVKPNETKT YFWKVQHHMA  1080
PTKDEFDCKA WAYFSDVDLE KDVHSGLIGP LLVCHTNTLN PAHGRQVTVQ EFALFFTIFD  1140
ETKSWYFTEN MERNCRAPCN IQMEDPTFKE NYRFHAINGY IMDTLPGLVM AQDQRIRWYL  1200
LSMGSNENIH SIHFSGHVFT VRKKEEYKMA LYNLYPGVFE TVEMLPSKAG IWRVECLIGE  1260
HLHAGMSTLF LVYSNKCQTP LGMASGHIRD FQITASGQYG QWAPKLARLH YSGSINAWST  1320
KEPFSWIKVD LLAPMIIHGI KTQGARQKFS SLYISQFIIM YSLDGKKWQT YRGNSTGTLM  1380
```

```
VFFGNVDSSG IKHNIFNPPI IARYIRLHPT HYSIRSTLRM ELMGCDLNSC SMPLGMESKA  1440
ISDAQITASS YFTNMFATWS PSKARLHLQG RSNAWRPQVN NPKEWLQVDF QKTMKVTGVT  1500
TQGVKSLLTS MYVKEFLISS SQDGHQWTLF FQNGKVKVFQ GNQDSFTPVV NSLDPPLLTR  1560
YLRIHPQSWV HQIALRMEVL GCEAQDLY                                    1588

SEQ ID NO: 11           moltype = AA  length = 19
FEATURE                 Location/Qualifiers
REGION                  1..19
                        note = signal peptide
source                  1..19
                        mol_type = protein
                        organism = synthetic construct
SEQUENCE: 11
MQIELSTCFF LCLLRFCFS                                              19

SEQ ID NO: 12           moltype = AA  length = 1438
FEATURE                 Location/Qualifiers
REGION                  1..1438
                        note = expression construct
source                  1..1438
                        mol_type = protein
                        organism = synthetic construct
SEQUENCE: 12
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNPPVLK RHQREITRTT LQSDQEEIDY DDTISVEMKK  780
EDFDIYDEDE NQSPRSFQKK TRHYFIAAVE RLWDYGMSSS PHVLRNRAQS GSVPQFKKVV  840
FQEFTDGSFT QPLYRGELNE HLGLLGPYIR AEVEDNIMVT FRNQASRPYS FYSSLISYEE  900
DQRQGAEPRK NFVKPNETKT YFWKVQHHMA PTKDEFDCKA WAYFSDVDLE KDVHSGLIGP  960
LLVCHTNTLN PAHGRQVTVQ EFALFFTIFD ETKSWYFTEN MERNCRAPCN IQMEDPTFKE  1020
NYRFHAINGY IMDTLPGLVM AQDQRIRWYL LSMGSNENIH SIHFSGHVFT VRKKEEYKMA  1080
LYNLYPGVFE TVEMLPSKAG IWRVECLIGE HLHAGMSTLF LVYSNKCQTP LGMASGHIRD  1140
FQITASGQYG QWAPKLARLH YSGSINAWST KEPFSWIKVD LLAPMIIHGI KTQGARQKFS  1200
SLYISQFIIM YSLDGKKWQT YRGNSTGTLM VFFGNVDSSG IKHNIFNPPI IARYIRLHPT  1260
HYSIRSTLRM ELMGCDLNSC SMPLGMESKA ISDAQITASS YFTNMFATWS PSKARLHLQG  1320
RSNAWRPQVN NPKEWLQVDF QKTMKVTGVT TQGVKSLLTS MYVKEFLISS SQDGHQWTLF  1380
FQNGKVKVFQ GNQDSFTPVV NSLDPPLLTR YLRIHPQSWV HQIALRMEVL GCEAQDLY    1438

SEQ ID NO: 13           moltype = DNA  length = 4371
FEATURE                 Location/Qualifiers
misc_feature            1..4371
                        note = expression construct
source                  1..4371
                        mol_type = other DNA
                        organism = synthetic construct
SEQUENCE: 13
atgcaaatag agctctccac ctgcttcttt ctgtgccttt tgcgattctg ctttagtgcc  60
accagaagat actacctggg tgcagtggaa ctgtcatggg actatatgca aagtgatctc  120
ggtgagctgc ctgtggacgc aagatttcct cctagagtgc caaaatcttt tccattcaac  180
acctcagtcg tgtacaaaaa gactctgttt gtagaattca cggatcacct tttcaacatc  240
gctaagccaa ggccaccctg gatgggtctg ctaggtccta ccatccaggc tgaggtttat  300
gatacagtgg tcattacact taagaacatg gcttcccatc ctgtcagtct tcatgctgtt  360
ggtgtatcct actggaaagc ttctgaggga gctgaatatg atgatcagac cagtcaaagg  420
gagaaagaag atgataaagt cttccctggt ggaagccata catatgtctg gcaggtcctg  480
aaagagaatg gtccaatggc ctctgaccca ctgtgcctta cctactcata tctttctcat  540
gtggacctgg taaaagactt gaattcaggc ctcattggag ccctactagt atgtagagaa  600
gggagtctgg ccaaggaaaa gacacagacc ttgcacaaat ttatactact tttgctgta   660
tttgatgaag ggaaaagttg gcactcagaa acaaagaact ccttgatgca ggatagggat  720
gctgcatctg ctcgggcctg gcctaaaatg cacacagtca atggttatgt aaacaggtct  780
ctgccaggtc tgattggatg ccacaggaaa tcagtctatt ggcatgtgat tggaatgggc  840
accactcctg aagtgcactc aatattcctc gaaggtcaca catttcttgt gaggaaccat  900
cgccaggcgt ccttggaaat ctcgccaata actttcctta ctgctcaaac actcttgatg  960
gaccttggac agtttctact gttttgtcat atctcttccc accaacatga tggcatggaa  1020
gcttatgtca aagtagacag ctgtccagag gaaccccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctccctt agtcctcgcc  1260
cccgatgaca gaagttataa aagtcaatat ttgaacaatg gccctcagcg gattggtagg  1320
aagtacaaaa aagtccgatt tatggcatac acagatgaaa cctttaagac tcgtgaagct  1380
```

```
attcagcatg aatcaggaat cttgggacct ttactttatg gggaagttgg agacacactg  1440
ttgattatat ttaagaatca agcaagcaga ccatataaca tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atcctcggtg cctgacccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt cctttctgtc ttcttctctg gatatacctt caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga accaagaagc  2280
ttctctcaaa acccaccagt cttgaaacgc catcaacggg aaataactcg tactactctt  2340
cagtcagatc aagaggaaat tgactatgat gataccatat cagttgaaat gaagaaggaa  2400
gattttgaca tttatgatga ggatgaaaat cagagccccc gcagctttca aaagaaaaca  2460
cgacactatt ttattgctgc agtggagagg ctctgggatt atgggatgag tagctcccca  2520
catgttctaa gaaacagggc tcagagtggc agtgtccctc agttcaagaa agttgttttc  2580
caggaattta ctgatggctc ctttactcag cccttatacc gtggagaact aaatgaacat  2640
ttgggactcc tggggccata tataagagca gaagttgaag ataatatcat ggtaactttc  2700
agaaatcagg cctctcgtcc ctattccttc tattctagcc ttatttctta tgaggaagat  2760
cagaggcaag gagcagaacc tagaaaaaac tttgtcaagc ctaatgaaac caaaacttac  2820
ttttggaaag tgcaacatca tatggcaccc actaaagatg agtttgactg caaagcctgg  2880
gcttatttct ctgatgttga cctggaaaaa gatgtgcact caggcctgat tggacccctt  2940
ctggtctgcc acactaacac actgaaccct gctcatggga gacaagtgac agtacaggaa  3000
tttgctctgt ttttcaccat ctttgatgag accaaaagct ggtacttcac tgaaaatatg  3060
gaaagaaact gcagggctcc ctgcaatatc cagatggaag atcccacttt taaagagaat  3120
tatcgcttcc atgcaatcaa tggctacata atggatacac tacctggctt agtaatggct  3180
caggatcaaa ggattcgatg gtatctgctc agcatgggca gcaatgaaaa catccattct  3240
attcatttca gtggacatgt gttcactgta cgaaaaaaag aggagtataa aatggcactg  3300
tacaatctct atccaggtgt ttttgagaca gtggaaatgt taccatccaa agctggaatt  3360
tggcgggtgg aatgccttat tggcgagcat ctacatgctg ggatgagcac actttttctg  3420
gtgtacagca ataagtgtca gactcccctg ggaatggctt ctggacacat tagagatttt  3480
cagattacag cttcaggaca atatggacag tgggccccaa agctggccag acttcattat  3540
tccggatcaa tcaatgcctg gagcaccaag gagccctttt cttggatcaa ggtggatctg  3600
ttggcaccaa tgattattca cggcatcaag acccagggtg cccgtcagaa gttctccagc  3660
ctctacatct ctcagtttat catcatgtat agtcttgatg ggaagaagtg gcagacttat  3720
cgaggaaatt ccactggaac cttaatggtc ttctttggca atgtggattc atctgggata  3780
aaacacaata tttttaaccc tccaattatt gctcgataca tccgtttgca cccaactcat  3840
tatagcattc gcagcactct tcgcatggag ttgatgggct gtgatttaaa tagttgcagc  3900
atgccattgg gaatggagag taaagcaata tcagatgcac agattactgc ttcatcctac  3960
tttaccaata tgtttgccac ctggtctcct tcaaaagctc gacttcacct ccaagggagg  4020
agtaatgcct ggagacctca ggtgaataat ccaaaagagt ggctgcaagt ggacttccag  4080
aagacaatga aagtcacagg agtaactact cagggagtaa aatctctgct taccagcatg  4140
tatgtgaagg agttcctcat ctccagcagt caagatggcc atcagtggac tctctttttt  4200
cagaatggca aagtaaaggt ttttcaggga aatcaagact ccttcacacc tgtggtgaac  4260
tctctagacc caccgttact gactcgctac cttcgaattc acccccagag ttgggtgcac  4320
cagattgccc tgaggatgga ggttctgggc tgcgaggcac aggacctcta c           4371
```

```
SEQ ID NO: 14          moltype = DNA  length = 7891
FEATURE                Location/Qualifiers
misc_feature           1..7891
                       note = expression construct
source                 1..7891
                       mol_type = other DNA
                       organism = synthetic construct
SEQUENCE: 14
ggccccaggt taatttttaa aaagcagtca aaggtcaaag tggcccttgg cagcatttac  60
tctctctatt gactttggtt aataatctca ggagcacaaa cattcctgga ggcaggagaa  120
gaaatcaaca tcctggactt atcctctggg cctctcccca ccttcgatgg ccccaggtta  180
atttttaaaa agcagtcaaa ggtcaaagtg gcccttggca gcatttactc tctctattga  240
ctttggttaa taatctcagg agcacaaaca ttcctggagg caggagaaga aatcaacatc  300
ctggacttat cctctgggcc tctccccacc gatatctacc tgctgatcgc ccggcccctg  360
ttcaaacatg tcctaatact ctgtcggggc aaaggtcggc agtagttttc catcttactc  420
aacatcctcc cagtgtacgt aggatcctgt ctgtctgcac atttcgtaga gcgagtgttc  480
cgatactcta atctcccggg gcaaaggtcg tattgactta ggttacttat tctccttttg  540
ttgactaagt caataatcag aatcagcagg tttggagtca gcttggcagg gatcagcagc  600
ctgggttgga aggagggggt ataaaagccc cttcaccagg agaagccgtc acacagatcc  660
acaagctcct gctaggaatt ctcaggagca caaacattcc tggaggcagg agaagaaatc  720
aacatcctgg acttatcctc tgggcctctc cccaccgata tctacctgct gatcgcccgg  780
cccctgttca aacatgtcct aatactctgt cggggcaaag gtcggcagta gttttccatc  840
ttactcaaca tcctcccagt gtacgtagga tcctgtctgt ctgcacattt cgtagagcga  900
gtgttccgat actctaatct cccggggcaa aggtcgtatt gacttaggtt acttattctc  960
cttttgttga ctaagtcaat aatcagaatc agcaggtttg gagtcagctt ggcagggatc  1020
agcagcctgg gttggaagga gggggtataa aagccccttc accaggagaa gccgtcacac  1080
agatccacaa gctcctgcta gagtcgctgc gcgctgcctt cgccccgtgc cccgctccgc  1140
cgccgcctcg cgccgcccgc cccggctctg actgaccgcg ttactcccac aggtgagcgg  1200
```

-continued

```
gcgggacggc ccttctcctc cgggctgtaa ttagcgcttg gtttattgac ggcttgtttc  1260
ttttctgtgg ctgcgtgaaa gccttgaggg gctccgggaa ggccctttgt gcggggggag  1320
cggctcgggg ggtgcgtgcg tgtgtgtgtg cgtggggagc gccgcgtgcg gctccgcgct  1380
gcccggcggc tgtgagcgct gcgggcgcgg cgcggggctt tgtgcgctcc gcagtgtgcg  1440
cgaggggagc gcggccgggg gcggtgcccc gcggtgcggg gggggctgcg aggggaacaa  1500
aggctgcgtg cggggtgtgt gcgtgggggg gtgagcaggg ggtgtgggcg cgtcggtcgg  1560
gctgcaaccc cccctgcacc cccctccccg agttgctgag cacggcccgg cttcgggtgc  1620
ggggctccgt acggggcgtg gcgcggggct cgccgtgccg ggcggggggt ggcggcaggt  1680
gggggtgccg ggcggggcgg ggccgcctcg ggccggggag ggctcggggg aggggcgcgg  1740
cggcccccgg agcgccggcg gctgtcgagg cgcggcgagc cgcagccatt gccttttatg  1800
gtaatcgtgc gagagggcgc agggacttcc tttgtcccaa atctgtgcgg agccgaaatc  1860
tgggaggcgc cgccgcaccc cctctagcgg gcgcggggcg aagcggtgcg gcgccggcag  1920
gaaggaaatg ggcggggagg gccttcgtgc gtcgccgcgc cgccgtcccc ttctccctct  1980
ccagcctcgg ggctgtccgc ggggggacgg ctgccttcgg gggggacggg gcagggcggg  2040
gttcggcttc tggcgtgtga ccggcggctc tagagcctct gctaaccttg ttcttgcctt  2100
cttctttttc ctacagctcc tgggcaacgt gctggttatt gtgctgtctc atcattttgg  2160
caaagaatta ctcgaggcca ccatgcagat tgaactgtcc acttgcttct tcctgtgcct  2220
cctgcggttt tgcttctcgg ccacccgccg gtattactta ggtgctgtgg aactgagctg  2280
ggactacatg cagtccgacc tgggagaact gccggtggac gcgagattcc cacctagagt  2340
cccgaagtcc ttcccattca acacctccgt ggtctacaaa aagaccctgt tcgtggagtt  2400
cactgaccac cttttcaata ttgccaagcc gcgccccccc tggatgggcc tgcttggtcc  2460
tacgatccaa gcagaggtct acgacaccgt ggtcatcaca ctgaagaaca tggcctcaca  2520
ccccgtgtcg ctgcatgctg tgggagtgtc ctactggaag gcctcagagg gtgccgaata  2580
tgatgaccag accagccaga gggaaaagga ggatgacaaa gtgttcccgg gtggcagcca  2640
cacttacgtg tggcaagtgc tgaaggaaaa cgggcctatg gcgtcggacc ccctatgcct  2700
gacctactcc tacctgtccc atgtggacct tgtgaaggat ctcaactcgg gactgatcgg  2760
cgccctcttg gtgtgcagag aaggcagcct ggcgaaggaa aagactcaga ccctgcacaa  2820
gttcattctg ttgtttgctg tgttcgatga aggaaagtcc tggcactcag aaaccaagaa  2880
ctcgctgatg caggatagag atgcggcctc ggccagagcc tggcctaaaa tgcacaccgt  2940
caacggatat gtgaacaggt cgctccctgg cctcatcggc tgccacagaa agtccgtgta  3000
ttggcatgtg atcggcatgg gtactactcc ggaagtgcat agtatctttc tggagggcca  3060
taccttcttg gtgcgcaacc acagacaggc ctcgctggaa atctcgccta tcactttctt  3120
gactgcgcag accctcctta tggaccttgg acagttcctg ctgttctgtc acatcagctc  3180
ccatcagcat gatgggatgg aggcctatgt caaagtggac tcctgccctg aggagccaca  3240
gctccggatg aagaacaatg aggaagcgga ggattacgac gacgacctga ctgacagcga  3300
aatggacgtc gtgcgattcg atgacgacaa cagcccgtcc ttcatccaaa ttagatcagt  3360
ggcgaagaag caccccaaga cctgggtgca ctacattgcc gccgaggaag aggactggga  3420
ctacgcgccg ctggtgctgg cgccagacga caggagctac aagtcccagt acctcaacaa  3480
cgggccgcag cgcattggca ggaagtacaa gaaagtccgc ttcatggcct acactgatga  3540
aaccttcaag acgagggaag ccatccagca cgagtcaggc atcctgggac cgctccttta  3600
cggcgaagtc ggggataccc tgctcatcat tttcaagaac caggcatcgc ggccctacaa  3660
catctaccct cacgggatca cagacgtgcg cccgctctac tcccgccggc tgcccaaggg  3720
agtgaagcac ctgaaggatt ttcccatcct gccgggagaa atcttcaagt acaagtggac  3780
cgtgactgtg gaagatggcc ctaccaagtc ggaccctcgc tgtctgaccc ggtactattc  3840
ctcgtttgtg aacatggagc gcgacctggc ctcggggctg attggtccgc tgctgatctg  3900
ctacaaggag tccgtggacc agcgcgggaa ccagatcatg tccgacaagc gcaacgtgat  3960
cctgttctct gtctttgatg aaaacagatc gtggtacttg actgagaata tccagcggtt  4020
cctgcccaac ccagcgggag tgcaactgga ggacccggag ttccaggcct caaacattat  4080
gcactctatc aacggctatg tgttcgactc gctccaactg agcgtgtgcc tgcatgaagt  4140
ggcatactgg tacattctgt ccatcggagc ccagaccgac ttcctgtccg tgttcttctc  4200
cggatacacc ttcaagcata agatggtgta cgaggacact ctgaccctct tcccattttc  4260
cggagaaact gtgttcatgt caatggaaaa cccgggcttg tggattctgg gttgccataa  4320
ctcggacttc cggaatagag ggatgaccgc cctgctgaaa gtgtccagct gtgacaagaa  4380
taccggcgat tactacgagg acagctatga ggacatctcc gcttatctgc tgtccaagaa  4440
caacgccatt gaacccaggt ccttctccca aaacggtgca ccgacctccg aaagcgccac  4500
cccagagtca ggacctggct cggaaccggc tacctcgggc tcagagacac cggggacttc  4560
cgagtccgca acccccgaga gtggacccgg atccgaacca gcaacctcag gatcagaaac  4620
cccgggaact tcggaatccg ccactcccga gtcgggacca ggcacctcca ctgagccttc  4680
cgagggaagc gcccccggat cccctgctgg atcccctacc agcactgaag aaggcacctc  4740
agaatccgcg accccctgagt ccggccctgg aagcgaaccc gccacctccg gttccgaaac  4800
ccctgggact agcgagagcg ccactccgga atcgggccca ggaagccctg ccggatcccc  4860
gaccagcacc gaggagggaa gccccgccgg gtcaccgact tccactgagg agggagcctc  4920
atcccccccc gtgctgaagc ggcatcaaag agagatcacc aggaccactc tccagtccga  4980
tcaggaagaa attgactacg acgatactat cagcgtggag atgaagaagg aggacttcga  5040
catctacgat gaggatgaga accagtcccc tcggagcttt cagaagaaaa cccgccacta  5100
cttcatcgct gccgtggagc ggctgtggga ttacgggatg tccagctcac cgcatgtgct  5160
gcggaataga gcgcagtcag gatcggtgcc ccagttcaag aaggtcgtgt tccaagagtt  5220
caccgacggg tccttcactc aacccctgta ccggggcgaa ctcaacgaac acctgggact  5280
gcttgggccg tatatcaggg cagaagtgga agataacatc atggtcacct tccgcaacca  5340
ggcctcccgg ccgtacagct tctactcttc actgatctcc tacgaggaag atcagcggca  5400
gggagccgag ccccggaaga acttcgtcaa gcctaacgaa actaagacct actttggaa  5460
ggtccagcat cacatggccc cgaccaaaga cgagttcgac tgtaaagcct gggcctactt  5520
ctccgatgtg gacctggaga aggacgtgca ctcgggactc attggcccgc tccttgtgtg  5580
ccatactaat accctgaacc ctgctcacgg tcgccaagtc acagtgcagg agttcgccct  5640
cttcttcacc atcttcgatg aaacaaagtc ctggtacttt actgagaaca tggaacgcaa  5700
ttgcagggca ccctgcaaca tccagatgga agatcccacc ttcaaggaaa actaccggtt  5760
tcatgccatt aacggctaca taatggacac gttgccagga ctggtcatgg cccaggacca  5820
gagaatccgg tggtatctgc tctccatggg ctccaacgaa aacattcaca gcattcattt  5880
ttccggccat gtgttcaccg tccggaagaa ggaagagtac aagatggctc tgtacaacct  5940
```

-continued

```
ctaccctgga gtgttcgaga ctgtggaaat gctgcctagc aaggccggca tttggagagt  6000
ggaatgcctg atcggagagc atttgcacgc cggaatgtcc accctgtttc ttgtgtactc  6060
caacaagtgc cagaccccgc tgggaatggc ctcaggtcat attagggatt tccagatcac  6120
tgcttcgggg cagtacgggc agtgggcacc taagttggcc cggctgcact actctggctc  6180
catcaatgcc tggtccacca aggaaccctt ctcctggatt aaggtggacc tcctggcccc  6240
aatgattatt cacggtatta agacccaggg tgcccgacag aagttctcct cactctacat  6300
ctcgcaattc atcataatgt acagcctgga tgggaagaag tggcagacct accggggaaa  6360
ctccactgga acgctcatgg tgtttttcgg caacgtggac tcctccggca ttaagcacaa  6420
catcttcaac cctccgatca ttgctcggta catccggctg cacccaactc actacagcat  6480
ccggtccacc ctgcggatgg aactgatggg ttgtgacctg aactcctgct ccatgcccct  6540
tgggatggaa tccaaggcca ttagcgatgc acagatcacc gcctcttcat acttcaccaa  6600
catgttcgcg acctggtccc cgtcgaaggc ccgcctgcac ctccaaggtc gctccaatgc  6660
gtggcggcct caagtgaaca accccaagga gtggctccag gtcgacttcc aaaagaccat  6720
gaaggtcacc ggagtgacca cccagggcgt gaagtccctg ctgacctcta tgtacgttaa  6780
ggagttcctc atctcctcaa gccaagacgg acatcagtgg accctgttct tccaaaacgg  6840
aaaagtcaaa gtattccagg gcaaccagga ctccttcacc cctgtggtca acagcctgga  6900
ccccccattg ctgacccgct acctccgcat ccacccccaa agctgggtcc accagatcgc  6960
actgcgcatg gaggtccttg gatgcgaagc ccaagatctg tactaagcgg ccgctcataa  7020
tcaacctctg gattacaaaa tttgtgaaag attgactggt attcttaact atgttgctcc  7080
ttttacgcta tgtggatacg ctgctttaat gcctttgtat catgctattg cttcccgtat  7140
ggctttcatt ttctcctcct tgtataaatc ctggttgctg tctctttatg aggagttgtg  7200
gcccgttgtc aggcaacgtg gcgtggtgtg cactgtgttt gctgacgcaa cccccactgg  7260
ttggggcatt gccaccacct gtcagctcct ttccgggact ttcgctttcc ccctccctat  7320
tgccacggcg gaactcatcg ccgcctgcct tgcccgctgc tggacagggg ctcggctgtt  7380
gggcactgac aattccgtgg tgttgtcggg gaaatcatcg tcctttcctt ggctgctcgc  7440
ctgtgttgcc acctggattc tgcgcgggac gtccttctgc tacgtccctt cggccctcaa  7500
tccagcggac cttccttccc gcggcctgct gccggctctg cggcctcttc cgcgtcttcg  7560
ccttcgccct cagacgagtc ggatctccct ttgggccgcc tccccgctgc ctaggcgact  7620
gtgccttcta gttgccagcc atctgttgtt tgcccctccc ccgtgccttc cttgaccctg  7680
gaaggtgcca ctcccactgt cctttcctaa taaaatgagg aaattgcatc gcattgtctg  7740
agtaggtgtc attctattct ggggggtggg gtggggcagg acagcaaggg ggaggattgg  7800
gaagacaata gcaggcatgc tggggaagac catgggcgcg ccaggcctgt cgacgcccgg  7860
gcggtaccgc gatcgctcgc gacgcataaa g                                  7891

SEQ ID NO: 15          moltype = DNA  length = 330
FEATURE                Location/Qualifiers
misc_feature           1..330
                       note = enhancer
source                 1..330
                       mol_type = other DNA
                       organism = synthetic construct
SEQUENCE: 15
ggccccaggt taatttttaa aaagcagtca aaggtcaaag tggcccttgg cagcatttac  60
tctctctatt gactttggtt aataatctca ggagcacaaa cattcctgga ggcaggagaa  120
gaaatcaaca tcctggactt atcctctggg cctctcccca ccttcgatgg ccccaggtta  180
atttttaaaa agcagtcaaa ggtcaaagtg gcccttggca gcatttactc tctctattga  240
ctttggttaa taatctcagg agcacaaaca ttcctggagg caggagaaga aatcaacatc  300
ctggacttat cctctgggcc tctccccacc                                    330

SEQ ID NO: 16          moltype = DNA  length = 345
FEATURE                Location/Qualifiers
misc_feature           1..345
                       note = promoter
source                 1..345
                       mol_type = other DNA
                       organism = synthetic construct
SEQUENCE: 16
gatatctacc tgctgatcgc ccggcccctg ttcaaacatg tcctaatact ctgtcggggc  60
aaaggtcggc agtagttttc catcttactc aacatcctcc cagtgtacgt aggatcctgt  120
ctgtctgcac atttcgtaga gcgagtgttc cgatactcta atctcccggg gcaaaggtcg  180
tattgactta ggttacttat tctccttttg ttgactaagt caataatcag aatcagcagg  240
tttggagtca gcttggcagg gatcagcagc ctgggttgga aggaggggt ataaaagccc  300
cttcaccagg agaagccgtc acacagatcc acaagctcct gctag                   345

SEQ ID NO: 17          moltype = DNA  length = 1489
FEATURE                Location/Qualifiers
misc_feature           1..1489
                       note = intron
source                 1..1489
                       mol_type = other DNA
                       organism = synthetic construct
SEQUENCE: 17
tcaggagcac aaacattcct ggaggcagga gaagaaatca acatcctgga cttatcctct  60
gggcctctcc ccaccgatat ctacctgctg atcgcccggc ccctgttcaa acatgtccta  120
atactctgtc ggggcaaagg tcggcagtag ttttccatct tactcaacat cctcccagtg  180
tacgtaggat cctgtctgtc tgcacatttc gtagagcgag tgttccgata ctctaatctc  240
ccggggcaaa ggtcgtattg acttaggtta cttattctcc ttttgttgac taagtcaata  300
atcagaatca gcaggtttgg agtcagcttg gcagggatca gcagcctggg ttggaaggag  360
ggggtataaa agccccttca ccaggagaag ccgtcacaca gatccacaag ctcctgctag  420
```

```
agtcgctgcg cgctgccttc gccccgtgcc ccgctccgcc gccgcctcgc gccgcccgcc  480
ccggctctga ctgaccgcgt tactcccaca ggtgagcggg cgggacggcc cttctcctcc  540
gggctgtaat tagcgcttgg tttattgacg gcttgtttct tttctgtggc tgcgtgaaag  600
ccttgagggg ctccgggaag gccctttgtg cggggggagc ggctcggggg gtgcgtgcgt  660
gtgtgtgtgc gtggggagcg ccgcgtgcgg ctccgcgctg cccggcggct gtgagcgctg  720
cgggcgcggc gcggggcttt gtgcgctccg cagtgtgcgc gaggggagcg cggccggggg  780
cggtgccccg cggtgcgggg ggggctgcga ggggaacaaa ggctgcgtgc ggggtgtgtg  840
cgtggggggg tgagcagggg gtgtgggcgc gtcggtcggg ctgcaacccc ccctgcaccc  900
ccctccccga gttgctgagc acggcccggc ttcgggtgcg gggctccgta cggggcgtgg  960
cgcggggctc gccgtgccgg gcgggggtg gcggcaggtg gggtgccgg gcggggcggg  1020
gccgcctcgg gccggggagg gctcgggga ggggcgcggc ggcccccgga gcgccggcgg  1080
ctgtcgaggc gcggcgagcc gcagccattg ccttttatgg taatcgtgcg agagggcgca  1140
gggacttcct ttgtcccaaa tctgtgcgga gccgaaatct gggaggcgcc gccgcacccc  1200
ctctagcggg cgcggggcga agcggtgcgg cgccggcagg aaggaaatgg gcggggaggg  1260
ccttcgtgcg tcgccgcgcc gccgtcccct tctccctctc cagcctcggg gctgtccgcg  1320
gggggacggc tgccttcggg ggggacgggg cagggcgggg ttcggcttct ggcgtgtgac  1380
cggcggctct agagcctctg ctaaccttgt tcttgccttc ttctttttcc tacagctcct  1440
gggcaacgtg ctggttattg tgctgtctca tcattttggc aaagaatta             1489
```

```
SEQ ID NO: 18          moltype = DNA  length = 595
FEATURE                Location/Qualifiers
misc_feature           1..595
                       note = WPRE
source                 1..595
                       mol_type = other DNA
                       organism = synthetic construct
SEQUENCE: 18
tcataatcaa cctctggatt acaaaatttg tgaaagattg actggtattc ttaactatgt  60
tgctcctttt acgctatgtg gatacgctgc tttaatgcct ttgtatcatg ctattgcttc  120
ccgtatggct ttcattttct cctccttgta taaatcctgg ttgctgtctc tttatgagga  180
gttgtggccc gttgtcaggc aacgtggcgt ggtgtgcact gtgtttgctg acgcaacccc  240
cactggttgg ggcattgcca ccacctgtca gctcctttcc gggactttcg ctttcccct  300
ccctattgcc acggcggaac tcatcgccgc ctgccttgcc cgctgctgga caggggctcg  360
gctgttgggc actgacaatt ccgtggtgtt gtcggggaaa tcatcgtcct ttccttggct  420
gctcgcctgt gttgccacct ggattctgcg cgggacgtcc ttctgctacg tcccttcggc  480
cctcaatcca gcggaccttc cttcccgcgg cctgctgccg gctctgcggc ctcttccgcg  540
tcttcgcctt cgccctcaga cgagtcggat ctccctttgg gccgcctccc cgctg       595
```

```
SEQ ID NO: 19          moltype = DNA  length = 211
FEATURE                Location/Qualifiers
misc_feature           1..211
                       note = bGHpA
source                 1..211
                       mol_type = other DNA
                       organism = synthetic construct
SEQUENCE: 19
cgactgtgcc ttctagttgc cagccatctg ttgtttgccc ctcccccgtg ccttccttga  60
ccctggaagg tgccactccc actgtccttt cctaataaaa tgaggaaatt gcatcgcatt  120
gtctgagtag gtgtcattct attctggggg gtggggtggg gcaggacagc aagggggagg  180
attgggaaga caatagcagg catgctgggg a                                 211
```

```
SEQ ID NO: 20          moltype = AA  length = 2332
FEATURE                Location/Qualifiers
source                 1..2332
                       mol_type = protein
                       organism = Homo sapiens
SEQUENCE: 20
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATT IPENDIEKTD PWFAHRTPMP  780
KIQNVSSSDL LMLLRQSPTP HGLSLSDLQE AKYETFSDDP SPGAIDSNNS LSEMTHFRPQ  840
LHHSGDMVFT PESGLQLRLN EKLGTTAATE LKKLDFKVSS TSNNLISTIP SDNLAAGTDN  900
TSSLGPPSMP VHYDSQLDTT LFGKKSSPLT ESGGPLSLSE ENNDSKLLES GLMNSQESSW  960
GKNVSSTESG RLFKGKRAHG PALLTKDNAL FKVSISLLKT NKTSNNSATN RKTHIDGPSL  1020
LIENSPSVWQ NILESDTEFK KVTPLIHDRM LMDKNATALR LNHMSNKTTS SKNMEMVQQK  1080
KEGPIPPDAQ NPDMSFFKML FLPESARWIQ RTHGKNSLNS GQGPSPKQLV SLGPEKSVEG  1140
QNFLSEKNKV VVGKGEFTKD VGLKEMVFPS SRNLFLTNLD NLHENNTHNQ EKKIQEEIEK  1200
KETLIQENVV LPQIHTVTGT KNFMKNLFLL STRQNVEGSY DGAYAPVLQD FRSLNDSTNR  1260
TKKHTAHFSK KGEEENLEGL GNQTKQIVEK YACTTRISPN TSQQNFVTQR SKRALKQFRL  1320
```

```
PLEETELEKR IIVDDTSTQW SKNMKHLTPS TLTQIDYNEK EKGAITQSPL SDCLTRSHSI  1380
PQANRSPLPI AKVSSFPSIR PIYLTRVLFQ DNSSHLPAAS YRKKDSGVQE SSHFLQGAKK  1440
NNLSLAILTL EMTGDQREVG SLGTSATNSV TYKKVENTVL PKPDLPKTSG KVELLPKVHI  1500
YQKDLFPTET SNGSPGHLDL VEGSLLQGTE GAIKWNEANR PGKVPFLRVA TESSAKTPSK  1560
LLDPLAWDNH YGTQIPKEEW KSQEKSPEKT AFKKKDTILS LNACESNHAI AAINEGQNKP  1620
EIEVTWAKQG RTERLCSQNP PVLKRHQREI TRTTLQSDQE EIDYDDTISV EMKKEDFDIY  1680
DEDENQSPRS FQKKTRHYFI AAVERLWDYG MSSSPHVLRN RAQSGSVPQF KKVVFQEFTD  1740
GSFTQPLYRG ELNEHLGLLG PYIRAEVEDN IMVTFRNQAS RPYSFYSSLI SYEEDQRQGA  1800
EPRKNFVKPN ETKTYFWKVQ HHMAPTKDEF DCKAWAYFSD VDLEKDVHSG LIGPLLVCHT  1860
NTLNPAHGRQ VTVQEFALFF TIFDETKSWY FTENMERNCR APCNIQMEDP TFKENYRFHA  1920
INGYIMDTLP GLVMAQDQRI RWYLLSMGSN ENIHSIHFSG HVFTVRKKEE YKMALYNLYP  1980
GVFETVEMLP SKAGIWRVEC LIGEHLHAGM STLFLVYSNK CQTPLGMASG HIRDFQITAS  2040
GQYGQWAPKL ARLHYSGSIN AWSTKEPFSW IKVDLLAPMI IHGIKTQGAR QKFSSLYISQ  2100
FIIMYSLDGK KWQTYRGNST GTLMVFFGNV DSSGIKHNIF NPPIIARYIR LHPTHYSIRS  2160
TLRMELMGCD LNSCSMPLGM ESKAISDAQI TASSYFTNMF ATWSPSKARL HLQGRSNAWR  2220
PQVNNPKEWL QVDFQKTMKV TGVTTQGVKS LLTSMYVKEF LISSSQDGHQ WTLFFQNGKV  2280
KVFQGNQDSF TPVVNSLDPP LLTRYLRIHP QSWVHQIALR MEVLGCEAQD LY          2332

SEQ ID NO: 21          moltype = DNA  length = 383
FEATURE                Location/Qualifiers
misc_feature           1..383
                       note = parvovirus
source                 1..383
                       mol_type = other DNA
                       organism = synthetic construct
SEQUENCE: 21
ccaaatcaga tgccgccggt cgccgccggt aggcgggact tccggtacaa gatggcggac  60
aattacgtca tttcctgtga cgtcatttcc tgtgacgtca cttccggtgg gcgggacttc  120
cggaattagg gttggctctg ggccagcttg cttggggttg ccttgacact aagacaagcg  180
gcgcgccgct tgatcttagt ggcacgtcaa ccccaagcgc tggcccagag ccaaccctaa  240
ttccggaagt cccgcccacc ggaagtgacg tcacaggaaa tgacgtcaca ggaaatgacg  300
taattgtccg ccatcttgta ccggaagtcc cgcctaccgg cggcgaccgg cggcatctga  360
tttggtgtct tcttttaaat ttt                                          383

SEQ ID NO: 22          moltype = DNA  length = 383
FEATURE                Location/Qualifiers
misc_feature           1..383
                       note = parvovirus
source                 1..383
                       mol_type = other DNA
                       organism = synthetic construct
SEQUENCE: 22
aaaatttaaa agaagacacc aaatcagatg ccgccggtcg ccgccggtag gcgggacttc  60
cggtacaaga tggcggacaa ttacgtcatt tcctgtgacg tcatttcctg tgacgtcact  120
tccggtgggc gggacttccg gaattagggt tggctctggg ccagcgcttg gggttgacgt  180
gccactaaga tcaagcggcg cgccgcttgt cttagtgtca aggcaacccc aagcaagctg  240
gcccagagcc aaccctaatt ccggaagtcc cgcccaccgg aagtgacgtc acaggaaatg  300
acgtcacagg aaatgacgta attgtccgcc atcttgtacc ggaagtcccg cctaccggcg  360
gcgaccggcg gcatctgatt tgg                                          383

SEQ ID NO: 23          moltype = DNA  length = 125
FEATURE                Location/Qualifiers
misc_feature           1..125
                       note = parvovirus
source                 1..125
                       mol_type = other DNA
                       organism = synthetic construct
SEQUENCE: 23
ccaaatcaga tgccgccggt cgccgccggt aggcgggact tccggtacag cgcgccgctg  60
taccggaagt cccgcctacc ggcggcgacc ggcggcatct gatttggtgt cttcttttaa  120
atttt                                                              125

SEQ ID NO: 24          moltype = DNA  length = 125
FEATURE                Location/Qualifiers
misc_feature           1..125
                       note = parvovirus
source                 1..125
                       mol_type = other DNA
                       organism = synthetic construct
SEQUENCE: 24
aaaatttaaa agaagacacc aaatcagatg ccgccggtcg ccgccggtag gcgggacttc  60
cggtacagcg gcgcgctgta ccggaagtcc cgcctaccgg cggcgaccgg cggcatctga  120
tttgg                                                              125

SEQ ID NO: 25          moltype = DNA  length = 114
FEATURE                Location/Qualifiers
misc_feature           1..114
                       note = parvovirus
source                 1..114
```

```
                         mol_type = other DNA
                         organism = synthetic construct
SEQUENCE: 25
ctcattggag ggttcgttcg ttcgaacgtt cgttcgcatg cgaacgaacg ttcgaacgaa  60
cgaaccctcc aatgagactc aaggacaaga ggatattttg cgcgccagga agtg        114

SEQ ID NO: 26            moltype = DNA  length = 114
FEATURE                  Location/Qualifiers
misc_feature             1..114
                         note = parvovirus
source                   1..114
                         mol_type = other DNA
                         organism = synthetic construct
SEQUENCE: 26
cacttcctgg cgcgcaaaat atcctcttgt ccttgagtct cattggaggg ttcgttcgtt  60
cgaacgttcg ttcgcatgcg aacgaacgtt cgaacgaacg aaccctccaa tgag        114

SEQ ID NO: 27            moltype = DNA  length = 408
FEATURE                  Location/Qualifiers
misc_feature             1..408
                         note = parvovirus
source                   1..408
                         mol_type = other DNA
                         organism = synthetic construct
SEQUENCE: 27
ctcattggag ggttcgttcg ttcgaaccag ccaatcaggg gagggggaag tgacgcaagt  60
tccggtcaca tgcttccggt gacgcacatc cggtgacgta gttcgcatgc ctgtctatcg  120
cctacccatc cctgtctgag atcaagggcg tgatcgtgca cagactggag agcgtgtcct  180
ataatatcgg ctctcaggag tggagcacca cagtgcccag atacgtggcc acccagggct  240
atctgatctc caacttcgac gcatgcgaac tacgtcaccg gatgtgcgtc accggaagca  300
tgtgaccgga acttgcgtca cttcccctc ccctgattgg ctggttcgaa cgaacgaacc  360
ctccaatgag actcaaggac aagaggatat tttgcgcgcc aggaagtg               408

SEQ ID NO: 28            moltype = DNA  length = 408
FEATURE                  Location/Qualifiers
misc_feature             1..408
                         note = parvovirus
source                   1..408
                         mol_type = other DNA
                         organism = synthetic construct
SEQUENCE: 28
cacttcctgg cgcgcaaaat atcctcttgt ccttgagtct cattggaggg ttcgttcgtt  60
cgaaccagcc aatcagggga gggggaagtg acgcaagttc cggtcacatg cttccggtga  120
cgcacatccg gtgacgtagt tcgcatgcct gtctatcgcc tacccatccc tgtctgagat  180
caagggcgtg atcgtgcaca gactggagag cgtgtcctat aatatcggct ctcaggagtg  240
gagcaccaca gtgcccagat acgtggccac ccagggctat ctgatctcca acttcgacgc  300
atgcgaacta cgtcaccgga tgtgcgtcac cggaagcatg tgaccggaac ttgcgtcact  360
tccccctccc ctgattggct ggttcgaacg aacgaaccct ccaatgag               408

SEQ ID NO: 29            moltype = DNA  length = 480
FEATURE                  Location/Qualifiers
misc_feature             1..480
                         note = parvovirus
source                   1..480
                         mol_type = other DNA
                         organism = synthetic construct
SEQUENCE: 29
ctcattggag ggttcgttcg ttcgaaccag ccaatcaggg gagggggaag tgacgcaagt  60
tccggtcaca tgcttccggt gacgcacatc cggtgacgta gttccggtca cgtgcttcct  120
gtcacgtgtt tccggtcgca tgcctgtcta tcgcctaccc atccctgtct gagatcaagg  180
gcgtgatcgt gcacagactg gagagcgtgt cctataatat cggctctcag gagtggagca  240
ccacagtgcc cagatacgtg gccacccagg gctatctgat ctccaacttc gacgcatgct  300
cacgtgaccg gaaacacgtg acaggaagca cgtgaccgga actacgtcac cggatgtgcg  360
tcaccggaag catgtgaccg gaacttgcgt cacttccccc tcccctgatt ggctggttcg  420
aacgaacgaa ccctccaatg agactcaagg acaagaggat attttgcgcg ccaggaagtg  480

SEQ ID NO: 30            moltype = DNA  length = 481
FEATURE                  Location/Qualifiers
misc_feature             1..481
                         note = parvovirus
source                   1..481
                         mol_type = other DNA
                         organism = synthetic construct
SEQUENCE: 30
cacttcctgg cgcgcaaaat atcctcttgt ccttgagtct cattggaggg ttcgttcgtt  60
cgaaccagcc aatcagggga gggggaagtg acgcaagttc cggtcacatg cttccggtga  120
cgcacatccg gtgacgtagt tccggtcacg tgcttcctgt cacgtgtttc cggtcacgtg  180
agcatgcctg tctatcgcct acccatccct gtctgagatc aagggcgtga tcgtgcacag  240
actggagagc gtgtcctata atatcggctc tcaggagtgg agcaccacag tgcccagata  300
```

```
cgtggccacc cagggctatc tgatctccaa cttcgacggc atgcgaccgg aaacacgtga  360
caggaagcac gtgaccggaa ctacgtcacc ggatgtgcgt caccggaagc atgtgaccgg  420
aacttgcgtc acttccccct cccctgattg gctggttcga acgaacgaac cctccaatga  480
g                                                                  481

SEQ ID NO: 31          moltype = DNA  length = 7053
FEATURE                Location/Qualifiers
source                 1..7053
                       mol_type = other DNA
                       organism = Homo sapiens
SEQUENCE: 31
atgcaaatag agctctccac ctgcttcttt ctgtgccttt tgcgattctg ctttagtgcc  60
accagaagat actacctggg tgcagtggaa ctgtcatggg actatatgca aagtgatctc  120
ggtgagctgc ctgtggacgc aagatttcct cctagagtgc caaaatcttt tccattcaac  180
acctcagtcg tgtacaaaaa gactctgttt gtagaattca cggatcacct tttcaacatc  240
gctaagccaa ggccaccctg gatgggtctg ctaggtccta ccatccaggc tgaggtttat  300
gatacagtgg tcattacact taagaacatg gcttcccatc ctgtcagtct tcatgctgtt  360
ggtgtatcct actggaaagc ttctgaggga gctgaatatg atgatcagac cagtcaaagg  420
gagaaagaag atgataaagt cttccctggt ggaagccata catatgtctg gcaggtcctg  480
aaagagaatg gtccaatggc ctctgaccca ctgtgcctta cctactcata tctttctcat  540
gtggacctgg taaaagactt gaattcaggc ctcattggag ccctactagt atgtagagaa  600
gggagtctgg ccaaggaaaa gacacagacc ttgcacaaat ttatactact ttttgctgta  660
tttgatgaag ggaaaagttg gcactcagaa acaaagaact ccttgatgca ggatagggat  720
gctgcatctg ctcgggcctg gcctaaaatg cacacagtca atggttatgt aaacaggtct  780
ctgccaggtc tgattggatg ccacaggaaa tcagtctatt ggcatgtgat tggaatgggc  840
accactcctg aagtgcactc aatattcctc gaaggtcaca catttcttgt gaggaaccat  900
cgccaggcgt ccttggaaat ctcgccaata actttcctta ctgctcaaac actcttgatg  960
gaccttggac agtttctact gttttgtcat atctcttccc accaacatga tggcatggaa  1020
gcttatgtca aagtagacag ctgtccagag gaaccccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctccctt agtcctcgcc  1260
cccgatgaca gaagttataa aagtcaatat ttgaacaatg gccctcagcg gattggtagg  1320
aagtacaaaa aagtccgatt tatggcatac acagatgaaa cctttaagac tcgtgaagct  1380
attcagcatg aatcaggaat cttgggacct ttactttatg gggaagttgg agacacactg  1440
ttgattatat ttaagaatca agcaagcaga ccatataaca tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atcctcggtg cctgacccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgtttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt ccttttctgtc ttcttctctg gatatacctt caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga accaagaagc  2280
ttctcccaga attcaagaca ccctagcact aggcaaaagc aatttaatgc caccacaatt  2340
ccagaaaatg acatagagaa gactgaccct tggtttgcac acagaacacc tatgcctaaa  2400
atacaaaatg tctcctctag tgatttgttg atgctcttgc gacagagtcc tactccacat  2460
gggctatcct tatctgatct ccaagaagcc aaatatgaga ctttttctga tgatccatca  2520
cctggagcaa tagacagtaa taacagcctg tctgaaatga cacacttcag gccacagctc  2580
catcacagtg ggacatggt atttacccct gagtcaggcc tccaattaag attaaatgag  2640
aaactgggga caactgcagc aacagagttg aagaaacttg atttcaaagt ttctagtaca  2700
tcaaataatc tgatttcaac aattccatca gacaatttgg cagcaggtac tgataataca  2760
agttccttag gacccccaag tatgccagtt cattatgata gtcaattaga taccactcta  2820
tttggcaaaa agtcatctcc ccttactgag tctggtggac ctctgagctt gagtgaagaa  2880
aataatgatt caaagttgtt agaatcaggt ttaatgaata gccaagaaag ttcatgggga  2940
aaaaatgtat cgtcaacaga gagtggtagg ttatttaaag ggaaaagagc tcatggacct  3000
gctttgttga ctaaagataa tgccttattc aaagttagca tctctttgtt aaagacaaac  3060
aaaacttcca ataattcagc aactaataga aagactcaca ttgatggccc atcattatta  3120
attgagaata gtccatcagt ctggcaaaat atattagaaa gtgacactga gtttaaaaaa  3180
gtgacacctt tgattcatga cagaatgctt atggacaaaa atgctacagc tttgaggcta  3240
aatcatatgt caaataaaac tacttcatca aaaaacatgg aaatggtcca acagaaaaaa  3300
gagggcccca ttccaccaga tgcacaaaat ccagatatgt cgttctttaa gatgctattc  3360
ttgccagaat cagcaaggtg gatacaaagg actcatggaa agaactctct gaactctggg  3420
caaggcccca gtccaaagca attagtatcc ttaggaccag aaaaatctgt ggaaggtcag  3480
aatttcttgt ctgagaaaaa caaagtggta gtaggaaagg gtgaatttac aaaggacgta  3540
ggactcaaag agatggtttt tccaagcagc agaaacctat ttcttactaa cttggataat  3600
ttacatgaaa ataatacaca caatcaagaa aaaaaaattc aggaagaaat agaaaagaag  3660
gaaacattaa tccaagagaa tgtagttttg cctcagatac atacagtgac tggcactaag  3720
aatttcatga agaacctttt cttactgagc actaggcaaa atgtagaagg ttcatatgac  3780
ggggcatatg ctccagtact tcaagatttt aggtcattaa atgattcaac aaatagaaca  3840
aagaaacaca cagctcattt ctcaaaaaaa ggggaggaag aaaacttgga aggcttggga  3900
aatcaaacca agcaaattgt agagaaatat gcatgcacca caaggatatc tcctaataca  3960
agccagcaga attttgtcac gcaacgtagt aagagagctt tgaaacaatt cagactccca  4020
ctagaagaaa cagaacttga aaaaaggata attgtggatg acacctcaac ccagtggtcc  4080
```

```
aaaaacatga aacatttgac cccgagcacc ctcacacaga tagactacaa tgagaaggag  4140
aaagggggcca ttactcagtc tcccttatca gattgcctta cgaggagtca tagcatccct  4200
caagcaaata gatctccatt acccattgca aaggtatcat catttccatc tattagacct  4260
atatatctga ccagggtcct attccaagac aactcttctc atcttccagc agcatcttat  4320
agaaagaaag attctggggt ccaagaaagc agtcatttct tacaaggagc caaaaaaaat  4380
aacctttctt tagccattct aaccttggag atgactggtg atcaaagaga ggttggctcc  4440
ctggggacaa gtgccacaaa ttcagtcaca tacaagaaag ttgagaacac tgttctcccg  4500
aaaccagact tgcccaaaac atctggcaaa gttgaattgc ttccaaaagt tcacatttat  4560
cagaaggacc tattccctac ggaaactagc aatgggtctc ctggccatct ggatctcgtg  4620
gaagggagcc ttcttcaggg aacagaggga gcgattaagt ggaatgaagc aaacagacct  4680
ggaaaagttc cctttctgag agtagcaaca gaaagctctg caaagactcc ctccaagcta  4740
ttggatcctc ttgcttggga taaccactat ggtactcaga taccaaaaga agagtggaaa  4800
tcccaagaga agtcaccaga aaaaacagct tttaagaaaa aggataccat tttgtccctg  4860
aacgcttgtg aaagcaatca tgcaatagca gcaataaatg agggacaaaa taagcccgaa  4920
atagaagtca cctgggcaaa gcaaggtagg actgaaaggc tgtgctctca aaacccacca  4980
gtcttgaaac gccatcaacg ggaaataact cgtactactc ttcagtcaga tcaagaggaa  5040
attgactatg atgataccat atcagttgaa atgaagaagg aagattttga catttatgat  5100
gaggatgaaa atcagagccc ccgcagcttt caaaagaaaa cacgacacta ttttattgct  5160
gcagtggaga ggctctggga ttatgggatg agtagctccc cacatgttct aagaaacagg  5220
gctcagagtg gcagtgtccc tcagttcaag aaagttgttt tccaggaatt tactgatggc  5280
tcctttactc agcccttata ccgtggagaa ctaaatgaac atttgggact cctggggcca  5340
tatataagag cagaagttga agataatatc atggtaactt tcagaaatca ggcctctcgt  5400
ccctattcct tctattctag ccttatttct tatgaggaag atcagaggca aggagcagaa  5460
cctagaaaaa actttgtcaa gcctaatgaa accaaaactt acttttggaa agtgcaacat  5520
catatggcac ccactaaaga tgagtttgac tgcaaagcct gggcttattt ctctgatgtt  5580
gacctggaaa aagatgtgca ctcaggcctg attggacccc ttctggtctg ccacactaac  5640
acactgaacc ctgctcatgg gagacaagtg acagtacagg aatttgctct gtttttcacc  5700
atctttgatg agaccaaaag ctggtacttc actgaaaata tggaaagaaa ctgcagggct  5760
ccctgcaata tccagatgga agatcccact tttaaagaga attatcgctt ccatgcaatc  5820
aatggctaca taatggatac actacctggc ttagtaatgg ctcaggatca aaggattcga  5880
tggtatctgc tcagcatggg cagcaatgaa aacatccatt ctattcattt cagtggacat  5940
gtgttcactg tacgaaaaaa agaggagtat aaaatggcac tgtacaatct ctatccaggt  6000
gtttttgaga cagtggaaat gttaccatcc aaagctggaa tttggcgggt ggaatgcctt  6060
attggcgagc atctacatgc tgggatgagc acactttttc tggtgtacag caataagtgt  6120
cagactcccc tgggaatggc ttctggacac attagagatt ttcagattac agcttcagga  6180
caatatggac agtgggcccc aaagctggcc agacttcatt attccggatc aatcaatgcc  6240
tggagcacca aggagccctt ttcttggatc aaggtggatc tgttggcacc aatgattatt  6300
cacggcatca agacccaggg tgcccgtcag aagttctcca gcctctacat ctctcagttt  6360
atcatcatgt atagtcttga tgggaagaag tggcagactt atcgaggaaa ttccactgga  6420
accttaatgg tcttctttgg caatgtggat tcatctggga taaaacacaa tatttttaac  6480
cctccaatta ttgctcgata catccgtttg cacccaactc attatagcat tcgcagcact  6540
cttcgcatgg agttgatggg ctgtgattta aatagttgca gcatgccatt gggaatggag  6600
agtaaagcaa tatcagatgc acagattact gcttcatcct actttaccaa tatgtttgcc  6660
acctggtctc cttcaaaagc tcgacttcac ctccaaggga ggagtaatgc ctggagacct  6720
caggtgaata atccaaaaga gtggctgcaa gtggacttcc agaagacaat gaaagtcaca  6780
ggagtaacta ctcagggagt aaaatctctg cttaccagca tgtatgtgaa ggagttcctc  6840
atctccagca gtcaagatgg ccatcagtgg actctctttt ttcagaatgg caaagtaaag  6900
gtttttcagg gaaatcaaga ctccttcaca cctgtggtga actctctaga cccaccgtta  6960
ctgactcgct accttcgaat tcacccccag agttgggtgc accagattgc cctgaggatg  7020
gaggttctgg gctgcgaggc acaggacctc tac                                7053

SEQ ID NO: 32          moltype = DNA  length = 4317
FEATURE                Location/Qualifiers
misc_feature           1..4317
                       note = expression construct
source                 1..4317
                       mol_type = other DNA
                       organism = synthetic construct
SEQUENCE: 32
gccactcgcc ggtactacct tggagccgtg gagctttcat gggactacat gcagagcgac  60
ctgggcgaac tccccgtgga tgccagattc ccccccgcg tgccaaagtc cttccccttt  120
aacacctccg tggtgtacaa gaaaaccctc tttgtcgagt tcactgacca cctgttcaac  180
atcgccaagc cgcgcccacc ttggatgggc ctcctgggac cgaccattca agctgaagtg  240
tacgacaccg tggtgatcac cctgaagaac atggcgtccc accccgtgtc cctgcatgcg  300
gtcggagtgt cctactggaa ggcctccgaa ggagctgagt acgacgacca gactagccag  360
cgggaaaagg aggacgataa agtgttcccg ggcggctcgc atacttacgt gtggcaagtc  420
ctgaaggaaa acggacctat ggcatccgat cctctgtgcc tgacttactc ctacctttcc  480
catgtggacc tcgtgaagga cctgaacagc gggctgattg gtgcacttct cgtgtgccgc  540
gaaggttcgc tcgctaagga aaagacccag accctccata agttcatcct tttgttcgct  600
gtgttcgatg aaggaaagtc atggcattcc gaaactaaga actcgctgat gcaggaccgg  660
gatgccgcct cagcccgcgc ctggcctaaa atgcatacag tcaacggata cgtgaatcgg  720
tcactgcccg ggctcatcgg ttgtcacaga aagtccgtgt actggcacgt catcggcatg  780
ggcactacgc ctgaagtgca ctccatcttc ctggaagggc acaccttcct cgtgcgcaac  840
caccgccagg cctctctgga aatctccccg attacctttc tgaccgccca gactctgctc  900
atggacctgg ggcagttcct tctcttctgc cacatctcca gccatcagca cgacggaatg  960
gaggcctacg tgaaggtgga ctcatgcccg gaagaacctc agttgcggat gaagaacaac  1020
gaggaggccg aggactatga cgacgatttg actgactccg agatggacgt cgtgcggttc  1080
gatgacgaca acagccccag cttcatccag attcgcagcg tggccaagaa gcaccccaaa  1140
acctgggtgc actacatcgc ggccgaggaa gaagattggg actacgcccc gttggtgctg  1200
```

```
gcacccgatg accggtcgta caagtcccag tatctgaaca atggtccgca gcggattggc  1260
agaaagtaca agaaagtgcg gttcatggcg tacactgacg aaacgtttaa gacccgggag  1320
gccattcaac atgagagcgg cattctggga ccactgctgt acggagaggt cggcgatacc  1380
ctgctcatca tcttcaaaaa ccaggcctcc cggccttaca acatctaccc tcacggaatc  1440
accgacgtgc ggccactcta ctcgcggcgc ctgccgaagg gcgtcaagca cctgaaagac  1500
ttccctatcc tgccgggcga aatcttcaag tataagtgga ccgtcaccgt ggaggacggg  1560
cccaccaaga gcgatcctag gtgtctgact cggtactact ccagcttcgt gaacatggaa  1620
cgggacctgg catcgggact cattggaccg ctgctgatct gctacaaaga gtcggtggat  1680
caacgcggca accagatcat gtccgacaag cgcaacgtga tcctgttctc cgtgtttgat  1740
gaaaacagat cctggtacct cactgaaaac atccagaggt tcctcccaaa ccccgcagga  1800
gtgcaactgg aggaccctga gtttcaggcc tcgaatatca tgcactcgat taacggttac  1860
gtgttcgact cgctgcagct gagcgtgtgc ctccatgaag tcgcttactg gtacattctg  1920
tccatcggcg cccagactga cttcctgagc gtgttctttt ccggttacac ctttaagcac  1980
aagatggtgt acgaagatac cctgaccctg ttccctttct ccggcgaaac ggtgttcatg  2040
tcgatggaga acccgggtct gtggattctg ggatgccaca acagcgactt tcggaaccgc  2100
ggaatgactg ccctgctgaa ggtgtcctca tgcgacaaga acaccggaga ctactacgag  2160
gactcctacg aggatatctc agcctacctc ctgtccaaga acaacgcgat cgagccgcgc  2220
agcttcagcc agaacccgcc tgtgctgaag aggcaccagc gagaaattac ccggaccacc  2280
ctccaatcgg atcaggagga aatcgactac gacgacacca tctcggtgga aatgaagaag  2340
gaagatttcg atatctacga cgaggacgaa aatcagtccc ctcgctcatt ccaaaagaaa  2400
actagacact actttatcgc cgcggtggaa agactgtggg actatggaat gtcatccagc  2460
cctcacgtcc ttcggaaccg ggcccagagc ggatcggtgc ctcagttcaa gaaagtggtg  2520
ttccaggagt tcaccgacgg cagcttcacc cagccgctgt accggggaga actgaacgaa  2580
cacctgggcc tgctcggtcc ctacatccgc gcggaagtgg aggataacat catggtgacc  2640
ttccgtaacc aagcatccag accttactcc ttctattcct ccctgatctc atacgaggag  2700
gaccagcgcc aaggcgccga gccccgcaag aacttcgtca agcccaacga gactaagacc  2760
tacttctgga aggtccaaca ccatatggcc ccgaccaagg atgagtttga ctgcaaggcc  2820
tgggcctact tctccgacgt ggaccttgag aaggatgtcc attccggcct gatcggggccg  2880
ctgctcgtgt gtcacaccaa caccctgaac ccagcgcatg gacgccaggt caccgtccag  2940
gagtttgctc tgttcttcac catttttgac gaaactaagt cctggtactt caccgagaat  3000
atggagcgaa actgtagagc gccctgcaat atccagatgg aagatccgac tttcaaggag  3060
aactatagat tccacgccat caacgggtac atcatggata ctctgccggg gctggtcatg  3120
gcccaggatc agaggattcg gtggtacttg ctgtcaatgg gatcgaacga aaacattcac  3180
tccattcact tctccggtca cgtgttcact gtgcgcaaga aggaggagta caagatggcg  3240
ctgtacaatc tgtaccccgg ggtgttcgaa actgtggaga tgctgccgtc caaggccggc  3300
atctggagag tggagtgcct gatcggagag cacctccacg cggggatgtc caccctcttc  3360
ctggtgtact cgaataagtg ccagaccccg ctgggcatgg cctcgggcca catcagagac  3420
ttccagatca cagcaagcgg acaatacggc caatgggcgc cgaagctggc ccgcttgcac  3480
tactccggat cgatcaacgc atggtccacc aaggaaccgt tctcgtggat taaggtggac  3540
ctcctggccc ctatgattat ccacggaatt aagacccagg gcgccaggca gaagttctcc  3600
tccctgtaca tctcgcaatt catcatcatg tacagcctgg acgggaagaa gtggcagact  3660
tacaggggaa actccaccgg caccctgatg gtctttttcg gcaacgtgga ttcctccggc  3720
attaagcaca acatcttcaa cccaccgatc atagccagat atattaggct ccacccccact  3780
cactactcaa tccgctcaac tcttcggatg gaactcatgg ggtgcgacct gaactcctgc  3840
tccatgccgt tggggatgga atcaaaggct attagcgacg cccagatcac cgcgagctcc  3900
tacttcacta acatgttcgc cacctggagc ccctccaagg ccaggctgca cttgcaggga  3960
cggtcaaatg cctggcggcc gcaagtgaac aatccgaagg aatggcttca agtggatttc  4020
caaaagacca tgaaagtgac cggagtcacc acccagggag tgaagtccct tctgacctcg  4080
atgtatgtga aggagttcct gattagcagc agccaggacg ggcaccagtg gaccctgttc  4140
ttccaaaacg gaaaggtcaa ggtgttccag gggaaccagg actcgttcac acccgtggtg  4200
aactccctgg accccccact gctgacgcgg tacttgagga ttcatcctca gtcctgggtc  4260
catcagattg cattgcgaat ggaagtcctg ggctgcgagg cccaggacct gtactga     4317

SEQ ID NO: 33          moltype = DNA  length = 4335
FEATURE                Location/Qualifiers
misc_feature           1..4335
                       note = expression construct
source                 1..4335
                       mol_type = other DNA
                       organism = synthetic construct
SEQUENCE: 33
gccacccgcc ggtattactt aggtgctgtg gaactgagct gggactacat gcagtccgac  60
ctgggagaac tgccggtgga cgcgagattc ccacctagag tcccgaagtc cttcccattc  120
aacacctccg tggtctacaa aaagaccctg ttcgtggagt tcactgacca ccttttcaat  180
attgccaagc cgcgcccccc ctggatgggc ctgcttggtc ctacgatcca agcagaggtc  240
tacgacaccg tggtcatcac actgaagaac atggcctcac accccgtgtc gctgcatgct  300
gtgggagtgt cctactggaa ggcctcagag ggtgccgaat atgatgacca gaccagccag  360
agggaaaagg aggatgacaa agtgttcccg ggtggcagcc acacttacgt gtggcaagtg  420
ctgaaggaaa acgggcctat ggcgtcggac cccctatgcc tgacctactc ctacctgtcc  480
catgtggacc ttgtgaagga tctcaactcg ggactgatcg gcgccctctt ggtgtgcaga  540
gaaggcagcc tggcgaagga aaagactcag accctgcaca agttcattct gttgtttgct  600
gtgttcgatg aaggaaagtc ctggcactca gaaaccaaga actcgctgat gcaggataga  660
gatgcggcct cggccagagc ctggcctaaa atgcacaccg tcaacggata tgtgaacagg  720
tcgctccctg gcctcatcgg ctgccacaga aagtccgtgt attggcatgt gatcggcatg  780
ggtactactc cggaagtgca tagtatcttt ctggagggcc ataccttctt ggtgcgcaac  840
cacagacagg cctcgctgga aatctcgcct atcacttttct tgactgcgca gaccctcctt  900
atggaccttg gacagttcct gctgttctgt cacatcagct cccatcagca tgatgggatg  960
gaggcctatg tcaaagtgga ctcctgccct gaggagccac agctccggat gaagaacaat  1020
gaggaagcgg aggattacga cgacgacctg actgacagcg aaatggacgt cgtgcgattc  1080
```

-continued gatgacgaca acagcccgtc cttcatccaa attagatcag tggcgaagaa gcaccccaag 1140
acctgggtgc actacattgc cgccgaggaa gaggactggg actacgcgcc gctggtgctg 1200
gcgccagacg acaggagcta caagtcccag tacctcaaca acgggccgca gcgcattggc 1260
aggaagtaca agaaagtccg cttcatggcc tacactgatg aaaccttcaa gacgagggaa 1320
gccatccagc acgagtcagg catcctggga ccgctccttt acggcgaagt cggggatacc 1380
ctgctcatca ttttcaagaa ccaggcatcg cggccctaca acatctaccc tcacgggatc 1440
acagacgtgc gcccgctcta ctcccgccgg ctgcccaagg gagtgaagca cctgaaggat 1500
tttcccatcc tgccgggaga aatcttcaag tacaagtgga ccgtgactgt ggaagatggc 1560
cctaccaagt cggaccctcg ctgtctgacc cggtactatt cctcgtttgt gaacatggag 1620
cgcgacctgg cctcggggct gattggtccg ctgctgatct gctacaagga gtccgtggac 1680
cagcgcggga accagatcat gtccgacaag cgcaacgtga tcctgttctc tgtctttgat 1740
gaaaacagat cgtggtactt gactgagaat atccagcggt tcctgcccaa cccagcggga 1800
gtgcaactgg aggacccgga gttccaggcc tcaaacatta tgcactctat caacggctat 1860
gtgttcgact cgctccaact gagcgtgtgc ctgcatgaag tggcatactg gtacattctg 1920
tccatcggag cccagaccga cttcctgtcc gtgttcttct ccggatacac cttcaagcat 1980
aagatggtgt acgaggacac tctgaccctc ttcccatttt ccggagaaac tgtgttcatg 2040
tcaatggaaa acccgggctt gtggattctg ggttgccata actcggactt ccggaataga 2100
gggatgaccg ccctgctgaa agtgtccagc tgtgacaaga ataccggcga ttactacgag 2160
gacagctatg aggacatctc cgcttatctg ctgtccaaga acaacgccat tgaacccagg 2220
tccttctccc aaaacggtgc accggcctca tccccccccg tgctgaagcg gcatcaaaga 2280
gagatcacca ggaccactct ccagtccgat caggaagaaa ttgactacga cgatactatc 2340
agcgtggaga tgaagaagga ggacttcgac atctacgatg aggatgagaa ccagtcccct 2400
cggagctttc agaagaaaac ccgccactac ttcatcgctg ccgtggagcg gctgtgggat 2460
tacgggatgt ccagctcacc gcatgtgctg cggaatagag cgcagtcagg atcggtgccc 2520
cagttcaaga aggtcgtgtt ccaagagttc accgacgggt ccttcactca acccctgtac 2580
cggggcgaac tcaacgaaca cctgggactg cttgggccgt atatcagggc agaagtggaa 2640
gataacatca tggtcacctt ccgcaaccag gcctcccggc cgtacagctt ctactcttca 2700
ctgatctcct acgaggaaga tcagcggcag ggagccgagc cccggaagaa cttcgtcaag 2760
cctaacgaaa ctaagaccta cttttggaag gtccagcatc acatggcccc gaccaaagac 2820
gagttcgact gtaaagcctg ggcctacttc tccgatgtgg acctggagaa ggacgtgcac 2880
tcgggactca ttggcccgct ccttgtgtgc catactaata ccctgaaccc tgctcacggt 2940
cgccaagtca cagtgcagga gttcgccctc ttcttcacca tcttcgatga aacaaagtcc 3000
tggtacttta ctgagaacat ggaacgcaat tgcagggcac cctgcaacat ccagatggaa 3060
gatcccacct tcaaggaaaa ctaccggttt catgccatta acggctacat aatggacacg 3120
ttgccaggac tggtcatggc ccaggaccag agaatccggt ggtatctgct ctccatgggc 3180
tccaacgaaa acattcacag cattcatttt tccggccatg tgttcaccgt ccggaagaag 3240
gaagagtaca agatggctct gtacaacctc taccctggag tgttcgagac tgtggaaatg 3300
ctgcctagca aggccggcat ttggagagtg gaatgcctga tcggagagca tttgcacgcc 3360
ggaatgtcca ccctgtttct tgtgtactcc aacaagtgcc agaccccgct gggaatggcc 3420
tcaggtcata ttagggattt ccagatcact gcttcggggc agtacgggca gtgggcacct 3480
aagttggccc ggctgcacta ctctggctcc atcaatgcct ggtccaccaa ggaacccttc 3540
tcctggatta aggtggacct cctggcccca atgattattc acggtattaa gacccagggt 3600
gcccgacaga agttctcctc actctacatc tcgcaattca tcataatgta cagcctggat 3660
gggaagaagt ggcagaccta ccggggaaac tccactggaa cgctcatggt gtttttcggc 3720
aacgtggact cctccggcat taagcacaac atcttcaacc ctccgatcat tgctcggtac 3780
atccggctgc acccaactca ctacagcatc cggtccaccc tgcggatgga actgatgggt 3840
tgtgacctga actcctgctc catgcccctt gggatggaat ccaaggccat tagcgatgca 3900
cagatcaccg cctcttcata cttcaccaac atgttcgcga cctggtcccc gtcgaaggcc 3960
cgcctgcacc tccaaggtcg ctccaatgcg tggcggcctc aagtgaacaa ccccaaggag 4020
tggctccagg tcgacttcca aaagaccatg aaggtcaccg gagtgaccac ccagggcgtg 4080
aagtccctgc tgacctctat gtacgttaag gagttcctca tctcctcaag ccaagacgga 4140
catcagtgga ccctgttctt ccaaaacgga aaagtcaaag tattccaggg caaccaggac 4200
tccttcaccc ctgtggtcaa cagcctggac cccccattgc tgacccgcta cctccgcatc 4260
cacccccaaa gctgggtcca ccagatcgca ctgcgcatgg aggtccttgg atgcgaagcc 4320
caagatctgt actaa 4335

SEQ ID NO: 34 moltype = DNA length = 4824
FEATURE Location/Qualifiers
misc_feature 1..4824
note = expression construct
source 1..4824
mol_type = other DNA
organism = synthetic construct
SEQUENCE: 34
atgcagattg agctgtccac ttgtttcttc ctgtgcctcc tgcgcttctg tttctccgcc 60
actcgccggt actaccttgg agccgtggag ctttcatggg actacatgca gagcgacctg 120
ggcgaactcc ccgtggatgc cagattcccc ccccgcgtgc caaagtcctt cccctttaac 180
acctccgtgg tgtacaagaa aaccctcttt gtcgagttca ctgaccacct gttcaacatc 240
gccaagccgc gcccaccttg gatgggcctc ctgggaccga ccattcaagc tgaagtgtac 300
gacaccgtgg tgatcaccct gaagaacatg gcgtcccacc ccgtgtccct gcatgcggtc 360
ggagtgtcct actggaaggc ctccgaagga gctgagtacg acgaccagac tagccagcgg 420
gaaaaggagg acgataaagt gttcccgggc ggctcgcata cttacgtgtg gcaagtcctg 480
aaggaaaacg gacctatggc atccgatcct ctgtgcctga cttactccta cctttcccat 540
gtggacctcg tgaaggacct gaacagcggg ctgattggtg cacttctcgt gtgccgcgaa 600
ggttcgctcg ctaaggaaaa gacccagacc ctccataagt tcatcctttt gttcgctgtg 660
ttcgatgaag gaaagtcatg gcattccgaa actaagaact cgctgatgca ggaccgggat 720
gccgcctcag cccgcgcctg gcctaaaatg catacagtca acggatacgt gaatcggtca 780
ctgcccgggc tcatcggttg tcacagaaag tccgtgtact ggcacgtcat cggcatgggc 840
actacgcctg aagtgcactc catcttcctg gaagggcaca ccttcctcgt gcgcaaccac 900

```
cgccaggcct ctctggaaat ctccccgatt acctttctga ccgcccagac tctgctcatg  960
gacctggggc agttccttct cttctgccac atctccagcc atcagcacga cggaatggag  1020
gcctacgtga aggtggactc atgcccggaa gaacctcagt tgcggatgaa gaacaacgag  1080
gaggccgagg actatgacga cgatttgact gactccgaga tggacgtcgt gcggttcgat  1140
gacgacaaca gccccagctt catccagatt cgcagcgtgg ccaagaagca ccccaaaacc  1200
tgggtgcact acatcgcggc cgaggaagaa gattgggact acgccccgtt ggtgctggca  1260
cccgatgacc ggtcgtacaa gtcccagtat ctgaacaatg gtccgcagcg gattggcaga  1320
aagtacaaga aagtgcggtt catggcgtac actgacgaaa cgtttaagac ccgggaggcc  1380
attcaacatg agagcggcat tctgggacca ctgctgtacg gagaggtcgg cgataccctg  1440
ctcatcatct tcaaaaacca ggcctcccgg ccttacaaca tctaccctca cggaatcacc  1500
gacgtgcggc cactctactc gcggcgcctg ccgaagggcg tcaagcacct gaaagacttc  1560
cctatcctgc cgggcgaaat cttcaagtat aagtggaccg tcaccgtgga ggacgggccc  1620
accaagagcg atcctaggtg tctgactcgg tactactcca gcttcgtgaa catggaacgg  1680
gacctggcat cgggactcat tggaccgctg ctgatctgct acaaagagtc ggtggatcaa  1740
cgcggcaacc agatcatgtc cgacaagcgc aacgtgatcc tgttctccgt gtttgatgaa  1800
aacagatcct ggtacctcac tgaaaacatc cagaggttcc tcccaaaccc cgcaggagtg  1860
caactggagg accctgagtt tcaggcctcg aatatcatgc actcgattaa cggttacgtg  1920
ttcgactcgc tgcaactgag cgtgtgcctc catgaagtcg cttactggta cattctgtcc  1980
atcggcgccc agactgactt cctgagcgtg ttcttttccg gttacacctt taagcacaag  2040
atggtgtacg aagataccct gaccctgttc cctttctccg gcgaaacggt gttcatgtcg  2100
atggagaacc cgggtctgtg gattctggga tgccacaaca gcgactttcg gaaccgcgga  2160
atgactgccc tgctgaaggt gtcctcatgc gacaagaaca ccggagacta ctacgaggac  2220
tcctacgagg atatctcagc ctacctcctg tccaagaaca acgcgatcga gccgcgcagc  2280
ttcagccaga acggcgcgcc aacatcagag agcgccaccc ctgaaagtgg tcccgggagc  2340
gagccagcca catctgggtc ggaaacgcca ggcacaagtg agtctgcaac tcccgagtcc  2400
ggacctggct ccgagcctgc cactagcggc tccgagactc cgggaacttc cgagagcgct  2460
acaccagaaa gcggacccgg aaccagtacc gaacctagcg agggctctgc tccgggcagc  2520
ccagccggct ctcctacatc cacggaggag ggcacttccg aatccgccac cccggagtca  2580
gggccaggat ctgaacccgc tacctcaggc agtgagacgc caggaacgag cgagtccgct  2640
acaccggaga gtgggccagg gagccctgct ggatctccta cgtccactga ggaagggtca  2700
ccagcgggct cgcccaccag cactgaagaa ggtgcctcga gcccgcctgt gctgaagagg  2760
caccagcgag aaattacccg gaccaccctc caatcggatc aggaggaaat cgactacgac  2820
gacaccatct cggtggaaat gaagaaggaa gatttcgata tctacgacga ggacgaaaat  2880
cagtcccctc gctcattcca aaagaaaact agacactact ttatcgccgc ggtggaaaga  2940
ctgtgggact atggaatgtc atccagccct cacgtccttc ggaaccgggc ccagagcgga  3000
tcggtgcctc agttcaagaa agtggtgttc caggagttca ccgacggcag cttcacccag  3060
ccgctgtacc ggggagaact gaacgaacac ctgggcctgc tcggtcccta catccgcgcg  3120
gaagtggagg ataacatcat ggtgaccttc cgtaaccaag catccagacc ttactccttc  3180
tattcctccc tgatctcata cgaggaggac cagcgccaag gcgccgagcc ccgcaagaac  3240
ttcgtcaagc ccaacgagac taagacctac ttctggaagg tccaacacca tatggccccg  3300
accaaggatg agtttgactg caaggcctgg gcctacttct ccgacgtgga ccttgagaag  3360
gatgtccatt ccggcctgat cggcccgctg ctcgtgtgtc acaccaacac cctgaaccca  3420
gcgcatggac gccaggtcac cgtccaggag tttgctctgt tcttcaccat ttttgacgaa  3480
actaagtcct ggtacttcac cgagaatatg gagcgaaact gtagagcgcc ctgcaatatc  3540
cagatggaag atccgacttt caaggagaac tatagattcc acgccatcaa cgggtacatc  3600
atggatactc tgccggggct ggtcatggcc caggatcaga ggattcggtg gtacttgctg  3660
tcaatgggat cgaacgaaaa cattcactcc attcacttct ccggtcacgt gttcactgtg  3720
cgcaagaagg aggagtacaa gatggcgctg tacaatctgt accccggggt gttcgaaact  3780
gtggagatgc tgccgtccaa ggccggcatc tggagagtgg agtgcctgat cggagagcac  3840
ctccacgcgg ggatgtccac cctcttcctg gtgtactcga ataagtgcca gaccccgctg  3900
ggcatggcct cgggccacat cagagacttc cagatcacag caagcggaca atacggccaa  3960
tgggcgccga agctggcccg cttgcactac tccggatcga tcaacgcatg gtccaccaag  4020
gaaccgttct cgtggattaa ggtggacctc ctggccccta tgattatcca cggaattaag  4080
acccagggcg ccaggcagaa gttctcctcc ctgtacatct cgcaattcat catcatgtac  4140
agcctggacg ggaagaagtg gcagacttac aggggaaact ccaccggcac cctgatggtc  4200
tttttcggca acgtggattc ctccggcatt aagcacaaca tcttcaaccc accgatcata  4260
gccagatata ttaggctcca ccccactcac tactcaatcc gctcaactct tcggatggaa  4320
ctcatggggt gcgacctgaa ctcctgctcc atgccgttgg ggatggaatc aaaggctatt  4380
agcgacgccc agatcaccgc gagctcctac ttcactaaca tgttcgccac ctggagcccc  4440
tccaaggcca ggctgcactt gcagggacgg tcaaatgcct ggcggccgca agtgaacaat  4500
ccgaaggaat ggcttcaagt ggatttccaa aagaccatga aagtgaccgg agtcaccacc  4560
cagggagtga agtcccttct gacctcgatg tatgtgaagg agttcctgat tagcagcagc  4620
caggacggcc accagtggac cctgttcttc caaaacggaa aggtcaaggt gttccagggg  4680
aaccaggact cgttcacacc cgtggtgaac tccctggacc ccccactgct gacgcggtac  4740
ttgaggattc atcctcagtc ctgggtccat cagattgcat tgcgaatgga agtcctgggc  4800
tgcgaggccc aggacctgta ctga                                         4824
```

```
SEQ ID NO: 35          moltype = DNA  length = 8458
FEATURE                Location/Qualifiers
source                 1..8458
                       mol_type = other DNA
                       organism = synthetic construct
SEQUENCE: 35
atcgatggcc ccaggttaat ttttaaaaag cagtcaaaag tccaagtggc ccttggcagc  60
atttactctc tctgtttgct ctggttaata atctcaggag cacaaacatt cctggaggca  120
ggagaagaaa tcaacatcct ggacttatcc tctgggcctc tccccacctt cgatggcccc  180
aggttaattt ttaaaaagca gtcaaaagtc caagtggccc ttggcagcat ttactctctc  240
tgtttgctct ggttaataat ctcaggagca caaacattcc tggaggcagg agaagaaatc  300
aacatcctgg acttatcctc tgggcctctc cccaccttcg aactagccac tagcctgagg  360
```

-continued

```
ctggtcaaaa ttgaacctcc tcctgctctg agcagcctgg ggggcagact aagcagaggg  420
ctgtgcagac ccacataaag agcctactgt gtgccaggca cttcacccga ggcacttcac  480
aagcatgctt gggaatgaaa cttccaactc tttgggatgc aggtgaaaca gttcctggtt  540
cagagaggtg aagcggcctg cctgaggcag cacagctctt ctttacagat gtgcttcccc  600
acctctaccc tgtctcacgg ccccccatgc cagcctgacg gttgtgtctg cctcagtcat  660
gctccatttt tccatcggga ccatcaagag ggtgtttgtg tctaaggctg actgggtaac  720
tttggatgag cggtctctcc gctctgagcc tgtttcctca tctgtcaaat gggctctaac  780
ccactctgat ctcccagggc ggcagtaagt cttcagcatc aggcattttg gggtgactca  840
gtaaatggta gatcttgcta ccagtggaac agccactaag gattctgcag tgagagcaga  900
gggccagcta agtggtactc tcccagagac tgtctgactc acgccacccc ctccaccttg  960
gacacaggac gctgtggttt ctgagccagg tacaatgact cctttcggta agtgcagtgg  1020
aagctgtaca ctgcccaggc aaagcgtccg ggcagcgtag gcgggcgact cagatcccag  1080
ccagtggact tagcccctgt ttgctcctcc gataactggg gtgaccttgg ttaatattca  1140
ccagcagcct cccccgttgc cctctggat ccactgctta aatacggacg aggacagggc  1200
cctgtctcct cagcttcagg caccaccact gacctgggac aggaattctc aggagcacaa  1260
acattcctgg aggcaggaga agaaatcaac atcctggact tatcctctgg gcctctcccc  1320
accgatatct acctgctgat cgcccggccc ctgttcaaac atgtcctaat actctgtcgg  1380
ggcaaaggtc ggcagtagtt ttccatctta ctcaacatcc tcccagtgta cgtaggatcc  1440
tgtctgtctg cacatttcgt agagcgagtg ttccgatact ctaatctccc ggggcaaagg  1500
tcgtattgac ttaggttact tattctcctt ttgttgacta agtcaataat cagaatcagc  1560
aggtttggag tcagcttggc agggatcagc agcctgggtt ggaaggaggg ggtataaaag  1620
ccccttcacc aggagaagcc gtcacacaga tccacaagct cctgctagag tcgctgcgcg  1680
ctgccttcgc cccgtgcccc gctccgccgc cgcctcgcgc cgcccgcccc ggctctgact  1740
gaccgcgtta ctcccacagg tgagcgggcg ggacggccct tctcctccgg gctgtaatta  1800
gcgcttggtt tattgacggc ttgtttcttt tctgtggctg cgtgaaagcc ttgaggggct  1860
ccgggaaggc cctttgtgcg gggggagcgg ctcggggggt gcgtgcgtgt gtgtgtgcgt  1920
ggggagcgcc gcgtgcggct ccgcgctgcc cggcggctgt gagcgctgcg ggcgcggcgc  1980
ggggctttgt gcgctccgca gtgtgcgcga ggggagcgcg gccgggggcg gtgccccgcg  2040
gtgcgggggg ggctgcgagg ggaacaaagg ctgcgtgcgg ggtgtgtgcg tgggggggtg  2100
agcagggggt gtgggcgcgt cggtcgggct gcaacccccc ctgcaccccc ctccccgagt  2160
tgctgagcac ggcccggctt cgggtgcggg gctccgtacg gggcgtggcg cggggctcgc  2220
cgtgccgggc ggggggtggc ggcaggtggg ggtgccgggc ggggcggggc cgcctcgggc  2280
cggggagggc tcgggggagg ggcgcggcgg cccccggagc gccggcggct gtcgaggcgc  2340
ggcgagccgc agccattgcc ttttatggta atcgtgcgag agggcgcagg gacttccttt  2400
gtcccaaatc tgtgcggagc cgaaatctgg gaggcgccgc cgcacccct ctagcgggcg  2460
cggggcgaag cggtgcggcg ccggcaggaa ggaaatgggc ggggagggcc ttcgtgcgtc  2520
gccgcgccgc cgtccccttc tccctctcca gcctcggggc tgtccgcggg gggacggctg  2580
ccttcggggg ggacggggca gggcggggtt cggcttctgg cgtgtgaccg gcggctctag  2640
agcctctgct aaccttgttc ttgccttctt ctttttccta cagctcctgg gcaacgtgct  2700
ggttattgtg ctgtctcatc attttggcaa agaattactc gaggccacca tgcagattga  2760
actgtccact tgcttcttcc tgtgcctcct gcggttttgc ttctcggcca cccgccggta  2820
ttacttaggt gctgtggaac tgagctggga ctacatgcag tccgacctgg gagaactgcc  2880
ggtggacgcg agattcccac ctagagtccc gaagtccttc ccattcaaca cctccgtggt  2940
ctacaaaaag accctgttcg tggagttcac tgaccacctt ttcaatattg ccaagccgcg  3000
ccccccctgg atgggcctgc ttggtcctac gatccaagca gaggtctacg acaccgtggt  3060
catcacactg aagaacatgg cctcacaccc cgtgtcgctg catgctgtgg gagtgtccta  3120
ctggaaggcc tcagagggtg ccgaatatga tgaccagacc agccagaggg aaaaggagga  3180
tgacaaagtg ttcccgggtg gcagccacac ttacgtgtgg caagtgctga aggaaaacgg  3240
gcctatggcg tcggaccccc tatgcctgac ctactcctac ctgtcccatg tggaccttgt  3300
gaaggatctc aactcgggac tgatcggcgc cctcttggtg tgcagagaag gcagcctggc  3360
gaaggaaaag actcagaccc tgcacaagtt cattctgttg tttgctgtgt tcgatgaagg  3420
aaagtcctgg cactcagaaa ccaagaactc gctgatgcag gatagagatg cggcctcggc  3480
cagagcctgg cctaaaatgc acaccgtcaa cggatatgtg aacaggtcgc tccctggcct  3540
catcggctgc cacagaaagt ccgtgtattg gcatgtgatc ggcatgggta ctactccgga  3600
agtgcatagt atctttctgg agggccatac cttcttggtg cgcaaccaca gacaggcctc  3660
gctggaaatc tcgcctatca ctttcttgac tgcgcagacc ctccttatgg accttggaca  3720
gttcctgctg ttctgtcaca tcagctccca tcagcatgat gggatggagg cctatgtcaa  3780
agtggactcc tgccctgagg agccacagct ccggatgaag aacaatgagg aagcggagga  3840
ttacgacgac gacctgactg acagcgaaat ggacgtcgtg cgattcgatg acgacaacag  3900
cccgtccttc atccaaatta gatcagtggc gaagaagcac cccaagacct gggtgcacta  3960
cattgccgcc gaggaagagg actgggacta cgcgccgctg gtgctggcgc cagacgacag  4020
gagctacaag tcccagtacc tcaacaacgg gccgcagcgc attggcagga agtacaagaa  4080
agtccgcttc atggcctaca ctgatgaaac cttcaagacg agggaagcca tccagcacga  4140
gtcaggcatc ctgggaccgc tcctttacgg cgaagtcggg gataccctgc tcatcatttt  4200
caagaaccag gcatcgcggc cctacaacat ctaccctcac gggatcacag acgtgcgccc  4260
gctctactcc cgccggctgc ccaagggagt gaagcacctg aaggatttc ccatcctgcc  4320
gggagaaatc ttcaagtaca agtggaccgt gactgtggaa gatggcccta ccaagtcgga  4380
ccctcgctgt ctgacccggt actattcctc gtttgtgaac atggagcgcg acctggcctc  4440
ggggctgatt ggtccgctgc tgatctgcta caaggagtcc gtggaccagc gcgggaacca  4500
gatcatgtcc gacaagcgca acgtgatcct gttctctgtc tttgatgaaa acagatcgtg  4560
gtacttgact gagaatatcc agcggttcct gcccaaccca gcgggagtgc aactggagga  4620
cccggagttc caggcctcaa acattatgca ctctatcaac ggctatgtgt tcgactcgct  4680
ccaactgagc gtgtgcctgc atgaagtggc atactggtac attctgtcca tcggagccca  4740
gaccgacttc ctgtccgtgt tcttctccgg atacaccttc aagcataaga tggtgtacga  4800
ggacactctg accctcttcc cattttccgg agaaactgtg ttcatgtcaa tggaaaaccc  4860
gggcttgtgg attctgggtt gccataactc ggacttccgg aatagaggga tgaccgccct  4920
gctgaaagtg tccagctgtg acaagaatac cggcgattac tacgaggaca gctatgagga  4980
catctccgct tatctgctgt ccaagaacaa cgccattgaa cccaggtcct tctcccaaaa  5040
cggtgcaccg acctccgaaa gcgccacccc agagtcagga cctggctcgg aaccggctac  5100
```

```
ctcgggctca gagacaccgg ggacttccga gtccgcaacc cccgagagtg gacccggatc  5160
cgaaccagca acctcaggat cagaaacccc gggaacttcg gaatccgcca ctcccgagtc  5220
gggaccaggc acctccactg agccttccga gggaagcgcc cccggatccc ctgctggatc  5280
ccctaccagc actgaagaag gcacctcaga atccgcgacc cctgagtccg gccctggaag  5340
cgaacccgcc acctccggtt ccgaaacccc tgggactagc gagagcgcca ctccggaatc  5400
gggcccagga agccctgccg gatccccgac cagcaccgag gagggaagcc ccgccgggtc  5460
accgacttcc actgaggagg gagcctcatc cccccccgtg ctgaagcggc atcaaagaga  5520
gatcaccagg accactctcc agtccgatca ggaagaaatt gactacgacg atactatcag  5580
cgtggagatg aagaaggagg acttcgacat ctacgatgag gatgagaacc agtcccctcg  5640
gagctttcag aagaaaaccc gccactactt catcgctgcc gtggagcggc tgtgggatta  5700
cgggatgtcc agctcaccgc atgtgctgcg gaatagagcg cagtcaggat cggtgcccca  5760
gttcaagaag gtcgtgttcc aagagttcac cgacgggtcc ttcactcaac ccctgtaccg  5820
gggcgaactc aacgaacacc tgggactgct tgggccgtat atcagggcag aagtggaaga  5880
taacatcatg gtcaccttcc gcaaccaggc ctcccggccg tacagcttct actcttcact  5940
gatctcctac gaggaagatc agcggcaggg agccgagccc cggaagaact tcgtcaagcc  6000
taacgaaact aagacctact tttggaaggt ccagcatcac atggccccga ccaaagacga  6060
gttcgactgt aaagcctggg cctacttctc cgatgtggac ctggagaagg acgtgcactc  6120
gggactcatt ggcccgctcc ttgtgtgcca tactaatacc ctgaaccctg ctcacggtcg  6180
ccaagtcaca gtgcaggagt tcgccctctt cttcaccatc ttcgatgaaa caaagtcctg  6240
gtactttact gagaacatgg aacgcaattg cagggcaccc tgcaacatcc agatggaaga  6300
tcccaccttc aaggaaaact accggtttca tgccattaac ggctacataa tggacacgtt  6360
gccaggactg gtcatggccc aggaccagag aatccggtgg tatctgctct ccatgggctc  6420
caacgaaaac attcacagca ttcatttttc cggccatgtg ttcaccgtcc ggaagaagga  6480
agagtacaag atggctctgt acaacctcta ccctggagtg ttcgagactg tggaaatgct  6540
gcctagcaag gccggcattt ggagagtgga atgcctgatc ggagagcatt tgcacgccgg  6600
aatgtccacc ctgtttcttg tgtactccaa caagtgccag accccgctgg gaatggcctc  6660
aggtcatatt agggatttcc agatcactgc ttcggggcag tacgggcagt gggcacctaa  6720
gttggcccgg ctgcactact ctggctccat caatgcctgg tccaccaagg aacccttctc  6780
ctggattaag gtggacctcc tggccccaat gattattcac ggtattaaga cccagggtgc  6840
ccgacagaag ttctcctcac tctacatctc gcaattcatc ataatgtaca gcctggatgg  6900
gaagaagtgg cagacctacc ggggaaactc cactggaacg ctcatggtgt ttttcggcaa  6960
cgtggactcc tccggcatta agcacaacat cttcaaccct ccgatcattg ctcggtacat  7020
ccggctgcac ccaactcact acagcatccg gtccaccctg cggatggaac tgatgggttg  7080
tgacctgaac tcctgctcca tgccccttgg gatggaatcc aaggccatta gcgatgcaca  7140
gatcaccgcc tcttcatact tcaccaacat gttcgcgacc tggtccccgt cgaaggcccg  7200
cctgcacctc caaggtcgct ccaatgcgtg gcggcctcaa gtgaacaacc ccaaggagtg  7260
gctccaggtc gacttccaaa agaccatgaa ggtcaccgga gtgaccaccc agggcgtgaa  7320
gtccctgctg acctctatgt acgttaagga gttcctcatc tcctcaagcc aagacggaca  7380
tcagtggacc ctgttcttcc aaaacggaaa agtcaaagta ttccagggca accaggactc  7440
cttcacccct gtggtcaaca gcctggaccc cccattgctg acccgctacc tccgcatcca  7500
cccccaaagc tgggtccacc agatcgcact gcgcatggag gtccttggat gcgaagccca  7560
agatctgtac taagcggccg ctcataatca acctctggat tacaaaattt gtgaaagatt  7620
gactggtatt cttaactatg ttgctccttt tacgctatgt ggatacgctg ctttaatgcc  7680
tttgtatcat gctattgctt cccgtatggc tttcattttc tcctccttgt ataaatcctg  7740
gttgctgtct ctttatgagg agttgtggcc cgttgtcagg caacgtggcg tggtgtgcac  7800
tgtgtttgct gacgcaaccc ccactggttg gggcattgcc accacctgtc agctcctttc  7860
cgggactttc gctttccccc tccctattgc cacggcggaa ctcatcgccg cctgccttgc  7920
ccgctgctgg acaggggctc ggctgttggg cactgacaat tccgtggtgt tgtcggggaa  7980
atcatcgtcc tttccttggc tgctcgcctg tgttgccacc tggattctgc gcgggacgtc  8040
cttctgctac gtcccttcgg ccctcaatcc agcggacctt ccttcccgcg gcctgctgcc  8100
ggctctgcgg cctcttccgc gtcttcgcct tcgccctcag acgagtcgga tctccctttg  8160
ggccgcctcc ccgctgccta ggcgactgtg ccttctagtt gccagccatc tgttgtttgc  8220
ccctcccccg tgccttcctt gaccctggaa ggtgccactc ccactgtcct ttcctaataa  8280
aatgaggaaa ttgcatcgca ttgtctgagt aggtgtcatt ctattctggg gggtggggtg  8340
gggcaggaca gcaaggggga ggattgggaa gacaatagca ggcatgctgg ggaagaccat  8400
gggcgcgcca ggcctgtcga cgcccgggcg gtaccgcgat cgctcgcgac gcataaag    8458

SEQ ID NO: 36           moltype = DNA  length = 1242
FEATURE                 Location/Qualifiers
source                  1..1242
                        mol_type = other DNA
                        organism = Homo sapiens
SEQUENCE: 36
atcgatggcc ccaggttaat ttttaaaaag cagtcaaaag tccaagtggc ccttggcagc  60
atttactctc tctgtttgct ctggttaata atctcaggag cacaaacatt cctggaggca  120
ggagaagaaa tcaacatcct ggacttatcc tctgggcctc tccccacctt cgatggcccc  180
aggttaattt ttaaaaagca gtcaaaagtc caagtggccc ttggcagcat ttactctctc  240
tgtttgctct ggttaataat ctcaggagca caaacattcc tggaggcagg agaagaaatc  300
aacatcctgg acttatcctc tgggcctctc cccaccttcg aactagccac tagcctgagg  360
ctggtcaaaa ttgaacctcc tcctgctctg agcagcctgg ggggcagact aagcagaggg  420
ctgtgcagac ccacataaag agcctactgt gtgccaggca cttcacccga ggcacttcac  480
aagcatgctt gggaatgaaa cttccaactc tttgggatgc aggtgaaaca gttcctggtt  540
cagagaggtg aagcggcctg cctgaggcag cacagctctt ctttacagat gtgcttcccc  600
acctctaccc tgtctcacgg ccccccatgc cagcctgacg gttgtgtctg cctcagtcat  660
gctccatttt tccatcggga ccatcaagag ggtgtttgtg tctaaggctg actgggtaac  720
tttggatgag cggtctctcc gctctgagcc tgtttcctca tctgtcaaat gggctctaac  780
ccactctgat ctcccagggc ggcagtaagt cttcagcatc aggcattttg ggtgactca   840
gtaaatggta gatcttgcta ccagtggaac agccactaag gattctgcag tgagagcaga  900
gggccagcta agtggtactc tcccagagac tgtctgactc acgccacccc ctccaccttg  960
```

-continued

```
gacacaggac gctgtggttt ctgagccagg tacaatgact cctttcggta agtgcagtgg  1020
aagctgtaca ctgcccaggc aaagcgtccg ggcagcgtag gcgggcgact cagatcccag  1080
ccagtggact tagcccctgt ttgctcctcc gataactggg gtgaccttgg ttaatattca  1140
ccagcagcct cccccgttgc ccctctggat ccactgctta aatacggacg aggacagggc  1200
cctgtctcct cagcttcagg caccaccact gacctgggac ag                     1242
```

OPTIMIZED FACTOR VIII GENES

RELATED APPLICATIONS

This application claims priority to U.S. Provisional Patent Application Ser. No. 63/236,225, filed Aug. 23, 2021, the disclosure of which is hereby incorporated by reference in its entirety.

REFERENCE TO SEQUENCE LISTING SUBMITTED ELECTRONICALLY

The content of the electronically submitted sequence listing in XML format (Name: 731947_SA9-484_ST26.xml; Size: 117,411 bytes; Date of Creation: Aug. 22, 2022) is incorporated herein by reference in its entirety.

BACKGROUND OF THE DISCLOSURE

A major impediment in providing a low-cost recombinant FVIII protein to patients is the high cost of commercial production. FVIII protein expresses poorly in heterologous expression systems, two to three orders of magnitude lower than similarly sized proteins. (Lynch et al., *Hum. Gene. Ther.;* 4:259-72 (1993). The poor expression of FVIII is due in part to the presence of cis-acting elements in the FVIII coding sequence that inhibit FVIII expression, such as transcriptional silencer elements (Hoeben et al., *Blood* 85:2447-2454 (1995)), matrix attachment-like sequences (MARs) (Fallux et al., *Mol. Cell. Biol.* 16:4264-4272 (1996)), and transcriptional elongation inhibitory elements (Koeberl et al., *Hum. Gene. Ther.;* 6:469-479 (1995)).

Thus, there exists a need in the art for FVIII sequences that express efficiently in heterologous systems.

SUMMARY OF THE DISCLOSURE

Disclosed are codon optimized nucleic acid molecules encoding a polypeptide with FVIII activity.

In certain aspects, disclosed herein is an isolated nucleic acid molecule comprising a nucleotide sequence at least 85% identical to SEQ ID NO: 9, wherein the nucleotide sequence encodes a polypeptide with factor VIII (FVIII) activity. In some embodiments, the nucleotide sequence is at least 90% identical to SEQ ID NO: 9. In some embodiments, the nucleotide sequence is at least 95%, at least 96%, at least 97%, at least 98%, at least 99%, or 100% identical to SEQ ID NO: 9. In some embodiments, the nucleotide sequence is at least 50% identical to SEQ ID NO: 9.

Also disclosed herein is an isolated nucleic acid molecule comprising the nucleotide sequence of SEQ ID NO: 9, wherein the nucleotide sequence encodes a polypeptide with Factor VIII activity.

Also disclosed herein is an isolated nucleic acid molecule comprising a nucleotide sequence at least 90%, at least 95%, at least 96%, at least 97%, at least 98%, at least 99%, or 100% identical to nucleotides 58-4824 of SEQ ID NO: 9. In some embodiments, the isolated nucleic acid molecule comprises nucleotides 58-4824 of SEQ ID NO: 9.

In certain aspects, disclosed herein is an isolated nucleic acid molecule comprising a nucleotide sequence at least 85% identical to SEQ ID NO: 33, wherein the nucleotide sequence encodes a polypeptide with factor VIII (FVIII) activity. In some embodiments, the nucleotide sequence is at least 90% identical to SEQ ID NO: 33. In some embodiments, the nucleotide sequence is at least 95%, at least 96%, at least 97%, at least 98%, at least 99%, or 100% identical to SEQ ID NO: 33. In some embodiments, the nucleotide sequence is at least 50% identical to SEQ ID NO: 33.

In some embodiments, the isolated nucleic acid molecule disclosed herein further comprises a nucleotide sequence encoding a signal peptide. In some embodiments, the nucleotide sequence encodes a signal peptide comprises the amino acid sequence of SEQ ID NO: 11.

In some embodiments, the isolated nucleic acid molecule disclosed herein is codon-optimized to contain fewer CpG motifs than SEQ ID NO: 32. In some embodiments, the isolated nucleic acid molecule disclosed herein has one or more CpG motifs depleted relative to SEQ ID NO: 32.

In another aspect, disclosed herein is an isolated nucleic acid molecule comprising a genetic cassette expressing a factor VIII (FVIII) polypeptide, wherein the genetic cassette comprises a nucleotide sequence at least 85% identical to SEQ ID NO: 14. In some embodiments, the genetic cassette comprises a nucleotide sequence that is at least 90% identical to SEQ ID NO: 14. In some embodiments, the genetic cassette comprises a nucleotide sequence that is at least 95%, at least 96%, at least 97%, at least 98%, at least 99%, or 100% identical to SEQ ID NO: 14. In some embodiments, the nucleotide sequence is at least 50% identical to SEQ ID NO: 14.

Also disclosed herein is an isolated nucleic acid molecule comprising a genetic cassette expressing a factor VIII (FVIII) polypeptide, wherein the genetic cassette comprises the nucleotide sequence of SEQ ID NO: 14.

In another aspect, disclosed herein is an isolated nucleic acid molecule comprising a genetic cassette expressing a factor VIII (FVIII) polypeptide, wherein the genetic cassette comprises a nucleotide sequence at least 85% identical to SEQ ID NO: 35. In some embodiments, the genetic cassette comprises a nucleotide sequence that is at least 90% identical to SEQ ID NO: 35. In some embodiments, the genetic cassette comprises a nucleotide sequence that is at least 95%, at least 96%, at least 97%, at least 98%, at least 99%, or 100% identical to SEQ ID NO: 35. In some embodiments, the nucleotide sequence is at least 50% identical to SEQ ID NO: 35.

Also disclosed herein is an isolated nucleic acid molecule comprising a genetic cassette expressing a factor VIII (FVIII) polypeptide, wherein the genetic cassette comprises the nucleotide sequence of SEQ ID NO: 35.

In another aspect, disclosed herein is an isolated nucleic acid molecule comprising a genetic cassette expressing a factor VIII (FVIII) polypeptide comprising: a nucleotide sequence encoding a FVIII protein comprising a nucleic acid sequence at least 85% identical to SEQ ID NO: 9 or SEQ ID NO: 33; a promoter controlling transcription of the nucleotide sequence, and a transcription termination sequence.

In some embodiments, the promoter is a liver-specific promoter. In some embodiments, the promoter is a mouse transthyretin (mTTR) promoter. In some embodiments, the promoter is a mTTR482 promoter. In some embodiments, the promoter comprises the nucleotide sequence of SEQ ID NO: 16.

In some embodiments, the transcription termination sequence is a polyadenylation (polyA) sequence. In some embodiments, the transcription termination sequence is a Bovine Growth Hormone Polyadenylation (bGHpA) signal sequence. In some embodiments, the transcription termination sequence comprises the nucleotide sequence of SEQ ID NO: 19.

In some embodiments, the isolated nucleic acid molecule further comprises an enhancer element. In some embodiments, the enhancer element is an A1MB2 enhancer element. In some embodiments, the A1MB2 enhancer element comprises the nucleotide sequence of SEQ ID NO: 15.

In some embodiments, the isolated nucleic acid molecule further comprises an intronic sequence. In some embodiments, the intronic sequence is a chimeric intron, a hybrid intron, or a synthetic intron. In some embodiments, the intronic sequence comprises the nucleotide sequence of SEQ ID NO: 17.

In some embodiments, the isolated nucleic acid molecule further comprises a post-transcriptional regulatory element. In some embodiments, the post-transcriptional regulatory element comprises a Woodchuck Posttranscriptional Regulatory Element (WPRE). In some embodiments, the WPRE comprises the nucleotide sequence of SEQ ID NO: 18.

In another aspect, disclosed herein is an isolated nucleic acid molecule comprising a genetic cassette expressing a factor VIII (FVIII) polypeptide, a first inverted terminal repeat (ITR), and a second ITR flanking the genetic cassette. In some embodiments, the first ITR and/or the second ITR are derived from a member of the viral family Parvoviridae. In some embodiments, the first ITR and/or the second ITR are derived from human Bocavirus (HBoV1), human erythrovirus (B19), Goose Parvovirus (GPV), or a variant thereof. In some embodiments, the first ITR and/or the second ITR comprises a polynucleotide sequence at least about 75% identical to SEQ ID NOs: 1, 2, or 21-30. In some embodiments, the first ITR comprises a polynucleotide sequence at least about 75% identical to SEQ ID NO: 1, and the second ITR comprises a polynucleotide sequence at least about 75% identical to SEQ ID NO: 2. In some embodiments, the first ITR comprises a polynucleotide sequence at least about 50% identical to SEQ ID NO: 1, and the second ITR comprises a polynucleotide sequence at least about 50% identical to SEQ ID NO: 2. In some embodiments, the first ITR comprises the polynucleotide sequence of SEQ ID NO: 1, and the second ITR comprises the polynucleotide sequence of SEQ ID NO: 2.

In another aspect, disclosed herein is an isolated nucleic acid molecule comprising a genetic cassette expressing a factor VIII (FVIII) polypeptide, wherein the genetic cassette comprises, from 5' to 3': an A1MB2 enhancer element comprising the nucleotide sequence of SEQ ID NO: 15, a liver-specific modified mouse transthyretin (mTTR) promoter (mTTR) comprising the nucleotide sequence of SEQ ID NO: 16, a chimeric intron comprising the nucleotide sequence of SEQ ID NO: 17, a nucleotide sequence encoding a FVIII protein comprising a nucleic acid sequence at least 85% identical to SEQ ID NO: 9 or SEQ ID NO: 33; a Woodchuck Posttranscriptional Regulatory Element (WPRE) comprising the nucleotide sequence of SEQ ID NO: 18; and a Bovine Growth Hormone Polyadenylation (bGHpA) signal comprising the nucleotide sequence of SEQ ID NO: 19.

In another aspect, disclosed herein is a vector comprising a nucleic acid molecule disclosed herein.

In another aspect, disclosed herein is a host cell comprising a nucleic acid molecule disclosed herein. Also disclosed herein are polypeptides produced by the host cell. In some embodiments, the host cell is an insect cell.

In another aspect, disclosed herein is a baculovirus system for production of a nucleic acid molecule disclosed herein. In some aspects, the nucleic acid molecule is produced in insect cells.

In another aspect, disclosed herein is a pharmaceutical composition comprising a nucleic acid molecule disclosed herein. In some embodiments, the pharmaceutical composition comprises a vector comprising a nucleic acid molecule disclosed herein. In some embodiments, the pharmaceutical composition further comprises a pharmaceutically acceptable excipient.

In another aspect, disclosed herein is a kit comprising a nucleic acid molecule disclosed herein and instructions for administering the nucleic acid molecule to a subject in need thereof.

In another aspect, disclosed herein is a method of producing a polypeptide with FVIII activity, comprising: culturing the host cell disclosed herein under conditions whereby a polypeptide with FVIII activity is produced, and recovering the polypeptide with FVIII activity.

In another aspect, disclosed herein is a method of increasing expression of a polypeptide with FVIII activity in a subject comprising administering a nucleic acid molecule comprising a nucleotide sequence at least 85% identical to SEQ ID NO: 9, SEQ ID NO: 33, SEQ ID NO: 35, or SEQ ID NO: 14. In some embodiments, the nucleic acid molecule comprises the nucleotide sequence of SEQ ID NO: 9. In some embodiments, the nucleic acid molecule comprises the nucleotide sequence of SEQ ID NO: 33. In some embodiments, the nucleic acid molecule comprises the nucleotide sequence of SEQ ID NO: 14. In some embodiments, the nucleic acid molecule comprises the nucleotide sequence of SEQ ID NO: 35.

In another aspect, disclosed herein is a method of treating a bleeding disorder in a subject comprising administering a nucleic acid molecule comprising a nucleotide sequence at least 85% identical to SEQ ID NO: 9, SEQ ID NO: 33, SEQ ID NO: 35, or SEQ ID NO: 14. In some embodiments, the nucleic acid molecule comprises the nucleotide sequence of SEQ ID NO: 9. In some embodiments, the nucleic acid molecule comprises the nucleotide sequence of SEQ ID NO: 33. In some embodiments, the nucleic acid molecule comprises the nucleotide sequence of SEQ ID NO: 14. In some embodiments, the nucleic acid molecule comprises the nucleotide sequence of SEQ ID NO: 35.

In another aspect, disclosed herein is a method of treating a bleeding disorder in a subject comprising administering a pharmaceutical composition comprising a nucleotide sequence at least 85% identical to SEQ ID NO: 9, SEQ ID NO: 33, SEQ ID NO: 35, or SEQ ID NO: 14. In some embodiments, the nucleic acid molecule comprises the nucleotide sequence of SEQ ID NO: 9. In some embodiments, the nucleic acid molecule comprises the nucleotide sequence of SEQ ID NO: 33. In some embodiments, the nucleic acid molecule comprises the nucleotide sequence of SEQ ID NO: 14. In some embodiments, the nucleic acid molecule comprises the nucleotide sequence of SEQ ID NO: 35.

In another aspect, disclosed herein is a method of treating hemophilia A in a subject comprising administering a pharmaceutical composition comprising a nucleotide sequence at least 85% identical to SEQ ID NO: 9, SEQ ID NO: 33, SEQ ID NO: 35, or SEQ ID NO: 14. In some embodiments, the nucleic acid molecule comprises the nucleotide sequence of SEQ ID NO: 9. In some embodiments, the nucleic acid molecule comprises the nucleotide sequence of SEQ ID NO: 33. In some embodiments, the nucleic acid molecule comprises the nucleotide sequence of SEQ ID NO: 14. In some embodiments, the nucleic acid molecule comprises the nucleotide sequence of SEQ ID NO: 35.

BRIEF DESCRIPTION OF THE DRAWINGS

FIG. 5A shows an image of agarose gel electrophoresis of the purified ceFVIIIXTEN (ceDNA) with AAV2 or HBoV1 ITRs obtained from the continuous-elution electrophoresis, as described in U.S. Patent Application No. 63/069,073. The purity is shown in comparison with the starting material (SM) with arrows indicating DNA bands corresponding to the size of FVIIIXTEN ceDNA vector (ceDNA), baculoviral DNA (vDNA) and Sf9 cell genomic DNA (gDNA). FIG. 5B shows a graphical representation of plasma FVIII activity levels measured by the Chromogenix Coatest® SP Factor VIII chromogenic assays. The plasma samples were collected at different intervals from hFVIIIR593C$^{+/+}$/HemA mice systemically injected via hydrodynamic tail-vein injection with 80, 40, or 12 μg/kg of ceFVIIIXTEN (ceDNA) flanked by the AAV2 or HBoV1 ITRs as indicated. Error bars represents standard deviation. The ITR sequences and their variants were described in previous U.S. Patent Application No. 63/069,073.

FIG. 6A shows a schematic diagram of FVIIIXTEN expression cassettes with either the liver-specific mTTR (SEQ ID NO: 3) or the A1AT promoter flanked by HBoV1 WT ITRs. FIG. 6B is an agarose gel electrophoresis image of single-stranded DNA (ssDNA) FVIIIXTEN HBoV1 generated by restriction enzyme digestion as described. FIG. 6C shows the FVIII expression levels normalized to percent of normal in mice injected with the mTTR or A1AT promoter constructs depicted in FIG. 6A. Error bars represent standard deviation.

FIG. 7A depicts an agarose gel electrophoresis image showing of full-length (8.3 kb) and truncated (6.0 kb) species of purified ceFVIIIXTEN (ceDNA) with AAV2 WT ITRs obtained from continuous-elution electrophoresis. FIG. 7B shows next-generation sequence (NGS) analyses of full-length 8.3 kb ceFVIIIXTEN (top panel) and of truncated 6.0 kb ceFVIIIXTEN (bottom panel) with AAV2 WT ITRs. FIG. 7C shows the FVIII expression levels normalized to percent of normal in mice injected with either the full-length or truncated ceFVIIIXTEN AAV2 constructs at either 80 or 40 μg/kg. Error bars represent standard deviation.

FIG. 8A shows an image of an agarose gel electrophoresis of the purified ceFVIIIXTEN (ceDNA) with AAV2 or HBoV1 ITRs obtained from the continuous-elution electrophoresis, as described in U.S. Patent Application No. 63/069,073. The purity is shown in comparison with the starting material (SM) with arrows indicating DNA bands corresponding to the size of FVIIIXTEN ceDNA vector (ceDNA), baculoviral DNA (vDNA) and Sf9 cell genomic DNA (gDNA). FIG. 8B shows the FVIII expression levels normalized to percent of normal in mice injected with either 80 or 40 μg/kg of ceFVIIIXTEN (ceDNA) flanked by the AAV2 or HBoV1 ITRs as indicated. Error bars represent standard deviation.

DETAILED DESCRIPTION

Figure 1:
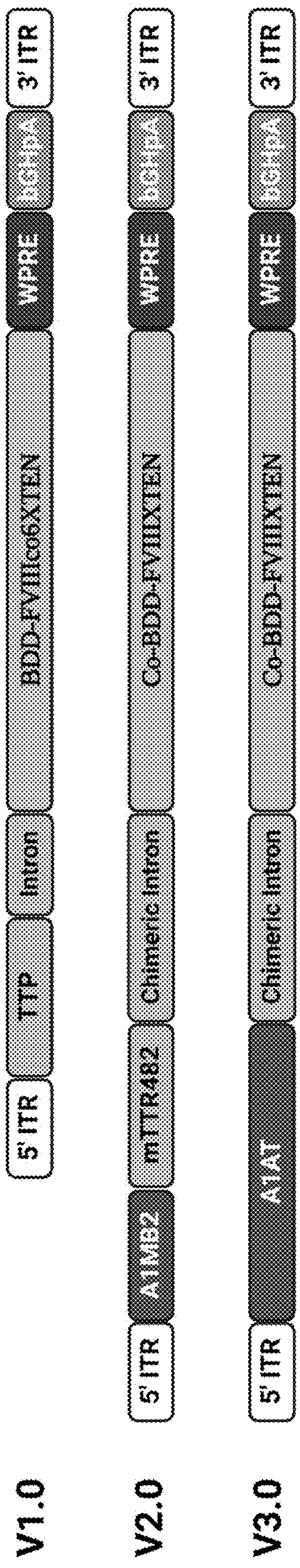
FIG. 1 shows schematic linear maps of human FVIIIXTEN expression constructs according to embodiments of the invention. The V1.0 cassette comprises codon optimized cDNA clone #6 encoding B-domain deleted human Factor VIII (BDD-FVIIIco6) fused with XTEN 144 peptide (FVIIIco6XTEN) under the regulation of Tristetraprolin (TTP) promoter, intron, the Woodchuck Posttranscriptional Regulatory Element (WPRE), and the Bovine Growth Hormone Polyadenylation (bGHpA) signal (see U.S. Publication No. 20190185543). The V2.0 cassette (SEQ ID NO: 14) comprises a codon optimized cDNA with further removal of CpG motifs encoding a B-domain deleted (BDD) codon-optimized human Factor VIII (BDDcoFVIII) fused with XTEN 144 peptide (FVIIIXTEN) under the regulation of liver-specific modified mouse transthyretin (mTTR) promoter (mTTR482) with enhancer element (A1MB2), hybrid synthetic intron (Chimeric Intron), the Woodchuck Posttranscriptional Regulatory Element (WPRE), and the Bovine Growth Hormone Polyadenylation (bGHpA) signal. The V3.0 cassette (SEQ ID NO: 35) comprises a codon optimized cDNA with further removal of CpG motifs encoding a B-domain deleted (BDD) codon-optimized human Factor VIII (Co-BDD-FVIII) fused with XTEN 144 peptide (FVIIIXTEN) under the regulation of liver-specific alpha-1-antitrypsin (A1 AT) promoter, hybrid synthetic intron (Chimeric Intron), the Woodchuck Posttranscriptional Regulatory Element (WPRE), and the Bovine Growth Hormone Polyadenylation (bGHpA) signal. FVIIIXTEN expression cassettes are flanked by parvoviral ITRs.

The present disclosure describes codon-optimized genes encoding polypeptides with Factor VIII (FVIII) activity. The present disclosure is directed to codon optimized nucleic acid molecules encoding polypeptides with Factor VIII activity, vectors, and host cells comprising optimized nucleic acid molecules, polypeptides encoded by optimized nucleic acid molecules, and methods of producing such polypeptides. The present disclosure is also directed to methods of treating bleeding disorders such as hemophilia comprising administering to the subject an optimized Factor VIII nucleic acid sequence, a vector comprising the optimized nucleic acid sequence, or the polypeptide encoded thereby.

The present disclosure meets an important need in the art by providing optimized FVIII sequences that demonstrate increased expression in host cells, improved yield of FVIII protein in methods to produce recombinant FVIII, and potentially result in greater therapeutic efficacy when used in gene therapy methods. In certain embodiments, the disclosure describes an isolated nucleic acid molecule comprising a nucleotide sequence which has sequence homology to the nucleotide sequence of SEQ ID NO: 9. In certain embodiments, the disclosure describes an isolated nucleic acid molecule comprising a nucleotide sequence which has sequence homology to the nucleotide sequence of SEQ ID NO: 33. In certain embodiments, the disclosure describes an isolated nucleic acid molecule comprising a nucleotide sequence which has sequence homology to the nucleotide sequence of SEQ ID NO: 14. In certain embodiments, the disclosure describes an isolated nucleic acid molecule comprising a nucleotide sequence which has sequence homology to the nucleotide sequence of SEQ ID NO: 35. In some embodiments, the genetic cassette further comprises a nucleotide sequence encoding an XTEN polypeptide.

In order to provide a clear understanding of the specification and claims, the following definitions are provided below.

Definitions

It is to be noted that the term "a" or "an" entity refers to one or more of that entity: for example, "a nucleotide sequence" is understood to represent one or more nucleotide sequences. As such, the terms "a" (or "an"), "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "isolated" for the purposes of the present disclosure designates a biological material (cell, polypeptide, polynucleotide, or a fragment, variant, or derivative thereof) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated." No particular level of purification is required. Recombinantly produced polypeptides and proteins expressed in host cells are considered isolated for the purpose of the disclosure, as are native or recombinant polypeptides which have been separated, fractionated, or partially or substantially purified by any suitable technique.

"Nucleic acids," "nucleic acid molecules," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then, that a single vector can contain just a single coding region or comprise two or more coding regions.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "genetic cassette" means a DNA sequence capable of directing expression of a particular polynucleotide sequence in an appropriate host cell, comprising a promoter operably linked to a polynucleotide sequence of interest. A genetic cassette may encompass nucleotide sequences located upstream (5' non-coding sequences), within, or downstream (3' non-coding sequences) of a coding region, and which influence the transcription, RNA processing, stability, or translation of the associated coding region. If a coding region is intended for expression in a eukaryotic cell, a polyadenylation signal and transcription termination sequence will usually be located 3' to the coding sequence. In some embodiments, the genetic cassette comprises a polynucleotide which encodes a gene product. In some embodiments, the genetic cassette comprises a polynucleotide which encodes a miRNA. In some embodiments, the genetic cassette comprises a heterologous polynucleotide sequence. A polynucleotide which encodes a product, e.g., a miRNA or a gene product (e.g., a polypeptide such as a therapeutic protein), can include a promoter and/or other expression (e.g., transcription or translation) control sequences operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other expression control sequences, besides a promoter, for example enhancers, operators, repressors, and transcription termination signals, can also be operably associated with a coding region to direct gene product expression.

"Expression control sequences" refer to regulatory nucleotide sequences, such as promoters, enhancers, terminators, and the like, that provide for the expression of a coding sequence in a host cell. Expression control sequences generally encompass any regulatory nucleotide sequence which facilitates the efficient transcription and translation of the coding nucleic acid to which it is operably linked. Non-limiting examples of expression control sequences include include promoters, enhancers, translation leader sequences, introns, polyadenylation recognition sequences, RNA processing sites, effector binding sites, or stem-loop structures. A variety of expression control sequences are known to those skilled in the art. These include, without limitation, expression control sequences which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other expression control sequences include those derived from vertebrate genes such as actin, heat shock protein, bovine growth hormone and rabbit β-globin, as well as other sequences capable of controlling gene expression in eukaryotic cells. Additional suitable expression control sequences include tissue-specific promoters and enhancers as well as lymphokine-inducible promoters (e.g., promoters inducible by interferons or interleukins). Other expression control sequences include intronic sequences, post-transcriptional regulatory elements, and polyadenylation signals. Additional exemplary expression control sequences are discussed elsewhere in the present disclosure.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. The term "yield," as used herein, refers to the amount of a polypeptide produced by the expression of a gene.

A "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers can also be considered to be reporters.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity. Additional exemplary promoters are discussed elsewhere in the present disclosure.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment can be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the disclosure and include norleucine, omithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g., M, F, W, S, Y, N, Q, C). These amino acids can participate in hydrophobic interactions and electrostatic interactions. As used herein, the term "charged amino acid" includes amino acids that can have non-zero net charge on their side chains (e.g., R, K, H, E, D). These amino acids can participate in hydrophobic interactions and electrostatic interactions.

Also included in the present disclosure are fragments or variants of polypeptides, and any combination thereof. The term "fragment" or "variant" when referring to polypeptide binding domains or binding molecules of the present disclosure include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences. "Identity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity are codified in publicly available computer programs. Sequence alignments and percent identity calculations can be performed using sequence analysis software such as the Megalign program of the LASERGENE bioinformatics computing suite (DNASTAR Inc., Madison, WI), the GCG suite of programs (Wisconsin Package Version 9.0, Genetics Computer Group (GCG), Madison, WI), BLASTP, BLASTN, BLASTX (Altschul et al., *J. Mol. Biol.* 215:403 (1990)), and DNASTAR (DNASTAR, Inc. 1228 S. Park St. Madison, WI 53715 USA). Within the context of this application, it will be understood that where sequence analysis software is used for analysis, that the results of the analysis will be based on the "default values" of the program referenced, unless otherwise specified. As used herein "default values" will mean any set of values or parameters which originally load with the software when first initialized. For the purposes of determining percent identity between an optimized BDD FVIII sequence of the disclosure and a reference sequence, only nucleotides in the reference sequence corresponding to nucleotides in the optimized BDD FVIII sequence of the disclosure are used to calculate percent identity. For example, when comparing a full length FVIII nucleotide sequence containing the B domain to an optimized B domain deleted (BDD) FVIII nucleotide sequence of the disclosure, the portion of the alignment including the A1, A2, A3, C1, and C2 domain will be used to calculate percent identity. The nucleotides in the portion of the full length FVIII sequence encoding the B domain (which will result in a large "gap" in the alignment) will not be counted as a mismatch. In addition, in determining percent identity between an optimized BDD FVIII sequence of the disclosure, or a designated portion thereof (e.g., nucleotides 2183-4474 and 4924-7006 of SEQ ID NO:14), and a reference sequence, percent identity will be calculated by aligning dividing the number of matched nucleotides by the total number of nucleotides in the complete sequence of the optimized BDD-FVIII sequence, or a designated portion thereof, as recited herein.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number corresponding to the number of the amino acid in mature native FVIII (SEQ ID NO: 20) to which the insertion site corresponds, which is immediately N-terminal to the position of the insertion. For example, the phrase "a3 comprises a heterologous moiety at an insertion site which corresponds to amino acid 1656 of SEQ ID NO: 24" indicates that the heterologous moiety is located between two amino acids corresponding to amino acid 1656 and amino acid 1657 of SEQ ID NO: 20.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid.

The terms "inserted," "is inserted," "inserted into" or grammatically related terms, as used herein refers to the position of a heterologous moiety in a recombinant FVIII polypeptide, relative to the analogous position in native mature human FVIII (SEQ ID NO: 20).

As used herein, the term "half-life" refers to a biological half-life of a particular polypeptide in vivo. Half-life can be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the β-phase.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

"Hemostasis," as used herein, means the stopping or slowing of bleeding or hemorrhage; or the stopping or slowing of blood flow through a blood vessel or body part.

"Hemostatic disorder," as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The isolated nucleic acid molecules, isolated polypeptides, or vectors comprising the isolated nucleic acid molecule of the disclosure can be used prophylactically. As used herein the term "prophylactic treatment" refers to the administration of a molecule prior to a bleeding episode. In one embodiment, the subject in need of a general hemostatic agent is undergoing, or is about to undergo, surgery. A polynucleotide, polypeptide, or vector of the disclosure can be administered prior to or after surgery as a prophylactic. The polynucleotide, polypeptide, or vector of the disclosure can be administered during or after surgery to control an acute bleeding episode. The surgery can include, but is not limited to, liver transplantation, liver resection, dental procedures, or stem cell transplantation.

The isolated nucleic acid molecules, isolated polypeptides, or vectors of the disclosure are also used for on-demand treatment. The term "on-demand treatment" refers to the administration of an isolated nucleic acid molecule, isolated polypeptide, or vector in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject can have trauma, uremia, a hereditary bleeding disorder (e.g., factor VII deficiency) a platelet disorder, or resistance owing to the development of antibodies to clotting factors.

"Treat," "treatment," "treating," as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term “treating” or “treatment” means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering an isolated nucleic acid molecule, isolated polypeptide or vector of the disclosure. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

“Administering,” as used herein, means to give a pharmaceutically acceptable Factor VIII-encoding nucleic acid molecule, Factor VIII polypeptide, or vector comprising a Factor VIII-encoding nucleic acid molecule of the disclosure to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. The nucleic acid molecules, polypeptides, and vectors can be administered as part of a pharmaceutical composition comprising at least one excipient.

As used herein, the phrase “subject in need thereof” includes subjects, such as mammalian subjects, that would benefit from administration of a nucleic acid molecule, a polypeptide, or vector of the disclosure, e.g., to improve hemostasis. In one embodiment, the subjects include, but are not limited to, individuals with hemophilia. In another embodiment, the subjects include, but are not limited to, the individuals who have developed a FVIII inhibitor and thus are in need of a bypass therapy. The subject can be an adult or a minor (e.g., under 12 years old).

As used herein, the term “clotting factor,” refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. An “activatable clotting factor” is a clotting factor in an inactive form (e.g., in its zymogen form) that is capable of being converted to an active form.

“Clotting activity,” as used herein, means the ability to participate in a cascade of biochemical reactions that culminates in the formation of a fibrin clot and/or reduces the severity, duration or frequency of hemorrhage or bleeding episode.

As used herein the terms “heterologous” or “exogenous” refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found.

As used herein, the term “heterologous nucleotide sequence” refers to a nucleotide sequence that does not naturally occur with a given polynucleotide sequence. In one embodiment, the heterologous nucleotide sequence encodes a polypeptide capable of extending the half-life of FVIII. In another embodiment, the heterologous nucleotide sequence encodes a polypeptide that increases the hydrodynamic radius of FVIII. In other embodiments, the heterologous nucleotide sequence encodes a polypeptide that improves one or more pharmacokinetic properties of FVIII without significantly affecting its biological activity or function (e.g., its procoagulant activity). In some embodiments, FVIII is linked or connected to the polypeptide encoded by the heterologous nucleotide sequence by a linker.

A “reference nucleotide sequence,” when used herein as a comparison to a nucleotide sequence of the disclosure, is a polynucleotide sequence essentially identical to the nucleotide sequence of the disclosure except that the portions corresponding to FVIII sequence are not optimized. In some embodiments, the reference nucleotide sequence for a nucleic acid molecule disclosed herein is SEQ ID NO: 32.

As used herein, the term “optimized,” with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, removal of CpG motifs, and two or more combinations thereof.

Polynucleotide Sequences

Certain aspects of the present disclosure aim to overcome deficiencies of AAV vectors for gene therapy. In particular, some aspects of the present disclosure are directed to a nucleic acid molecule comprising a genetic cassette, e.g., encoding a therapeutic protein and/or a miRNA. In some embodiments, the genetic cassette encodes a therapeutic protein. In some embodiments, the therapeutic protein comprises a clotting factor. In some embodiments, the genetic cassette encodes a miRNA. In some embodiments, the nucleic acid molecule further comprises at least one non-coding region. In certain embodiments, the at least one non-coding region comprises a promoter sequence, an intron, a regulatory element, a 3'UTR poly(A) sequence, or any combination thereof. In some embodiments, the regulatory element is a post-transcriptional regulatory element.

In one embodiment, the genetic cassette is a single stranded nucleic acid. In another embodiment, the genetic cassette is a double stranded nucleic acid. In another embodiment, the genetic cassette is a closed-end double stranded nucleic acid (ceDNA).

In some embodiments, the genetic cassette comprises a nucleotide sequence encoding a FVIII polypeptide, wherein the nucleotide sequence is codon optimized. In some embodiments, the genetic cassette comprises a nucleotide sequence encoding a codon optimized FVIII driven by a mTTR promoter and synthetic intron. In some embodiments, the genetic cassette comprises a nucleotide sequence which is disclosed in International Application No. PCT/US2017/015879, which is incorporated by reference in its entirety. In some embodiments, the genetic cassette is a "hFVIIIco6XTEN" genetic cassette as described in PCT/US2017/015879. In some embodiments, the genetic cassette comprises SEQ ID NO: 32.

In some embodiments, the genetic cassette comprises codon optimized cDNA encoding B-domain deleted (BDD) codon-optimized human Factor VIII (BDDcoFVIII) fused with XTEN 144 peptide. In some embodiments, the genetic cassette comprises the nucleotide sequence set forth as SEQ ID NO: 9. In some embodiments, the genetic cassette comprises the nucleotide sequence set forth as SEQ ID NO: 14. In some embodiments, the genetic cassette has the nucleotide sequence of SEQ ID NO: 14. In some embodiments, the genetic cassette comprises the nucleotide sequence set forth as SEQ ID NO: 33. In some embodiments, the genetic cassette comprises the nucleotide sequence set forth as SEQ ID NO: 35. In some embodiments, the genetic cassette further comprises a nucleotide sequence encoding an XTEN polypeptide.

In some embodiments, the genetic cassette comprises a nucleotide sequence encoding a codon optimized FVIII driven by a mTTR promoter and synthetic intron. In some embodiments, the genetic cassette further comprises a a Woodchuck Posttranscriptional Regulatory Element (WPRE). In some embodiments, the genetic cassette further comprises the Bovine Growth Hormone Polyadenylation (bGHpA) signal.

In some embodiments, the present disclosure is directed to codon optimized nucleic acid molecules encoding a polypeptide with FVIII activity. In some embodiments, the polynucleotide encodes a full-length FVIII polypeptide. In other embodiments, the nucleic acid molecule encodes a B domain-deleted (BDD) FVIII polypeptide, wherein all or a portion of the B domain of FVIII is deleted. In one particular embodiment, the nucleic acid molecule encodes a polypeptide comprising an amino acid sequence having at least about 80%, at least about 85%, at least about 86%, at least about 87%, at least about 88%, at least about 89%, at least about 90%, at least about 95%, at least about 96%, at least about 97%, at least about 98%, or at least about 99% sequence identity to SEQ ID NO: 10 or a fragment thereof.

In some embodiments, the nucleic acid molecule of the disclosure encodes a FVIII polypeptide comprising a signal peptide or a fragment thereof. In other embodiments, the nucleic acid molecule encodes a FVIII polypeptide which lacks a signal peptide. In some embodiments, the signal peptide comprises the amino acid sequence of SEQ ID NO: 11.

"A polypeptide with FVIII activity" as used herein means a functional FVIII polypeptide in its normal role in coagulation, unless otherwise specified. The term a polypeptide with FVIII activity includes a functional fragment, variant, analog, or derivative thereof that retains the function of full-length wild-type Factor VIII in the coagulation pathway. "A polypeptide with FVIII activity" is used interchangeably with FVIII protein, FVIII polypeptide, or FVIII. Examples of FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. In one embodiment, a polypeptide having FVIII activity comprises two polypeptide chains, the first chain having the FVIII heavy chain and the second chain having the FVIII light chain. In another embodiment, the polypeptide having FVIII activity is single chain FVIII. Single chain FVIII can contain one or more mutation or substitutions at amino acid residue 1645 and/or 1648 corresponding to mature human FVIII sequence (SEQ ID NO: 20). See International Application No. PCT/US2012/045784, incorporated herein by reference in its entirety. The FVIII protein can be the human, porcine, canine, rat, or murine FVIII protein. In addition, comparisons between FVIII from humans and other species have identified conserved residues that are likely to be required for function. See, e.g., Cameron et al. (1998) Thromb. Haemost. 79:317-22; and U.S. Pat. No. 6,251,632.

A number of tests are available to assess the FVIII activity of a polypeptide: activated partial thromboplastin time (aPTT) test, chromogenic assay, ROTEM® assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM® analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The "B domain" of FVIII, as used herein, is the same as the B domain known in the art that is defined by internal amino acid sequence identity and sites of proteolytic cleavage by thrombin, e.g., residues Ser741-Arg1648 of full length human FVIII (SEQ ID NO: 20). The other human FVIII domains are defined by the following amino acid residues: A1, residues Ala1-Arg372; A2, residues Ser373-Arg740; A3, residues Ser1690-11e2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. An example of a BDD FVIII is REFACTO® recombinant BDD FVIII (Wyeth Pharmaceuticals, Inc.).

A "B domain deleted FVIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. Other examples of B domain deleted FVIII are disclosed in Hoeben R. C., et al. (1990) *J. Biol. Chem.* 265 (13): 7318-7323; Meulien et al. (1988), *Protein Eng.* 2(4): 301-6; Toole et al. (1986) Proc. Natl. Acad. Sci. U.S.A. 83, 5939-5942; Eaton, et al. (1986) Biochemistry 25:8343-8347; (Sarver, et al. (1987) DNA 6:553-564; European Patent No. 295597; and International Publication Nos. WO 91/09122, WO 88/00831, and WO 87/04187, each of which is incorporated herein by reference in its entirety. Each of the foregoing deletions can be made in any FVIII sequence.

Codon Optimization

In one embodiment, the present disclosure provides an isolated nucleic acid molecule comprising a nucleotide sequence that encodes a polypeptide with FVIII activity, wherein the nucleic acid sequence has been codon optimized. In another embodiment, the starting nucleic acid sequence that encodes a polypeptide with FVIII activity and that is subject to codon optimization is SEQ ID NO: 32. In some embodiments, the sequence that encodes a polypeptide with FVIII activity is codon optimized for human expression. In other embodiments, the sequence that encodes a polypeptide with FVIII activity is codon optimized for murine expression.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

In other embodiments, the nucleic acid molecules disclosed herein are further optimized by removal of one or more CpG motifs and/or the methylation of at least one CpG motif. As used herein, "CpG motif" refers to a dinucleotide sequence containing an unmethylated cytosine linked by a phosphate bond to a guanosine. The term "CpG motif" encompasses both methylated and unmethylated CpG dinucleotides. Unmethylated CpG motifs are common in nucleic acid of bacterial and viral origin (e.g., plasmid DNA) but are suppressed and largely methylated in vertebrate DNA. Thus unmethylated CpG motifs stimulate the mammalian host to mount a rapid inflammatory response. Klinman, et al. (1996). PNAS 93:2879-2883. Exemplary methods of CpG removal are described in Yew, N. S., et al. (2002). Mol Ther. 5(6):731-738 and International Application No. PCT/US2001/010309. In some embodiments, the nucleic acid molecules disclosed herein have been modified to contain fewer CpG motifs (i.e. "CpG reduced" or "CpG depleted"). In one embodiment, the CpG motifs located within a codon triplet for a selected amino acid is changed to a codon triplet for the same amino acid lacking a CpG motif. In some embodiments, the nucleic acid molecules disclosed herein have been optimized to reduce innate immune response.

In some embodiments, disclosed herein is a nucleic acid molecule comprising a nucleotide sequence having at least 50%, 55%, 60%, 65%, 70%, 75%, 80%, 85%, 90%, 95%, or 100% sequence identity to SEQ ID NO: 9.

In some embodiments, disclosed herein is a nucleic acid molecule comprising a nucleotide sequence having at least 50%, 55%, 60%, 65%, 70%, 75%, 80%, 85%, 90%, 95%, or 100% sequence identity to SEQ ID NO: 33.

In some embodiments, disclosed herein is a nucleic acid molecule comprising a nucleotide sequence having at least 50%, 55%, 60%, 65%, 70%, 75%, 80%, 85%, 90%, 95%, or 100% sequence identity to SEQ ID NO: 14.

In some embodiments, disclosed herein is a nucleic acid molecule comprising a nucleotide sequence having at least 50%, 55%, 60%, 65%, 70%, 75%, 80%, 85%, 90%, 95%, or 100% sequence identity to SEQ ID NO: 35.

Heterologous Nucleotide Sequences

In some embodiments, the isolated nucleic acid molecules of the disclosure further comprise a heterologous nucleotide sequence. In some embodiments, the isolated nucleic acid molecules of the disclosure further comprise at least one heterologous nucleotide sequence. The heterologous nucleotide sequence can be linked with the optimized BDD-FVIII nucleotide sequences of the disclosure at the 5' end, at the 3' end, or inserted into the middle of the optimized BDD-FVIII nucleotide sequence. Thus, in some embodiments, the heterologous amino acid sequence encoded by the heterologous nucleotide sequence is linked to the N-terminus or the C-terminus of the FVIII amino acid sequence encoded by the nucleotide sequence or inserted between two amino acids in the FVIII amino acid sequence. In some embodiments, the heterologous amino acid sequence can be inserted between two amino acids at one or more insertion site. In some embodiments, the heterologous amino acid sequence can be inserted within the FVIII polypeptide encoded by the nucleic acid molecule of the disclosure at any site disclosed in International Publication No. WO 2013/123457 A1, WO 2015/106052 A1 or U.S. Publication No. 2015/0158929 A1, each of which are incorporated by reference in their entirety.

In some embodiments, the heterologous amino acid sequence encoded by the heterologous nucleotide sequence is inserted within the B domain or a fragment thereof. In some embodiments, the heterologous amino acid sequence is inserted within the FVIII immediately downstream of an amino acid corresponding to amino acid 745 of wild type mature human FVIII (SEQ ID NO: 20). In one particular embodiment, the FVIII comprises a deletion of amino acids 746-1637, corresponding to wild type mature human FVIII (SEQ ID NO: 20), and the heterologous amino acid sequence encoded by the heterologous nucleotide sequence is inserted immediately downstream of amino acid 745, corresponding to wild type mature human FVIII (SEQ ID NO: 20). The insertion sites of FVIII referenced herein indicate the amino acid position corresponding to the amino acid position of wild type mature human FVIII (SEQ ID NO: 20).

In some embodiments, the heterologous moiety is a peptide or a polypeptide with either unstructured or structured characteristics that are associated with the prolongation of in vivo half-life when incorporated in a protein of the disclosure. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In one particular embodiment, the heterologous amino acid sequence is an immunoglobulin constant region or a portion thereof, transferrin, albumin, or a PAS sequence. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In certain embodiments, a heterologous moiety improves one or more pharmacokinetic properties of the FVIII protein without significantly affecting its biological activity or function. In some embodiments, a heterologous moiety increases the in vivo and/or in vitro half-life of the FVIII protein of the disclosure. In vivo half-life of a FVIII protein can be determined by any methods known to those of skill in the art, e.g., activity assays (chromogenic assay or one stage clotting aPTT assay), ELISA, ROTEM™, etc.

In other embodiments, a heterologous moiety increases stability of the FVIII protein of the disclosure or a fragment thereof (e.g., a fragment comprising a heterologous moiety after proteolytic cleavage of the FVIII protein). As used herein, the term "stability" refers to an art-recognized measure of the maintenance of one or more physical properties of the FVIII protein in response to an environmental condition (e.g., an elevated or lowered temperature). In certain aspects, the physical property can be the maintenance of the covalent structure of the FVIII protein (e.g., the absence of proteolytic cleavage, unwanted oxidation or deamidation). In other aspects, the physical property can also be the presence of the FVIII protein in a properly folded state (e.g., the absence of soluble or insoluble aggregates or precipitates). In one aspect, the stability of the FVIII protein is measured by assaying a biophysical property of the FVIII protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics. Other advantageous properties which may be conferred by introducing an XTEN sequence include enhanced conformational flexibility, enhanced aqueous solubility, high degree of protease resistance, low immunogenicity, low binding to mammalian receptors, or increased hydrodynamic (or Stokes) radii.

XTEN can have varying lengths for insertion into or linkage to FVIII. In some embodiments, the XTEN sequence useful for the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues. In one particular embodiment, the XTEN comprises an amino acid sequence of longer than 42 amino acids and shorter than 144 amino acids in length.

The XTEN sequence of the disclosure can comprise one or more sequence motif of 5 to 14 (e.g., 9 to 14) amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids (e.g., 5 amino acids) selected from the group consisting of glycine (G), alanine (A), serine (S), threonine (T), glutamate (E) and proline (P). See US 2010-0239554 A1.

Examples of XTEN sequences that can be used as heterologous moieties in chimeric proteins of the disclosure are disclosed, e.g., in U.S. Patent Publication Nos. 2010/0239554 A1, 2010/0323956 A1, 2011/0046060 A1, 2011/0046061 A, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

The one or more XTEN sequences can be inserted at the C-terminus or at the N-terminus of the amino acid sequence encoded by the nucleotide sequence or inserted between two amino acids in the amino acid sequence encoded by the nucleotide sequence. For example, the XTEN can be inserted between two amino acids at one or more insertion sites. Examples of sites within FVIII that are permissible for XTEN insertion can be found in, e.g., International Publication No. WO 2013/123457 A1 or U.S. Publication No. 2015/0158929 A1, which are herein incorporated by reference in their entirety.

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, heterologous nucleotide sequences encoding peptide linkers can be inserted between the optimized FVIII polynucleotide sequences of the disclosure and a heterologous nucleotide sequence encoding, for example, one of the heterologous moieties described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the disclosure is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the disclosure result in a chimeric molecule having a heterologous cleavage site.

In one embodiment, an FVIII polypeptide encoded by a nucleic acid molecule of the instant disclosure comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used in a construct of the disclosure, e.g., to connect an FVIII protein to an Fc region. Some exemplary linkers that can be used in connection with the disclosure include, e.g., polypeptides comprising GlySer amino acids described in more detail below.

In one embodiment, the peptide linker is synthetic, i.e., non-naturally occurring. In one embodiment, a peptide linker includes peptides (or polypeptides) (which can or cannot be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

In another embodiment, a peptide linker comprises or consists of a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker. In one embodiment, a peptide linker of the disclosure comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the disclosure are at least one amino acid in length and can be of varying lengths. In one embodiment, a peptide linker of the disclosure is from about 1 to about 50 amino acids in length. As used in this context, the term "about" indicates +/− two amino acid residues. Since linker length must be a positive integer, the length of from about 1 to about 50 amino acids in length, means a length of from 1-3 to 48-52 amino acids in length. In another embodiment, a peptide linker of the disclosure is from about 10 to about 20 amino acids in length. In another embodiment, a peptide linker of the disclosure is from about 15 to about 50 amino acids in length. In another embodiment, a peptide linker of the disclosure is from about 20 to about 45 amino acids in length. In another embodiment, a peptide linker of the disclosure is from about 15 to about 35 or about 20 to about 30 amino acids in length. In another embodiment, a peptide linker of the disclosure is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the disclosure is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

Expression Control Sequences

In some embodiments, the nucleic acid molecule or vector of the disclosure further comprises at least one expression control sequence. For example, the isolated nucleic acid molecule of the disclosure can be operably linked to at least one expression control sequence. The expression control sequence can, for example, be a promoter sequence or promoter-enhancer combination.

Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the disclosure includes expression of a transgene under the control of a tissue specific promoter and/or enhancer. In another embodiment, the promoter or other expression control sequence selectively enhances expression of the transgene in liver cells. In certain embodiments, the promoter or other expression control sequence selectively enhances expression of the transgene in hepatocytes, sinusoidal cells, and/or endothelial cells. In one particular embodiment, the promoter or other expression control sequence selective enhances expression of the transgene in endothelial cells. In certain embodiments, the promoter or other expression control sequence selective enhances expression of the transgene in muscle cells, the central nervous system, the eye, the liver, the heart, or any combination thereof. Examples of liver specific promoters include, but are not limited to, a mouse transthyretin promoter (mTTR), a native human factor VIII promoter, human alpha-1-antitrypsin promoter (hAAT), human albumin minimal promoter, and mouse albumin promoter. In some embodiments, the nucleic acid molecules disclosed herein comprise a mTTR promoter. The mTTR promoter is described in Costa et al. (1986) Mol. Cell. Biol. 6:4697. The FVIII promoter is described in Figueiredo and Brownlee, 1995, J. Biol. Chem. 270:11828-11838. In some embodiments, the promoter is selected from a liver specific promoter (e.g., al-antitrypsin (AAT)), a muscle specific promoter (e.g., muscle creatine kinase (MCK), myosin heavy chain alpha (αMHC), myoglobin (MB), and desmin (DES)), a synthetic promoter (e.g., SPc5-12, 2R5Sc5-12, dMCK, and tMCK), or any combination thereof.

In some embodiments, the transgene expression is targeted to the liver. In certain embodiments, the transgene expression is targeted to hepatocytes. In other embodiment, the transgene expression is targeted to endothelial cells. In one particular embodiment, the transgene expression is targeted to any tissue that naturally expressed endogenous FVIII. In some embodiments, the transgene expression is targeted to the central nervous system. In certain embodiments, the transgene expression is targeted to neurons. In some embodiments, the transgene expression is targeted to afferent neurons. In some embodiments, the transgene expression is targeted to efferent neurons. In some embodiments, the transgene expression is targeted to interneurons. In some embodiments, the transgene expression is targeted to glial cells. In some embodiments, the transgene expression is targeted to astrocytes. In some embodiments, the transgene expression is targeted to oligodendrocytes. In some embodiments, the transgene expression is targeted to microglia. In some embodiments, the transgene expression is targeted to ependymal cells. In some embodiments, the transgene expression is targeted to Schwann cells. In some embodiments, the transgene expression is targeted to satellite cells. In some embodiments, the transgene expression is targeted to muscle tissue. In some embodiments, the transgene expression is targeted to smooth muscle. In some embodiments, the transgene expression is targeted to cardiac muscle. In some embodiments, the transgene expression is targeted to skeletal muscle. In some embodiments, the transgene expression is targeted to the eye. In some embodiments, the transgene expression is targeted to a photoreceptor cell. In some embodiments, the transgene expression is targeted to retinal ganglion cell.

Other promoters useful in the nucleic acid molecules disclosed herein include a mouse transthyretin promoter (mTTR), a native human factor VIII promoter, a human alpha-1-antitrypsin promoter (hAAT), a human albumin minimal promoter, a mouse albumin promoter, a tristetraprolin (TTP; also known as ZFP36) promoter, a CASI promoter, a CAG promoter, a cytomegalovirus (CMV) promoter, an α1-antitrypsin (AAT) promoter, a muscle creatine kinase (MCK) promoter, myosin heavy chain alpha (αMHC) promoter, a myoglobin (MB) promoter, desmin (DES) promoter, a SPc5-12 promoter, a 2R5Sc5-12 promoter, a dMCK promoter, and a tMCK promoter, a phosphoglycerate kinase (PGK) promoter, or any combinations thereof.

In some embodiments, the nucleic acid molecules disclosed herein comprise a transthyretin (TTR) promoter. In some embodiments, the promoter is a mouse transthyretin (mTTR) promoter. Non-limiting examples of mTTR promoters include the mTTR202 promoter, mTTR202opt promoter, and mTTR482 promoter, as disclosed in U.S. Publication No. US2019/0048362, which is incorporated by reference herein in its entirety. In some embodiments, the promoter is a liver-specific modified mouse transthyretin (mTTR) promoter. In some embodiments, the promoter is the liver-specific modified mouse transthyretin (mTTR) promoter mTTR482. Examples of mTTR482 promoters are described in Kyostio-Moore et al. (2016) Mol Ther Methods Clin Dev. 3:16006, and Nambiar B. et al. (2017) Hum Gene Ther Methods, 28(1):23-28. In some embodiments, the promoter is a liver-specific modified mouse transthyretin (mTTR) promoter comprising the nucleic acid sequence of SEQ ID NO: 16.

Expression levels can be further enhanced to achieve therapeutic efficacy using one or more enhancer elements. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al. (1992) J. Biol. Chem. 267:20765-20773; Rouet et al. (1995), Nucleic Acids Res. 23:395-404; Rouet et al (1998) Biochem.

J. 334:577-584; III et al. (1997) Blood Coagulation Fibrinolysis 8: S23-S30). In some embodiments, the enhancer is derived from liver specific transcription factor binding sites, such as EBP, DBP, HNF1, HNF3, HNF4, HNF6, with Enh1, comprising HNF1, (sense)-HNF3, (sense)-HNF4, (antisense)-HNF1, (antisense)-HNF6, (sense)-EBP, (antisense)-HNF4 (antisense).

In some embodiments, the enhancer element comprises one or two modified prothrombin enhancers (pPrT2), one or two alpha 1-microbikunin enhancers (A1MB2), a modified mouse albumin enhancer (mEalb), a hepatitis B virus enhancer II (HE11), or a CRM8 enhancer. In some embodiments, the A1MB2 enhancer is the enhancer disclosed in International Application No. PCT/US2019/055917. In some embodiments, the enhancer element is A1MB2. In some embodiments, the enhancer element includes multiple copies of the AIMB2 enhancer sequence. In some embodiments, the A1MB2 enhancer is positioned 5' to the nucleic acid sequence encoding the FVIII polypeptide. In some embodiments, the A1MB2 enhancer is positioned 5' to the promoter sequence, such as the mTTR promoter. In some embodiments, the enhancer element is the A1MB2 enhancer comprising the nucleic acid sequence of SEQ ID NO: 15.

In some embodiments, the nucleic acid molecules disclosed herein comprise an intron or intronic sequence. In some embodiments, the intronic sequence is a naturally occurring intronic sequence. In some embodiments, the intronic sequence is a synthetic sequence. In some embodiments, the intronic sequence is derived from a naturally occurring intronic sequence. In some embodiments, the intronic sequence is a hybrid synthetic intron or chimeric intron. In some embodiments, the intronic sequence is a chimeric intron that consists of chicken beta-actin/rabbit beta-globin intron and has been modified to eliminate five existing ATG sequences to reduce false translation starts. In certain embodiments, the intronic sequence comprises the SV40 small T intron. In some embodiments, the intronic sequence is positioned 5' to the nucleic acid sequence encoding the FVIII polypeptide. In some embodiments, the chimeric intron is positioned 5' to a promoter sequence, such as the mTTR promoter. In some embodiments, the chimeric intron comprises the nucleic acid sequence of SEQ ID NO: 17.

In some embodiments, the nucleic acid molecules disclosed herein comprise a post-transcriptional regulatory element. In certain embodiments, the regulatory element comprises a mutated woodchuck hepatitis virus regulatory element (WPRE). WPRE is believed to enhance the expression of viral vector-delivered transgenes. Examples of WPRE are described in Zufferey et al. (1999) J Virol., 73(4):2886-2892; Loeb et al. (1999) Hum Gene Ther. 10(14):2295-2305. In some embodiments, the WPRE is positioned 3' to the nucleic acid sequence encoding the FVIII polypeptide. In some embodiments, the WPRE comprises the nucleic acid sequence of SEQ ID NO: 18.

In some embodiments, the nucleic acid molecules disclosed herein comprise a transcription terminator. In some embodiments, the transcription terminator is a polyadenylation (poly(A)) sequence. Non-limiting examples of transcriptional terminators include those derived from the bovine growth hormone polyadenylation signal (BGHpA), the Simian virus 40 polyadenylation signal (SV40pA), or a synthetic polyadenylation signal. In one embodiment, the 3'UTR poly(A) tail comprises an actin poly(A) site. In one embodiment, the 3'UTR poly(A) tail comprises a hemoglobin poly(A) site. In some embodiments, the transcriptional terminator is BGHpA. Examples of BGHpA transcriptional terminators are described in Woychik et al. (1984) PNAS 81:3944-3948. In some embodiments, the transcriptionalo terminator is positioned at the 3' end of the genetic cassette encoding the nucleic acid sequence encoding the FVIII polypeptide. In some embodiments, the transcriptional terminator is a BGHpA comprising the nucleic acid sequence of SEQ ID NO: 19.

In some embodiments, the nucleic acid molecule disclosed herein comprises one or more DNA nuclear targeting sequences (DTSs). A DTS promotes translocation of DNA molecules containing such sequences into the nucleus. In certain embodiments, the DTS comprises an SV40 enhancer sequence. In certain embodiments, the DTS comprises a c-Myc enhancer sequence. In some embodiments, the nucleic acid molecule comprises DTSs that are located between the first ITR and the second ITR. In some embodiments, the nucleic acid molecule comprises a DTS located 3' to the first ITR and 5' to the transgene (e.g. FVIII protein). In some embodiments, the nucleic acid molecule comprises a DTS located 3' to the transgene and 5' to the second ITR on the nucleic acid molecule.

In some embodiments, the nucleic acid molecule disclosed herein comprises a toll-like receptor 9 (TLR9) inhibition sequence. Exemplary TLR9 inhibition sequences are described in, e.g., Trieu et al. (2006) Crit Rev Immunol. 26(6):527-44; Ashman et al. Int'l Immunology 23(3): 203-14.

Inverted Terminal Repeat (ITR) Sequences

Certain aspects of the present disclosure are directed to a nucleic acid molecule comprising a first ITR, e.g., a 5' ITR, and second ITR, e.g., a 3' ITR. Typically, ITRs are involved in parvovirus (e.g., AAV) DNA replication and rescue, or excision, from prokaryotic plasmids (Samulski et al., 1983, 1987; Senapathy et al., 1984; Gottlieb and Muzyczka, 1988). In addition, ITRs appear to be the minimum sequences required for AAV proviral integration and for packaging of AAV DNA into virions (McLaughlin et al., 1988; Samulski et al., 1989). These elements are essential for efficient multiplication of a parvovirus genome. It is hypothesized that the minimal defining elements indispensable for ITR function are a Rep-binding site and a terminal resolution site plus a variable palindromic sequence allowing for hairpin formation. Palindromic nucleotide regions normally function together in cis as origins of DNA replication and as packaging signals for the virus. Complimentary sequences in the ITRs fold into a hairpin structure during DNA replication. In some embodiments, the ITRs fold into a hairpin T-shaped structure. In other embodiments, the ITRs fold into non-T-shaped hairpin structures, e.g., into a U-shaped hairpin structure. Data suggests that the T-shaped hairpin structures of AAV ITRs may inhibit the expression of a transgene flanked by the ITRs. See, e.g., Zhou et al. (2017) *Scientific Reports* 7:5432. By utilizing an ITR that does not form T-shaped hairpin structures, this form of inhibition may be avoided. Therefore, in certain aspects, a polynucleotide comprising a non-AAV ITR has an improved transgene expression compared to a polynucleotide comprising an AAV ITR that forms a T-shaped hairpin.

As used herein, an "inverted terminal repeat" (or "ITR") refers to a nucleic acid subsequence located at either the 5' or 3' end of a single stranded nucleic acid sequence, which comprises a set of nucleotides (initial sequence) followed downstream by its reverse complement, i.e., palindromic sequence. The intervening sequence of nucleotides between the initial sequence and the reverse complement can be any length including zero. In one embodiment, the ITR useful for the present disclosure comprises one or more "palindromic sequences." An ITR can have any number of functions. In some embodiments, an ITR described herein forms a hairpin structure. In some embodiments, the ITR forms a T-shaped hairpin structure. In some embodiments, the ITR forms a non-T-shaped hairpin structure, e.g., a U-shaped hairpin structure. In some embodiments, the ITR promotes the long-term survival of the nucleic acid molecule in the nucleus of a cell. In some embodiments, the ITR promotes the permanent survival of the nucleic acid molecule in the nucleus of a cell (e.g., for the entire life-span of the cell). In some embodiments, the ITR promotes the stability of the nucleic acid molecule in the nucleus of a cell. In some embodiments, the ITR promotes the retention of the nucleic acid molecule in the nucleus of a cell. In some embodiments, the ITR promotes the persistence of the nucleic acid molecule in the nucleus of a cell. In some embodiments, the ITR inhibits or prevents the degradation of the nucleic acid molecule in the nucleus of a cell.

Therefore, an "ITR" as used herein can fold back on itself and form a double stranded segment. For example, the sequence GATCXXXXGATC comprises an initial sequence of GATC and its complement (3'CTAG5') when folded to form a double helix. In some embodiments, the ITR comprises a continuous palindromic sequence (e.g., GATC-GATC) between the initial sequence and the reverse complement. In some embodiments, the ITR comprises an interrupted palindromic sequence (e.g., GATCXXXX-GATC) between the initial sequence and the reverse complement. In some embodiments, the complementary sections of the continuous or interrupted palindromic sequence interact with each other to form a "hairpin loop" structure. As used herein, a "hairpin loop" structure results when at least two complimentary sequences on a single-stranded nucleotide molecule base-pair to form a double stranded section. In some embodiments, only a portion of the ITR forms a hairpin loop. In other embodiments, the entire ITR forms a hairpin loop.

In the present disclosure, at least one ITR is an ITR of a non-adenovirus associated virus (non-AAV). In certain embodiments, the ITR is an ITR of a non-AAV member of the viral family Parvoviridae. In some embodiments, the ITR is an ITR of a non-AAV member of the genus *Dependovirus* or the genus *Erythrovirus.*

In some embodiments, the ITR is an ITR of a non-AAV genome from Bocavirus, *Dependovirus, Erythrovirus*, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus and any combination thereof. In certain embodiments, the ITR is derived from human Bocavirus (HBoV1). In certain embodiments, the ITR is derived from erythrovirus parvovirus B19 (human virus). In some embodiments, the ITR is derived from a Dependoparvovirus. In one embodiment, the Dependoparvovirus is a *Dependovirus* Goose parvovirus (GPV) strain. In a specific embodiment, the GPV strain is attenuated, e.g., GPV strain 82-0321V. In another specific embodiment, the GPV strain is pathogenic, e.g., GPV strain B. In some embodiments, the ITR is an ITR of a goose parvovirus (GPV) or a Muscovy duck parvovirus (MDPV).

In some embodiments, the ITR is an ITR of an erythrovirus parvovirus B19 (also known as parvovirus B19—also referred to herein as "B19", primate erythroparvovirus 1, B19 virus, and erythrovirus). In some embodiments, the ITR is an ITR of a human Bocavirus (HBoV1).

In certain embodiments, one ITR of two ITRs is an ITR of an AAV. In other embodiments, one ITR of two ITRs in the construct is an ITR of an AAV serotype selected from serotype 1, 2, 3, 4, 5, 6, 7, 8, 9, 10, 11 and any combination thereof. In one particular embodiment, the ITR is derived from AAV serotype 2, e.g., an ITR of AAV serotype 2.

In certain aspects of the present disclosure, the nucleic acid molecule comprises two ITRs, a 5' ITR and a 3' ITR, wherein the 5' ITR is located at the 5' terminus of the nucleic acid molecule, and the 3' ITR is located at the 3' terminus of the nucleic acid molecule. The first ITR and the second ITR of the nucleic acid molecule can be derived from the same genome, e.g., from the genome of the same virus, or from different genomes, e.g., from the genomes of two or more different virus genomes (also known as "hybrid" ITRs). In some embodiments, first ITR is derived from B19 and the second ITR is derived from GPV. In some embodiments, first ITR is derived from GPV and the second ITR is derived from B19.

In certain embodiments, the first ITR and/or the second ITR comprises or consists of all or a portion of an ITR derived from human Bocavirus (HBoV1). In certain embodiments, the first ITR and/or the second ITR comprises or consists of all or a portion of an ITR derived from HBoV1. In some embodiments, the second ITR is a reverse complement of the first ITR. In some embodiments, the first ITR is a reverse complement of the second ITR. In some embodiments, the first ITR and/or the second ITR derived from HBoV1 is capable of forming a hairpin structure. In certain embodiments, the hairpin structure does not comprise a T-shaped hairpin.

In some embodiments, the first ITR and/or the second ITR comprises or consists of a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NOs: SEQ ID NOs: 1, 2, 21-30, wherein the first ITR and/or the second ITR retains a functional property of the wild type ITR from which it is derived. In some embodiments, the first ITR and/or the second ITR is derived from a wild type HBoV1 ITR. In some embodiments, the first ITR and/or the second ITR is derived from a wild type B19 ITR. In some embodiments, the first ITR and/or the second ITR is derived from a wild type GPV ITR.

In some embodiments, the first ITR and/or the second ITR comprises or consists of a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NOs: 1, 2, 21-30, wherein the first ITR and/or the second ITR is capable of forming a hairpin structure. In certain embodiments, the hairpin structure does not comprise a T-shaped hairpin.

It will be appreciated to those of skill in the art that any of the first ITR sequences described herein can be matched with any of the second ITR sequences described herein. In some embodiments, the first ITR sequence described herein is a 5' ITR sequence. In some embodiments, the second ITR sequence described herein is a 3' ITR sequence. In some embodiments, the second ITR sequence described herein is a 5' ITR sequence. In some embodiments, the first ITR sequence described herein is a 3' ITR sequence. Those of skill in the art will be able to determine the suitable orientation of the first and the second ITR described herein with respect to the architecture of a genetic cassette.

In another particular embodiment, the ITR is a synthetic sequence genetically engineered to include at its 5' and 3' ends ITRs not derived from an AAV genome. In another particular embodiment, the ITR is a synthetic sequence genetically engineered to include at its 5' and 3' ends ITRs derived from one or more of non-AAV genomes. The two ITRs present in the nucleic acid molecule of the invention can be the same or different non-AAV genomes. In particular, the ITRs can be derived from the same non-AAV genome. In a specific embodiment, the two ITRs present in the nucleic acid molecule of the invention are the same, and can in particular be AAV2 ITRs.

In some embodiments, the ITR sequence comprises one or more palindromic sequence. A palindromic sequence of an ITR disclosed herein includes, but is not limited to, native palindromic sequences (i.e., sequences found in nature), synthetic sequences (i.e., sequences not found in nature), such as pseudo palindromic sequences, and combinations or modified forms thereof.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures. In some embodiments, the first ITR and/or the second ITR does not form a T-shaped hairpin structure. In certain embodiments, the first ITR and/or the second ITR forms a non-T-shaped hairpin structure. In some embodiments, the non-T-shaped hairpin structure comprises a U-shaped hairpin structure.

In some embodiments, an ITR in a nucleic acid molecule described herein may be a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and are preferred when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements may be preferred when expression is desired only at certain times or at certain locations, or when it is desirable to titrate the level of expression using an inducing agent. Transcriptionally active elements can also be tissue-specific; that is, they exhibit activity only in certain tissues or cell types.

Transcriptionally active elements, can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements may alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these may be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng and Nickoloff (1992) Anal. Biochem. 200:81-88). Another way to create transcriptionally-activated ITRs involves the introduction of a restriction site at a desired location in the ITR. In addition, multiple transcriptionally activate elements can be incorporated into a transcriptionally-activated ITR, using methods known in the art.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBa box, CArG box, CCAC box, or any other element involved in transcription as known in the art.

Vector Systems

Some embodiments of the present disclosure are directed to vectors comprising one or more codon optimized nucleic acid molecules encoding a polypeptide with FVIII activity described herein, host cells comprising the vectors, and methods of treating a bleeding disorder using the vectors. The present disclosure meets an important need in the art by providing a vector comprising an optimized FVIII sequence that demonstrates increased expression in a subject and potentially result in greater therapeutic efficacy when used in gene therapy methods.

Suitable vectors for the disclosure include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure will include optimized polynucleotides encoding the BDD FVIII protein described herein. In one embodiment, the optimized coding sequences for the BDD FVIII protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. In one embodiment, the virus is an adeno-associated virus, a double-stranded DNA virus. The adeno-associated virus can be engineered to be replication-deficient and is capable of infecting a wide range of cell types and species.

One or more of different AAV vector sequences derived from nearly any serotype can be used in accord with the present disclosure. Choice of a particular AAV vector sequence will be guided by known parameters such as tropism of interest, required vector yields, etc. Generally, the AAV serotypes have genomic sequences of significant homology at the amino acid and the nucleic acid levels, provide a related set of genetic functions, produce virions which are related, and replicate and assemble similarly. For the genomic sequence of the various AAV serotypes and an overview of the genomic similarities see, e.g., GenBank Accession number U89790; GenBank Accession number J01901; GenBank Accession number AF043303; GenBank Accession number AF085716; Chlorini et al. (1997) J. Vir. 71: 6823-33; Srivastava et al. (1983) J. Vir. 45:555-64; Chlorini et al. (1999) J. Vir. 73:1309-1319; Rutledge et al. (1998), J. Vir. 72:309-319; or Wu et al. (2000) J. Vir. 74: 8635-47. AAV serotypes 1, 2, 3, 4 and 5 are an illustrative source of AAV nucleotide sequences for use in the context of the present disclosure. AAV6, AAV7, AAV8 or AAV9 or newly developed AAV-like particles obtained by e.g. capsid shuffling techniques and AAV capsid libraries, or from newly designed, developed or evolved ITR's are also suitable for certain disclosure applications. See Dalkara et al. (2013), Sci. Transl. Med. 5(189): 189ra76; Kotterman M A (2014) Nat. Rev. Genet. 15(7):455.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA). Other plasmids are well-known to those of ordinary skill in the art. Additionally, plasmids can be custom designed using standard molecular biology techniques to remove and/or add specific fragments of DNA.

In certain embodiments, it will be useful to include within the vector one or more miRNA target sequences which, for example, are operably linked to the optimized FVIII transgene. More than one copy of a miRNA target sequence included in the vector can increase the effectiveness of the system. For example, vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the vector in antisense orientation. Examples of the miRNA target sequences are described at WO2007/000668, WO2004/094642, WO2010/055413, or WO2010/125471, which are incorporated herein by reference in their entireties. However in certain other embodiments, the vector will not include any miRNA target sequence. Choice of whether or not to include an miRNA target sequence (and how many) will be guided by known parameters such as the intended tissue target, the level of expression required, etc.

Host Cells

The disclosure also provides a host cell comprising a nucleic acid molecule or vector of the disclosure. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present disclosure are preferably of mammalian origin; most preferably of human or mouse origin. Those skilled in the art are credited with ability to preferentially determine particular host cell lines which are best suited for their purpose. Exemplary host cell lines include, but are not limited to, CHO, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3. times.63-Ag3.653 (mouse myeloma), BFA-1c1BPT (bovine endothelial cells), RAJI (human lymphocyte), PER.C6®, NSO, CAP, BHK21, and HEK 293 (human kidney). In one particular embodiment, the host cell is selected from the group consisting of: a CHO cell, a HEK293 cell, a BHK21 cell, a PER.C6® cell, a NSO cell, and a CAP cell. Host cell lines are typically available from commercial services, the American Tissue Culture Collection, or from published literature.

Introduction of the isolated nucleic acid molecules or vectors of the disclosure into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Plasmids can be introduced into the host via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules or vectors of the disclosure are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, CA). In another embodiment, the medium is CD17 (Invitrogen, Carlsbad, CA). Selection of a medium appropriate for the particular cell line used is within the level of those ordinary skilled in the art.

In some embodiments, host cells suitable for use in the present invention are of insect origin. In some embodiments, a suitable insect host cell includes, for example, a cell line isolated from *Spodoptera frugiperda* (Sf) or a cell line isolated from Trichoplusia ni (Tni). Those of skill in the art will readily be able to determine the suitability of any Sf or Tni cell line. Exemplary insect host cells include, without limitation, Sf9 cells, Sf21 cells, and High Five™ cells. Exemplary insect host cells also include, without limitation, any Sf or Tni cell line that is free from adventitious virus contamination, e.g., Sf-rhabdovirus-negative (Sf-RVN) and Tn-nodavirus-negative (Tn-NVN) cells. Other suitable host insect cells are known to those of skill in the art. In one particular embodiment, the insect host cells are Sf9 cells.

Aspects of the present disclosure provide a method of cloning a nucleic acid molecule described herein, comprising inserting a nucleic acid molecule capable of complex secondary structures into a suitable vector, and introducing the resulting vector into a suitable bacterial host strain. As known in the art, complex secondary structures (e.g., long palindromic regions) of nucleic acids may be unstable and difficult to clone in bacterial host strains. For example, nucleic acid molecules comprising a first ITR and a second ITR (e.g., non-AAV parvoviral ITRs, e.g., HBoV1 ITRs) of the present disclosure may be difficult to clone using conventional methodologies. Long DNA palindromes inhibit DNA replication and are unstable in the genomes of *E. coli, Bacillus, Streptococcus, Streptomyces, S. cerevisiae*, mice, and humans. These effects result from the formation of hairpin or cruciform structures by intrastrand base pairing. In *E. coli* the inhibition of DNA replication can be significantly overcome in SbcC or SbcD mutants. SbcD is the nuclease subunit, and SbcC is the ATPase subunit of the SbcCD complex. The *E. coli* SbcCD complex is an exonuclease complex responsible for preventing the replication of long palindromes. The SbcCD complex is a nuclear with ATP-dependent double-stranded DNA exonuclease activity and ATP-independent single-stranded DNA endonuclease activity. SbcCD may recognize DNA palindromes and collapse replication forks by attacking hairpin structures that arise.

In certain embodiments, a suitable bacterial host strain is incapable of resolving cruciform DNA structures. In certain embodiments, a suitable bacterial host strain comprises a disruption in the SbcCD complex. In some embodiments, the disruption in the SbcCD complex comprises a genetic disruption in the SbcC gene and/or SbcD gene. In certain embodiments, the disruption in the SbcCD complex comprises a genetic disruption in the SbcC gene. Various bacterial host strains that comprise a genetic disruption in the SbcC gene are known in the art. For example, without limitation, the bacterial host strain PMC103 comprises the genotype sbcC, recD, mcrA, ΔmcrBCF; the bacterial host strain PMC107 comprises the genotype recBC, recJ, sbcBC, mcrA, ΔmcrBCF; and the bacterial host strain SURE comprises the genotype recB, recJ, sbcC, mcrA, ΔmcrBCF, umuC, uvrC. Accordingly, in some embodiments a method of cloning a nucleic acid molecule described herein comprises inserting a nucleic acid molecule capable of complex secondary structures into a suitable vector, and introducing the resulting vector into host strain PMC103, PMC107, or SURE. In certain embodiments, the method of cloning a nucleic acid molecule described herein comprises inserting a nucleic acid molecule capable of complex secondary structures into a suitable vector, and introducing the resulting vector into host strain PMC103.

Suitable vectors are known in the art and described elsewhere herein. In certain embodiments, a suitable vector for use in a cloning methodology of the present disclosure is a low copy vector. In certain embodiments, a suitable vector for use in a cloning methodology of the present disclosure is pBR322.

Accordingly, the present disclosure provides a method of cloning a nucleic acid molecule, comprising inserting a nucleic acid molecule capable of complex secondary structures into a suitable vector, and introducing the resulting vector into a bacterial host strain comprising a disruption in the SbcCD complex, wherein the nucleic acid molecule comprises a first inverted terminal repeat (ITR) and a second ITR, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NOs. 12-23 or a functional derivative thereof.

Production of Polypeptides

The disclosure also provides a polypeptide encoded by a nucleic acid molecule of the disclosure. In other embodiments, the polypeptide of the disclosure is encoded by a vector comprising the isolated nucleic molecules of the disclosure. In yet other embodiments, the polypeptide of the disclosure is produced by a host cell comprising the isolated nucleic molecules of the disclosure.

In other embodiments, the disclosure also provides a method of producing a polypeptide with FVIII activity, comprising culturing a host cell of the disclosure under conditions whereby a polypeptide with FVIII activity is produced, and recovering the polypeptide with FVIII activity. In some embodiments, the expression of the polypeptide with FVIII activity is increased relative to a host cell cultured under the same conditions but comprising a reference nucleotide sequence comprising SEQ ID NO: 32, a parental FVIII nucleotide sequence.

In other embodiments, the disclosure provides a method of increasing the expression of a polypeptide with FVIII activity comprising culturing a host cell of the disclosure under conditions whereby a polypeptide with FVIII activity is expressed by the nucleic acid molecule, wherein the expression of the polypeptide with FVIII activity is increased relative to a host cell cultured under the same conditions comprising a reference nucleic acid molecule comprising SEQ ID NO: 32.

In other embodiments, the disclosure provides a method of improving yield of a polypeptide with FVIII activity comprising culturing a host cell under conditions whereby a polypeptide with FVIII activity is produced by the nucleic acid molecule, wherein the yield of polypeptide with FVIII activity is increased relative to a host cell cultured under the same conditions comprising a reference nucleic acid sequence comprising SEQ ID NO: 32.

A variety of methods are available for recombinantly producing a FVIII protein from the optimized nucleic acid molecule of the disclosure. A polynucleotide of the desired sequence can be produced by de novo solid-phase DNA synthesis or by PCR mutagenesis of an earlier prepared polynucleotide. Oligonucleotide-mediated mutagenesis is one method for preparing a substitution, insertion, deletion, or alteration (e.g., altered codon) in a nucleotide sequence. For example, the starting DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide of the disclosure.

For recombinant protein production, an optimized polynucleotide sequence of the disclosure encoding the FVIII protein is inserted into an appropriate expression vehicle, i.e., a vector which contains the necessary elements for the transcription and translation of the inserted coding sequence, or in the case of an RNA viral vector, the necessary elements for replication and translation.

The polynucleotide sequence of the disclosure is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14: 725) and electroporation (Neumann et al. 1982, *EMBO, J.* 1: 841). A variety of host-expression vector systems can be utilized to express the FVIII proteins described herein in eukaryotic cells. In one embodiment, the eukaryotic cell is an animal cell, including mammalian cells (e.g. HEK293 cells, PER.C6®, CHO, BHK, Cos, HeLa cells). A polynucleotide sequence of the disclosure can also code fora signal sequence that will permit the FVIII protein to be secreted. One skilled in the art will understand that while the FVIII protein is translated the signal sequence is cleaved by the cell to form the mature protein. Various signal sequences are known in the art, e.g., native factor VII signal sequence, native factor IX signal sequence and the mouse IgK light chain signal sequence. Alternatively, where a signal sequence is not included the FVIII protein can be recovered by lysing the cells.

The FVIII protein of the disclosure can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad.Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the FVIII protein described herein coding sequence can be ligated into the vector in frame with the lac Z coding region so that a hybrid protein is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., PreCission Protease (Pharmacia, Peapack, N. J.)) for easy removal of the tag after purification.

For the purposes of this disclosure, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation.

An example of a vector useful for expressing an optimized FVIII sequence is NEOSPLA (U.S. Pat. No. 6,159,730). This vector contains the cytomegalovirus promoter/ enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the disclosure of the instant disclosure can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate to the production of the FVIII polypeptide, and assayed for FVIII polypeptide synthesis. Exemplary assay techniques include enzyme-linked immunosorbent assay (ELISA), radioimmunoassay (RIA), or fluorescence-activated cell sorter analysis (FACS), immunohistochemistry and the like.

In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

The host cell line used for protein expression is preferably of mammalian origin; most preferably of human or mouse origin, as the isolated nucleic acids of the disclosure have been optimized for expression in human cells. Exemplary host cell lines have been described above. In one embodiment of the method to produce a polypeptide with FVIII activity, the host cell is a HEK293 cell. In another embodiment of the method to produce a polypeptide with FVIII activity, the host cell is a CHO cell.

Genes encoding the polypeptides of the disclosure can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella; Bacillaceae*, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

Alternatively, optimized nucleotide sequences of the disclosure can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) can optionally be attached or included within the polypeptide sequence to facilitate downstream purification.

Once expressed, the FVIII protein can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred for pharmaceutical uses, with 98 to 99% or more homogeneity being most preferred.

Pharmaceutical Compositions

Compositions containing an isolated nucleic acid molecule, a polypeptide having FVIII activity encoded by the nucleic acid molecule, a vector, or a host cell of the present disclosure can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the disclosure for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the disclosure can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See, e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the disclosure is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present disclosure are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a polypeptide having Factor VIII activity, an optimized nucleic acid molecule encoding the polypeptide having Factor VIII activity, the vector comprising the nucleic acid molecule, or the host cell comprising the vector, and a pharmaceutically acceptable carrier. In some embodiments, the composition is administered by a route selected from the group consisting of topical administration, intraocular administration, parenteral administration, intrathecal administration, subdural administration and oral administration. The parenteral administration can be intravenous or subcutaneous administration.

Methods of Treatment

In some aspects, the present disclosure is directed to methods of treating a disease or condition in a subject in need thereof, comprising administering a nucleic acid molecule, a vector, a polypeptide, or a pharmaceutical composition disclosed herein.

In some embodiments, the disclosure is directed to methods of treating a bleeding disorder. In some embodiments, the disclosure is directed to methods of treating hemophilia A.

The isolated nucleic acid molecule, vector, or polypeptide can be administered intravenously, subcutaneously, intramuscularly, or via any mucosal surface, e.g., orally, sublingually, buccally, sublingually, nasally, rectally, vaginally or via pulmonary route. The isolated nucleic acid molecule, vector, or polypeptide can also be administered intraneurally, intraocularly, and intrathecally. The clotting factor protein can be implanted within or linked to a biopolymer solid support that allows for the slow release of the chimeric protein to the desired site.

In one embodiment, the route of administration of the isolated nucleic acid molecule, vector, or polypeptide is parenteral. The term parenteral as used herein includes intravenous, intraarterial, intraperitoneal, intramuscular, subcutaneous, rectal or vaginal administration. In some embodiments, the isolated nucleic acid molecule, vector, or polypeptide is administered intravenously. While all these forms of administration are clearly contemplated as being within the scope of the disclosure, a form for administration would be a solution for injection, in particular for intravenous or intraarterial injection or drip.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The nucleic acid molecule, vector, or polypeptides of the disclosure can optionally be administered in combination with other agents that are effective in treating the disorder or condition in need of treatment (e.g., prophylactic or therapeutic).

As used herein, the administration of isolated nucleic acid molecules, vectors, or polypeptides of the disclosure in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the isolated nucleic acid molecule, vector, or polypeptide of the instant disclosure can be used in conjunction or combination with an agent or agents (e.g., to provide a combined therapeutic regimen). Exemplary agents with which a polypeptide or polynucleotide of the disclosure can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polynucleotides or polypeptides of the instant disclosure can vary by subject or can be administered according to what is known in the art. See, e.g., Bruce A Chabner et al., *Antineoplastic Agents*, in Goodman & Gilman's The Pharmacological Basis of Therapeutics 1233-1287 ((Joel G. Hardman et al., eds., 9$^{th}$ ed. 1996). In another embodiment, an amount of such an agent consistent with the standard of care is administered.

In one embodiment, also disclosed herein is a kit, comprising the nucleic acid molecule disclosed herein and instructions for administering the nucleic acid molecule to a subject in need thereof. In another embodiment, disclosed herein is a baculovirus system for production of the nucleic acid molecule provided herein. The nucleic acid molecule is produced in insect cells. In another embodiment, a nanoparticle delivery system for expression constructs is provided. The expression construct comprises the nucleic acid molecule disclosed herein.

Gene Therapy

In some embodiments, the nucleic acid molecule disclosed herein is used in gene therapy. The optimized FVIII nucleic acid molecules disclosed herein can be used in any context where expression of FVIII is required. In some embodiments, the nucleic acid molecules comprise the nucleotide sequence of SEQ ID NO: 9. In some embodiments, the nucleic acid molecules comprise the nucleotide sequence of SEQ ID NO: 33. In some embodiments, the nucleic acid molecules comprise the nucleotide sequence of SEQ ID NO: 14. In some embodiments, the nucleic acid molecules comprise the nucleotide sequence of SEQ ID NO: 35.

For example, somatic gene therapy has been explored as a possible treatment for hemophilia A. Gene therapy is a particularly appealing treatment for hemophilia because of its potential to cure the disease through continuous endogenous production of FVIII following a single administration of vector. Hemophilia A is well suited for a gene replacement approach because its clinical manifestations are entirely attributable to the lack of a single gene product (FVIII) that circulates in minute amounts (200 ng/ml) in the plasma.

In one aspect, the nucleic acid molecule described herein may be used in AAV gene therapy. AAV is able to infect a number of mammalian cells. See, e.g., Tratschin et al. (1985) Mol. Cell Biol. 5:3251-3260 and Grimm et al. (1999) Hum. Gene Ther. 10:2445-2450. A rAAV vector carries a nucleic acid sequence encoding a gene of interest, or fragment thereof, under the control of regulatory sequences which direct expression of the product of the gene in cells. In some embodiments, the rAAV is formulated with a carrier and additional components suitable for administration.

In another aspect, the nucleic acid molecule described herein may be used in lentiviral gene therapy. Lentiviruses are RNA viruses wherein the viral genome is RNA. When a host cell is infected with a lentivirus, the genomic RNA is reverse transcribed into a DNA intermediate which is integrated very efficiently into the chromosomal DNA of infected cells. In some embodiments, the lentivirus is formulated with a carrier and additional components suitable for administration. In another aspect, the nucleic acid molecule described herein may be used in adenoviral therapy. A review of the use of adenovirus for gene therapy can be found e.g. in Wold et al. (2013) Curr Gene Ther. 13(6):421-33). In another aspect, the nucleic acid molecule described herein may be used in non-viral gene therapy.

An optimized FVIII protein of the disclosure can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the iliopsoas sheath would be therapeutically beneficial. In one embodiment, the bleeding disease or disorder is hemophilia. In another embodiment, the bleeding disease or disorder is hemophilia A. This involves administration of an optimized FVIII encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. In other embodiments, the sequences are incorporated into a non-viral vector known to those skilled in the art.

In another aspect, the methods disclosed herein provide techniques for the targeted, specific alteration of the genetic information (e.g. genome) of living organisms. As used herein, the term "alteration" or "alteration of genetic information" refers to any change in the genome of a cell. In the context of treating genetic disorders, alterations may include, but are not limited to, insertion, deletion and/or correction.

In some aspects, alterations may also include a gene knock-in, knock-out or knock down. As used herein, the term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a cDNA encoding the wild-type protein may be inserted into the genome of a cell carrying a mutant gene. Knock-in strategies need not replace the defective gene, in whole or in part. In some cases, a knock-in strategy may further involve substitution of an existing sequence with the provided sequence, e.g., substitution of a mutant allele with a wildtype copy. The term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. The term "knock-down" as used herein refers to reduction in the expression of a gene or its gene product(s). As a result of a gene knock-down, the protein activity or function may be attenuated or the protein levels may be reduced or eliminated.

In some embodiments, the nucleic acid sequences disclosed herein are used for genome editing. Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double strand DNA breaks at particular locations within the genome. Such breaks can be and regularly are repaired by natural, endogenous cellular processes, such as homology-directed repair (HDR) and non-homologous end joining (NHEJ), as recently reviewed in Cox et al. (2015). Nature Medicine 21(2): 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process, see, e.g., Cho and Greenberg (2015). Nature 518, 174-76. In some instances, it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, such as the CRISPR endonuclease system and others.

In another aspect, the nucleic acid molecule described herein may be used in lipid nanoparticle (LNP)-mediated delivery of FVIII ceDNA. Lipid nanoparticles formed from cationic lipids with other lipid components, such as neutral lipids, cholesterol, PEG, PEGylated lipids, and oligonucleotides have been used to block degradation of nucleic acids in plasma and facilitate the cellular uptake of oligonucleotides. Such lipid nanoparticles may be used to deliver the nucleic acid molecule described herein to subjects.

The disclosure provides a method of increasing expression of a polypeptide with FVIII activity in a subject comprising administering the isolated nucleic acid molecule of the disclosure to a subject in need thereof, wherein the expression of the polypeptide is increased relative to a reference nucleic acid molecule comprising SEQ ID NO: 32. The disclosure also provides a method of increasing expression of a polypeptide with FVIII activity in a subject comprising administering a vector of the disclosure to a subject in need thereof, wherein the expression of the polypeptide is increased relative to a vector comprising a reference nucleic acid molecule.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1: Modified FVIIIXTEN Expression Cassette

It was hypothesized that the transgene expression level can be increased by codon-optimizing the coding sequence for the targeted hosts. Higher level of FVIII expression has been demonstrated using a V1.0 FVIIIco6XTEN expression cassette (SEQ ID NO: 32)(FIG. 1) in previous studies as described in U.S. Publication No. 20190185543. However, to further improve the target specificity and reduce immunogenicity, the FVIIIXTEN expression cassette was codon-optimized with CpG motifs depleted to reduce the innate immune response raised against the DNA vector encoding FVIIIXTEN expression cassette with parvoviral ITRs. In this study, the modified V2.0 FVIIIXTEN expression cassette comprises of a codon optimized cDNA encoding B-domain deleted human Factor VIII (BDDcoFVIII) fused with XTEN 144 peptide (FVIIIXTEN) under the regulation of liver-specific modified mouse transthyretin (mTTR) promoter (mTTR482) with enhancer element (A1MB2), hybrid synthetic intron (Chimeric Intron), the Woodchuck Posttranscriptional Regulatory Element (WPRE), and the Bovine Growth Hormone Polyadenylation (bGHpA) signal (SEQ ID NO: 14).(FIG. 1). The in vivo functionality of the modified V2.0 FVIIIXTEN expression cassette has been demonstrated with different parvoviral ITRs in a form of single-stranded (ss) or closed-end (ce) DNA by systemic delivery via hydrodynamic tail-vein injections in hFVIIIR593C$^{+/+}$/HemA mice.

Example 2: Single-Stranded FVIIIXTEN (ssFVIIIXTEN) DNA

Modified FVIIIXTEN Shown Significantly Higher Levels of Activity in Vivo

It was hypothesized that the hairpin formed within the ITR region drives the long-term persistent expression of transgene at higher level. To validate the functionality of modified FVIIIXTEN expression cassette in vivo, single-stranded DNA (ssDNA) comprising of V1.0 or V2.0 human FVIIIXTEN with preformed erythrovirus B19 ITRs was tested in hFVIIIR593C$^{+/+}$/HemA mice. These mice contain a human FVIII-R593C transgene, designed with the murine albumin (Alb) promoter driving expression of an altered human coagulation factor VIII (FVIII) cDNA harboring a mutation that is frequently observed in patients with mild hemophilia A. These mice also carry a knock-out of the FVIII gene and are deficient for endogenous FVIIIprotein. These double mutant mice are tolerant of human FVIII injection and have no FVIII activity. They produce very little inhibitory antibodies and lack FVIII responsive T cells or B cells after treatment with human FVIII. The hFVIIIR593C$^{+/+}$/HemA mouse is further described in Bril, et al. (2006) Thromb. Haemost. 95(2): 341-7.

Figure 2:
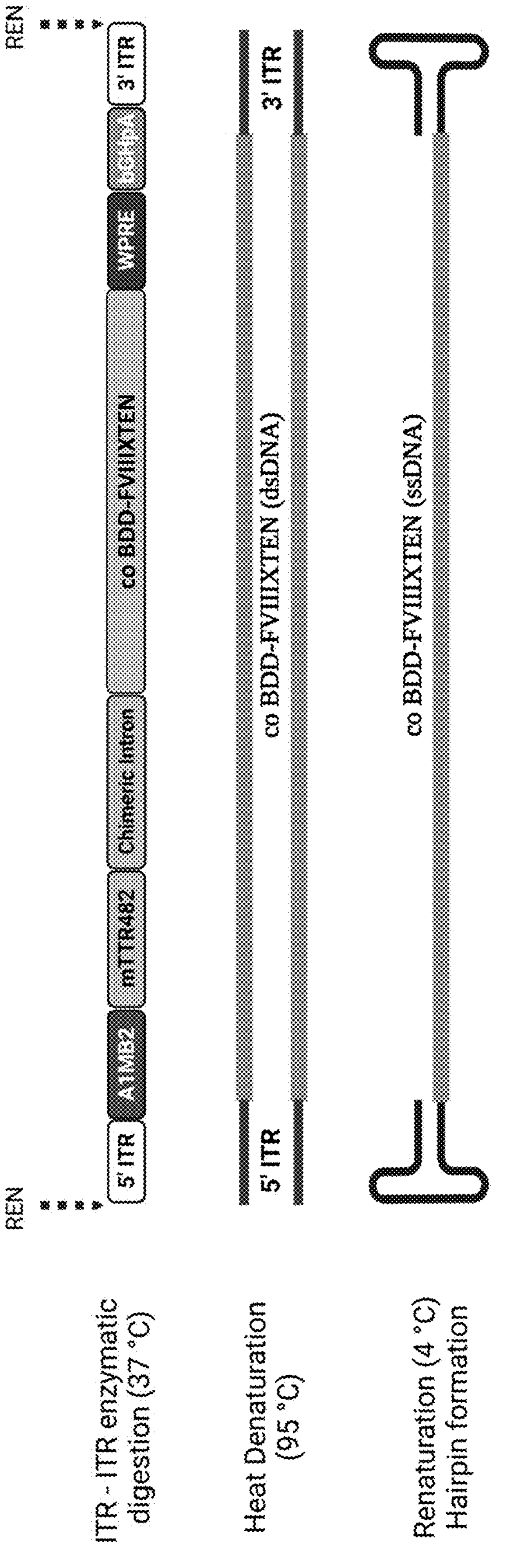
FIG. 2 shows a schematic representation of approach used for ssDNA generation, where a FVIIIXTEN expression cassette flanked by the parvoviral ITRs was digested with restriction enzymes that recognize the ITR related sequence and produce blunt-end DNA, and heat denatured (denaturation) the double-stranded DNA products (FVIII expression cassette and plasmid backbone) of digestion at 95° C. followed by cooling down (renaturation) at 4° C. to allow the palindromic ITR sequences to fold. The resulting ssFVIIIXTEN (ssDNA) was used for systemic delivery via hydrodynamic tail-vein injections in HemA mice.

The ssFVIIIXTEN with preformed B19 ITRs was generated by denaturing the double-stranded DNA fragment products (FVIII expression cassette and plasmid backbone) of MscI digestion at 95° C. (denaturation) and then cooling down at 4° C. (renaturation) to allow the palindromic ITR sequences to fold (FIG. 2). The ssFVIIIXTEN was then systemically injected via hydrodynamic tail-vein injections at 800 μg/kg hFVIIIR593C$^{+/+}$/HemA mice. Plasma samples were collected from injected mice at indicated intervals for 5.5 months and the FVIII activity was measured by the Chromogenix Coatest® SP Factor VIII chromogenic assay, according to the manufacturer's instructions.

Figure 3:
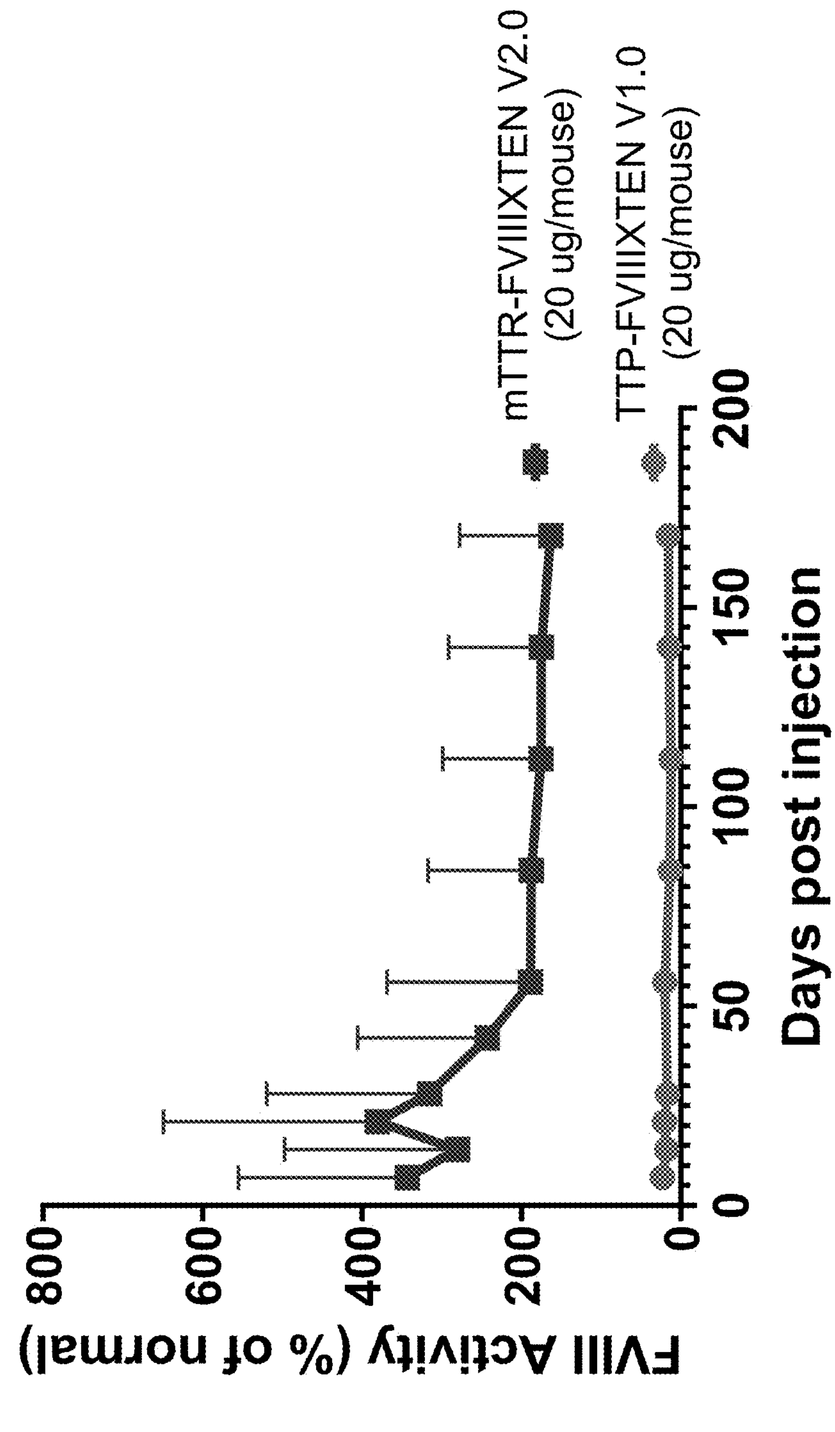
FIG. 3 shows a graphical representation of plasma FVIII activity levels measured by the Chromogenix Coatest® SP Factor VIII chromogenic assays. The blood samples were collected at different intervals from hFVIIIR593C$^{+/+}$/HemA mice systemically injected via hydrodynamic tail-vein injection with 800 μg/kg of single-stranded V1.0 or V2.0 ssFVIIIXTEN (ssDNA) flanked by the B19 ITRs. Error bars represents standard deviation.

The plasma FVIII activity normalized to percent of normal for V1.0 and V2.0 ssFVIIIXTEN injected animals is shown in FIG. 3. The results showed significant improvement in FVIII activity in V2.0 injected cohorts in comparison to V1.0 ssFVIIIXTEN. However, there was initial drop in FVIII expression observed up to day 56 but then the levels were stabilized up to day 168 suggesting the persistent expression of parvoviral ITRs flanked V2.0 ssFVIIIXTEN from the liver of injected animals. Thus, these results validate the functionality of modified FVIIIXTEN with long-term persistent expression of FVIII activity in comparison to V1.0 in vivo.

Human Bocavirus (HBoV1) ITRs Shown Supraphysiological Levels of FVIII Expression in Vivo To determine the impact of ITRs on stability and long-term persistency of transgene expression, the improved version of FVIIIXTEN was tested with human Bocavirus (HBoV1), human erythrovirus B19, Goose Parvovirus (GPV), or their variant ITRs in vivo. These ITRs were engineered based on the thermostability and ITR-specific elements required for the long-term persistency of viral genome in their respective hosts. Tested ITR variants and predicted secondary structure is described in previous U.S. Patent Application No. 63/069,114. Individual variant ITR was cloned into the synthetic FVIIIXTEN expression construct using Golden Gate Assembly and verified by sequencing at the Genewiz sequencing facility. Sequence verified constructs were then used for generating ssFVIIIXTEN (ssDNA), as described above, and then systemically injected in hFVIIIR593C$^{+/+}$/HemA mice via hydrodynamic tail-vein injection at 200, 800, or 1600 μg/kg. Plasma samples were collected from injected mice at indicated interval for 5.5 months and the FVIII activity was measured by the Chromogenix Coatest® SP Factor VIII chromogenic assay, according to the manufacturer's instructions.

Figure 4:
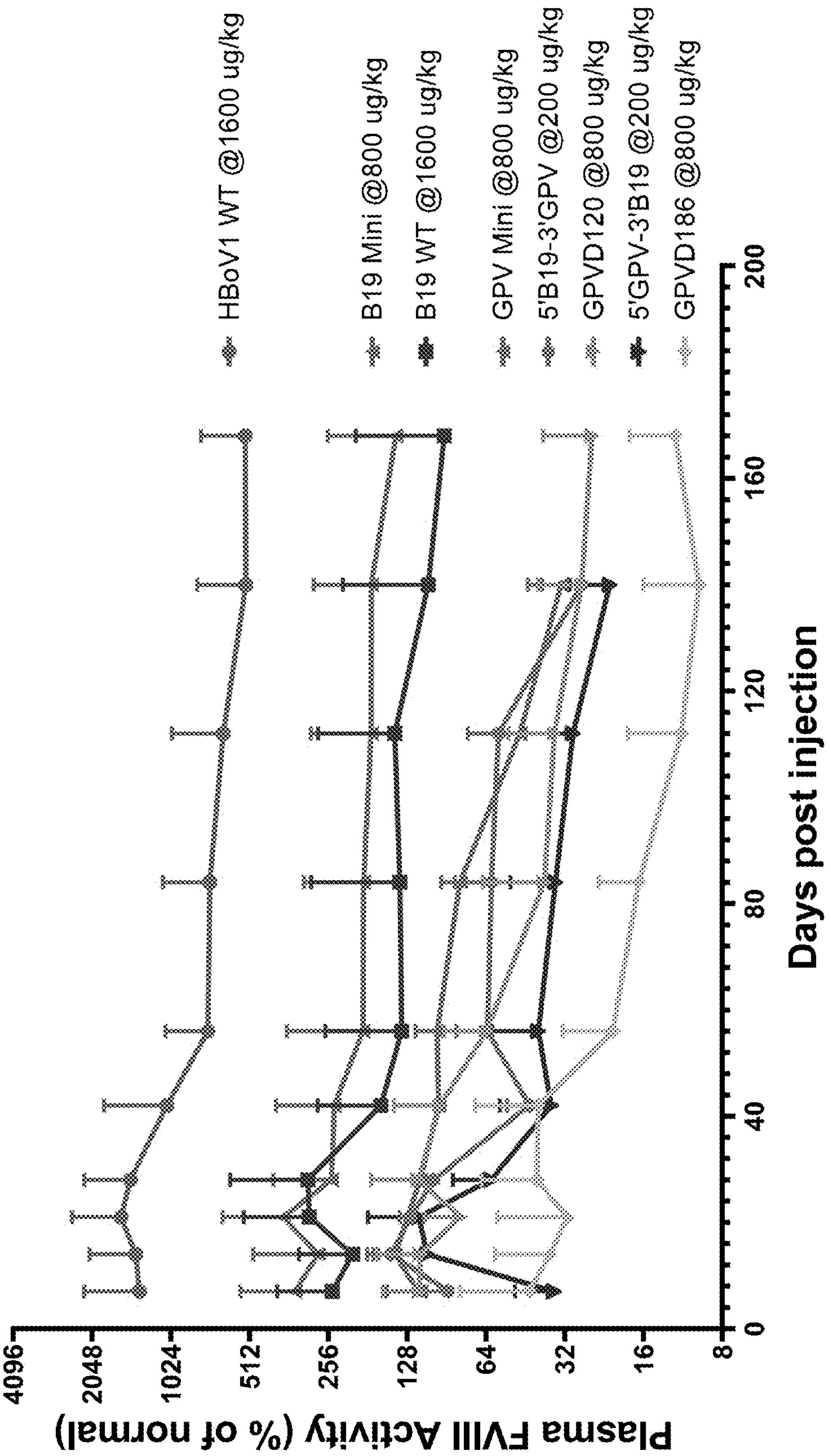
FIG. 4 shows a graphical representation of plasma FVIII activity levels measured by the Chromogenix Coatest® SP Factor VIII chromogenic assays. The plasma samples were collected at different intervals from hFVIIIR593C$^{+/+}$/HemA mice systemically injected via hydrodynamic tail-vein injection with 200, 800, or 1600 μg/kg of single-stranded V2.0 ssFVIIIXTEN (ssDNA) flanked by human Bocavirus (HBoV1), human erythrovirus (B19), Goose Parvovirus (GPV), or their variant ITRs or their combinations as indicated. Two hybrid ITR sets were also tested (5'B19-3'GPV and 5'GPV-3'B19). Error bars represent standard deviation. The ITR sequences and their variants were described in previous U.S. Patent Application No. 63/069,114.

The plasma FVIII activity normalized to percent of normal for V2.0 ssFVIIIXTEN injected animals is shown in FIG. 4. The results showed long-term persistent FVIIIXTEN expression in all the parvoviral ITRs tested albeit with varying levels. All variants or hybrids of GPV ITRs tested showed continuous decline in the levels of FVIIIXTEN expression in comparison with other parvoviral ITRs. In contrary, HBoV1 and B19 ITRs showed initial decline in FVIIIXTEN up to day 56 and then stabilized through day 168 suggesting the ITR-dependent persistency of FVIIIXTEN transgene in vivo. Unlike GPV ITRs, both B19 and HBoV1 ITRs showed significantly higher levels of FVIII expression irrespective of the variant tested suggesting the ITR-dependent stability of FVIIIXTEN transgene in vivo.

Among different parvoviral ITRs tested, HBoV1 ITRs showed significantly higher levels (>1000%) of normal FVIII activity in hFVIIIR593C$^{+/+}$/HemA mice. (FIG. 4). These results validate the functionality of the modified FVIIIXTEN expression with different parvoviral ITRs and demonstrate the ITR-dependent stability as well as persistency of transgene expression in vivo.

Example 3: Closed End FVIIIXTEN (ceFVIIIXTEN) DNA

Though ssFVIIIXTEN (ssDNA) was effective in expressing a modified FVIIIXTEN expression cassette in vivo, there are several limitations associated with ssDNA to be used as a non-viral gene therapy vector. One of them is the level of endotoxin contamination due to the prokaryotic host (*E. coli*) used for generating plasmid DNA, which also contains the extraneous sequences, such as antibiotic resistance gene and prokaryotic origin of replication, needed for selection and amplification in *E. coli*. To address these challenges and limitations, a eukaryotic cell-based system was developed to generate DNA therapeutic drug substance in a form of closed-end DNA (ceDNA) comprising of the FVIIIXTEN expression cassette with parvoviral ITRs. The genetic organization of ceDNA, resembles recombinant AAV vector DNA, but differs in conformation.

Figure 5A:
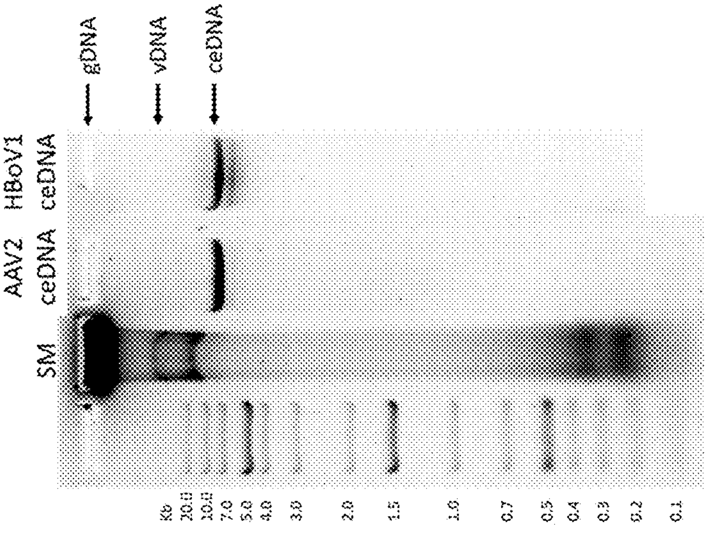
FIGS. 5A-5B are representations of the purified ceFVIIIXTEN (ceDNA) obtained from the baculovirus system and their efficacies in vivo.

To generate this DNA vector, the baculovirus insect cell system was leveraged, which is widely used for the biologics manufacturing and is the only platform approved by the FDA for recombinant influenza vaccine manufacturing. Three different approaches of ceDNA production were employed in the baculovirus system, as described in U.S. Patent Application No. 63/069,073. An exemplary purified ceDNA encoding modified FVIIIXTEN with AAV2 or HBoV1 ITRs in comparison with the starting material (SM) is shown in FIG. 5A.

To validate the functionality of modified FVIIIXTEN as expressed from ceDNA, purified ceFVIIIXTEN was injected systemically via hydrodynamic tail-vein injections in hFVIIIR593C$^{+/+}$/HemA mice at 0.3 μg, 1.0 μg, or 2.0 μg/mouse, which is equivalent to 12 μg, 40 μg, and 80 μg/kg, respectively. Plasma samples from injected mice were collected at indicated interval and FVIII activity was measured by the chromogenic assay, as described above.

Figure 5B:
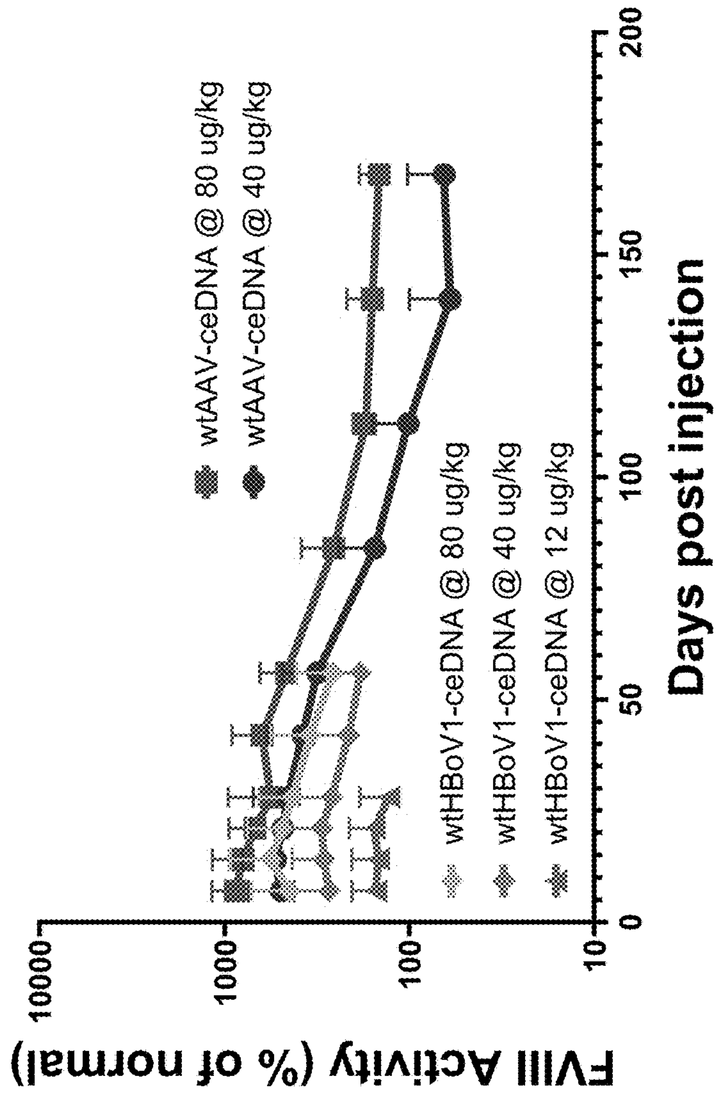

The plasma FVIII activity normalized to percent of normal for ceFVIIIXTEN injected animals is shown in FIG. 5B. The results showed dose-dependent response in HemA mice with supraphysiological levels (>500% of normal) of FVIII expression observed in the highest dose tested up to day 56 post injection. Interestingly, similar level of expression was achieved when the mice were injected with ssFVIIIXTEN at 1600 μg/kg, which is at least 20× higher the dose of ceFVIIIXTEN (80 μg/kg) (FIG. 4). This data suggests that ceDNA provides higher level of FVIII expression in comparison to the ssDNA form. Thus, these studies validate the functionality of modified FVIIIXTEN as expressed from either ssDNA or ceDNA and confirms that codon optimization along with use of optimized ITRs can produce a functional transgene and improve its long-term persistency.

Example 4: Modified FVIIIXTEN Expression Cassette

The V2.0 FVIIIXTEN expression cassette contains a mTTR promoter and enhancer element (see FIG. 1). However, this promoter is mouse-liver specific and is not well-studied or characterized to determine the liver-specificity in large animal models or in human patients. Therefore, in this study V3.0 FVIIIXTEN expression cassette (SEQ ID NO: 35) was generated by replacing the mTTR promoter and enhancer element with human liver-specific alpha-1-antitrypsin (A1AT) promoter (SEQ ID NO: 36) in the V2.0 expression cassette (FIG. 1).

Example 5: FVIIIXTEN HBoV1 mTTR vs A1AT ssDNA in Vivo Efficacy

Figure 6A:
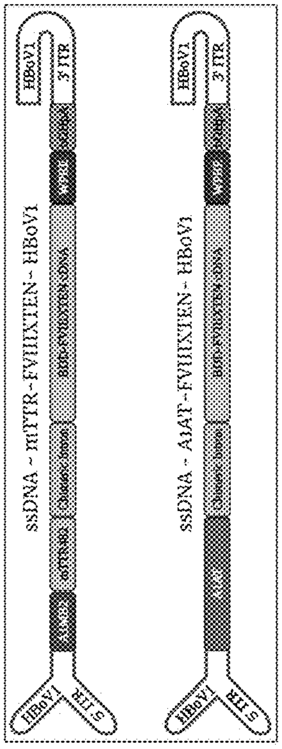
FIG. 6A-6C shows the testing of the liver-specific mTTR and human A1AT promoter driving expression of FVIIIXTEN in HBoV1 ITR constructs.
Figure 6B:
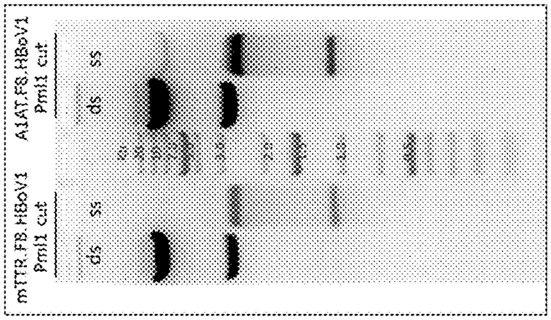

To validate the functionality of the mTTR versus the A1AT promoter in vivo, single-stranded DNA (ssDNA) comprising codon-optimized human FVIIIXTEN (ssFVIIIXTEN) with preformed HBoV1 ITRs, generating the constructs depicted in FIG. 6A. The ssFVIIIXTEN with preformed HBoV1 ITRs was generated by denaturing the double-stranded DNA (dsDNA) fragment products (mTTR or A1AT FVIII expression cassette and plasmid backbone) of PmlI digestion at 95° C. and then cooling down at 4° C. to allow the palindromic ITR sequences to fold. The resulting ssFVIIIXTEN was checked by 0.8 to 1.2% agarose gel electrophoresis. The gel analysis showed half the size of dsDNA for ssFVIIIXTEN suggesting efficient hairpin formation (FIG. 6B).

The ssFVIIIXTEN was systemically injected into hFVIIIR593C$^{+/+}$/HemA mice via hydrodynamic tail-vein injections at 10 μg/mouse. Plasma samples were collected from injected mice at 7 day intervals for 5.5 months. Plasma FVIII activity was measured by the Chromogenix Coatest® SP Factor VIII chromogenic assay, according to the manufacturer's instructions.

Figure 6C:
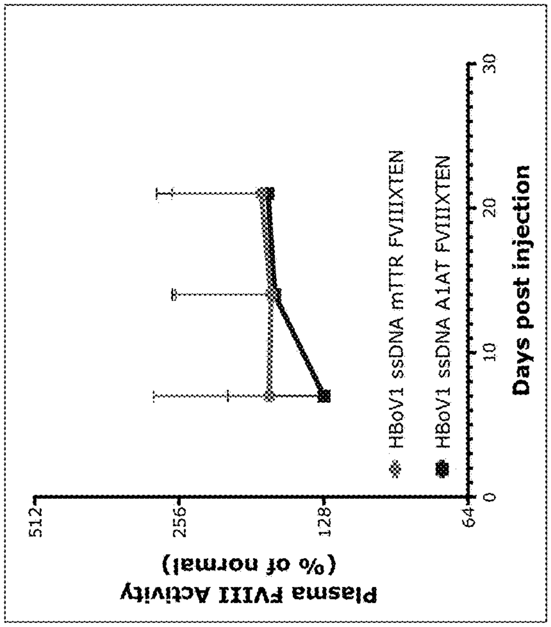

The plasma FVIII activity normalized to percent of normal for ssFVIIIXTEN injected animals is shown in FIG. 6C. These results showed equivalent levels of FVIII expression up to day 21 post-injection, suggesting there is no significant difference in FVIIIXTEN levels expressed by the mTTR or A1AT promoter in hFVIIIR593C+/+/HemA mice animal model.

Example 6: FVIIIXTEN AAV2 Full-Length vs Truncated ceDNA in Vivo Efficacy

Adeno-associated Virus (AAV) vector is known to produce different replicative forms of viral genome (e.g. monomer, dimer, or multimer) through ITR-ITR concatamerization. We previously observed that a closed-end DNA (ceDNA) vector comprising the V2.0 codon-optimized FVIIIXTEN (ceFVIIIXTEN) flanked by AAV2 WT ITRs produced a truncated species of ceFVIIIXTEN along with the monomeric and multimeric forms of vector genome in the baculovirus system. See, e.g., International Application No. PCT/US21/47218)

Figure 7A:
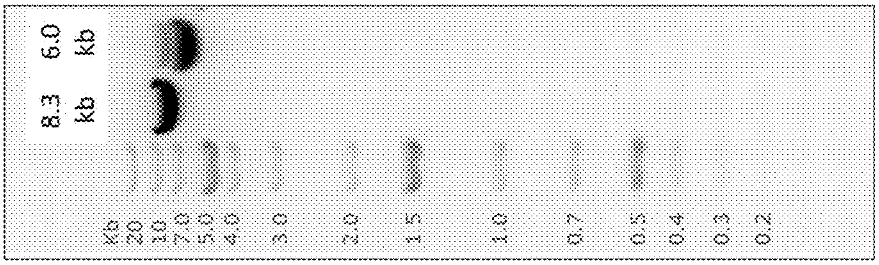
FIG. 7A-7C show the study results for the purified ceFVIIIXTEN AAV2 (ceDNA) species obtained from the baculovirus system.

In this study, to further investigate the properties of the truncated species of ceFVIIIXTEN, we purified both full-length and truncated species of ceFVIIIXTEN by continuous-elution electrophoresis, as described in International Application No. PCT/US21/47218. The purity of both species of ceFVIIIXTEN was determined by agarose gel electrophoresis and the results showed major bands corresponding to the size of full-length (8.3 kb) and truncated (6.0 kb) species of ceFVIIIXTEN (FIG. 7A).

Figure 7B:
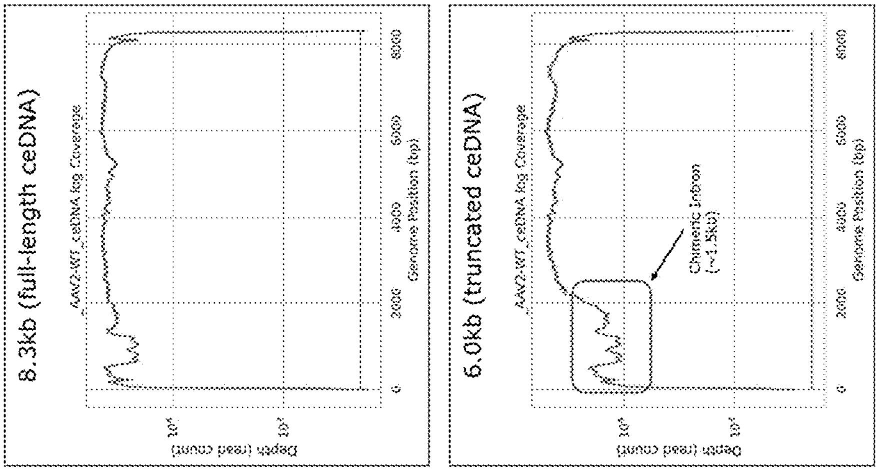

To further validate the nucleotide sequences of both species of ceFVIIIXTEN, we performed next-generation sequence (NGS) analyses on purified ceFVIIIXTEN materials using the MiSeq Illumina Sequence Analyzer. The NGS results, shown in FIG. 7B, showed >80% coverage for the full-length ceFVIIIXTEN sequence reads (top panel) and >75% coverage for the truncated ceFVIIIXTEN species (bottom panel) with some impurities coming from the host cell and/or baculoviral genome. Further analyses of NGS data revealed that the truncated ceFVIIIXTEN reads were missing a large portion of the chimeric intron region while retaining the ITRs sequences at the 5' end of the ceFVIIIXTEN (FIG. 7B, bottom panel).

Figure 7C:
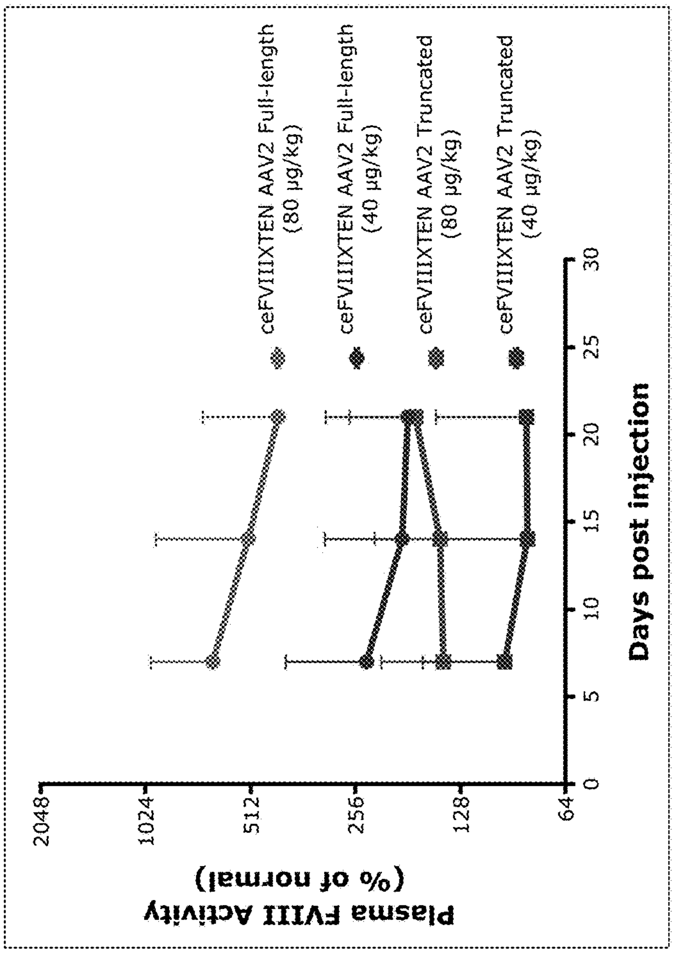

To further validate the functionality of the truncated species of ceFVIIIXTEN, purified full-length or truncated species of ceFVIIIXTEN was systemically injected in hFVIIIR593C+/+/HemA mice via hydrodynamic tail-vein injections at either 40 or 80 μg/kg. Plasma samples were collected from injected mice at 7 day intervals and plasma FVIII activity was measured by the Chromogenix Coatest® SP Factor VIII chromogenic assay, according to the manufacturer's instructions. The plasma FVIII activity normalized to percent of normal for ceFVIIIXTEN injected animals is shown in FIG. 7C.

The results showed supraphysiological levels of FVIII expression in full-length ceFVIIIXTEN injected cohorts. However, animals injected with truncated ceFVIIIXTEN-showed 2-fold lower FVIII expression at both doses tested up to day 21 post injections (FIG. 7C). This data further supports the contribution of the chimeric intron to the improvement in the expression levels of the V2.0 codon-optimized FVIIIXTEN in vivo (FIG. 7C).

Example 7: FVIIIXTEN Closed-End DNA (ceFVIIIXTEN) in Vivo Efficacy

Figure 8A:
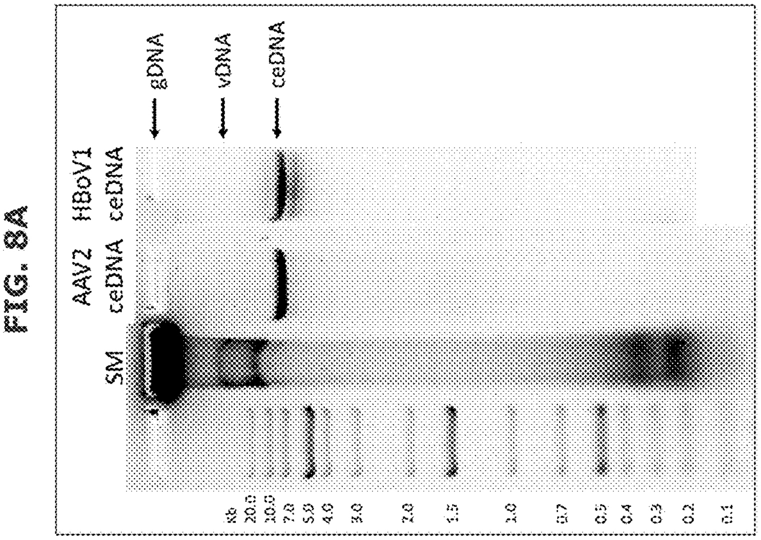
FIGS. 8A-8B are representations of the purified ceFVIIIXTEN (ceDNA) obtained from the baculovirus system and their efficacies in vivo.

In this study, we investigated the in vivo efficacy of ceDNAencoding modified FVIIIXTEN and flanked by either AAV2 or HBoV1 ITRs. ceFVIIIXTEN DNA was generated in the baculovirus system using either AAV2 or HBoV1 ITRs as described previously (see, e.g. International Application No. PCT/US21/47218). Agarose gel was used to analyze the purity of each ceDNA in comparison to the starting material (SM) is shown in FIG. 8A.

Purified ceFVIIIXTEN was injected systemically via hydrodynamic tail-vein injections in hFVIIIR593C+/+/HemA mice at either 1.0 μg or 2.0 μg/mouse, which is equivalent to either 40 μg or 80 μg/kg, respectively. Plasma samples from injected mice were collected at interval and FVIII activity was measured by the chromogenic assay, as described above.

Figure 8B:
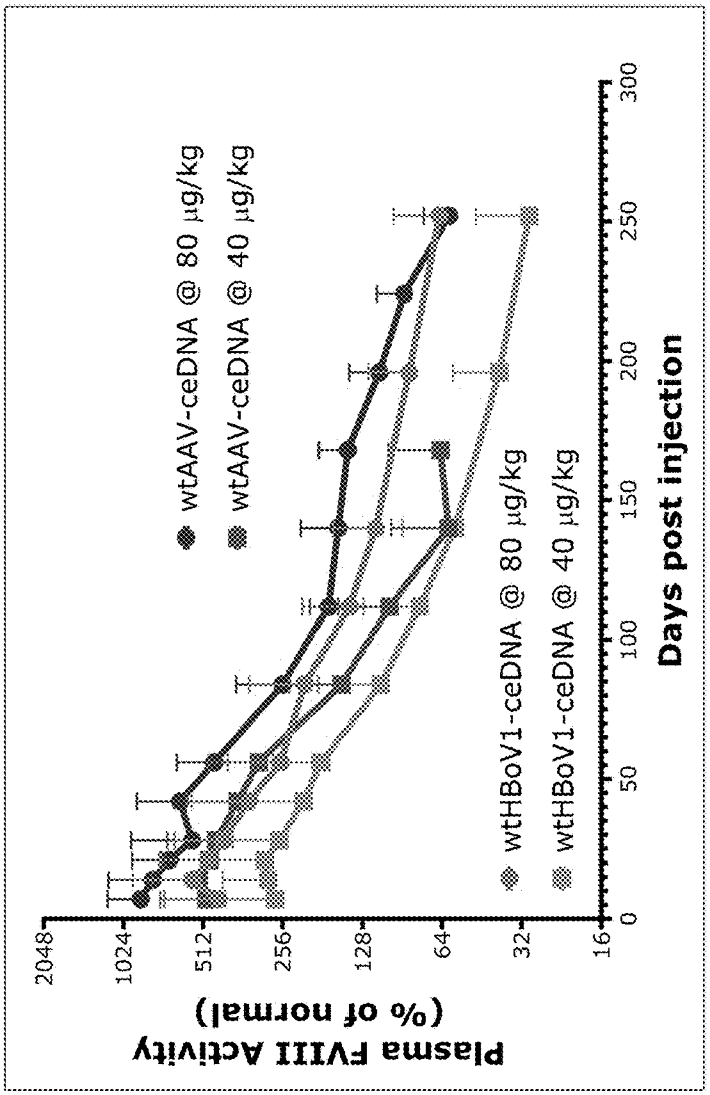

The plasma FVIII activity normalized to percent of normal for ceFVIIIXTEN injected animals is shown in FIG. 8B.

The results showed comparable FVIII expression levels for ceDNA vectors flanked by either AAV2 or HBoV1 ITRs. As seen previously, FVIII expression levels gradually declined in treated animals up to day 256, suggesting the loss of vector over time in the liver hepatocytes. These studies validate the functionality and long-term persistence of modified V2.0 FVIIIXTEN as expressed from ceDNA vectors comprising AAV2 or HBoV1 ITRs.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

All patents and publications cited herein are incorporated by reference herein in their entirety.

SEQUENCES

TABLE 1

Additional Nucleotide and Amino Acid Sequences

| SEQ ID NO/ Description | Nucleotide or amino acid sequence |
|---|---|
| SEQ ID NO. 1: HBoV1 5' ITR | GTGGTTGTACAGACGCCATCTTGGAATCCAATATGTCTGCCGGCTCAGTCATGCCTGCGCTGCGCGCAGCGCGCTGCG<br>CGCGCGCATGATCTAATCGCCGGCAGACATATTGGATTCCAAGATGGCGTCTGTACAACCAC |
| SEQ ID NO. 2: HBoV1 3' ITR | TTGCTTATGCAATCGCGAAACTCTATATCTTTTAATGTGTTGTTGTTGTACATGCGCCATCTTAGTTTTATATCAGCT<br>GGCGCCTTAGTTATATAACATGCATGTTATATAACTAAGGCGCCAGCTGATATAAAACTAAGATGGCGCATGTACAAC<br>AACAACACATTAAAAGATATAGAGTTTCGCGATTGCATAAGCAA |
| SEQ ID NO. 3: HBoV1-5'ITR-mTTR482-Intron-coBDDFVHIX TEN (V2.0)-WPRE-bGHPolyA-HBoV1-3'ITR | GTATACCTGCAGGCTAGCCACGTGTTGTTGTTGTACATGCGCCATCTTAGTTTTATATCAGCTGGCGCCTTAGTTATA<br>TAACATGCATGTTATATAACTAAGGCGCCAGCTGATATAAAACTAAGATGGCGCATGTACAACAACAACACATTAAAA<br>GATATAGAGTTTCGCGATTGCAAGCTTGGCCCCAGGTTAATTTTTAAAAAGCAGTCAAAGGTCAAAGTGGCCCTTGGC<br>AGCATTTACTCTCTCTATTGACTTTGGTTAATAATCTCAGGAGCACAAACATTCCTGGAGGCAGGAGAAGAAATCAAC<br>ATCCTGGACTTATCCTCTGGGCCTCTCCCCACCTTCGATGGCCCCAGGTTAATTTTTAAAAAGCAGTCAAAGGTCAAA<br>GTGGCCCTTGGCAGCATTTACTCTCTCTATTGACTTTGGTTAATAATCTCAGGAGCACAAACATTCCTGGAGGCAGGA<br>GAAGAAATCAACATCCTGGACTTATCCTCTGGGCCTCTCCCCACCGATATCTACCTGCTGATCGCCCGGCCCCTGTTC<br>AAACATGTCCTAATACTCTGTCGGGGCAAAGGTCGGCAGTAGTTTTCCATCTTACTCAACATCCTCCCAGTGTACGTA<br>GGATCCTGTCTGTCTGCACATTTCGTAGAGCGAGTGTTCCGATACTCTAATCTCCCGGGGCAAAGGTCGTATTGACTT<br>AGGTTACTTATTCTCCTTTTGTTGACTAAGTCAATAATCAGAATCAGCAGGTTTGGAGTCAGCTTGGCAGGGATCAGC<br>AGCCTGGGTTGGAAGGAGGGGGTATAAAAGCCCCTTCACCAGGAGAAGCCGTCACACAGATCCACAAGCTCCTGCTAG<br>GAATTCTCAGGAGCACAAACATTCCTGGAGGCAGGAGAAGAAATCAACATCCTGGACTTATCCTCTGGGCCTCTCCCC<br>ACCGATATCTACCTGCTGATCGCCCGGCCCCTGTTCAAACATGTCCTAATACTCTGTCGGGGCAAAGGTCGGCAGTAG<br>TTTTCCATCTTACTCAACATCCTCCCAGTGTACGTAGGATCCTGTCTGTCTGCACATTTCGTAGAGCGAGTGTTCCGA |

TABLE 1-continued

| Additional Nucleotide and Amino Acid Sequences | |
|---|---|
| SEQ ID NO/ Description | Nucleotide or amino acid sequence |
| | TACTCTAATCTCCCGGGGCAAAGGTCGTATTGACTTAGGTTACTTATTCTCCTTTTGTTGACTAAGTCAATAATCAGA ATCAGCAGGTTTGGAGTCAGCTTGGCAGGGATCAGCAGCCTGGGTTGGAAGGAGGGGGTATAAAAGCCCCTTCACCAG GAGAAGCCGTCACACAGATCCACAAGCTCCTGCTAGAGTCGCTGCGCGCTGCCTTCGCCCCGTGCCCCGCTCCGCCGC CGCCTCGCGCCGCCCGCCCCGGCTCTGACTGACCGCGTTACTCCCACAGGTGAGCGGGCGGGACGGCCCTTCTCCTCC GGGCTGTAATTAGCGCTTGGTTTATTGACGGCTTGTTTCTTTTCTGTGGCTGCGTGAAAGCCTTGAGGGGCTCCGGGA AGGCCCTTTGTGCGGGGGGAGCGGCTCGGGGGGTGCGTGCGTGTGTGTGTGCGTGGGGAGCGCCGCGTGCGGCTCCGC GCTGCCCGGCGGCTGTGAGCGCTGCGGGCGCGGCGCGGGGCTTTGTGCGCTCCGCAGTGTGCGCGAGGGGAGCGCGGC CGGGGGCGGTGCCCCGCGGTGCGGGGGGGGCTGCGAGGGGAACAAAGGCTGCGTGCGGGGTGTGTGCGTGGGGGGGTG AGCAGGGGGTGTGGGCGCGTCGGTCGGGCTGCAACCCCCCCTGCACCCCCCTCCCCGAGTTGCTGAGCACGGCCCGGC TTCGGGTGCGGGGCTCCGTACGGGGCGTGGCGCGGGGCTCGCCGTGCCGGGCGGGGGGTGGCGGCAGGTGGGGGTGCC GGGCGGGGCGGGGCCGCCTCGGGCCGGGGAGGGCTCGGGGGAGGGGCGCGGCGGCCCCCGGAGCGCCGGCGGCTGTCG AGGCGCGGCGAGCCGCAGCCATTGCCTTTTATGGTAATCGTGCGAGAGGGCGCAGGGACTTCCTTTGTCCCAAATCTG TGCGGAGCCGAAATCTGGGAGGCGCCGCCGCACCCCCTCTAGCGGGCGCGGGGCGAAGCGGTGCGGCGCCGGCAGGAA GGAAATGGGCGGGGAGGGCCTTCGTGCGTCGCCGCGCCGCCGTCCCCTTCTCCCTCTCCAGCCTCGGGGCTGTCCGCG GGGGGACGGCTGCCTTCGGGGGGGACGGGGCAGGGCGGGGTTCGGCTTCTGGCGTGTGACCGGCGGCTCTAGAGCCTC TGCTAACCTTGTTCTTGCCTTCTTCTTTTTCCTACAGCTCCTGGGCAACGTGCTGGTTATTGTGCTGTCTCATCATTT TGGCAAAGAATTACTCGAGGCCACCATGCAGATTGAACTGTCCACTTGCTTCTTCCTGTGCCTCCTGCGGTTTTGCTT CTCGGCCACCCGCCGGTATTACTTAGGTGCTGTGGAACTGAGCTGGGACTACATGCAGTCCGACCTGGGAGAACTGCC GGTGGACGCGAGATTCCCACCTAGAGTCCCGAAGTCCTTCCCATTCAACACCTCCGTGGTCTACAAAAAGACCCTGTT CGTGGAGTTCACTGACCACCTTTTCAATATTGCCAAGCCGCGCCCCCCCTGGATGGGCCTGCTTGGTCCTACGATCCA AGCAGAGGTCTACGACACCGTGGTCATCACACTGAAGAACATGGCCTCACACCCCGTGTCGCTGCATGCTGTGGGAGT GTCCTACTGGAAGGCCTCAGAGGGTGCCGAATATGATGACCAGACCAGCCAGAGGGAAAAGGAGGATGACAAAGTGTT CCCGGGTGGCAGCCACACTTACGTGTGGCAAGTGCTGAAGGAAAACGGGCCTATGGCGTCGGACCCCCTATGCCTGAC CTACTCCTACCTGTCCCATGTGGACCTTGTGAAGGATCTCAACTCGGGACTGATCGGCGCCCTCTTGGTGTGCAGAGA AGGCAGCCTGGCGAAGGAAAAGACTCAGACCCTGCACAAGTTCATTCTGTTGTTTGCTGTGTTCGATGAAGGAAAGTC CTGGCACTCAGAAACCAAGAACTCGCTGATGCAGGATAGAGATGCGGCCTCGGCCAGAGCCTGGCCTAAAATGCACAC CGTCAACGGATATGTGAACAGGTCGCTCCCTGGCCTCATCGGCTGCCACAGAAAGTCCGTGTATTGGCATGTGATCGG CATGGGTACTACTCCGGAAGTGCATAGTATCTTTCTGGAGGGCCATACCTTCTTGGTGCGCAACCACAGACAGGCCTC GCTGGAAATCTCGCCTATCACTTTCTTGACTGCGCAGACCCTCCTTATGGACCTTGGACAGTTCCTGCTGTTCTGTCA CATCAGCTCCCATCAGCATGATGGGATGGAGGCCTATGTCAAAGTGGACTCCTGCCCTGAGGAGCCACAGCTCCGGAT GAAGAACAATGAGGAAGCGGAGGATTACGACGACGACCTGACTGACAGCGAAATGGACGTCGTGCGATTCGATGACGA CAACAGCCCGTCCTTCATCCAAATTAGATCAGTGGCGAAGAAGCACCCCAAGACCTGGGTGCACTACATTGCCGCCGA GGAAGAGGACTGGGACTACGCGCCGCTGGTGCTGGCGCCAGACGACAGGAGCTACAAGTCCCAGTACCTCAACAACGG GCCGCAGCGCATTGGCAGGAAGTACAAGAAAGTCCGCTTCATGGCCTACACTGATGAAACCTTCAAGACGAGGGAAGC CATCCAGCACGAGTCAGGCATCCTGGGACCGCTCCTTTACGGCGAAGTCGGGGATACCCTGCTCATCATTTTCAAGAA CCAGGCATCGCGGCCCTACAACATCTACCCTCACGGGATCACAGACGTGCGCCCGCTCTACTCCCGCCGGCTGCCCAA GGGAGTGAAGCACCTGAAGGATTTTCCCATCCTGCCGGGAGAAATCTTCAAGTACAAGTGGACCGTGACTGTGGAAGA TGGCCCTACCAAGTCGGACCCTCGCTGTCTGACCCGGTACTATTCCTCGTTTGTGAACATGGAGCGCGACCTGGCCTC GGGGCTGATTGGTCCGCTGCTGATCTGCTACAAGGAGTCCGTGGACCAGCGCGGGAACCAGATCATGTCCGACAAGCG CAACGTGATCCTGTTCTCTGTCTTTGATGAAAACAGATCGTGGTACTTGACTGAGAATATCCAGCGGTTCCTGCCCAA CCCAGCGGGAGTGCAACTGGAGGACCCGGAGTTCCAGGCCTCAAACATTATGCACTCTATCAACGGCTATGTGTTCGA CTCGCTCCAACTGAGCGTGTGCCTGCATGAAGTGGCATACTGGTACATTCTGTCCATCGGAGCCCAGACCGACTTCCT GTCCGTGTTCTTCTCCGGATACACCTTCAAGCATAAGATGGTGTACGAGGACACTCTGACCCTCTTCCCATTTTCCGG AGAAACTGTGTTCATGTCAATGGAAAACCCGGGCTTGTGGATTCTGGGTTGCCATAACTCGGACTTCCGGAATAGAGG GATGACCGCCCTGCTGAAAGTGTCCAGCTGTGACAAGAATACCGGCGATTACTACGAGGACAGCTATGAGGACATCTC CGCTTATCTGCTGTCCAAGAACAACGCCATTGAACCCAGGTCCTTCTCCCAAAACGGTGCACCGACCTCCGAAAGCGC CACCCCAGAGTCAGGACCTGGCTCGGAACCGGCTACCTCGGGCTCAGAGACACCGGGGACTTCCGAGTCCGCAACCCC CGAGAGTGGACCCGGATCCGAACCAGCAACCTCAGGATCAGAAACCCCGGGAACTTCGGAATCCGCCACTCCCGAGTC GGGACCAGGCACCTCCACTGAGCCTTCCGAGGGAAGCGCCCCCGGATCCCCTGCTGGATCCCCTACCAGCACTGAAGA AGGCACCTCAGAATCCGCGACCCCTGAGTCCGGCCCTGGAAGCGAACCCGCCACCTCCGGTTCCGAAACCCCTGGGAC TAGCGAGAGCGCCACTCCGGAATCGGGCCCAGGAAGCCCTGCCGGATCCCCGACCAGCACCGAGGAGGGAAGCCCCGC CGGGTCACCGACTTCCACTGAGGAGGGAGCCTCATCCCCCCCCGTGCTGAAGCGGCATCAAAGAGAGATCACCAGGAC CACTCTCCAGTCCGATCAGGAAGAAATTGACTACGACGATACTATCAGCGTGGAGATGAAGAAGGAGGACTTCGACAT CTACGATGAGGATGAGAACCAGTCCCCTCGGAGCTTTCAGAAGAAAACCCGCCACTACTTCATCGCTGCCGTGGAGCG GCTGTGGGATTACGGGATGTCCAGCTCACCGCATGTGCTGCGGAATAGAGCGCAGTCAGGATCGGTGCCCCAGTTCAA GAAGGTCGTGTTCCAAGAGTTCACCGACGGGTCCTTCACTCAACCCCTGTACCGGGGCGAACTCAACGAACACCTGGG ACTGCTTGGGCCGTATATCAGGGCAGAAGTGGAAGATAACATCATGGTCACCTTCCGCAACCAGGCCTCCCGGCCGTA CAGCTTCTACTCTTCACTGATCTCCTACGAGGAAGATCAGCGGCAGGGAGCCGAGCCCCGGAAGAACTTCGTCAAGCC TAACGAAACTAAGACCTACTTTTGGAAGGTCCAGCATCACATGGCCCCGACCAAAGACGAGTTCGACTGTAAAGCCTG GGCCTACTTCTCCGATGTGGACCTGGAGAAGGACGTGCACTCGGGACTCATTGGCCCGCTCCTTGTGTGCCATACTAA TACCCTGAACCCTGCTCACGGTCGCCAAGTCACAGTGCAGGAGTTCGCCCTCTTCTTCACCATCTTCGATGAAACAAA GTCCTGGTACTTTACTGAGAACATGGAACGCAATTGCAGGGCACCCTGCAACATCCAGATGGAAGATCCCACCTTCAA GGAAAACTACCGGTTTCATGCCATTAACGGCTACATAATGGACACGTTGCCAGGACTGGTCATGGCCCAGGACCAGAG AATCCGGTGGTATCTGCTCTCCATGGGCTCCAACGAAAACATTCACAGCATTCATTTTTCCGGCCATGTGTTCACCGT CCGGAAGAAGGAAGAGTACAAGATGGCTCTGTACAACCTCTACCCTGGAGTGTTCGAGACTGTGGAAATGCTGCCTAG CAAGGCCGGCATTTGGAGAGTGGAATGCCTGATCGGAGAGCATTTGCACGCCGGAATGTCCACCCTGTTTCTTGTGTA CTCCAACAAGTGCCAGACCCCGCTGGGAATGGCCTCAGGTCATATTAGGGATTTCCAGATCACTGCTTCGGGGCAGTA CGGGCAGTGGGCACCTAAGTTGGCCCGGCTGCACTACTCTGGCTCCATCAATGCCTGGTCCACCAAGGAACCCTTCTC CTGGATTAAGGTGGACCTCCTGGCCCCAATGATTATTCACGGTATTAAGACCCAGGGTGCCCGACAGAAGTTCTCCTC ACTCTACATCTCGCAATTCATCATAATGTACAGCCTGGATGGGAAGAAGTGGCAGACCTACCGGGGAAACTCCACTGG AACGCTCATGGTGTTTTTCGGCAACGTGGACTCCTCCGGCATTAAGCACAACATCTTCAACCCTCCGATCATTGCTCG GTACATCCGGCTGCACCCAACTCACTACAGCATCCGGTCCACCCTGCGGATGGAACTGATGGGTTGTGACCTGAACTC CTGCTCCATGCCCCTTGGGATGGAATCCAAGGCCATTAGCGATGCACAGATCACCGCCTCTTCATACTTCACCAACAT GTTCGCGACCTGGTCCCCGTCGAAGGCCCGCCTGCACCTCCAAGGTCGCTCCAATGCGTGGCGGCCTCAAGTGAACAA CCCCAAGGAGTGGCTCCAGGTCGACTTCCAAAAGACCATGAAGGTCACCGGAGTGACCACCCAGGGCGTGAAGTCCCT |

TABLE 1-continued

Additional Nucleotide and Amino Acid Sequences

| SEQ ID NO/ Description | Nucleotide or amino acid sequence |
| --- | --- |
| | GCTGACCTCTATGTACGTTAAGGAGTTCCTCATCTCCTCAAGCCAAGACGGACATCAGTGGACCCTGTTCTTCCAAAA<br>CGGAAAAGTCAAAGTATTCCAGGGCAACCAGGACTCCTTCACCCCTGTGGTCAACAGCCTGGACCCCCCATTGCTGAC<br>CCGCTACCTCCGCATCCACCCCCAAAGCTGGGTCCACCAGATCGCACTGCGCATGGAGGTCCTTGGATGCGAAGCCCA<br>AGATCTGTACTAAGCGGCCGCTCATAATCAACCTCTGGATTACAAAATTTGTGAAAGATTGACTGGTATTCTTAACTA<br>TGTTGCTCCTTTTACGCTATGTGGATACGCTGCTTTAATGCCTTTGTATCATGCTATTGCTTCCCGTATGGCTTTCAT<br>TTTCTCCTCCTTGTATAAATCCTGGTTGCTGTCTCTTTATGAGGAGTTGTGGCCCGTTGTCAGGCAACGTGGCGTGGT<br>GTGCACTGTGTTTGCTGACGCAACCCCCACTGGTTGGGGCATTGCCACCACCTGTCAGCTCCTTTCCGGGACTTTCGC<br>TTTCCCCCTCCCTATTGCCACGGCGGAACTCATCGCCGCCTGCCTTGCCCGCTGCTGGACAGGGGCTCGGCTGTTGGG<br>CACTGACAATTCCGTGGTGTTGTCGGGGAAATCATCGTCCTTTCCTTGGCTGCTCGCCTGTGTTGCCACCTGGATTCT<br>GCGCGGGACGTCCTTCTGCTACGTCCCTTCGGCCCTCAATCCAGCGGACCTTCCTTCCCGCGGCCTGCTGCCGGCTCT<br>GCGGCCTCTTCCGCGTCTTCGCCTTCGCCCTCAGACGAGTCGGATCTCCCTTTGGGCCGCCTCCCCGCTGCCTAGGCG<br>ACTGTGCCTTCTAGTTGCCAGCCATCTGTTGTTTGCCCCTCCCCCGTGCCTTCCTTGACCCTGGAAGGTGCCACTCCC<br>ACTGTCCTTTCCTAATAAAATGAGGAAATTGCATCGCATTGTCTGAGTAGGTGTCATTCTATTCTGGGGGGTGGGGTG<br>GGGCAGGACAGCAAGGGGGAGGATTGGGAAGACAATAGCAGGCATGCTGGGGAAGACCATGGGCGCGCCAGGCCTGTC<br>GACGCCCGGGCGGTACCGCGATCGCTCGCGACGCATAAAGTATATGTGACGTGGTTGTACAGACGCCATCTTGGAATC<br>CAATATGTCTGCCGGCGATTAGATCATGCGCGCGCAGCGCGCTGCGCGCAGCGCAGGCATGACTGAGCCGGCAGAC<br>ATATTGGATTCCAAGATGGCGTCTGTACAACCACGTGCTTAAGCTGCAGACTAGTGAGCTCGTTAAC |
| SEQ ID NO. 4: Sf codon optimized HBoV1 NS1 | GCGGCCGCGGATCCGCCACCATGGCATTCAATCCGCCCGTAATACGCGCATTTTCACAACCCGCCTTTACGTATGTCT<br>TTAAGTTTCCGTACCCTCAATGGAAAGAGAAAGAGTGGCTACTGCACGCGTTGCTTGCCCACGGCACCGAGCAGTCCA<br>TGATTCAATTACGTAACTGTGCCCCACACCCGGACGAGGATATTATCCGGGACGATCTTCTAATAAGTTTGGAAGATA<br>GGCATTTCGGGGCGGTCCTGTGTAAAGCGGTATACATGGCTACTACCACGTTGATGTCTCACAAGCAACGCAATATGT<br>TCCCAAGGTGCGACATAATCGTTCAGTCAGAGTTAGGTGAAAAAAATTTACATTGTCATATTATCGTTGGAGGCGAAG<br>GCCTATCAAAGAGAAACGCTAAGAGCTCTTGCGCTCAGTTTTACGGACTTATATTAGCAGAAATTATCCAGCGCTGTA<br>AGAGTTTACTAGCCACCCGTCCGTTTGAGCCGGAAGAAGCGGATATATTTCATACGTTGAAGAAAGCGGAGCGCGAGG<br>CCTGGGGTGGAGTTACTGGCGGTAACATGCAAATCTTACAATACAGGGACCGTCGGGGTGACCTGCATGCACAGACTG<br>TTGATCCCCTCAGATTCTTCAAAAATTATTTGTTACCGAAGAACCGATGCATAAGTAGTTACAGCAAACCTGATGTCT<br>GTACTAGCCCTGATAACTGGTTCATTCTGGCCGAAAAAACGTACTCGCATACACTTATCAATGGATTGCCGCTTCCCG<br>AGCACTATCGAAAAAACTATCATGCCACCCTGGATAATGAAGTTATACCTGGACCACAGACTATGGCGTATGGAGGGA<br>GAGGCCCTTGGGAACATTTACCCGAGGTGGGTGACCAGAGGCTTGCCGCAAGTTCCGTGAGCACTACGTATAAGCCAA<br>ACAAGAAGGAGAAGCTAATGCTCAACCTCCTCGACAAGTGTAAGGAGTTGAATCTTCTAGTTTATGAGGATCTTGTAG<br>CGAACTGCCCAGAGCTGCTGCTCATGCTAGAAGGCCAACCTGGAGGTGCTCGACTCATCGAGCAAGTACTAGGAATGC<br>ATCACATCAATGTATGCTCGAATTTCACCGCGCTAACGTACCTCTTCCATCTGCATCCGGTGACATCGCTGGATAGTG<br>ACAACAAAGCGTTACAGCTTTTACTAATTCAAGGGTACAACCCCCTGGCAGTGGGGCATGCTCTCTGTTGTGTGTTAA<br>ACAAACAATTTGGTAAACAGAACACAGTCTGTTTTTACGGGCCAGCATCTACTGGGAAAACAAATATGGCAAAAGCGA<br>TTGTGCAGGGAATCCGGCTATATGGCTGCGTCAACCATCTTAACAAGGGTTTTGTTTTCAATGATTGTCGACAACGCC<br>TCGTAGTCTGGTGGGAGGAATGCCTAATGCACCAGGACTGGGTGGAGCCAGCAAAGTGTATTCTTGGCGGGACCGAAT<br>GTCGTATCGACGTCAAGCACAGAGATTCTGTCCTATTGACACAAACGCCTGTAATAATTTCGACTAATCACGACATTT<br>ACGCCGTCGTGGGAGGGAATTCGGTGTCTCACGTTCACGCTGCGCCTCTCAAAGAACGGGTTATTCAGCTGAATTTTA<br>TGAAACAACTCCCCCAAACTTTTGGTGAGATAACCGCCACAGAAATCGCTGCTCTGCTACAGTGGTGCTTTAATGAAT<br>ATGACTGCACCCTGACAGGTTTCAAACAGAAGTGGAATTTGGACAAGATACCTAACTCATTCCCGTTGGGGGTATTGT<br>GCCCAACACATTCCCAAGATTTCACACTTCACGAAAATGGGTATTGCACGGACTGCGGGGGCTACCTTCCCCACTCCG<br>CTGATAATTCAATGTATACCGATCGGGCTAGCGAAACATCCACCGGCGACATAACGCCCTCCAAATGATTCGAATCTA<br>GAGCCTGCAGTCTCGAGGCATGCGGTACC |
| SEQ ID NO. 5: Outside Primer | GTGGACGTGAAAGAAACC |
| SEQ ID NO. 6: Inside Primer | GGTCATAGCTGTTTCCTGTG |
| SEQ ID NO. 7: hr5.ie1.neo.p 10PAS | ATTAAGCTTCCGCGTAAAACACAATCAAGTATGAGTCATAAGCTGATGTCATGTTTTGCACACGGCTCATAACCGAAC<br>TGGCTTTACGAGTAGAATTCTACTTGTAACGCACGATCAGTGGATGATGTCATTTGTTTTTCAAATCGAGATGATGTC<br>ATGTTTTGCACACGGCTCATAAACTCGCTTTACGGGTAGAATTCTACGTGTAACGCACGATCGATTGATGAGTCATTT<br>GTTTTGCAATATGATATCATACAATATGACTCATTTGTTTTTCAAAACCGAACTTGATTTACGGGTAGAATTCTACTT<br>GTAAAGCACAATCAAAAAGATGATGTCATTTGTTTTTCAAAACTGAACTCGCTTTACGAGTAGAATTCTACGTGTAAA<br>ACACAATCAAGAAATGATGTCATTTGTTATAAAAATAAAAGCTGATGTCATGTTTTGCACATGGCTCATAACTAAACT<br>CGCTTTACGGGTAGAATTCTACGCGTCGATGTCTTTGTGATGCGCGCGACATTTTTGTAGGTTATTGATAAAATGA<br>ACGGATACGTTGCCCGACATTATCATTAAATCCTTGGCGTAGAATTTGTCGGGTCCATTGTCCGTGTGCGCTAGCATG<br>CCCGTAACGGACCTCGTACTTTTGGCTTCAAAGGTTTTGCGCACAGACAAAATGTGCCACACTTGCAGCTCTGCATGT<br>GTGCGCGTTACCACAAATCCCAACGGCGCAGTGTACTTGTTGTATGCAAATAAATCTCGATAAAGGCGCGGCGCGCGA<br>ATGCAGCTGATCACGTACGCTCCTCGTGTTCCGTTCAAGGACGGTGTTATCGACCTCAGATTAATGTTTATCGGCCGA<br>CTGTTTTCGTATCCGCTCACCAAACGCGTTTTTGCATTAACATTGTATGTCGGCGGATGTTCTATATCTAATTTGAAT<br>AAATAAACGATAACCGCGTTGGTTTTAGAGGGCATAATAAAAGAAATATTGTTATCGTGTTCGCCATTAGGGCAGTAT<br>AAATTGACGTTCATGTTGGATATTGTTTCAGTTGCAAGTTGACACTGGCGGCGACAAGATCGTGAACAACCAAGTGAC<br>GCGGCCGCATTTGTAAAAAAAAAATAAATAAAAATGATCGAGCAGGACGGCCTGCACGCTGGTTCTCCAGCTGCTTGG<br>GTCGAGCGTCTGTTCGGTTACGACTGGGCTCAGCAGACCATCGGTTGCTCCGACGCTGCTGTGTTCCGTCTGTCCGCT<br>CAGGGTCGTCCCGTGCTGTTCGTCAAGACCGACCTGTCCGGTGCTCTGAACGAGCTGCAGGACGAGGCTGCTCGTCTG<br>TCCTGGCTGGCTACCACTGGTGTCCCTTGCGCTGCTGTCCTGGACGTGGTCACTGAGGCTGGTCGTGACTGGCTGCTG<br>CTGGGAGAAGTGCCTGGACAGGACCTGCTGTCCAGCCACCTGGCTCCAGCTGAGAAGGTGTCCATCATGGCTGACGCT<br>ATGCGTCGTCTGCACACCCTGGACCCTGCTACCTGCCCCTTCGACCACCAAGCTAAGCACCGTATCGAGCGTGCTCGT<br>ACCCGTATGGAAGCTGGCCTGGTGGACCAGGACGACCTGGACGAAGAACACCAGGGACTGGCCCCTGCTGAGCTGTTC |

TABLE 1-continued

Additional Nucleotide and Amino Acid Sequences

| SEQ ID NO/ Description | Nucleotide or amino acid sequence |
|---|---|
| | GCTCGTCTGAAGGCTCGTATGCCCGACGGCGAGGACCTGGTGGTTACTCACGGCGACGCTTGCCTGCCCAACATCATG<br>GTCGAGAACGGTCGTTTCTCCGGTTTCATCGACTGCGGTCGTCTGGGTGTCGCTGACCGTTACCAGGATATCGCTCTG<br>GCTACCCGTGATATCGCTGAGGAACTGGGTGGCGAGTGGGCTGACAGATTCCTGGTGCTGTACGGTATCGCTGCTCCC<br>GACTCCCAGCGTATCGCTTTCTACCGTCTGCTGGACGAGTTCTTCTAAGCCCCTTGTAAACGCCACAATTGTGTTTGT<br>TGCAAATAAACCCATGATTATTTGATTAAAATTGTTGTTTTCTTTGTTCATAGACAATAGTGTGTTTTGCCTAAACGG<br>GTACC |
| SEQ ID NO. 8: hr5.ie1.eGFP. p10PAS | ATTAAGCTTCCGCGTAAAACACAATCAAGTATGAGTCATAAGCTGATGTCATGTTTTGCACACGGCTCATAACCGAAC<br>TGGCTTTACGAGTAGAATTCTACTTGTAACGCACGATCAGTGGATGATGTCATTTGTTTTTCAAATCGAGATGATGTC<br>ATGTTTTGCACACGGCTCATAAACTCGCTTTACGGGTAGAATTCTACGTGTAACGCACGATCGATTGATGAGTCATTT<br>GTTTTGCAATATGATATCATACAATATGACTCATTTGTTTTTCAAAACCGAACTTGATTTACGGGTAGAATTCTACTT<br>GTAAAGCACAATCAAAAAGATGATGTCATTTGTTTTTCAAAACTGAACTCGCTTTACGAGTAGAATTCTACGTGTAAA<br>ACACAATCAAGAAATGATGTCATTTGTTATAAAAATAAAAGCTGATGTCATGTTTTGCACATGGCTCATAACTAAACT<br>CGCTTTACGGGTAGAATTCTACGCGCGTCGATGTCTTTGTGATGCGCGCGACATTTTTGTAGGTTATTGATAAAATGA<br>ACGGATACGTTGCCCGACATTATCATTAAATCCTTGGCGTAGAATTTGTCGGGTCCATTGTCCGTGTGCGCTAGCATG<br>CCCGTAACGGACCTCGTACTTTTGGCTTCAAAGGTTTTGCGCACAGACAAAATGTGCCACACTTGCAGCTCTGCATGT<br>GTGCGCGTTACCACAAATCCCAACGGCGCAGTGTACTTGTTGTATGCAAATAAATCTCGATAAAGGCGCGGCGCGCGA<br>ATGCAGCTGATCACGTACGCTCCTCGTGTTCCGTTCAAGGACGGTGTTATCGACCTCAGATTAATGTTTATCGGCCGA<br>CTGTTTTCGTATCCGCTCACCAAACGCGTTTTTGCATTAACATTGTATGTCGGCGGATGTTCTATATCTAATTTGAAT<br>AAATAAACGATAACCGCGTTGGTTTTAGAGGGCATAATAAAAGAAATATTGTTATCGTGTTCGCCATTAGGGCAGTAT<br>AAATTGACGTTCATGTTGGATATTGTTTCAGTTGCAAGTTGACACTGGCGGCGACAAGATCGTGAACAACCAAGTGAC<br>GCGGCCGCATTTGTAAAAAAAAAATAAATAAAAATGGTGTCCAAGGGCGAGGAACTGTTCACCGGTGTCGTGCCCATC<br>CTGGTCGAACTGGACGGCGACGTGAACGGTCACAAGTTCTCCGTGTCTGGCGAAGGCGAGGGCGACGCTACCTACGGA<br>AAGCTGACCCTGAAGTTCATCTGCACCACCGGCAAGCTGCCCGTGCCTTGGCCTACCCTGGTCACCACTCTGACCTAC<br>GGTGTCCAGTGCTTCTCCCGTTACCCCGACCACATGAAGCAGCACGATTTCTTCAAGTCCGCTATGCCCGAGGGTTAC<br>GTGCAAGAGCGTACCATCTTCTTCAAGGACGACGGCAACTACAAGACCCGTGCTGAAGTGAAGTTCGAAGGCGACACC<br>CTCGTGAACCGTATCGAGCTGAAGGGTATCGACTTCAAGGAAGATGGAAACATCCTGGGCCACAAGCTCGAGTACAAC<br>TACAACTCCCACAACGTGTACATCATGGCCGACAAGCAAAAGAACGGCATCAAAGTGAACTTCAAGATCCGCCACAAC<br>ATCGAGGACGGTTCCGTGCAGCTGGCTGACCACTACCAGCAGAACACCCCCATCGGCGACGGTCCTGTGCTGCTGCCT<br>GACAACCACTACCTGTCCACCCAGTCCGCTCTGTCCAAGGACCCCAACGAGAAGCGTGACCACATGGTGCTGCTCGAG<br>TTCGTGACCGCTGCTGGTATCACCCTGGGCATGGACGAGCTGTACAAGTAAGCCCCTTGTAAACGCCACAATTGTGTT<br>TGTTGCAAATAAACCCATGATTATTTGATTAAAATTGTTGTTTTCTTTGTTCATAGACAATAGTGTGTTTTGCCTAAA<br>CGGGTACC |
| SEQ ID NO:9 Nucleotide sequence encoding coBDDFVIHX TEN (V2.0) | ATGCAGATTGAACTGTCCACTTGCTTCTTCCTGTGCCTCCTGCGGTTTTGCTTCTCGGCCACCCGCCGGTATTACTTA<br>GGTGCTGTGGAACTGAGCTGGGACTACATGCAGTCCGACCTGGGAGAACTGCCGGTGGACGCGAGATTCCCACCTAGA<br>GTCCCGAAGTCCTTCCCATTCAACACCTCCGTGGTCTACAAAAAGACCCTGTTCGTGGAGTTCACTGACCACCTTTTC<br>AATATTGCCAAGCCGCGCCCCCCCTGGATGGGCCTGCTTGGTCCTACGATCCAAGCAGAGGTCTACGACACCGTGGTC<br>ATCACACTGAAGAACATGGCCTCACACCCCGTGTCGCTGCATGCTGTGGGAGTGTCCTACTGGAAGGCCTCAGAGGGT<br>GCCGAATATGATGACCAGACCAGCCAGAGGGAAAAGGAGGATGACAAAGTGTTCCCGGGTGGCAGCCACACTTACGTG<br>TGGCAAGTGCTGAAGGAAAACGGGCCTATGGCGTCGGACCCCCTATGCCTGACCTACTCCTACCTGTCCCATGTGGAC<br>CTTGTGAAGGATCTCAACTCGGGACTGATCGGCGCCCTCTTGGTGTGCAGAGAAGGCAGCCTGGCGAAGGAAAAGACT<br>CAGACCCTGCACAAGTTCATTCTGTTGTTTGCTGTGTTCGATGAAGGAAAGTCCTGGCACTCAGAAACCAAGAACTCG<br>CTGATGCAGGATAGAGATGCGGCCTCGGCCAGAGCCTGGCCTAAAATGCACACCGTCAACGGATATGTGAACAGGTCG<br>CTCCCTGGCCTCATCGGCTGCCACAGAAAGTCCGTGTATTGGCATGTGATCGGCATGGGTACTACTCCGGAAGTGCAT<br>AGTATCTTTCTGGAGGGCCATACCTTCTTGGTGCGCAACCACAGACAGGCCTCGCTGGAAATCTCGCCTATCACTTTC<br>TTGACTGCGCAGACCCTCCTTATGGACCTTGGACAGTTCCTGCTGTTCTGTCACATCAGCTCCCATCAGCATGATGGG<br>ATGGAGGCCTATGTCAAAGTGGACTCCTGCCCTGAGGAGCCACAGCTCCGGATGAAGAACAATGAGGAAGCGGAGGAT<br>TACGACGACGACCTGACTGACAGCGAAATGGACGTCGTGCGATTCGATGACGACAACAGCCCGTCCTTCATCCAAATT<br>AGATCAGTGGCGAAGAAGCACCCCAAGACCTGGGTGCACTACATTGCCGCCGAGGAAGAGGACTGGGACTACGCGCCG<br>CTGGTGCTGGCGCCAGACGACAGGAGCTACAAGTCCCAGTACCTCAACAACGGGCCGCAGCGCATTGGCAGGAAGTAC<br>AAGAAAGTCCGCTTCATGGCCTACACTGATGAAACCTTCAAGACGAGGGAAGCCATCCAGCACGAGTCAGGCATCCTG<br>GGACCGCTCCTTTACGGCGAAGTCGGGGATACCCTGCTCATCATTTTCAAGAACCAGGCATCGCGGCCCTACAACATC<br>TACCCTCACGGGATCACAGACGTGCGCCCGCTCTACTCCCGCCGGCTGCCCAAGGGAGTGAAGCACCTGAAGGATTTT<br>CCCATCCTGCCGGGAGAAATCTTCAAGTACAAGTGGACCGTGACTGTGGAAGATGGCCCTACCAAGTCGGACCCTCGC<br>TGTCTGACCCGGTACTATTCCTCGTTTGTGAACATGGAGCGCGACCTGGCCTCGGGGCTGATTGGTCCGCTGCTGATC<br>TGCTACAAGGAGTCCGTGGACCAGCGCGGGAACCAGATCATGTCCGACAAGCGCAACGTGATCCTGTTCTCTGTCTTT<br>GATGAAAACAGATCGTGGTACTTGACTGAGAATATCCAGCGGTTCCTGCCCAACCCAGCGGGAGTGCAACTGGAGGAC<br>CCGGAGTTCCAGGCCTCAAACATTATGCACTCTATCAACGGCTATGTGTTCGACTCGCTCCAACTGAGCGTGTGCCTG<br>CATGAAGTGGCATACTGGTACATTCTGTCCATCGGAGCCCAGACCGACTTCCTGTCCGTGTTCTTCTCCGGATACACC<br>TTCAAGCATAAGATGGTGTACGAGGACACTCTGACCCTCTTCCCATTTTCCGGAGAAACTGTGTTCATGTCAATGGAA<br>AACCCGGGCTTGTGGATTCTGGGTTGCCATAACTCGGACTTCCGGAATAGAGGGATGACCGCCCTGCTGAAAGTGTCC<br>AGCTGTGACAAGAATACCGGCGATTACTACGAGGACAGCTATGAGGACATCTCCGCTTATCTGCTGTCCAAGAACAAC<br>GCCATTGAACCCAGGTCCTTCTCCCAAAACGGTGCACCGACCTCCGAAAGCGCCACCCCAGAGTCAGGACCTGGCTCG<br>GAACCGGCTACCTCGGGCTCAGAGACACCGGGGACTTCCGAGTCCGCAACCCCCGAGAGTGGACCCGGATCCGAACCA<br>GCAACCTCAGGATCAGAAACCCCGGGAACTTCGGAATCCGCCACTCCCGAGTCGGGACCAGGCACCTCCACTGAGCCT<br>TCCGAGGGAAGCGCCCCCGGATCCCCTGCTGGATCCCCTACCAGCACTGAAGAAGGCACCTCAGAATCCGCGACCCCT<br>GAGTCCGGCCCTGGAAGCGAACCCGCCACCTCCGGTTCCGAAACCCCTGGGACTAGCGAGAGCGCCACTCCGGAATCG<br>GGCCCAGGAAGCCCTGCCGGATCCCCGACCAGCACCGAGGAGGGAAGCCCCGCCGGGTCACCGACTTCCACTGAGGAG<br>GGAGCCTCATCCCCCCCCGTGCTGAAGCGGCATCAAAGAGAGATCACCAGGACCACTCTCCAGTCCGATCAGGAAGAA<br>ATTGACTACGACGATACTATCAGCGTGGAGATGAAGAAGGAGGACTTCGACATCTACGATGAGGATGAGAACCAGTCC<br>CCTCGGAGCTTTCAGAAGAAAACCCGCCACTACTTCATCGCTGCCGTGGAGCGGCTGTGGGATTACGGGATGTCCAGC<br>TCACCGCATGTGCTGCGGAATAGAGCGCAGTCAGGATCGGTGCCCCAGTTCAAGAAGGTCGTGTTCCAAGAGTTCACC<br>GACGGGTCCTTCACTCAACCCCTGTACCGGGGCGAACTCAACGAACACCTGGGACTGCTTGGGCCGTATATCAGGGCA<br>GAAGTGGAAGATAACATCATGGTCACCTTCCGCAACCAGGCCTCCCGGCCGTACAGCTTCTACTCTTCACTGATCTCC |

TABLE 1-continued

| Additional Nucleotide and Amino Acid Sequences | |
|---|---|
| SEQ ID NO/ Description | Nucleotide or amino acid sequence |
| | TACGAGGAAGATCAGCGGCAGGGAGCCGAGCCCCGGAAGAACTTCGTCAAGCCTAACGAAACTAAGACCTACTTTTGG<br>AAGGTCCAGCATCACATGGCCCCGACCAAAGACGAGTTCGACTGTAAAGCCTGGGCCTACTTCTCCGATGTGGACCTG<br>GAGAAGGACGTGCACTCGGGACTCATTGGCCCGCTCCTTGTGTGCCATACTAATACCCTGAACCCTGCTCACGGTCGC<br>CAAGTCACAGTGCAGGAGTTCGCCCTCTTCTTCACCATCTTCGATGAAACAAAGTCCTGGTACTTTACTGAGAACATG<br>GAACGCAATTGCAGGGCACCCTGCAACATCCAGATGGAAGATCCCACCTTCAAGGAAAACTACCGGTTTCATGCCATT<br>AACGGCTACATAATGGACACGTTGCCAGGACTGGTCATGGCCCAGGACCAGAGAATCCGGTGGTATCTGCTCTCCATG<br>GGCTCCAACGAAAACATTCACAGCATTCATTTTTCCGGCCATGTGTTCACCGTCCGGAAGAAGGAAGAGTACAAGATG<br>GCTCTGTACAACCTCTACCCTGGAGTGTTCGAGACTGTGGAAATGCTGCCTAGCAAGGCCGGCATTTGGAGAGTGGAA<br>TGCCTGATCGGAGAGCATTTGCACGCCGGAATGTCCACCCTGTTTCTTGTGTACTCCAACAAGTGCCAGACCCCGCTG<br>GGAATGGCCTCAGGTCATATTAGGGATTTCCAGATCACTGCTTCGGGGCAGTACGGGCAGTGGGCACCTAAGTTGGCC<br>CGGCTGCACTACTCTGGCTCCATCAATGCCTGGTCCACCAAGGAACCCTTCTCCTGGATTAAGGTGGACCTCCTGGCC<br>CCAATGATTATTCACGGTATTAAGACCCAGGGTGCCCGACAGAAGTTCTCCTCACTCTACATCTCGCAATTCATCATA<br>ATGTACAGCCTGGATGGGAAGAAGTGGCAGACCTACCGGGGAAACTCCACTGGAACGCTCATGGTGTTTTTCGGCAAC<br>GTGGACTCCTCCGGCATTAAGCACAACATCTTCAACCCTCCGATCATTGCTCGGTACATCCGGCTGCACCCAACTCAC<br>TACAGCATCCGGTCCACCCTGCGGATGGAACTGATGGGTTGTGACCTGAACTCCTGCTCCATGCCCCTTGGGATGGAA<br>TCCAAGGCCATTAGCGATGCACAGATCACCGCCTCTTCATACTTCACCAACATGTTCGCGACCTGGTCCCCGTCGAAG<br>GCCCGCCTGCACCTCCAAGGTCGCTCCAATGCGTGGCGGCCTCAAGTGAACAACCCCAAGGAGTGGCTCCAGGTCGAC<br>TTCCAAAAGACCATGAAGGTCACCGGAGTGACCACCCAGGGCGTGAAGTCCCTGCTGACCTCTATGTACGTTAAGGAG<br>TTCCTCATCTCCTCAAGCCAAGACGGACATCAGTGGACCCTGTTCTTCCAAAACGGAAAAGTCAAAGTATTCCAGGGC<br>AACCAGGACTCCTTCACCCCTGTGGTCAACAGCCTGGACCCCCCATTGCTGACCCGCTACCTCCGCATCCACCCCCAA<br>AGCTGGGTCCACCAGATCGCACTGCGCATGGAGGTCCTTGGATGCGAAGCCCAAGATCTGTACTAA |
| SEQ ID NO: 10 Amino acid sequence of coBDDFVHIX TEN (V2.0) | ATRRYYLGAVELSWDYMQSDLGELPVDARFPPRVPKSFPFNTSVVYKKTLFVEFTDHLFNIAKPRPPWMGLLGPTIQA<br>EVYDTVVITLKNMASHPVSLHAVGVSYWKASEGAEYDDQTSQREKEDDKVFPGGSHTYVWQVLKENGPMASDPLCLTY<br>SYLSHVDLVKDLNSGLIGALLVCREGSLAKEKTQTLHKFILLFAVFDEGKSWHSETKNSLMQDRDAASARAWPKMHTV<br>NGYVNRSLPGLIGCHRKSVYWHVIGMGTTPEVHSIFLEGHTFLVRNHRQASLEISPITFLTAQTLLMDLGQFLLFCHI<br>SSHQHDGMEAYVKVDSCPEEPQLRMKNNEEAEDYDDDLTDSEMDVVRFDDDNSPSFIQIRSVAKKHPKTWVHYIAAEE<br>EDWDYAPLVLAPDDRSYKSQYLNNGPQRIGRKYKKVRFMAYTDETFKTREAIQHESGILGPLLYGEVGDTLLIIFKNQ<br>ASRPYNIYPHGITDVRPLYSRRLPKGVKHLKDFPILPGEIFKYKWTVTVEDGPTKSDPRCLTRYYSSFVNMERDLASG<br>LIGPLLICYKESVDQRGNQIMSDKRNVILFSVFDENRSWYLTENIQRFLPNPAGVQLEDPEFQASNIMHSINGYVFDS<br>LQLSVCLHEVAYWYILSIGAQTDFLSVFFSGYTFKHKMVYEDTLTLFPFSGETVFMSMENPGLWILGCHNSDFRNRGM<br>TALLKVSSCDKNTGDYYEDSYEDISAYLLSKNNAIEPRSFSQNGAPTSESATPESGPGSEPATSGSETPGTSESATPE<br>SGPGSEPATSGSETPGTSESATPESGPGTSTEPSEGSAPGSPAGSPTSTEEGTSESATPESGPGSEPATSGSETPGTS<br>ESATPESGPGSPAGSPTSTEEGSPAGSPTSTEEGASSPPVLKRHQREITRTTLQSDQEEIDYDDTISVEMKKEDFDIY<br>DEDENQSPRSFQKKTRHYFIAAVERLWDYGMSSSPHVLRNRAQSGSVPQFKKVVFQEFTDGSFTQPLYRGELNEHLGL<br>LGPYIRAEVEDNIMVTFRNQASRPYSFYSSLISYEEDQRQGAEPRKNFVKPNETKTYFWKVQHHMAPTKDEFDCKAWA<br>YFSDVDLEKDVHSGLIGPLLVCHTNTLNPAHGRQVTVQEFALFFTIFDETKSWYFTENMERNCRAPCNIQMEDPTFKE<br>NYRFHAINGYIMDTLPGLVMAQDQRIRWYLLSMGSNENIHSIHFSGHVFTVRKKEEYKMALYNLYPGVFETVEMLPSK<br>AGIWRVECLIGEHLHAGMSTLFLVYSNKCQTPLGMASGHIRDFQITASGQYGQWAPKLARLHYSGSINAWSTKEPFSW<br>IKVDLLAPMIIHGIKTQGARQKFSSLYISQFIIMYSLDGKKWQTYRGNSTGTLMVFFGNVDSSGIKHNIFNPPIIARY<br>IRLHPTHYSIRSTLRMELMGCDLNSCSMPLGMESKAISDAQITASSYFTNMFATWSPSKARLHLQGRSNAWRPQVNNP<br>KEWLQVDFQKTMKVTGVTTQGVKSLLTSMYVKEFLISSSQDGHQWTLFFQNGKVKVFQGNQDSFTPVVNSLDPPLLTR<br>YLRIHPQSWVHQIALRMEVLGCEAQDLY |
| SEQ ID NO: 11 Signal peptide of coBDDFVHIX TEN (V2.0) | MQIELSTCFFLCLLRFCFS |
| SEQ ID NO: 12 Amino acid sequence of BDD mature human FVIII | ATRRYYLGAVELSWDYMQSDLGELPVDARFPPRVPKSFPFNTSVVYKKTLFVEFTDHLFNIAKPRPPWMGLLGPTIQA<br>EVYDTVVITLKNMASHPVSLHAVGVSYWKASEGAEYDDQTSQREKEDDKVFPGGSHTYVWQVLKENGPMASDPLCLTY<br>SYLSHVDLVKDLNSGLIGALLVCREGSLAKEKTQTLHKFILLFAVFDEGKSWHSETKNSLMQDRDAASARAWPKMHTV<br>NGYVNRSLPGLIGCHRKSVYWHVIGMGTTPEVHSIFLEGHTFLVRNHRQASLEISPITFLTAQTLLMDLGQFLLFCHI<br>SSHQHDGMEAYVKVDSCPEEPQLRMKNNEEAEDYDDDLTDSEMDVVRFDDDNSPSFIQIRSVAKKHPKTWVHYIAAEE<br>EDWDYAPLVLAPDDRSYKSQYLNNGPQRIGRKYKKVRFMAYTDETFKTREAIQHESGILGPLLYGEVGDTLLIIFKNQ<br>ASRPYNIYPHGITDVRPLYSRRLPKGVKHLKDFPILPGEIFKYKWTVTVEDGPTKSDPRCLTRYYSSFVNMERDLASG<br>LIGPLLICYKESVDQRGNQIMSDKRNVILFSVFDENRSWYLTENIQRFLPNPAGVQLEDPEFQASNIMHSINGYVFDS<br>LQLSVCLHEVAYWYILSIGAQTDFLSVFFSGYTFKHKMVYEDTLTLFPFSGETVFMSMENPGLWILGCHNSDFRNRGM<br>TALLKVSSCDKNTGDYYEDSYEDISAYLLSKNNAIEPRSFSQNPPVLKRHQREITRTTLQSDQEEIDYDDTISVEMKK<br>EDFDIYDEDENQSPRSFQKKTRHYFIAAVERLWDYGMSSSPHVLRNRAQSGSVPQFKKVVFQEFTDGSFTQPLYRGEL<br>NEHLGLLGPYIRAEVEDNIMVTFRNQASRPYSFYSSLISYEEDQRQGAEPRKNFVKPNETKTYFWKVQHHMAPTKDEF<br>DCKAWAYFSDVDLEKDVHSGLIGPLLVCHTNTLNPAHGRQVTVQEFALFFTIFDETKSWYFTENMERNCRAPCNIQME<br>DPTFKENYRFHAINGYIMDTLPGLVMAQDQRIRWYLLSMGSNENIHSIHFSGHVFTVRKKEEYKMALYNLYPGVFETV<br>EMLPSKAGIWRVECLIGEHLHAGMSTLFLVYSNKCQTPLGMASGHIRDFQITASGQYGQWAPKLARLHYSGSINAWST<br>KEPFSWIKVDLLAPMIIHGIKTQGARQKFSSLYISQFIIMYSLDGKKWQTYRGNSTGTLMVFFGNVDSSGIKHNIFNP<br>PIIARYIRLHPTHYSIRSTLRMELMGCDLNSCSMPLGMESKAISDAQITASSYFTNMFATWSPSKARLHLQGRSNAWR<br>PQVNNPKEWLQVDFQKTMKVTGVTTQGVKSLLTSMYVKEFLISSSQDGHQWTLFFQNGKVKVFQGNQDSFTPVVNSLD<br>PPLLTRYLRIHPQSWVHQIALRMEVLGCEAQDLY |

TABLE 1-continued

Additional Nucleotide and Amino Acid Sequences

| SEQ ID NO/ Description | Nucleotide or amino acid sequence |
|---|---|
| SEQ ID NO: 13 Nucleotide sequence encoding BDD mature human FVIII | ATGCAAATAGAGCTCTCCACCTGCTTCTTTCTGTGCCTTTTGCGATTCTGCTTTAGTGCCACCAGAAGATACTACCTG<br>GGTGCAGTGGAACTGTCATGGGACTATATGCAAAGTGATCTCGGTGAGCTGCCTGTGGACGCAAGATTTCCTCCTAGA<br>GTGCCAAAATCTTTTCCATTCAACACCTCAGTCGTGTACAAAAAGACTCTGTTTGTAGAATTCACGGATCACCTTTTC<br>AACATCGCTAAGCCAAGGCCACCCTGGATGGGTCTGCTAGGTCCTACCATCCAGGCTGAGGTTTATGATACAGTGGTC<br>ATTACACTTAAGAACATGGCTTCCCATCCTGTCAGTCTTCATGCTGTTGGTGTATCCTACTGGAAAGCTTCTGAGGGA<br>GCTGAATATGATGATCAGACCAGTCAAAGGGAGAAAGAAGATGATAAAGTCTTCCCTGGTGGAAGCCATACATATGTC<br>TGGCAGGTCCTGAAAGAGAATGGTCCAATGGCCTCTGACCCACTGTGCCTTACCTACTCATATCTTTCTCATGTGGAC<br>CTGGTAAAAGACTTGAATTCAGGCCTCATTGGAGCCCTACTAGTATGTAGAGAAGGGAGTCTGGCCAAGGAAAAGACA<br>CAGACCTTGCACAAATTTATACTACTTTTTGCTGTATTTGATGAAGGGAAAAGTTGGCACTCAGAAACAAAGAACTCC<br>TTGATGCAGGATAGGGATGCTGCATCTGCTCGGGCCTGGCCTAAAATGCACACAGTCAATGGTTATGTAAACAGGTCT<br>CTGCCAGGTCTGATTGGATGCCACAGGAAATCAGTCTATTGGCATGTGATTGGAATGGGCACCACTCCTGAAGTGCAC<br>TCAATATTCCTCGAAGGTCACACATTTCTTGTGAGGAACCATCGCCAGGCGTCCTTGGAAATCTCGCCAATAACTTTC<br>CTTACTGCTCAAACACTCTTGATGGACCTTGGACAGTTTCTACTGTTTTGTCATATCTCTTCCCACCAACATGATGGC<br>ATGGAAGCTTATGTCAAAGTAGACAGCTGTCCAGAGGAACCCCAACTACGAATGAAAAATAATGAAGAAGCGGAAGAC<br>TATGATGATGATCTTACTGATTCTGAAATGGATGTGGTCAGGTTTGATGATGACAACTCTCCTTCCTTTATCCAAATT<br>CGCTCAGTTGCCAAGAAGCATCCTAAAACTTGGGTACATTACATTGCTGCTGAAGAGGAGGACTGGGACTATGCTCCC<br>TTAGTCCTCGCCCCCGATGACAGAAGTTATAAAAGTCAATATTTGAACAATGGCCCTCAGCGGATTGGTAGGAAGTAC<br>AAAAAAGTCCGATTTATGGCATACACAGATGAAACCTTTAAGACTCGTGAAGCTATTCAGCATGAATCAGGAATCTTG<br>GGACCTTTACTTTATGGGGAAGTTGGAGACACACTGTTGATTATATTTAAGAATCAAGCAAGCAGACCATATAACATC<br>TACCCTCACGGAATCACTGATGTCCGTCCTTTGTATTCAAGGAGATTACCAAAAGGTGTAAAACATTTGAAGGATTTT<br>CCAATTCTGCCAGGAGAAATATTCAAATATAAATGGACAGTGACTGTAGAAGATGGGCCAACTAAATCAGATCCTCGG<br>TGCCTGACCCGCTATTACTCTAGTTTCGTTAATATGGAGAGAGATCTAGCTTCAGGACTCATTGGCCCTCTCCTCATC<br>TGCTACAAAGAATCTGTAGATCAAAGAGGAAACCAGATAATGTCAGACAAGAGGAATGTCATCCTGTTTTCTGTATTT<br>GATGAGAACCGAAGCTGGTACCTCACAGAGAATATACAACGCTTTCTCCCCAATCCAGCTGGAGTGCAGCTTGAGGAT<br>CCAGAGTTCCAAGCCTCCAACATCATGCACAGCATCAATGGCTATGTTTTTGATAGTTTGCAGTTGTCAGTTTGTTTG<br>CATGAGGTGGCATACTGGTACATTCTAAGCATTGGAGCACAGACTGACTTCCTTTCTGTCTTCTTCTCTGGATATACC<br>TTCAAACACAAAATGGTCTATGAAGACACACTCACCCTATTCCCATTCTCAGGAGAAACTGTCTTCATGTCGATGGAA<br>AACCCAGGTCTATGGATTCTGGGGTGCCACAACTCAGACTTTCGGAACAGAGGCATGACCGCCTTACTGAAGGTTTCT<br>AGTTGTGACAAGAACACTGGTGATTATTACGAGGACAGTTATGAAGATATTTCAGCATACTTGCTGAGTAAAAACAAT<br>GCCATTGAACCAAGAAGCTTCTCTCAAAACCCACCAGTCTTGAAACGCCATCAACGGGAAATAACTCGTACTACTCTT<br>CAGTCAGATCAAGAGGAAATTGACTATGATGATACCATATCAGTTGAAATGAAGAAGGAAGATTTTGACATTTATGAT<br>GAGGATGAAAATCAGAGCCCCCGCAGCTTTCAAAAGAAAACACGACACTATTTTATTGCTGCAGTGGAGAGGCTCTGG<br>GATTATGGGATGAGTAGCTCCCCACATGTTCTAAGAAACAGGGCTCAGAGTGGCAGTGTCCCTCAGTTCAAGAAAGTT<br>GTTTTCCAGGAATTTACTGATGGCTCCTTTACTCAGCCCTTATACCGTGGAGAACTAAATGAACATTTGGGACTCCTG<br>GGGCCATATATAAGAGCAGAAGTTGAAGATAATATCATGGTAACTTTCAGAAATCAGGCCTCTCGTCCCTATTCCTTC<br>TATTCTAGCCTTATTTCTTATGAGGAAGATCAGAGGCAAGGAGCAGAACCTAGAAAAAACTTTGTCAAGCCTAATGAA<br>ACCAAAACTTACTTTTGGAAAGTGCAACATCATATGGCACCCACTAAAGATGAGTTTGACTGCAAAGCCTGGGCTTAT<br>TTCTCTGATGTTGACCTGGAAAAAGATGTGCACTCAGGCCTGATTGGACCCCTTCTGGTCTGCCACACTAACACACTG<br>AACCCTGCTCATGGGAGACAAGTGACAGTACAGGAATTTGCTCTGTTTTTCACCATCTTTGATGAGACCAAAAGCTGG<br>TACTTCACTGAAAATATGGAAAGAAACTGCAGGGCTCCCTGCAATATCCAGATGGAAGATCCCACTTTTAAAGAGAAT<br>TATCGCTTCCATGCAATCAATGGCTACATAATGGATACACTACCTGGCTTAGTAATGGCTCAGGATCAAAGGATTCGA<br>TGGTATCTGCTCAGCATGGGCAGCAATGAAAACATCCATTCTATTCATTTCAGTGGACATGTGTTCACTGTACGAAAA<br>AAAGAGGAGTATAAAATGGCACTGTACAATCTCTATCCAGGTGTTTTTGAGACAGTGGAAATGTTACCATCCAAAGCT<br>GGAATTTGGCGGGTGGAATGCCTTATTGGCGAGCATCTACATGCTGGGATGAGCACACTTTTTCTGGTGTACAGCAAT<br>AAGTGTCAGACTCCCCTGGGAATGGCTTCTGGACACATTAGAGATTTTCAGATTACAGCTTCAGGACAATATGGACAG<br>TGGGCCCCAAAGCTGGCCAGACTTCATTATTCCGGATCAATCAATGCCTGGAGCACCAAGGAGCCCTTTTCTTGGATC<br>AAGGTGGATCTGTTGGCACCAATGATTATTCACGGCATCAAGACCCAGGGTGCCCGTCAGAAGTTCTCCAGCCTCTAC<br>ATCTCTCAGTTTATCATCATGTATAGTCTTGATGGGAAGAAGTGGCAGACTTATCGAGGAAATTCCACTGGAACCTTA<br>ATGGTCTTCTTTGGCAATGTGGATTCATCTGGGATAAAACACAATATTTTTAACCCTCCAATTATTGCTCGATACATC<br>CGTTTGCACCCAACTCATTATAGCATTCGCAGCACTCTTCGCATGGAGTTGATGGGCTGTGATTTAAATAGTTGCAGC<br>ATGCCATTGGGAATGGAGAGTAAAGCAATATCAGATGCACAGATTACTGCTTCATCCTACTTTACCAATATGTTTGCC<br>ACCTGGTCTCCTTCAAAAGCTCGACTTCACCTCCAAGGGAGGAGTAATGCCTGGAGACCTCAGGTGAATAATCCAAAA<br>GAGTGGCTGCAAGTGGACTTCCAGAAGACAATGAAAGTCACAGGAGTAACTACTCAGGGAGTAAAATCTCTGCTTACC<br>AGCATGTATGTGAAGGAGTTCCTCATCTCCAGCAGTCAAGATGGCCATCAGTGGACTCTCTTTTTTCAGAATGGCAAA<br>GTAAAGGTTTTTCAGGGAAATCAAGACTCCTTCACACCTGTGGTGAACTCTCTAGACCCACCGTTACTGACTCGCTAC<br>CTTCGAATTCACCCCCAGAGTTGGGTGCACCAGATTGCCCTGAGGATGGAGGTTCTGGGCTGCGAGGCACAGGACCTC<br>TAG |
| SEQ ID NO: 14 V2.0 Expression cassette mTTR482-Intron-coBDDFVIHX TEN (V2.0)-WERE-bGHPolyA | GGCCCCAGGTTAATTTTTAAAAAGCAGTCAAAGGTCAAAGTGGCCCTTGGCAGCATTTACTCTCTCTATTGACTTTGG<br>TTAATAATCTCAGGAGCACAAACATTCCTGGAGGCAGGAGAAGAAATCAACATCCTGGACTTATCCTCTGGGCCTCTC<br>CCCACCTTCGATGGCCCCAGGTTAATTTTTAAAAAGCAGTCAAAGGTCAAAGTGGCCCTTGGCAGCATTTACTCTCTC<br>TATTGACTTTGGTTAATAATCTCAGGAGCACAAACATTCCTGGAGGCAGGAGAAGAAATCAACATCCTGGACTTATCC<br>TCTGGGCCTCTCCCCACCGATATCTACCTGCTGATCGCCCGGCCCCTGTTCAAACATGTCCTAATACTCTGTCGGGGC<br>AAAGGTCGGCAGTAGTTTTCCATCTTACTCAACATCCTCCCAGTGTACGTAGGATCCTGTCTGTCTGCACATTTCGTA<br>GAGCGAGTGTTCCGATACTCTAATCTCCCGGGGCAAAGGTCGTATTGACTTAGGTTACTTATTCTCCTTTTGTTGACT<br>AAGTCAATAATCAGAATCAGCAGGTTTGGAGTCAGCTTGGCAGGGATCAGCAGCCTGGGTTGGAAGGAGGGGGTATAA<br>AAGCCCCTTCACCAGGAGAAGCCGTCACACAGATCCACAAGCTCCTGCTAGGAATTCTCAGGAGCACAAACATTCCTG<br>GAGGCAGGAGAAGAAATCAACATCCTGGACTTATCCTCTGGGCCTCTCCCCACCGATATCTACCTGCTGATCGCCCGG<br>CCCCTGTTCAAACATGTCCTAATACTCTGTCGGGGCAAAGGTCGGCAGTAGTTTTCCATCTTACTCAACATCCTCCCA<br>GTGTACGTAGGATCCTGTCTGTCTGCACATTTCGTAGAGCGAGTGTTCCGATACTCTAATCTCCCGGGGCAAAGGTCG<br>TATTGACTTAGGTTACTTATTCTCCTTTTGTTGACTAAGTCAATAATCAGAATCAGCAGGTTTGGAGTCAGCTTGGCA<br>GGGATCAGCAGCCTGGGTTGGAAGGAGGGGGTATAAAAGCCCCTTCACCAGGAGAAGCCGTCACACAGATCCACAAGC<br>TCCTGCTAGAGTCGCTGCGCGCTGCCTTCGCCCCGTGCCCCGCTCCGCCGCCGCCTCGCGCCGCCCGCCCCGGCTCTG<br>ACTGACCGCGTTACTCCCACAGGTGAGCGGGCGGGACGGCCCTTCTCCTCCGGGCTGTAATTAGCGCTTGGTTTATTG |

TABLE 1-continued

Additional Nucleotide and Amino Acid Sequences

| SEQ ID NO/ Description | Nucleotide or amino acid sequence |
| --- | --- |
| | ACGGCTTGTTTCTTTTCTGTGGCTGCGTGAAAGCCTTGAGGGGCTCCGGGAAGGCCCTTTGTGCGGGGGGAGCGGCTC<br>GGGGGGTGCGTGCGTGTGTGTGTGCGTGGGGAGCGCCGCGTGCGGCTCCGCGCTGCCCGGCGGCTGTGAGCGCTGCGG<br>GCGCGGCGCGGGGCTTTGTGCGCTCCGCAGTGTGCGCGAGGGGAGCGCGGCCGGGGGCGGTGCCCCGCGGTGCGGGGG<br>GGGCTGCGAGGGGAACAAAGGCTGCGTGCGGGGTGTGTGCGTGGGGGGGTGAGCAGGGGGTGTGGGCGCGTCGGTCGG<br>GCTGCAACCCCCCCTGCACCCCCCTCCCCGAGTTGCTGAGCACGGCCCGGCTTCGGGTGCGGGGCTCCGTACGGGGCG<br>TGGCGCGGGGCTCGCCGTGCCGGGCGGGGGGTGGCGGCAGGTGGGGGTGCCGGGCGGGGCGGGGCCGCCTCGGGCCGG<br>GGAGGGCTCGGGGGAGGGGCGCGGCGGCCCCCGGAGCGCCGGCGGCTGTCGAGGCGCGGCGAGCCGCAGCCATTGCCT<br>TTTATGGTAATCGTGCGAGAGGGCGCAGGGACTTCCTTTGTCCCAAATCTGTGCGGAGCCGAAATCTGGGAGGCGCCG<br>CCGCACCCCCTCTAGCGGGCGCGGGGCGAAGCGGTGCGGCGCCGGCAGGAAGGAAATGGGCGGGGAGGGCCTTCGTGC<br>GTCGCCGCGCCGCCGTCCCCTTCTCCCTCTCCAGCCTCGGGGCTGTCCGCGGGGGGACGGCTGCCTTCGGGGGGGACG<br>GGGCAGGGCGGGGTTCGGCTTCTGGCGTGTGACCGGCGGCTCTAGAGCCTCTGCTAACCTTGTTCTTGCCTTCTTCTT<br>TTTCCTACAGCTCCTGGGCAACGTGCTGGTTATTGTGCTGTCTCATCATTTTGGCAAAGAATTACTCGAGGCCACCAT<br>GCAGATTGAACTGTCCACTTGCTTCTTCCTGTGCCTCCTGCGGTTTTGCTTCTCGGCCACCCGCCGGTATTACTTAGG<br>TGCTGTGGAACTGAGCTGGGACTACATGCAGTCCGACCTGGGAGAACTGCCGGTGGACGCGAGATTCCCACCTAGAGT<br>CCCGAAGTCCTTCCCATTCAACACCTCCGTGGTCTACAAAAAGACCCTGTTCGTGGAGTTCACTGACCACCTTTTCAA<br>TATTGCCAAGCCGCGCCCCCCCTGGATGGGCCTGCTTGGTCCTACGATCCAAGCAGAGGTCTACGACACCGTGGTCAT<br>CACACTGAAGAACATGGCCTCACACCCCGTGTCGCTGCATGCTGTGGGAGTGTCCTACTGGAAGGCCTCAGAGGGTGC<br>CGAATATGATGACCAGACCAGCCAGAGGGAAAAGGAGGATGACAAAGTGTTCCCGGGTGGCAGCCACACTTACGTGTG<br>GCAAGTGCTGAAGGAAAACGGGCCTATGGCGTCGGACCCCCTATGCCTGACCTACTCCTACCTGTCCCATGTGGACCT<br>TGTGAAGGATCTCAACTCGGGACTGATCGGCGCCCTCTTGGTGTGCAGAGAAGGCAGCCTGGCGAAGGAAAAGACTCA<br>GACCCTGCACAAGTTCATTCTGTTGTTTGCTGTGTTCGATGAAGGAAAGTCCTGGCACTCAGAAACCAAGAACTCGCT<br>GATGCAGGATAGAGATGCGGCCTCGGCCAGAGCCTGGCCTAAAATGCACACCGTCAACGGATATGTGAACAGGTCGCT<br>CCCTGGCCTCATCGGCTGCCACAGAAAGTCCGTGTATTGGCATGTGATCGGCATGGGTACTACTCCGGAAGTGCATAG<br>TATCTTTCTGGAGGGCCATACCTTCTTGGTGCGCAACCACAGACAGGCCTCGCTGGAAATCTCGCCTATCACTTTCTT<br>GACTGCGCAGACCCTCCTTATGGACCTTGGACAGTTCCTGCTGTTCTGTCACATCAGCTCCCATCAGCATGATGGGAT<br>GGAGGCCTATGTCAAAGTGGACTCCTGCCCTGAGGAGCCACAGCTCCGGATGAAGAACAATGAGGAAGCGGAGGATTA<br>CGACGACGACCTGACTGACAGCGAAATGGACGTCGTGCGATTCGATGACGACAACAGCCCGTCCTTCATCCAAATTAG<br>ATCAGTGGCGAAGAAGCACCCCAAGACCTGGGTGCACTACATTGCCGCCGAGGAAGAGGACTGGGACTACGCGCCGCT<br>GGTGCTGGCGCCAGACGACAGGAGCTACAAGTCCCAGTACCTCAACAACGGGCCGCAGCGCATTGGCAGGAAGTACAA<br>GAAAGTCCGCTTCATGGCCTACACTGATGAAACCTTCAAGACGAGGGAAGCCATCCAGCACGAGTCAGGCATCCTGGG<br>ACCGCTCCTTTACGGCGAAGTCGGGGATACCCTGCTCATCATTTTCAAGAACCAGGCATCGCGGCCCTACAACATCTA<br>CCCTCACGGGATCACAGACGTGCGCCCGCTCTACTCCCGCCGGCTGCCCAAGGGAGTGAAGCACCTGAAGGATTTTCC<br>CATCCTGCCGGGAGAAATCTTCAAGTACAAGTGGACCGTGACTGTGGAAGATGGCCCTACCAAGTCGGACCCTCGCTG<br>TCTGACCCGGTACTATTCCTCGTTTGTGAACATGGAGCGCGACCTGGCCTCGGGGCTGATTGGTCCGCTGCTGATCTG<br>CTACAAGGAGTCCGTGGACCAGCGCGGGAACCAGATCATGTCCGACAAGCGCAACGTGATCCTGTTCTCTGTCTTTGA<br>TGAAAACAGATCGTGGTACTTGACTGAGAATATCCAGCGGTTCCTGCCCAACCCAGCGGGAGTGCAACTGGAGGACCC<br>GGAGTTCCAGGCCTCAAACATTATGCACTCTATCAACGGCTATGTGTTCGACTCGCTCCAACTGAGCGTGTGCCTGCA<br>TGAAGTGGCATACTGGTACATTCTGTCCATCGGAGCCCAGACCGACTTCCTGTCCGTGTTCTTCTCCGGATACACCTT<br>CAAGCATAAGATGGTGTACGAGGACACTCTGACCCTCTTCCCATTTTCCGGAGAAACTGTGTTCATGTCAATGGAAAA<br>CCCGGGCTTGTGGATTCTGGGTTGCCATAACTCGGACTTCCGGAATAGAGGGATGACCGCCCTGCTGAAAGTGTCCAG<br>CTGTGACAAGAATACCGGCGATTACTACGAGGACAGCTATGAGGACATCTCCGCTTATCTGCTGTCCAAGAACAACGC<br>CATTGAACCCAGGTCCTTCTCCCAAAACGGTGCACCGACCTCCGAAAGCGCCACCCCAGAGTCAGGACCTGGCTCGGA<br>ACCGGCTACCTCGGGCTCAGAGACACCGGGGACTTCCGAGTCCGCAACCCCCGAGAGTGGACCCGGATCCGAACCAGC<br>AACCTCAGGATCAGAAACCCCGGGAACTTCGGAATCCGCCACTCCCGAGTCGGGACCAGGCACCTCCACTGAGCCTTC<br>CGAGGGAAGCGCCCCCGGATCCCCTGCTGGATCCCCTACCAGCACTGAAGAAGGCACCTCAGAATCCGCGACCCCTGA<br>GTCCGGCCCTGGAAGCGAACCCGCCACCTCCGGTTCCGAAACCCCTGGGACTAGCGAGAGCGCCACTCCGGAATCGGG<br>CCCAGGAAGCCCTGCCGGATCCCCGACCAGCACCGAGGAGGGAAGCCCCGCCGGGTCACCGACTTCCACTGAGGAGGG<br>AGCCTCATCCCCCCCCGTGCTGAAGCGGCATCAAAGAGAGATCACCAGGACCACTCTCCAGTCCGATCAGGAAGAAAT<br>TGACTACGACGATACTATCAGCGTGGAGATGAAGAAGGAGGACTTCGACATCTACGATGAGGATGAGAACCAGTCCCC<br>TCGGAGCTTTCAGAAGAAAACCCGCCACTACTTCATCGCTGCCGTGGAGCGGCTGTGGGATTACGGGATGTCCAGCTC<br>ACCGCATGTGCTGCGGAATAGAGCGCAGTCAGGATCGGTGCCCCAGTTCAAGAAGGTCGTGTTCCAAGAGTTCACCGA<br>CGGGTCCTTCACTCAACCCCTGTACCGGGGCGAACTCAACGAACACCTGGGACTGCTTGGGCCGTATATCAGGGCAGA<br>AGTGGAAGATAACATCATGGTCACCTTCCGCAACCAGGCCTCCCGGCCGTACAGCTTCTACTCTTCACTGATCTCCTA<br>CGAGGAAGATCAGCGGCAGGGAGCCGAGCCCCGGAAGAACTTCGTCAAGCCTAACGAAACTAAGACCTACTTTTGGAA<br>GGTCCAGCATCACATGGCCCCGACCAAAGACGAGTTCGACTGTAAAGCCTGGGCCTACTTCTCCGATGTGGACCTGGA<br>GAAGGACGTGCACTCGGGACTCATTGGCCCGCTCCTTGTGTGCCATACTAATACCCTGAACCCTGCTCACGGTCGCCA<br>AGTCACAGTGCAGGAGTTCGCCCTCTTCTTCACCATCTTCGATGAAACAAAGTCCTGGTACTTTACTGAGAACATGGA<br>ACGCAATTGCAGGGCACCCTGCAACATCCAGATGGAAGATCCCACCTTCAAGGAAAACTACCGGTTTCATGCCATTAA<br>CGGCTACATAATGGACACGTTGCCAGGACTGGTCATGGCCCAGGACCAGAGAATCCGGTGGTATCTGCTCTCCATGGG<br>CTCCAACGAAAACATTCACAGCATTCATTTTTCCGGCCATGTGTTCACCGTCCGGAAGAAGGAAGAGTACAAGATGGC<br>TCTGTACAACCTCTACCCTGGAGTGTTCGAGACTGTGGAAATGCTGCCTAGCAAGGCCGGCATTTGGAGAGTGGAATG<br>CCTGATCGGAGAGCATTTGCACGCCGGAATGTCCACCCTGTTTCTTGTGTACTCCAACAAGTGCCAGACCCCGCTGGG<br>AATGGCCTCAGGTCATATTAGGGATTTCCAGATCACTGCTTCGGGGCAGTACGGGCAGTGGGCACCTAAGTTGGCCCG<br>GCTGCACTACTCTGGCTCCATCAATGCCTGGTCCACCAAGGAACCCTTCTCCTGGATTAAGGTGGACCTCCTGGCCCC<br>AATGATTATTCACGGTATTAAGACCCAGGGTGCCCGACAGAAGTTCTCCTCACTCTACATCTCGCAATTCATCATAAT<br>GTACAGCCTGGATGGGAAGAAGTGGCAGACCTACCGGGGAAACTCCACTGGAACGCTCATGGTGTTTTTCGGCAACGT<br>GGACTCCTCCGGCATTAAGCACAACATCTTCAACCCTCCGATCATTGCTCGGTACATCCGGCTGCACCCAACTCACTA<br>CAGCATCCGGTCCACCCTGCGGATGGAACTGATGGGTTGTGACCTGAACTCCTGCTCCATGCCCCTTGGGATGGAATC<br>CAAGGCCATTAGCGATGCACAGATCACCGCCTCTTCATACTTCACCAACATGTTCGCGACCTGGTCCCCGTCGAAGGC<br>CCGCCTGCACCTCCAAGGTCGCTCCAATGCGTGGCGGCCTCAAGTGAACAACCCCAAGGAGTGGCTCCAGGTCGACTT<br>CCAAAAGACCATGAAGGTCACCGGAGTGACCACCCAGGGCGTGAAGTCCCTGCTGACCTCTATGTACGTTAAGGAGTT<br>CCTCATCTCCTCAAGCCAAGACGGACATCAGTGGACCCTGTTCTTCCAAAACGGAAAAGTCAAAGTATTCCAGGGCAA<br>CCAGGACTCCTTCACCCCTGTGGTCAACAGCCTGGACCCCCCATTGCTGACCCGCTACCTCCGCATCCACCCCCAAAG<br>CTGGGTCCACCAGATCGCACTGCGCATGGAGGTCCTTGGATGCGAAGCCCAAGATCTGTACTAAGCGGCCGCTCATAA<br>TCAACCTCTGGATTACAAAATTTGTGAAAGATTGACTGGTATTCTTAACTATGTTGCTCCTTTTACGCTATGTGGATA |

TABLE 1-continued

Additional Nucleotide and Amino Acid Sequences

| SEQ ID NO/ Description | Nucleotide or amino acid sequence |
|---|---|
| | CGCTGCTTTAATGCCTTTGTATCATGCTATTGCTTCCCGTATGGCTTTCATTTTCTCCTCCTTGTATAAATCCTGGTTGCTGTCTCTTTATGAGGAGTTGTGGCCCGTTGTCAGGCAACGTGGCGTGGTGTGCACTGTGTTTGCTGACGCAACCCCCACTGGTTGGGGCATTGCCACCACCTGTCAGCTCCTTTCCGGGACTTTCGCTTTCCCCCTCCCTATTGCCACGGCGGAACTCATCGCCGCCTGCCTTGCCCGCTGCTGGACAGGGGCTCGGCTGTTGGGCACTGACAATTCCGTGGTGTTGTCGGGGAAATCATCGTCCTTTCCTTGGCTGCTCGCCTGTGTTGCCACCTGGATTCTGCGCGGGACGTCCTTCTGCTACGTCCCTTCGGCCCTCAATCCAGCGGACCTTCCTTCCCGCGGCCTGCTGCCGGCTCTGCGGCCTCTTCCGCGTCTTCGCCTTCGCCCTCAGACGAGTCGGATCTCCCTTTGGGCCGCCTCCCCGCTGCCTAGGCGACTGTGCCTTCTAGTTGCCAGCCATCTGTTGTTTGCCCCTCCCCCGTGCCTTCCTTGACCCTGGAAGGTGCCACTCCCACTGTCCTTTCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGACAATAGCAGGCATGCTGGGGAAGACCATGGGCGCGCCAGGCCTGTCGACGCCCGGGCGGTACCGCGATCGCTCGCGACGCATAAAG |
| SEQ ID NO: 15 A1MB2 enhancer | GGCCCCAGGTTAATTTTTAAAAAGCAGTCAAAGGTCAAAGTGGCCCTTGGCAGCATTTACTCTCTCTATTGACTTTGGTTAATAATCTCAGGAGCACAAACATTCCTGGAGGCAGGAGAAGAAATCAACATCCTGGACTTATCCTCTGGGCCTCTCCCCACCTTCGATGGCCCCAGGTTAATTTTTAAAAAGCAGTCAAAGGTCAAAGTGGCCCTTGGCAGCATTTACTCTCTCTATTGACTTTGGTTAATAATCTCAGGAGCACAAACATTCCTGGAGGCAGGAGAAGAAATCAACATCCTGGACTTATCCTCTGGGCCTCTCCCCACC |
| SEQ ID NO: 16 mTTR promoter | GATATCTACCTGCTGATCGCCCGGCCCCTGTTCAAACATGTCCTAATACTCTGTCGGGGCAAAGGTCGGCAGTAGTTTTCCATCTTACTCAACATCCTCCCAGTGTACGTAGGATCCTGTCTGTCTGCACATTTCGTAGAGCGAGTGTTCCGATACTCTAATCTCCCGGGGCAAAGGTCGTATTGACTTAGGTTACTTATTCTCCTTTTGTTGACTAAGTCAATAATCAGAATCAGCAGGTTTGGAGTCAGCTTGGCAGGGATCAGCAGCCTGGGTTGGAAGGAGGGGGTATAAAAGCCCCTTCACCAGGAGAAGCCGTCACACAGATCCACAAGCTCCTGCTAG |
| SEQ ID NO: 17 Chimeric Intron | TCAGGAGCACAAACATTCCTGGAGGCAGGAGAAGAAATCAACATCCTGGACTTATCCTCTGGGCCTCTCCCCACCGATATCTACCTGCTGATCGCCCGGCCCCTGTTCAAACATGTCCTAATACTCTGTCGGGGCAAAGGTCGGCAGTAGTTTTCCATCTTACTCAACATCCTCCCAGTGTACGTAGGATCCTGTCTGTCTGCACATTTCGTAGAGCGAGTGTTCCGATACTCTAATCTCCCGGGGCAAAGGTCGTATTGACTTAGGTTACTTATTCTCCTTTTGTTGACTAAGTCAATAATCAGAATCAGCAGGTTTGGAGTCAGCTTGGCAGGGATCAGCAGCCTGGGTTGGAAGGAGGGGGTATAAAAGCCCCTTCACCAGGAGAAGCCGTCACACAGATCCACAAGCTCCTGCTAGAGTCGCTGCGCGCTGCCTTCGCCCCGTGCCCCGCTCCGCCGCCGCCTCGCGCCGCCCGCCCCGGCTCTGACTGACCGCGTTACTCCCACAGGTGAGCGGGCGGGACGGCCCTTCTCCTCCGGGCTGTAATTAGCGCTTGGTTTATTGACGGCTTGTTTCTTTTCTGTGGCTGCGTGAAAGCCTTGAGGGGCTCCGGGAAGGCCCTTTGTGCGGGGGGAGCGGCTCGGGGGGTGCGTGCGTGTGTGTGTGCGTGGGGAGCGCCGCGTGCGGCTCCGCGCTGCCCGGCGGCTGTGAGCGCTGCGGGCGCGGCGCGGGGCTTTGTGCGCTCCGCAGTGTGCGCGAGGGGAGCGCGGCCGGGGGCGGTGCCCCGCGGTGCGGGGGGGGCTGCGAGGGGAACAAAGGCTGCGTGCGGGGTGTGTGCGTGGGGGGGTGAGCAGGGGGTGTGGGCGCGTCGGTCGGGCTGCAACCCCCCCTGCACCCCCCTCCCCGAGTTGCTGAGCACGGCCCGGCTTCGGGTGCGGGGCTCCGTACGGGGCGTGGCGCGGGGCTCGCCGTGCCGGGCGGGGGGTGGCGGCAGGTGGGGGTGCCGGGCGGGGCGGGGCCGCCTCGGGCCGGGGAGGGCTCGGGGGAGGGGCGCGGCGGCCCCCGGAGCGCCGGCGGCTGTCGAGGCGCGGCGAGCCGCAGCCATTGCCTTTTATGGTAATCGTGCGAGAGGGCGCAGGGACTTCCTTTGTCCCAAATCTGTGCGGAGCCGAAATCTGGGAGGCGCCGCCGCACCCCCTCTAGCGGGCGCGGGGCGAAGCGGTGCGGCGCCGGCAGGAAGGAAATGGGCGGGGAGGGCCTTCGTGCGTCGCCGCGCCGCCGTCCCCTTCTCCCTCTCCAGCCTCGGGGCTGTCCGCGGGGGGACGGCTGCCTTCGGGGGGGACGGGGCAGGGCGGGGTTCGGCTTCTGGCGTGTGACCGGCGGCTCTAGAGCCTCTGCTAACCTTGTTCTTGCCTTCTTCTTTTTCCTACAGCTCCTGGGCAACGTGCTGGTTATTGTGCTGTCTCATCATTTTGGCAAAGAATTA |
| SEQ ID NO: 18 WERE | TCATAATCAACCTCTGGATTACAAAATTTGTGAAAGATTGACTGGTATTCTTAACTATGTTGCTCCTTTTACGCTATGTGGATACGCTGCTTTAATGCCTTTGTATCATGCTATTGCTTCCCGTATGGCTTTCATTTTCTCCTCCTTGTATAAATCCTGGTTGCTGTCTCTTTATGAGGAGTTGTGGCCCGTTGTCAGGCAACGTGGCGTGGTGTGCACTGTGTTTGCTGACGCAACCCCCACTGGTTGGGGCATTGCCACCACCTGTCAGCTCCTTTCCGGGACTTTCGCTTTCCCCCTCCCTATTGCCACGGCGGAACTCATCGCCGCCTGCCTTGCCCGCTGCTGGACAGGGGCTCGGCTGTTGGGCACTGACAATTCCGTGGTGTTGTCGGGGAAATCATCGTCCTTTCCTTGGCTGCTCGCCTGTGTTGCCACCTGGATTCTGCGCGGGACGTCCTTCTGCTACGTCCCTTCGGCCCTCAATCCAGCGGACCTTCCTTCCCGCGGCCTGCTGCCGGCTCTGCGGCCTCTTCCGCGTCTTCGCCTTCGCCCTCAGACGAGTCGGATCTCCCTTTGGGCCGCCTCCCCGCTG |
| SEQ ID NO: 19 bGHpA | CGACTGTGCCTTCTAGTTGCCAGCCATCTGTTGTTTGCCCCTCCCCCGTGCCTTCCTTGACCCTGGAAGGTGCCACTCCCACTGTCCTTTCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGACAATAGCAGGCATGCTGGGGA |
| SEQ ID NO: 20 Amino acid sequence of wild type human mature FVIII protein | ATRRYYLGAVELSWDYMQSDLGELPVDARFPPRVPKSFPFNTSVVYKKTLFVEFTDHLFNIAKPRPPWMGLLGPTIQAEVYDTWITLKNMASHPVSLHAVGVSYWKASEGAEYDDQTSQREKEDDKVFPGGSHTYVWQVLKENGPMASDPLCLTYSYLSHVDLVKDLNSGLIGALLVCREGSLAKEKTQTLHKFILLFAVFDEGKSWHSETKNSLMQDRDAASARAWPKMHTVNGYVNRSLPGLIGCHRKSVYWHVIGMGTTPEVHSIFLEGHTFLVRNHRQASLEISPITFLTAQTLLMDLGQFLLFCHISSHQHDGMEAYVKVDSCPEEPQLRMKNNEEAEDYDDDLTDSEMDVVRFDDDNSPSFIQIRSVAKKHPKTWVHYIAAEEEDWDYAPLVLAPDDRSYKSQYLNNGPQRIGRKYKKVRFMAYTDETFKTREAIQHESGILGPLLYGEVGDTLLIIFKNQASRPYNIYPHGITDVRPLYSRRLPKGVKHLKDFPILPGEIFKYKWTVTVEDGPTKSDPRCLTRYYSSFVNMERDLASGLIGPLLICYKESVDQRGNQIMSDKRNVILFSVFDENRSWYLTENIQRFLPNPAGVQLEDPEFQASNIMHSINGYVFDSLQLSVCLHEVAYWYILSIGAQTDFLSVFFSGYTFKHKMVYEDTLTLFPFSGETVFMSMENPGLWILGCHNSDFRNRGMTALLKVSSCDKNTGDYYEDSYEDISAYLLSKNNAIEPRSFSQNSRHPSTRQKQFNATTIPENDIEKTDPWFAHRTPMPKIQNVSSSDLLMLLRQSPTPHGLSLSDLQEAKYETFSDDPSPGAIDSNNSLSEMTHFRPQLHHSGDMVFTPESGLQLRLNEKLGTTAATELKKLDFKVSSTSNNLISTIPSDNLAAGTDNTSSLGPPSMPVHYDSQLDTTLFGKKSSPLTESGGPLSLSEENNDSKLLESGLMNSQESSWGKNVSSTESGRLFKGKRAHGPALLTKDNALFKVSISLLKTNKTSNNSATNRKTHIDGPSLLIENSPSVWQNILESDTEFKKVTPLIHDRMLMDKNATALRLNHMSNKTTSSKNMEMVQQKKEGPIPPDAQNPDMSFFKMLFLPESARWIQRTHGKNSLNSGQGPSPKQLVSLGPEKSVEGQNFLSEKNKVVVGKGEFTKDVGLKEMVFPSSRNLFLTNLDNLHENNTHNQEKKIQEEIEKKETLIQENVVLPQIHTVTGTKNFMKNLFLLSTRQNVEGSYDGAYAPVLQDFRSLNDSTNRTKKHTAHFSKKGEEENLEGLGNQTKQIVEKYACTTRISPNTSQQNFVTQRSKRALKQFRLPLEETE |

TABLE 1-continued

Additional Nucleotide and Amino Acid Sequences

| SEQ ID NO/ Description | Nucleotide or amino acid sequence |
|---|---|
| | LEKRIIVDDTSTQWSKNMKHLTPSTLTQIDYNEKEKGAITQSPLSDCLTRSHSIPQANRSPLPIAKVSSFPSIRPIYL<br>TRVLFQDNSSHLPAASYRKKDSGVQESSHFLQGAKKNNLSLAILTLEMTGDQREVGSLGTSATNSVTYKKVENTVLPK<br>PDLPKTSGKVELLPKVHIYQKDLFPTETSNGSPGHLDLVEGSLLQGTEGAIKWNEANRPGKVPFLRVATESSAKTPSK<br>LLDPLAWDNHYGTQIPKEEWKSQEKSPEKTAFKKKDTILSLNACESNHAIAAINEGQNKPEIEVTWAKQGRTERLCSQ<br>NPPVLKRHQREITRTTLQSDQEEIDYDDTISVEMKKEDFDIYDEDENQSPRSFQKKTRHYFIAAVERLWDYGMSSSPH<br>VLRNRAQSGSVPQFKKVVFQEFTDGSFTQPLYRGELNEHLGLLGPYIRAEVEDNIMVTFRNQASRPYSFYSSLISYEE<br>DQRQGAEPRKNFVKPNETKTYFWKVQHHMAPTKDEFDCKAWAYFSDVDLEKDVHSGLIGPLLVCHTNTLNPAHGRQVT<br>VQEFALFFTIFDETKSWYFTENMERNCRAPCNIQMEDPTFKENYRFHAINGYIMDTLPGLVMAQDQRIRWYLLSMGSN<br>ENIHSIHFSGHVFTVRKKEEYKMALYNLYPGVFETVEMLPSKAGIWRVECLIGEHLHAGMSTLFLVYSNKCQTPLGMA<br>SGHIRDFQITASGQYGQWAPKLARLHYSGSINAWSTKEPFSWIKVDLLAPMIIHGIKTQGARQKFSSLYISQFIIMYS<br>LDGKKWQTYRGNSTGTLMVFFGNVDSSGIKHNIFNPPIIARYIRLHPTHYSIRSTLRMELMGCDLNSCSMPLGMESKA<br>ISDAQITASSYFTNMFATWSPSKARLHLQGRSNAWRPQVNNPKEWLQVDFQKTMKVTGVTTQGVKSLLTSMYVKEFLI<br>SSSQDGHQWTLFFQNGKVKVFQGNQDSFTPVVNSLDPPLLTRYLRIHPQSWVHQIALRMEVLGCEAQDLY |
| SEQ ID NO:<br>21<br>B19 WT 5' | CCAAATCAGATGCCGCCGGTCGCCGCCGGTAGGCGGGACTTCCGGTACAAGATGGCGGACAATTACGTCATTTCCTGT<br>GACGTCATTTCCTGTGACGTCACTTCCGGTGGGCGGGACTTCCGGAATTAGGGTTGGCTCTGGGCCAGCTTGCTTGGG<br>GTTGCCTTGACACTAAGACAAGCGGCGCGCCGCTTGATCTTAGTGGCACGTCAACCCCAAGCGCTGGCCCAGAGCCAA<br>CCCTAATTCCGGAAGTCCCGCCCACCGGAAGTGACGTCACAGGAAATGACGTCACAGGAAATGACGTAATTGTCCGCC<br>ATCTTGTACCGGAAGTCCCGCCTACCGGCGGCGACCGGCGGCATCTGATTTGGTGTCTTCTTTTAAATTTT |
| SEQ ID NO:<br>22<br>B19 WT 3' | AAAATTTAAAAGAAGACACCAAATCAGATGCCGCCGGTCGCCGCCGGTAGGCGGGACTTCCGGTACAAGATGGCGGAC<br>AATTACGTCATTTCCTGTGACGTCATTTCCTGTGACGTCACTTCCGGTGGGCGGGACTTCCGGAATTAGGGTTGGCTC<br>TGGGCCAGCGCTTGGGGTTGACGTGCCACTAAGATCAAGCGGCGCGCCGCTTGTCTTAGTGTCAAGGCAACCCCAAGC<br>AAGCTGGCCCAGAGCCAACCCTAATTCCGGAAGTCCCGCCCACCGGAAGTGACGTCACAGGAAATGACGTCACAGGAA<br>ATGACGTAATTGTCCGCCATCTTGTACCGGAAGTCCCGCCTACCGGCGGCGACCGGCGGCATCTGATTTGG |
| SEQ ID NO:<br>23<br>5'_B19_<br>minimal | CCAAATCAGATGCCGCCGGTCGCCGCCGGTAGGCGGGACTTCCGGTACAGCGCGCCGCTGTACCGGAAGTCCCGCCTA<br>CCGGCGGCGACCGGCGGCATCTGATTTGGTGTCTTCTTTTAAATTTT |
| SEQ ID NO:<br>24<br>3'_B19_<br>minimal | AAAATTTAAAAGAAGACACCAAATCAGATGCCGCCGGTCGCCGCCGGTAGGCGGGACTTCCGGTACAGCGGCGCGCTG<br>TACCGGAAGTCCCGCCTACCGGCGGCGACCGGCGGCATCTGATTTGG |
| SEQ ID NO:<br>25<br>5'_GPV_<br>minimal | CTCATTGGAGGGTTCGTTCGTTCGAACGTTCGTTCGCATGCGAACGAACGTTCGAACGAACGAACCCTCCAATGAGAC<br>TCAAGGACAAGAGGATATTTTGCGCGCCAGGAAGTG |
| SEQ ID NO:<br>26<br>3'_GPV_<br>minimal | CACTTCCTGGCGCGCAAAATATCCTCTTGTCCTTGAGTCTCATTGGAGGGTTCGTTCGTTCGAACGTTCGTTCGCATG<br>CGAACGAACGTTCGAACGAACGAACCCTCCAATGAG |
| SEQ ID NO:<br>27<br>5'_GPV_A186 | CTCATTGGAGGGTTCGTTCGTTCGAACCAGCCAATCAGGGGAGGGGGAAGTGACGCAAGTTCCGGTCACATGCTTCCG<br>GTGACGCACATCCGGTGACGTAGTTCGCATGCCTGTCTATCGCCTACCCATCCCTGTCTGAGATCAAGGGCGTGATCG<br>TGCACAGACTGGAGAGCGTGTCCTATAATATCGGCTCTCAGGAGTGGAGCACCACAGTGCCCAGATACGTGGCCACCC<br>AGGGCTATCTGATCTCCAACTTCGACGCATGCGAACTACGTCACCGGATGTGCGTCACCGGAAGCATGTGACCGGAAC<br>TTGCGTCACTTCCCCCTCCCCTGATTGGCTGGTTCGAACGAACGAACCCTCCAATGAGACTCAAGGACAAGAGGATAT<br>TTTGCGCGCCAGGAAGTG |
| SEQ ID NO:<br>28<br>3'_GPV_A186 | CACTTCCTGGCGCGCAAAATATCCTCTTGTCCTTGAGTCTCATTGGAGGGTTCGTTCGTTCGAACCAGCCAATCAGGG<br>GAGGGGGAAGTGACGCAAGTTCCGGTCACATGCTTCCGGTGACGCACATCCGGTGACGTAGTTCGCATGCCTGTCTAT<br>CGCCTACCCATCCCTGTCTGAGATCAAGGGCGTGATCGTGCACAGACTGGAGAGCGTGTCCTATAATATCGGCTCTCA<br>GGAGTGGAGCACCACAGTGCCCAGATACGTGGCCACCCAGGGCTATCTGATCTCCAACTTCGACGCATGCGAACTACG<br>TCACCGGATGTGCGTCACCGGAAGCATGTGACCGGAACTTGCGTCACTTCCCCCTCCCCTGATTGGCTGGTTCGAACG<br>AACGAACCCTCCAATGAG |
| SEQ ID NO:<br>29<br>5'_GPV_A120 | CTCATTGGAGGGTTCGTTCGTTCGAACCAGCCAATCAGGGGAGGGGGAAGTGACGCAAGTTCCGGTCACATGCTTCCG<br>GTGACGCACATCCGGTGACGTAGTTCCGGTCACGTGCTTCCTGTCACGTGTTTCCGGTCGCATGCCTGTCTATCGCCT<br>ACCCATCCCTGTCTGAGATCAAGGGCGTGATCGTGCACAGACTGGAGAGCGTGTCCTATAATATCGGCTCTCAGGAGT<br>GGAGCACCACAGTGCCCAGATACGTGGCCACCCAGGGCTATCTGATCTCCAACTTCGACGCATGCTCACGTGACCGGA<br>AACACGTGACAGGAAGCACGTGACCGGAACTACGTCACCGGATGTGCGTCACCGGAAGCATGTGACCGGAACTTGCGT<br>CACTTCCCCCTCCCCTGATTGGCTGGTTCGAACGAACGAACCCTCCAATGAGACTCAAGGACAAGAGGATATTTTGCG<br>CGCCAGGAAGTG |
| SEQ ID NO:<br>30<br>3'_GPV_A120 | CACTTCCTGGCGCGCAAAATATCCTCTTGTCCTTGAGTCTCATTGGAGGGTTCGTTCGTTCGAACCAGCCAATCAGGG<br>GAGGGGGAAGTGACGCAAGTTCCGGTCACATGCTTCCGGTGACGCACATCCGGTGACGTAGTTCCGGTCACGTGCTTC<br>CTGTCACGTGTTTCCGGTCACGTGAGCATGCCTGTCTATCGCCTACCCATCCCTGTCTGAGATCAAGGGCGTGATCGT<br>GCACAGACTGGAGAGCGTGTCCTATAATATCGGCTCTCAGGAGTGGAGCACCACAGTGCCCAGATACGTGGCCACCCA<br>GGGCTATCTGATCTCCAACTTCGACGGCATGCGACCGGAAACACGTGACAGGAAGCACGTGACCGGAACTACGTCACC<br>GGATGTGCGTCACCGGAAGCATGTGACCGGAACTTGCGTCACTTCCCCCTCCCCTGATTGGCTGGTTCGAACGAACGA<br>ACCCTCCAATGAG |

TABLE 1-continued

Additional Nucleotide and Amino Acid Sequences

| SEQ ID NO/ Description | Nucleotide or amino acid sequence |
|---|---|
| SEQ ID NO: 31 Nucleic acid sequence of wild type human FVIII | ATGCAAATAGAGCTCTCCACCTGCTTCTTTCTGTGCCTTTTGCGATTCTGCTTTAGTGCCACCAGAAGATACTACCTG<br>GGTGCAGTGGAACTGTCATGGGACTATATGCAAAGTGATCTCGGTGAGCTGCCTGTGGACGCAAGATTTCCTCCTAGA<br>GTGCCAAAATCTTTTCCATTCAACACCTCAGTCGTGTACAAAAAGACTCTGTTTGTAGAATTCACGGATCACCTTTTC<br>AACATCGCTAAGCCAAGGCCACCCTGGATGGGTCTGCTAGGTCCTACCATCCAGGCTGAGGTTTATGATACAGTGGTC<br>ATTACACTTAAGAACATGGCTTCCCATCCTGTCAGTCTTCATGCTGTTGGTGTATCCTACTGGAAAGCTTCTGAGGGA<br>GCTGAATATGATGATCAGACCAGTCAAAGGGAGAAAGAAGATGATAAAGTCTTCCCTGGTGGAAGCCATACATATGTC<br>TGGCAGGTCCTGAAAGAGAATGGTCCAATGGCCTCTGACCCACTGTGCCTTACCTACTCATATCTTTCTCATGTGGAC<br>CTGGTAAAAGACTTGAATTCAGGCCTCATTGGAGCCCTACTAGTATGTAGAGAAGGGAGTCTGGCCAAGGAAAAGACA<br>CAGACCTTGCACAAATTTATACTACTTTTTGCTGTATTTGATGAAGGGAAAAGTTGGCACTCAGAAACAAAGAACTCC<br>TTGATGCAGGATAGGGATGCTGCATCTGCTCGGGCCTGGCCTAAAATGCACACAGTCAATGGTTATGTAAACAGGTCT<br>CTGCCAGGTCTGATTGGATGCCACAGGAAATCAGTCTATTGGCATGTGATTGGAATGGGCACCACTCCTGAAGTGCAC<br>TCAATATTCCTCGAAGGTCACACATTTCTTGTGAGGAACCATCGCCAGGCGTCCTTGGAAATCTCGCCAATAACTTTC<br>CTTACTGCTCAAACACTCTTGATGGACCTTGGACAGTTTCTACTGTTTTGTCATATCTCTTCCCACCAACATGATGGC<br>ATGGAAGCTTATGTCAAAGTAGACAGCTGTCCAGAGGAACCCCAACTACGAATGAAAAATAATGAAGAAGCGGAAGAC<br>TATGATGATGATCTTACTGATTCTGAAATGGATGTGGTCAGGTTTGATGATGACAACTCTCCTTCCTTTATCCAAATT<br>CGCTCAGTTGCCAAGAAGCATCCTAAAACTTGGGTACATTACATTGCTGCTGAAGAGGAGGACTGGGACTATGCTCCC<br>TTAGTCCTCGCCCCCGATGACAGAAGTTATAAAAGTCAATATTTGAACAATGGCCCTCAGCGGATTGGTAGGAAGTAC<br>AAAAAAGTCCGATTTATGGCATACACAGATGAAACCTTTAAGACTCGTGAAGCTATTCAGCATGAATCAGGAATCTTG<br>GGACCTTTACTTTATGGGGAAGTTGGAGACACACTGTTGATTATATTTAAGAATCAAGCAAGCAGACCATATAACATC<br>TACCCTCACGGAATCACTGATGTCCGTCCTTTGTATTCAAGGAGATTACCAAAAGGTGTAAAACATTTGAAGGATTTT<br>CCAATTCTGCCAGGAGAAATATTCAAATATAAATGGACAGTGACTGTAGAAGATGGGCCAACTAAATCAGATCCTCGG<br>TGCCTGACCCGCTATTACTCTAGTTTCGTTAATATGGAGAGAGATCTAGCTTCAGGACTCATTGGCCCTCTCCTCATC<br>TGCTACAAAGAATCTGTAGATCAAAGAGGAAACCAGATAATGTCAGACAAGAGGAATGTCATCCTGTTTTCTGTATTT<br>GATGAGAACCGAAGCTGGTACCTCACAGAGAATATACAACGCTTTCTCCCCAATCCAGCTGGAGTGCAGCTTGAGGAT<br>CCAGAGTTCCAAGCCTCCAACATCATGCACAGCATCAATGGCTATGTTTTTGATAGTTTGCAGTTGTCAGTTTGTTTG<br>CATGAGGTGGCATACTGGTACATTCTAAGCATTGGAGCACAGACTGACTTCCTTTCTGTCTTCTTCTCTGGATATACC<br>TTCAAACACAAAATGGTCTATGAAGACACACTCACCCTATTCCCATTCTCAGGAGAAACTGTCTTCATGTCGATGGAA<br>AACCCAGGTCTATGGATTCTGGGGTGCCACAACTCAGACTTTCGGAACAGAGGCATGACCGCCTTACTGAAGGTTTCT<br>AGTTGTGACAAGAACACTGGTGATTATTACGAGGACAGTTATGAAGATATTTCAGCATACTTGCTGAGTAAAAACAAT<br>GCCATTGAACCAAGAAGCTTCTCCCAGAATTCAAGACACCCTAGCACTAGGCAAAAGCAATTTAATGCCACCACAATT<br>CCAGAAAATGACATAGAGAAGACTGACCCTTGGTTTGCACACAGAACACCTATGCCTAAAATACAAAATGTCTCCTCT<br>AGTGATTTGTTGATGCTCTTGCGACAGAGTCCTACTCCACATGGGCTATCCTTATCTGATCTCCAAGAAGCCAAATAT<br>GAGACTTTTTCTGATGATCCATCACCTGGAGCAATAGACAGTAATAACAGCCTGTCTGAAATGACACACTTCAGGCCA<br>CAGCTCCATCACAGTGGGGACATGGTATTTACCCCTGAGTCAGGCCTCCAATTAAGATTAAATGAGAAACTGGGGACA<br>ACTGCAGCAACAGAGTTGAAGAAACTTGATTTCAAAGTTTCTAGTACATCAAATAATCTGATTTCAACAATTCCATCA<br>GACAATTTGGCAGCAGGTACTGATAATACAAGTTCCTTAGGACCCCCAAGTATGCCAGTTCATTATGATAGTCAATTA<br>GATACCACTCTATTTGGCAAAAAGTCATCTCCCCTTACTGAGTCTGGTGGACCTCTGAGCTTGAGTGAAGAAAATAAT<br>GATTCAAAGTTGTTAGAATCAGGTTTAATGAATAGCCAAGAAAGTTCATGGGGAAAAAATGTATCGTCAACAGAGAGT<br>GGTAGGTTATTTAAAGGGAAAAGAGCTCATGGACCTGCTTTGTTGACTAAAGATAATGCCTTATTCAAAGTTAGCATC<br>TCTTTGTTAAAGACAAACAAAACTTCCAATAATTCAGCAACTAATAGAAAGACTCACATTGATGGCCCATCATTATTA<br>ATTGAGAATAGTCCATCAGTCTGGCAAAATATATTAGAAAGTGACACTGAGTTTAAAAAAGTGACACCTTTGATTCAT<br>GACAGAATGCTTATGGACAAAAATGCTACAGCTTTGAGGCTAAATCATATGTCAAATAAAACTACTTCATCAAAAAAC<br>ATGGAAATGGTCCAACAGAAAAAAGAGGGCCCCATTCCACCAGATGCACAAAATCCAGATATGTCGTTCTTTAAGATG<br>CTATTCTTGCCAGAATCAGCAAGGTGGATACAAAGGACTCATGGAAAGAACTCTCTGAACTCTGGGCAAGGCCCCAGT<br>CCAAAGCAATTAGTATCCTTAGGACCAGAAAAATCTGTGGAAGGTCAGAATTTCTTGTCTGAGAAAAACAAAGTGGTA<br>GTAGGAAAGGGTGAATTTACAAAGGACGTAGGACTCAAAGAGATGGTTTTTCCAAGCAGCAGAAACCTATTTCTTACT<br>AACTTGGATAATTTACATGAAAATAATACACACAATCAAGAAAAAAAAATTCAGGAAGAAATAGAAAAGAAGGAAACA<br>TTAATCCAAGAGAATGTAGTTTTGCCTCAGATACATACAGTGACTGGCACTAAGAATTTCATGAAGAACCTTTTCTTA<br>CTGAGCACTAGGCAAAATGTAGAAGGTTCATATGACGGGGCATATGCTCCAGTACTTCAAGATTTTAGGTCATTAAAT<br>GATTCAACAAATAGAACAAAGAAACACACAGCTCATTTCTCAAAAAAAGGGGAGGAAGAAAACTTGGAAGGCTTGGGA<br>AATCAAACCAAGCAAATTGTAGAGAAATATGCATGCACCACAAGGATATCTCCTAATACAAGCCAGCAGAATTTTGTC<br>ACGCAACGTAGTAAGAGAGCTTTGAAACAATTCAGACTCCCACTAGAAGAAACAGAACTTGAAAAAAGGATAATTGTG<br>GATGACACCTCAACCCAGTGGTCCAAAAACATGAAACATTTGACCCCGAGCACCCTCACACAGATAGACTACAATGAG<br>AAGGAGAAAGGGGCCATTACTCAGTCTCCCTTATCAGATTGCCTTACGAGGAGTCATAGCATCCCTCAAGCAAATAGA<br>TCTCCATTACCCATTGCAAAGGTATCATCATTTCCATCTATTAGACCTATATATCTGACCAGGGTCCTATTCCAAGAC<br>AACTCTTCTCATCTTCCAGCAGCATCTTATAGAAAGAAAGATTCTGGGGTCCAAGAAAGCAGTCATTTCTTACAAGGA<br>GCCAAAAAAAATAACCTTTCTTTAGCCATTCTAACCTTGGAGATGACTGGTGATCAAAGAGAGGTTGGCTCCCTGGGG<br>ACAAGTGCCACAAATTCAGTCACATACAAGAAAGTTGAGAACACTGTTCTCCCGAAACCAGACTTGCCCAAAACATCT<br>GGCAAAGTTGAATTGCTTCCAAAAGTTCACATTTATCAGAAGGACCTATTCCCTACGGAAACTAGCAATGGGTCTCCT<br>GGCCATCTGGATCTCGTGGAAGGGAGCCTTCTTCAGGGAACAGAGGGAGCGATTAAGTGGAATGAAGCAAACAGACCT<br>GGAAAAGTTCCCTTTCTGAGAGTAGCAACAGAAAGCTCTGCAAAGACTCCCTCCAAGCTATTGGATCCTCTTGCTTGG<br>GATAACCACTATGGTACTCAGATACCAAAAGAAGAGTGGAAATCCCAAGAGAAGTCACCAGAAAAAACAGCTTTTAAG<br>AAAAAGGATACCATTTTGTCCCTGAACGCTTGTGAAAGCAATCATGCAATAGCAGCAATAAATGAGGGACAAAATAAG<br>CCCGAAATAGAAGTCACCTGGGCAAAGCAAGGTAGGACTGAAAGGCTGTGCTCTCAAAACCCACCAGTCTTGAAACGC<br>CATCAACGGGAAATAACTCGTACTACTCTTCAGTCAGATCAAGAGGAAATTGACTATGATGATACCATATCAGTTGAA<br>ATGAAGAAGGAAGATTTTGACATTTATGATGAGGATGAAAATCAGAGCCCCCGCAGCTTTCAAAAGAAAACACGACAC<br>TATTTTATTGCTGCAGTGGAGAGGCTCTGGGATTATGGGATGAGTAGCTCCCCACATGTTCTAAGAAACAGGGCTCAG<br>AGTGGCAGTGTCCCTCAGTTCAAGAAAGTTGTTTTCCAGGAATTTACTGATGGCTCCTTTACTCAGCCCTTATACCGT<br>GGAGAACTAAATGAACATTTGGGACTCCTGGGGCCATATATAAGAGCAGAAGTTGAAGATAATATCATGGTAACTTTC<br>AGAAATCAGGCCTCTCGTCCCTATTCCTTCTATTCTAGCCTTATTTCTTATGAGGAAGATCAGAGGCAAGGAGCAGAA<br>CCTAGAAAAAACTTTGTCAAGCCTAATGAAACCAAAACTTACTTTTGGAAAGTGCAACATCATATGGCACCCACTAAA<br>GATGAGTTTGACTGCAAAGCCTGGGCTTATTTCTCTGATGTTGACCTGGAAAAAGATGTGCACTCAGGCCTGATTGGA<br>CCCCTTCTGGTCTGCCACACTAACACACTGAACCCTGCTCATGGGAGACAAGTGACAGTACAGGAATTTGCTCTGTTT<br>TTCACCATCTTTGATGAGACCAAAAGCTGGTACTTCACTGAAAATATGGAAAGAACTGCAGGGCTCCCTGCAATATC |

TABLE 1-continued

Additional Nucleotide and Amino Acid Sequences

| SEQ ID NO/ Description | Nucleotide or amino acid sequence |
| --- | --- |
| | CAGATGGAAGATCCCACTTTTAAAGAGAATTATCGCTTCCATGCAATCAATGGCTACATAATGGATACACTACCTGGC<br>TTAGTAATGGCTCAGGATCAAAGGATTCGATGGTATCTGCTCAGCATGGGCAGCAATGAAAACATCCATTCTATTCAT<br>TTCAGTGGACATGTGTTCACTGTACGAAAAAAAGAGGAGTATAAAATGGCACTGTACAATCTCTATCCAGGTGTTTTT<br>GAGACAGTGGAAATGTTACCATCCAAAGCTGGAATTTGGCGGGTGGAATGCCTTATTGGCGAGCATCTACATGCTGGG<br>ATGAGCACACTTTTTCTGGTGTACAGCAATAAGTGTCAGACTCCCCTGGGAATGGCTTCTGGACACATTAGAGATTTT<br>CAGATTACAGCTTCAGGACAATATGGACAGTGGGCCCCAAAGCTGGCCAGACTTCATTATTCCGGATCAATCAATGCC<br>TGGAGCACCAAGGAGCCCTTTTCTTGGATCAAGGTGGATCTGTTGGCACCAATGATTATTCACGGCATCAAGACCCAG<br>GGTGCCCGTCAGAAGTTCTCCAGCCTCTACATCTCTCAGTTTATCATCATGTATAGTCTTGATGGGAAGAAGTGGCAG<br>ACTTATCGAGGAAATTCCACTGGAACCTTAATGGTCTTCTTTGGCAATGTGGATTCATCTGGGATAAAACACAATATT<br>TTTAACCCTCCAATTATTGCTCGATACATCCGTTTGCACCCAACTCATTATAGCATTCGCAGCACTCTTCGCATGGAG<br>TTGATGGGCTGTGATTTAAATAGTTGCAGCATGCCATTGGGAATGGAGAGTAAAGCAATATCAGATGCACAGATTACT<br>GCTTCATCCTACTTTACCAATATGTTTGCCACCTGGTCTCCTTCAAAAGCTCGACTTCACCTCCAAGGGAGGAGTAAT<br>GCCTGGAGACCTCAGGTGAATAATCCAAAAGAGTGGCTGCAAGTGGACTTCCAGAAGACAATGAAAGTCACAGGAGTA<br>ACTACTCAGGGAGTAAAATCTCTGCTTACCAGCATGTATGTGAAGGAGTTCCTCATCTCCAGCAGTCAAGATGGCCAT<br>CAGTGGACTCTCTTTTTTCAGAATGGCAAAGTAAAGGTTTTTCAGGGAAATCAAGACTCCTTCACACCTGTGGTGAAC<br>TCTCTAGACCCACCGTTACTGACTCGCTACCTTCGAATTCACCCCCAGAGTTGGGTGCACCAGATTGCCCTGAGGATG<br>GAGGTTCTGGGCTGCGAGGCACAGGACCTCTAC |
| SEQ ID NO: 32 Nucleotide sequence encoding BDD-co6FVIII (V1.0) (no XTEN) | GCCACTCGCCGGTACTACCTTGGAGCCGTGGAGCTTTCATGGGACTACATGCAGAGCGACCTGGGCGAACTCCCCGTG<br>GATGCCAGATTCCCCCCCGCGTGCCAAAGTCCTTCCCCTTTAACACCTCCGTGGTGTACAAGAAAACCCTCTTTGTC<br>GAGTTCACTGACCACCTGTTCAACATCGCCAAGCCGCGCCCACCTTGGATGGGCCTCCTGGGACCGACCATTCAAGCT<br>GAAGTGTACGACACCGTGGTGATCACCCTGAAGAACATGGCGTCCCACCCCGTGTCCCTGCATGCGGTCGGAGTGTCC<br>TACTGGAAGGCCTCCGAAGGAGCTGAGTACGACGACCAGACTAGCCAGCGGGAAAAGGAGGACGATAAAGTGTTCCCG<br>GGCGGCTCGCATACTTACGTGTGGCAAGTCCTGAAGGAAAACGGACCTATGGCATCCGATCCTCTGTGCCTGACTTAC<br>TCCTACCTTTCCCATGTGGACCTCGTGAAGGACCTGAACAGCGGGCTGATTGGTGCACTTCTCGTGTGCCGCGAAGGT<br>TCGCTCGCTAAGGAAAAGACCCAGACCCTCCATAAGTTCATCCTTTTGTTCGCTGTGTTCGATGAAGGAAAGTCATGG<br>CATTCCGAAACTAAGAACTCGCTGATGCAGGACCGGGATGCCGCCTCAGCCCGCGCCTGGCCTAAAATGCATACAGTC<br>AACGGATACGTGAATCGGTCACTGCCCGGGCTCATCGGTTGTCACAGAAAGTCCGTGTACTGGCACGTCATCGGCATG<br>GGCACTACGCCTGAAGTGCACTCCATCTTCCTGGAAGGGCACACCTTCCTCGTGCGCAACCACCGCCAGGCCTCTCTG<br>GAAATCTCCCCGATTACCTTTCTGACCGCCCAGACTCTGCTCATGGACCTGGGGCAGTTCCTTCTCTTCTGCCACATC<br>TCCAGCCATCAGCACGACGGAATGGAGGCCTACGTGAAGGTGGACTCATGCCCGGAAGAACCTCAGTTGCGGATGAAG<br>AACAACGAGGAGGCCGAGGACTATGACGACGATTTGACTGACTCCGAGATGGACGTCGTGCGGTTCGATGACGACAAC<br>AGCCCCAGCTTCATCCAGATTCGCAGCGTGGCCAAGAAGCACCCCAAAACCTGGGTGCACTACATCGCGGCCGAGGAA<br>GAAGATTGGGACTACGCCCCGTTGGTGCTGGCACCCGATGACCGGTCGTACAAGTCCCAGTATCTGAACAATGGTCCG<br>CAGCGGATTGGCAGAAAGTACAAGAAAGTGCGGTTCATGGCGTACACTGACGAAACGTTTAAGACCCGGGAGGCCATT<br>CAACATGAGAGCGGCATTCTGGGACCACTGCTGTACGGAGAGGTCGGCGATACCCTGCTCATCATCTTCAAAAACCAG<br>GCCTCCCGGCCTTACAACATCTACCCTCACGGAATCACCGACGTGCGGCCACTCTACTCGCGGCGCCTGCCGAAGGGC<br>GTCAAGCACCTGAAAGACTTCCCTATCCTGCCGGGCGAAATCTTCAAGTATAAGTGGACCGTCACCGTGGAGGACGGG<br>CCCACCAAGAGCGATCCTAGGTGTCTGACTCGGTACTACTCCAGCTTCGTGAACATGGAACGGGACCTGGCATCGGGA<br>CTCATTGGACCGCTGCTGATCTGCTACAAAGAGTCGGTGGATCAACGCGGCAACCAGATCATGTCCGACAAGCGCAAC<br>GTGATCCTGTTCTCCGTGTTTGATGAAAACAGATCCTGGTACCTCACTGAAAACATCCAGAGGTTCCTCCCAAACCCC<br>GCAGGAGTGCAACTGGAGGACCCTGAGTTTCAGGCCTCGAATATCATGCACTCGATTAACGGTTACGTGTTCGACTCG<br>CTGCAGCTGAGCGTGTGCCTCCATGAAGTCGCTTACTGGTACATTCTGTCCATCGGCGCCCAGACTGACTTCCTGAGC<br>GTGTTCTTTTCCGGTTACACCTTTAAGCACAAGATGGTGTACGAAGATACCCTGACCCTGTTCCCTTTCTCCGGCGAA<br>ACGGTGTTCATGTCGATGGAGAACCCGGGTCTGTGGATTCTGGGATGCCACAACAGCGACTTTCGGAACCGCGGAATG<br>ACTGCCCTGCTGAAGGTGTCCTCATGCGACAAGAACACCGGAGACTACTACGAGGACTCCTACGAGGATATCTCAGCC<br>TACCTCCTGTCCAAGAACAACGCGATCGAGCCGCGCAGCTTCAGCCAGAACCCGCCTGTGCTGAAGAGGCACCAGCGA<br>GAAATTACCCGGACCACCCTCCAATCGGATCAGGAGGAAATCGACTACGACGACACCATCTCGGTGGAAATGAAGAAG<br>GAAGATTTCGATATCTACGACGAGGACGAAAATCAGTCCCCTCGCTCATTCCAAAAGAAAACTAGACACTACTTTATC<br>GCCGCGGTGGAAAGACTGTGGGACTATGGAATGTCATCCAGCCCTCACGTCCTTCGGAACCGGGCCCAGAGCGGATCG<br>GTGCCTCAGTTCAAGAAAGTGGTGTTCCAGGAGTTCACCGACGGCAGCTTCACCCAGCCGCTGTACCGGGGAGAACTG<br>AACGAACACCTGGGCCTGCTCGGTCCCTACATCCGCGCGGAAGTGGAGGATAACATCATGGTGACCTTCCGTAACCAA<br>GCATCCAGACCTTACTCCTTCTATTCCTCCCTGATCTCATACGAGGAGGACCAGCGCCAAGGCGCCGAGCCCCGCAAG<br>AACTTCGTCAAGCCCAACGAGACTAAGACCTACTTCTGGAAGGTCCAACACCATATGGCCCCGACCAAGGATGAGTTT<br>GACTGCAAGGCCTGGGCCTACTTCTCCGACGTGGACCTTGAGAAGGATGTCCATTCCGGCCTGATCGGGCCGCTGCTC<br>GTGTGTCACACCAACACCCTGAACCCAGCGCATGGACGCCAGGTCACCGTCCAGGAGTTTGCTCTGTTCTTCACCATT<br>TTTGACGAAACTAAGTCCTGGTACTTCACCGAGAATATGGAGCGAAACTGTAGAGCGCCCTGCAATATCCAGATGGAA<br>GATCCGACTTTCAAGGAGAACTATAGATTCCACGCCATCAACGGGTACATCATGGATACTCTGCCGGGGCTGGTCATG<br>GCCCAGGATCAGAGGATTCGGTGGTACTTGCTGTCAATGGGATCGAACGAAAACATTCACTCCATTCACTTCTCCGGT<br>CACGTGTTCACTGTGCGCAAGAAGGAGGAGTACAAGATGGCGCTGTACAATCTGTACCCCGGGGTGTTCGAAACTGTG<br>GAGATGCTGCCGTCCAAGGCCGGCATCTGGAGAGTGGAGTGCCTGATCGGAGAGCACCTCCACGCGGGGATGTCCACC<br>CTCTTCCTGGTGTACTCGAATAAGTGCCAGACCCCGCTGGGCATGGCCTCGGGCCACATCAGAGACTTCCAGATCACA<br>GCAAGCGGACAATACGGCCAATGGGCGCCGAAGCTGGCCCGCTTGCACTACTCCGGATCGATCAACGCATGGTCCACC<br>AAGGAACCGTTCTCGTGGATTAAGGTGGACCTCCTGGCCCCTATGATTATCCACGGAATTAAGACCCAGGGCGCCAGG<br>CAGAAGTTCTCCTCCCTGTACATCTCGCAATTCATCATCATGTACAGCCTGGACGGGAAGAAGTGGCAGACTTACAGG<br>GGAAACTCCACCGGCACCCTGATGGTCTTTTTCGGCAACGTGGATTCCTCCGGCATTAAGCACAACATCTTCAACCCA<br>CCGATCATAGCCAGATATATTAGGCTCCACCCCACTCACTACTCAATCCGCTCAACTCTTCGGATGGAACTCATGGGG<br>TGCGACCTGAACTCCTGCTCCATGCCGTTGGGGATGGAATCAAAGGCTATTAGCGACGCCCAGATCACCGCGAGCTCC<br>TACTTCACTAACATGTTCGCCACCTGGAGCCCCTCCAAGGCCAGGCTGCACTTGCAGGGACGGTCAAATGCCTGGCGG<br>CCGCAAGTGAACAATCCGAAGGAATGGCTTCAAGTGGATTTCCAAAAGACCATGAAAGTGACCGGAGTCACCACCCAG<br>GGAGTGAAGTCCCTTCTGACCTCGATGTATGTGAAGGAGTTCCTGATTAGCAGCAGCCAGGACGGGCACCAGTGGACC<br>CTGTTCTTCCAAAACGGAAAGGTCAAGGTGTTCCAGGGGAACCAGGACTCGTTCACACCCGTGGTGAACTCCCTGGAC<br>CCCCCACTGCTGACGCGGTACTTGAGGATTCATCCTCAGTCCTGGGTCCATCAGATTGCATTGCGAATGGAAGTCCTG<br>GGCTGCGAGGCCCAGGACCTGTACTGA |

TABLE 1-continued

Additional Nucleotide and Amino Acid Sequences

| SEQ ID NO/ Description | Nucleotide or amino acid sequence |
|---|---|
| SEQ ID NO: 33<br>Nucleotide sequence encoding coBDDFVIII (V2.0) (no XTEN) | GCCACCCGCCGGTATTACTTAGGTGCTGTGGAACTGAGCTGGGACTACATGCAGTCCGACCTGGGAGAACTGCCGGTG<br>GACGCGAGATTCCCACCTAGAGTCCCGAAGTCCTTCCCATTCAACACCTCCGTGGTCTACAAAAAGACCCTGTTCGTG<br>GAGTTCACTGACCACCTTTTCAATATTGCCAAGCCGCGCCCCCCCTGGATGGGCCTGCTTGGTCCTACGATCCAAGCA<br>GAGGTCTACGACACCGTGGTCATCACACTGAAGAACATGGCCTCACACCCCGTGTCGCTGCATGCTGTGGGAGTGTCC<br>TACTGGAAGGCCTCAGAGGGTGCCGAATATGATGACCAGACCAGCCAGAGGGAAAAGGAGGATGACAAAGTGTTCCCG<br>GGTGGCAGCCACACTTACGTGTGGCAAGTGCTGAAGGAAAACGGGCCTATGGCGTCGGACCCCCTATGCCTGACCTAC<br>TCCTACCTGTCCCATGTGGACCTTGTGAAGGATCTCAACTCGGGACTGATCGGCGCCCTCTTGGTGTGCAGAGAAGGC<br>AGCCTGGCGAAGGAAAAGACTCAGACCCTGCACAAGTTCATTCTGTTGTTTGCTGTGTTCGATGAAGGAAAGTCCTGG<br>CACTCAGAAACCAAGAACTCGCTGATGCAGGATAGAGATGCGGCCTCGGCCAGAGCCTGGCCTAAAATGCACACCGTC<br>AACGGATATGTGAACAGGTCGCTCCCTGGCCTCATCGGCTGCCACAGAAAGTCCGTGTATTGGCATGTGATCGGCATG<br>GGTACTACTCCGGAAGTGCATAGTATCTTTCTGGAGGGCCATACCTTCTTGGTGCGCAACCACAGACAGGCCTCGCTG<br>GAAATCTCGCCTATCACTTTCTTGACTGCGCAGACCCTCCTTATGGACCTTGGACAGTTCCTGCTGTTCTGTCACATC<br>AGCTCCCATCAGCATGATGGGATGGAGGCCTATGTCAAAGTGGACTCCTGCCCTGAGGAGCCACAGCTCCGGATGAAG<br>AACAATGAGGAAGCGGAGGATTACGACGACGACCTGACTGACAGCGAAATGGACGTCGTGCGATTCGATGACGACAAC<br>AGCCCGTCCTTCATCCAAATTAGATCAGTGGCGAAGAAGCACCCCAAGACCTGGGTGCACTACATTGCCGCCGAGGAA<br>GAGGACTGGGACTACGCGCCGCTGGTGCTGGCGCCAGACGACAGGAGCTACAAGTCCCAGTACCTCAACAACGGGCCG<br>CAGCGCATTGGCAGGAAGTACAAGAAAGTCCGCTTCATGGCCTACACTGATGAAACCTTCAAGACGAGGGAAGCCATC<br>CAGCACGAGTCAGGCATCCTGGGACCGCTCCTTTACGGCGAAGTCGGGGATACCCTGCTCATCATTTTCAAGAACCAG<br>GCATCGCGGCCCTACAACATCTACCCTCACGGGATCACAGACGTGCGCCCGCTCTACTCCCGCCGGCTGCCCAAGGGA<br>GTGAAGCACCTGAAGGATTTTCCCATCCTGCCGGGAGAAATCTTCAAGTACAAGTGGACCGTGACTGTGGAAGATGGC<br>CCTACCAAGTCGGACCCTCGCTGTCTGACCCGGTACTATTCCTCGTTTGTGAACATGGAGCGCGACCTGGCCTCGGGG<br>CTGATTGGTCCGCTGCTGATCTGCTACAAGGAGTCCGTGGACCAGCGCGGGAACCAGATCATGTCCGACAAGCGCAAC<br>GTGATCCTGTTCTCTGTCTTTGATGAAAACAGATCGTGGTACTTGACTGAGAATATCCAGCGGTTCCTGCCCAACCCA<br>GCGGGAGTGCAACTGGAGGACCCGGAGTTCCAGGCCTCAAACATTATGCACTCTATCAACGGCTATGTGTTCGACTCG<br>CTCCAACTGAGCGTGTGCCTGCATGAAGTGGCATACTGGTACATTCTGTCCATCGGAGCCCAGACCGACTTCCTGTCC<br>GTGTTCTTCTCCGGATACACCTTCAAGCATAAGATGGTGTACGAGGACACTCTGACCCTCTTCCCATTTTCCGGAGAA<br>ACTGTGTTCATGTCAATGGAAAACCCGGGCTTGTGGATTCTGGGTTGCCATAACTCGGACTTCCGGAATAGAGGGATG<br>ACCGCCCTGCTGAAAGTGTCCAGCTGTGACAAGAATACCGGCGATTACTACGAGGACAGCTATGAGGACATCTCCGCT<br>TATCTGCTGTCCAAGAACAACGCCATTGAACCCAGGTCCTTCTCCCAAAACGGTGCACCGGCCTCATCCCCCCCCGTG<br>CTGAAGCGGCATCAAAGAGAGATCACCAGGACCACTCTCCAGTCCGATCAGGAAGAAATTGACTACGACGATACTATC<br>AGCGTGGAGATGAAGAAGGAGGACTTCGACATCTACGATGAGGATGAGAACCAGTCCCCTCGGAGCTTTCAGAAGAAA<br>ACCCGCCACTACTTCATCGCTGCCGTGGAGCGGCTGTGGGATTACGGGATGTCCAGCTCACCGCATGTGCTGCGGAAT<br>AGAGCGCAGTCAGGATCGGTGCCCCAGTTCAAGAAGGTCGTGTTCCAAGAGTTCACCGACGGGTCCTTCACTCAACCC<br>CTGTACCGGGGCGAACTCAACGAACACCTGGGACTGCTTGGGCCGTATATCAGGGCAGAAGTGGAAGATAACATCATG<br>GTCACCTTCCGCAACCAGGCCTCCCGGCCGTACAGCTTCTACTCTTCACTGATCTCCTACGAGGAAGATCAGCGGCAG<br>GGAGCCGAGCCCCGGAAGAACTTCGTCAAGCCTAACGAAACTAAGACCTACTTTTGGAAGGTCCAGCATCACATGGCC<br>CCGACCAAAGACGAGTTCGACTGTAAAGCCTGGGCCTACTTCTCCGATGTGGACCTGGAGAAGGACGTGCACTCGGGA<br>CTCATTGGCCCGCTCCTTGTGTGCCATACTAATACCCTGAACCCTGCTCACGGTCGCCAAGTCACAGTGCAGGAGTTC<br>GCCCTCTTCTTCACCATCTTCGATGAAACAAAGTCCTGGTACTTTACTGAGAACATGGAACGCAATTGCAGGGCACCC<br>TGCAACATCCAGATGGAAGATCCCACCTTCAAGGAAAACTACCGGTTTCATGCCATTAACGGCTACATAATGGACACG<br>TTGCCAGGACTGGTCATGGCCCAGGACCAGAGAATCCGGTGGTATCTGCTCTCCATGGGCTCCAACGAAAACATTCAC<br>AGCATTCATTTTTCCGGCCATGTGTTCACCGTCCGGAAGAAGGAAGAGTACAAGATGGCTCTGTACAACCTCTACCCT<br>GGAGTGTTCGAGACTGTGGAAATGCTGCCTAGCAAGGCCGGCATTTGGAGAGTGGAATGCCTGATCGGAGAGCATTTG<br>CACGCCGGAATGTCCACCCTGTTTCTTGTGTACTCCAACAAGTGCCAGACCCCGCTGGGAATGGCCTCAGGTCATATT<br>AGGGATTTCCAGATCACTGCTTCGGGGCAGTACGGGCAGTGGGCACCTAAGTTGGCCCGGCTGCACTACTCTGGCTCC<br>ATCAATGCCTGGTCCACCAAGGAACCCTTCTCCTGGATTAAGGTGGACCTCCTGGCCCCAATGATTATTCACGGTATT<br>AAGACCCAGGGTGCCCGACAGAAGTTCTCCTCACTCTACATCTCGCAATTCATCATAATGTACAGCCTGGATGGGAAG<br>AAGTGGCAGACCTACCGGGGAAACTCCACTGGAACGCTCATGGTGTTTTTCGGCAACGTGGACTCCTCCGGCATTAAG<br>CACAACATCTTCAACCCTCCGATCATTGCTCGGTACATCCGGCTGCACCCAACTCACTACAGCATCCGGTCCACCCTG<br>CGGATGGAACTGATGGGTTGTGACCTGAACTCCTGCTCCATGCCCCTTGGGATGGAATCCAAGGCCATTAGCGATGCA<br>CAGATCACCGCCTCTTCATACTTCACCAACATGTTCGCGACCTGGTCCCCGTCGAAGGCCCGCCTGCACCTCCAAGGT<br>CGCTCCAATGCGTGGCGGCCTCAAGTGAACAACCCCAAGGAGTGGCTCCAGGTCGACTTCCAAAAGACCATGAAGGTC<br>ACCGGAGTGACCACCCAGGGCGTGAAGTCCCTGCTGACCTCTATGTACGTTAAGGAGTTCCTCATCTCCTCAAGCCAA<br>GACGGACATCAGTGGACCCTGTTCTTCCAAAACGGAAAAGTCAAAGTATTCCAGGGCAACCAGGACTCCTTCACCCCT<br>GTGGTCAACAGCCTGGACCCCCCATTGCTGACCCGCTACCTCCGCATCCACCCCCAAAGCTGGGTCCACCAGATCGCA<br>CTGCGCATGGAGGTCCTTGGATGCGAAGCCCAAGATCTGTACTAA |
| SEQ ID NO: 34<br>V1.0 Expression cassette TTP-Intron-BDDFVIIIco6 XTEN (V1.0)-WPRE-bGHPolyA | ATGCAGATTGAGCTGTCCACTTGTTTCTTCCTGTGCCTCCTGCGCTTCTGTTTCTCCGCCACTCGCCGGTACTACCTT<br>GGAGCCGTGGAGCTTTCATGGGACTACATGCAGAGCGACCTGGGCGAACTCCCCGTGGATGCCAGATTCCCCCCCCGC<br>GTGCCAAAGTCCTTCCCCTTTAACACCTCCGTGGTGTACAAGAAAACCCTCTTTGTCGAGTTCACTGACCACCTGTTC<br>AACATCGCCAAGCCGCGCCCACCTTGGATGGGCCTCCTGGGACCGACCATTCAAGCTGAAGTGTACGACACCGTGGTG<br>ATCACCCTGAAGAACATGGCGTCCCACCCCGTGTCCCTGCATGCGGTCGGAGTGTCCTACTGGAAGGCCTCCGAAGGA<br>GCTGAGTACGACGACCAGACTAGCCAGCGGGAAAAGGAGGACGATAAAGTGTTCCCGGGCGGCTCGCATACTTACGTG<br>TGGCAAGTCCTGAAGGAAAACGGACCTATGGCATCCGATCCTCTGTGCCTGACTTACTCCTACCTTTCCCATGTGGAC<br>CTCGTGAAGGACCTGAACAGCGGGCTGATTGGTGCACTTCTCGTGTGCCGCGAAGGTTCGCTCGCTAAGGAAAAGACC<br>CAGACCCTCCATAAGTTCATCCTTTTGTTCGCTGTGTTCGATGAAGGAAAGTCATGGCATTCCGAAACTAAGAACTCG<br>CTGATGCAGGACCGGGATGCCGCCTCAGCCCGCGCCTGGCCTAAAATGCATACAGTCAACGGATACGTGAATCGGTCA<br>CTGCCCGGGCTCATCGGTTGTCACAGAAAGTCCGTGTACTGGCACGTCATCGGCATGGGCACTACGCCTGAAGTGCAC<br>TCCATCTTCCTGGAAGGGCACACCTTCCTCGTGCGCAACCACCGCCAGGCCTCTCTGGAAATCTCCCCGATTACCTTT<br>CTGACCGCCCAGACTCTGCTCATGGACCTGGGGCAGTTCCTTCTCTTCTGCCACATCTCCAGCCATCAGCACGACGGA<br>ATGGAGGCCTACGTGAAGGTGGACTCATGCCCGGAAGAACCTCAGTTGCGGATGAAGAACAACGAGGAGGCCGAGGAC<br>TATGACGACGATTTGACTGACTCCGAGATGGACGTCGTGCGGTTCGATGACGACAACAGCCCCAGCTTCATCCAGATT<br>CGCAGCGTGGCCAAGAAGCACCCCAAAACCTGGGTGCACTACATCGCGGCCGAGGAAGAAGATTGGGACTACGCCCCG<br>TTGGTGCTGGCACCCGATGACCGGTCGTACAAGTCCCAGTATCTGAACAATGGTCCGCAGCGGATTGGCAGAAAGTAC<br>AAGAAAGTGCGGTTCATGGCGTACACTGACGAAACGTTTAAGACCCGGGAGGCCATTCAACATGAGAGCGGCATTCTG |

TABLE 1-continued

Additional Nucleotide and Amino Acid Sequences

| SEQ ID NO/ Description | Nucleotide or amino acid sequence |
| --- | --- |
| | GGACCACTGCTGTACGGAGAGGTCGGCGATACCCTGCTCATCATCTTCAAAAACCAGGCCTCCCGGCCTTACAACATC<br>TACCCTCACGGAATCACCGACGTGCGGCCACTCTACTCGCGGCGCCTGCCGAAGGGCGTCAAGCACCTGAAAGACTTC<br>CCTATCCTGCCGGGCGAAATCTTCAAGTATAAGTGGACCGTCACCGTGGAGGACGGGCCCACCAAGAGCGATCCTAGG<br>TGTCTGACTCGGTACTACTCCAGCTTCGTGAACATGGAACGGGACCTGGCATCGGGACTCATTGGACCGCTGCTGATC<br>TGCTACAAAGAGTCGGTGGATCAACGCGGCAACCAGATCATGTCCGACAAGCGCAACGTGATCCTGTTCTCCGTGTTT<br>GATGAAAACAGATCCTGGTACCTCACTGAAAACATCCAGAGGTTCCTCCCAAACCCCGCAGGAGTGCAACTGGAGGAC<br>CCTGAGTTTCAGGCCTCGAATATCATGCACTCGATTAACGGTTACGTGTTCGACTCGCTGCAACTGAGCGTGTGCCTC<br>CATGAAGTCGCTTACTGGTACATTCTGTCCATCGGCGCCCAGACTGACTTCCTGAGCGTGTTCTTTTCCGGTTACACC<br>TTTAAGCACAAGATGGTGTACGAAGATACCCTGACCCTGTTCCCTTTCTCCGGCGAAACGGTGTTCATGTCGATGGAG<br>AACCCGGGTCTGTGGATTCTGGGATGCCACAACAGCGACTTTCGGAACCGCGGAATGACTGCCCTGCTGAAGGTGTCC<br>TCATGCGACAAGAACACCGGAGACTACTACGAGGACTCCTACGAGGATATCTCAGCCTACCTCCTGTCCAAGAACAAC<br>GCGATCGAGCCGCGCAGCTTCAGCCAGAACGGCGCGCCAACATCAGAGAGCGCCACCCCTGAAAGTGGTCCCGGGAGC<br>GAGCCAGCCACATCTGGGTCGGAAACGCCAGGCACAAGTGAGTCTGCAACTCCCGAGTCCGGACCTGGCTCCGAGCCT<br>GCCACTAGCGGCTCCGAGACTCCGGGAACTTCCGAGAGCGCTACACCAGAAAGCGGACCCGGAACCAGTACCGAACCT<br>AGCGAGGGCTCTGCTCCGGGCAGCCCAGCCGGCTCTCCTACATCCACGGAGGAGGGCACTTCCGAATCCGCCACCCCG<br>GAGTCAGGGCCAGGATCTGAACCCGCTACCTCAGGCAGTGAGACGCCAGGAACGAGCGAGTCCGCTACACCGGAGAGT<br>GGGCCAGGGAGCCCTGCTGGATCTCCTACGTCCACTGAGGAAGGGTCACCAGCGGGCTCGCCCACCAGCACTGAAGAA<br>GGTGCCTCGAGCCCGCCTGTGCTGAAGAGGCACCAGCGAGAAATTACCCGGACCACCCTCCAATCGGATCAGGAGGAA<br>ATCGACTACGACGACACCATCTCGGTGGAAATGAAGAAGGAAGATTTCGATATCTACGACGAGGACGAAAATCAGTCC<br>CCTCGCTCATTCCAAAAGAAAACTAGACACTACTTTATCGCCGCGGTGGAAAGACTGTGGGACTATGGAATGTCATCC<br>AGCCCTCACGTCCTTCGGAACCGGGCCCAGAGCGGATCGGTGCCTCAGTTCAAGAAAGTGGTGTTCCAGGAGTTCACC<br>GACGGCAGCTTCACCCAGCCGCTGTACCGGGGAGAACTGAACGAACACCTGGGCCTGCTCGGTCCCTACATCCGCGCG<br>GAAGTGGAGGATAACATCATGGTGACCTTCCGTAACCAAGCATCCAGACCTTACTCCTTCTATTCCTCCCTGATCTCA<br>TACGAGGAGGACCAGCGCCAAGGCGCCGAGCCCCGCAAGAACTTCGTCAAGCCCAACGAGACTAAGACCTACTTCTGG<br>AAGGTCCAACACCATATGGCCCCGACCAAGGATGAGTTTGACTGCAAGGCCTGGGCCTACTTCTCCGACGTGGACCTT<br>GAGAAGGATGTCCATTCCGGCCTGATCGGGCCGCTGCTCGTGTGTCACACCAACACCCTGAACCCAGCGCATGGACGC<br>CAGGTCACCGTCCAGGAGTTTGCTCTGTTCTTCACCATTTTTGACGAAACTAAGTCCTGGTACTTCACCGAGAATATG<br>GAGCGAAACTGTAGAGCGCCCTGCAATATCCAGATGGAAGATCCGACTTTCAAGGAGAACTATAGATTCCACGCCATC<br>AACGGGTACATCATGGATACTCTGCCGGGGCTGGTCATGGCCCAGGATCAGAGGATTCGGTGGTACTTGCTGTCAATG<br>GGATCGAACGAAAACATTCACTCCATTCACTTCTCCGGTCACGTGTTCACTGTGCGCAAGAAGGAGGAGTACAAGATG<br>GCGCTGTACAATCTGTACCCCGGGGTGTTCGAAACTGTGGAGATGCTGCCGTCCAAGGCCGGCATCTGGAGAGTGGAG<br>TGCCTGATCGGAGAGCACCTCCACGCGGGGATGTCCACCCTCTTCCTGGTGTACTCGAATAAGTGCCAGACCCCGCTG<br>GGCATGGCCTCGGGCCACATCAGAGACTTCCAGATCACAGCAAGCGGACAATACGGCCAATGGGCGCCGAAGCTGGCC<br>CGCTTGCACTACTCCGGATCGATCAACGCATGGTCCACCAAGGAACCGTTCTCGTGGATTAAGGTGGACCTCCTGGCC<br>CCTATGATTATCCACGGAATTAAGACCCAGGGCGCCAGGCAGAAGTTCTCCTCCCTGTACATCTCGCAATTCATCATC<br>ATGTACAGCCTGGACGGGAAGAAGTGGCAGACTTACAGGGGAAACTCCACCGGCACCCTGATGGTCTTTTTCGGCAAC<br>GTGGATTCCTCCGGCATTAAGCACAACATCTTCAACCCACCGATCATAGCCAGATATATTAGGCTCCACCCCACTCAC<br>TACTCAATCCGCTCAACTCTTCGGATGGAACTCATGGGGTGCGACCTGAACTCCTGCTCCATGCCGTTGGGGATGGAA<br>TCAAAGGCTATTAGCGACGCCCAGATCACCGCGAGCTCCTACTTCACTAACATGTTCGCCACCTGGAGCCCCTCCAAG<br>GCCAGGCTGCACTTGCAGGGACGGTCAAATGCCTGGCGGCCGCAAGTGAACAATCCGAAGGAATGGCTTCAAGTGGAT<br>TTCCAAAAGACCATGAAAGTGACCGGAGTCACCACCCAGGGAGTGAAGTCCCTTCTGACCTCGATGTATGTGAAGGAG<br>TTCCTGATTAGCAGCAGCCAGGACGGGCACCAGTGGACCCTGTTCTTCCAAAACGGAAAGGTCAAGGTGTTCCAGGGG<br>AACCAGGACTCGTTCACACCCGTGGTGAACTCCCTGGACCCCCCACTGCTGACGCGGTACTTGAGGATTCATCCTCAG<br>TCCTGGGTCCATCAGATTGCATTGCGAATGGAAGTCCTGGGCTGCGAGGCCCAGGACCTGTACTGA |
| SEQ ID NO: 35<br>V3.0<br>Expression cassette<br>Human-codon optimized<br>A1AT-Intron-BDDFVHIXTEN-WPRE-bGHPolyA | ATCGATGGCCCCAGGTTAATTTTTAAAAAGCAGTCAAAAGTCCAAGTGGCCCTTGGCAGCATTTACTCTCTCTGTTTG<br>CTCTGGTTAATAATCTCAGGAGCACAAACATTCCTGGAGGCAGGAGAAGAAATCAACATCCTGGACTTATCCTCTGGG<br>CCTCTCCCCACCTTCGATGGCCCCAGGTTAATTTTTAAAAAGCAGTCAAAAGTCCAAGTGGCCCTTGGCAGCATTTAC<br>TCTCTCTGTTTGCTCTGGTTAATAATCTCAGGAGCACAAACATTCCTGGAGGCAGGAGAAGAAATCAACATCCTGGAC<br>TTATCCTCTGGGCCTCTCCCCACCTTCGAACTAGCCACTAGCCTGAGGCTGGTCAAAATTGAACCTCCTCCTGCTCTG<br>AGCAGCCTGGGGGGCAGACTAAGCAGAGGGCTGTGCAGACCCACATAAAGAGCCTACTGTGTGCCAGGCACTTCACCC<br>GAGGCACTTCACAAGCATGCTTGGGAATGAAACTTCCAACTCTTTGGGATGCAGGTGAAACAGTTCCTGGTTCAGAGA<br>GGTGAAGCGGCCTGCCTGAGGCAGCACAGCTCTTCTTTACAGATGTGCTTCCCCACCTCTACCCTGTCTCACGGCCCC<br>CCATGCCAGCCTGACGGTTGTGTCTGCCTCAGTCATGCTCCATTTTTCCATCGGGACCATCAAGAGGGTGTTTGTGTC<br>TAAGGCTGACTGGGTAACTTTGGATGAGCGGTCTCTCCGCTCTGAGCCTGTTTCCTCATCTGTCAAATGGGCTCTAAC<br>CCACTCTGATCTCCCAGGGCGGCAGTAAGTCTTCAGCATCAGGCATTTTGGGGTGACTCAGTAAATGGTAGATCTTGC<br>TACCAGTGGAACAGCCACTAAGGATTCTGCAGTGAGAGCAGAGGGCCAGCTAAGTGGTACTCTCCCAGAGACTGTCTG<br>ACTCACGCCACCCCCTCCACCTTGGACACAGGACGCTGTGGTTTCTGAGCCAGGTACAATGACTCCTTTCGGTAAGTG<br>CAGTGGAAGCTGTACACTGCCCAGGCAAAGCGTCCGGGCAGCGTAGGCGGGCGACTCAGATCCCAGCCAGTGGACTTA<br>GCCCCTGTTTGCTCCTCCGATAACTGGGGTGACCTTGGTTAATATTCACCAGCAGCCTCCCCCGTTGCCCCTCTGGAT<br>CCACTGCTTAAATACGGACGAGGACAGGGCCCTGTCTCCTCAGCTTCAGGCACCACCACTGACCTGGGACAGGAATTC<br>TCAGGAGCACAAACATTCCTGGAGGCAGGAGAAGAAATCAACATCCTGGACTTATCCTCTGGGCCTCTCCCCACCGAT<br>ATCTACCTGCTGATCGCCCGGCCCCTGTTCAAACATGTCCTAATACTCTGTCGGGGCAAAGGTCGGCAGTAGTTTTCC<br>ATCTTACTCAACATCCTCCCAGTGTACGTAGGATCCTGTCTGTCTGCACATTTCGTAGAGCGAGTGTTCCGATACTCT<br>AATCTCCCGGGGCAAAGGTCGTATTGACTTAGGTTACTTATTCTCCTTTTGTTGACTAAGTCAATAATCAGAATCAGC<br>AGGTTTGGAGTCAGCTTGGCAGGGATCAGCAGCCTGGGTTGGAAGGAGGGGGTATAAAAGCCCCTTCACCAGGAGAAG<br>CCGTCACACAGATCCACAAGCTCCTGCTAGAGTCGCTGCGCGCTGCCTTCGCCCCGTGCCCCGCTCCGCCGCCGCCTC<br>GCGCCGCCCGCCCCGGCTCTGACTGACCGCGTTACTCCCACAGGTGAGCGGGCGGGACGGCCCTTCTCCTCCGGGCTG<br>TAATTAGCGCTTGGTTTATTGACGGCTTGTTTCTTTTCTGTGGCTGCGTGAAAGCCTTGAGGGGCTCCGGGAAGGCCC<br>TTTGTGCGGGGGGAGCGGCTCGGGGGGTGCGTGCGTGTGTGTGTGCGTGGGGAGCGCCGCGTGCGGCTCCGCGCTGCC<br>CGGCGGCTGTGAGCGCTGCGGGCGCGGCGCGGGGCTTTGTGCGCTCCGCAGTGTGCGCGAGGGGAGCGCGGCCGGGGG<br>CGGTGCCCCGCGGTGCGGGGGGGGCTGCGAGGGGAACAAAGGCTGCGTGCGGGGTGTGTGCGTGGGGGGGTGAGCAGG<br>GGGTGTGGGCGCGTCGGTCGGGCTGCAACCCCCCCTGCACCCCCCTCCCCGAGTTGCTGAGCACGGCCCGGCTTCGGG<br>TGCGGGGCTCCGTACGGGGCGTGGCGCGGGGCTCGCCGTGCCGGGCGGGGGGTGGCGGCAGGTGGGGGTGCCGGGCGG<br>GGCGGGGCCGCCTCGGGCCGGGGAGGGCTCGGGGGAGGGGCGCGGCGGCCCCCGGAGCGCCGGCGGCTGTCGAGGCGC |

TABLE 1-continued

Additional Nucleotide and Amino Acid Sequences

| SEQ ID NO/ Description | Nucleotide or amino acid sequence |
|---|---|
| | GGCGAGCCGCAGCCATTGCCTTTTATGGTAATCGTGCGAGAGGGCGCAGGGACTTCCTTTGTCCCAAATCTGTGCGGA |
| | GCCGAAATCTGGGAGGCGCCGCCGCACCCCCTCTAGCGGGCGCGGGGCGAAGCGGTGCGGCGCCGGCAGGAAGGAAAT |
| | GGGCGGGGAGGGCCTTCGTGCGTCGCCGCGCCGCCGTCCCCTTCTCCCTCTCCAGCCTCGGGGCTGTCCGCGGGGGGA |
| | CGGCTGCCTTCGGGGGGGACGGGGCAGGGCGGGGTTCGGCTTCTGGCGTGTGACCGGCGGCTCTAGAGCCTCTGCTAA |
| | CCTTGTTCTTGCCTTCTTCTTTTTCCTACAGCTCCTGGGCAACGTGCTGGTTATTGTGCTGTCTCATCATTTTGGCAA |
| | AGAATTACTCGAGGCCACCATGCAGATTGAACTGTCCACTTGCTTCTTCCTGTGCCTCCTGCGGTTTTGCTTCTCGGC |
| | CACCCGCCGGTATTACTTAGGTGCTGTGGAACTGAGCTGGGACTACATGCAGTCCGACCTGGGAGAACTGCCGGTGGA |
| | CGCGAGATTCCCACCTAGAGTCCCGAAGTCCTTCCCATTCAACACCTCCGTGGTCTACAAAAAGACCCTGTTCGTGGA |
| | GTTCACTGACCACCTTTTCAATATTGCCAAGCCGCGCCCCCCCTGGATGGGCCTGCTTGGTCCTACGATCCAAGCAGA |
| | GGTCTACGACACCGTGGTCATCACACTGAAGAACATGGCCTCACACCCCGTGTCGCTGCATGCTGTGGGAGTGTCCTA |
| | CTGGAAGGCCTCAGAGGGTGCCGAATATGATGACCAGACCAGCCAGAGGGAAAAGGAGGATGACAAAGTGTTCCCGGG |
| | TGGCAGCCACACTTACGTGTGGCAAGTGCTGAAGGAAAACGGGCCTATGGCGTCGGACCCCCTATGCCTGACCTACTC |
| | CTACCTGTCCCATGTGGACCTTGTGAAGGATCTCAACTCGGGACTGATCGGCGCCCTCTTGGTGTGCAGAGAAGGCAG |
| | CCTGGCGAAGGAAAAGACTCAGACCCTGCACAAGTTCATTCTGTTGTTTGCTGTGTTCGATGAAGGAAAGTCCTGGCA |
| | CTCAGAAACCAAGAACTCGCTGATGCAGGATAGAGATGCGGCCTCGGCCAGAGCCTGGCCTAAAATGCACACCGTCAA |
| | CGGATATGTGAACAGGTCGCTCCCTGGCCTCATCGGCTGCCACAGAAAGTCCGTGTATTGGCATGTGATCGGCATGGG |
| | TACTACTCCGGAAGTGCATAGTATCTTTCTGGAGGGCCATACCTTCTTGGTGCGCAACCACAGACAGGCCTCGCTGGA |
| | AATCTCGCCTATCACTTTCTTGACTGCGCAGACCCTCCTTATGGACCTTGGACAGTTCCTGCTGTTCTGTCACATCAG |
| | CTCCCATCAGCATGATGGGATGGAGGCCTATGTCAAAGTGGACTCCTGCCCTGAGGAGCCACAGCTCCGGATGAAGAA |
| | CAATGAGGAAGCGGAGGATTACGACGACGACCTGACTGACAGCGAAATGGACGTCGTGCGATTCGATGACGACAACAG |
| | CCCGTCCTTCATCCAAATTAGATCAGTGGCGAAGAAGCACCCCAAGACCTGGGTGCACTACATTGCCGCCGAGGAAGA |
| | GGACTGGGACTACGCGCCGCTGGTGCTGGCGCCAGACGACAGGAGCTACAAGTCCCAGTACCTCAACAACGGGCCGCA |
| | GCGCATTGGCAGGAAGTACAAGAAAGTCCGCTTCATGGCCTACACTGATGAAACCTTCAAGACGAGGGAAGCCATCCA |
| | GCACGAGTCAGGCATCCTGGGACCGCTCCTTTACGGCGAAGTCGGGGATACCCTGCTCATCATTTTCAAGAACCAGGC |
| | ATCGCGGCCCTACAACATCTACCCTCACGGGATCACAGACGTGCGCCCGCTCTACTCCCGCCGGCTGCCCAAGGGAGT |
| | GAAGCACCTGAAGGATTTTCCCATCCTGCCGGGAGAAATCTTCAAGTACAAGTGGACCGTGACTGTGGAAGATGGCCC |
| | TACCAAGTCGGACCCTCGCTGTCTGACCCGGTACTATTCCTCGTTTGTGAACATGGAGCGCGACCTGGCCTCGGGGCT |
| | GATTGGTCCGCTGCTGATCTGCTACAAGGAGTCCGTGGACCAGCGCGGGAACCAGATCATGTCCGACAAGCGCAACGT |
| | GATCCTGTTCTCTGTCTTTGATGAAAACAGATCGTGGTACTTGACTGAGAATATCCAGCGGTTCCTGCCCAACCCAGC |
| | GGGAGTGCAACTGGAGGACCCGGAGTTCCAGGCCTCAAACATTATGCACTCTATCAACGGCTATGTGTTCGACTCGCT |
| | CCAACTGAGCGTGTGCCTGCATGAAGTGGCATACTGGTACATTCTGTCCATCGGAGCCCAGACCGACTTCCTGTCCGT |
| | GTTCTTCTCCGGATACACCTTCAAGCATAAGATGGTGTACGAGGACACTCTGACCCTCTTCCCATTTTCCGGAGAAAC |
| | TGTGTTCATGTCAATGGAAAACCCGGGCTTGTGGATTCTGGGTTGCCATAACTCGGACTTCCGGAATAGAGGGATGAC |
| | CGCCCTGCTGAAAGTGTCCAGCTGTGACAAGAATACCGGCGATTACTACGAGGACAGCTATGAGGACATCTCCGCTTA |
| | TCTGCTGTCCAAGAACAACGCCATTGAACCCAGGTCCTTCTCCCAAAACGGTGCACCGACCTCCGAAAGCGCCACCCC |
| | AGAGTCAGGACCTGGCTCGGAACCGGCTACCTCGGGCTCAGAGACACCGGGGACTTCCGAGTCCGCAACCCCCGAGAG |
| | TGGACCCGGATCCGAACCAGCAACCTCAGGATCAGAAACCCCGGGAACTTCGGAATCCGCCACTCCCGAGTCGGGACC |
| | AGGCACCTCCACTGAGCCTTCCGAGGGAAGCGCCCCCGGATCCCCTGCTGGATCCCCTACCAGCACTGAAGAAGGCAC |
| | CTCAGAATCCGCGACCCCTGAGTCCGGCCCTGGAAGCGAACCCGCCACCTCCGGTTCCGAAACCCCTGGGACTAGCGA |
| | GAGCGCCACTCCGGAATCGGGCCCAGGAAGCCCTGCCGGATCCCCGACCAGCACCGAGGAGGGAAGCCCCGCCGGGTC |
| | ACCGACTTCCACTGAGGAGGGAGCCTCATCCCCCCCCGTGCTGAAGCGGCATCAAAGAGAGATCACCAGGACCACTCT |
| | CCAGTCCGATCAGGAAGAAATTGACTACGACGATACTATCAGCGTGGAGATGAAGAAGGAGGACTTCGACATCTACGA |
| | TGAGGATGAGAACCAGTCCCCTCGGAGCTTTCAGAAGAAAACCCGCCACTACTTCATCGCTGCCGTGGAGCGGCTGTG |
| | GGATTACGGGATGTCCAGCTCACCGCATGTGCTGCGGAATAGAGCGCAGTCAGGATCGGTGCCCCAGTTCAAGAAGGT |
| | CGTGTTCCAAGAGTTCACCGACGGGTCCTTCACTCAACCCCTGTACCGGGGCGAACTCAACGAACACCTGGGACTGCT |
| | TGGGCCGTATATCAGGGCAGAAGTGGAAGATAACATCATGGTCACCTTCCGCAACCAGGCCTCCCGGCCGTACAGCTT |
| | CTACTCTTCACTGATCTCCTACGAGGAAGATCAGCGGCAGGGAGCCGAGCCCCGGAAGAACTTCGTCAAGCCTAACGA |
| | AACTAAGACCTACTTTTGGAAGGTCCAGCATCACATGGCCCCGACCAAAGACGAGTTCGACTGTAAAGCCTGGGCCTA |
| | CTTCTCCGATGTGGACCTGGAGAAGGACGTGCACTCGGGACTCATTGGCCCGCTCCTTGTGTGCCATACTAATACCCT |
| | GAACCCTGCTCACGGTCGCCAAGTCACAGTGCAGGAGTTCGCCCTCTTCTTCACCATCTTCGATGAAACAAAGTCCTG |
| | GTACTTTACTGAGAACATGGAACGCAATTGCAGGGCACCCTGCAACATCCAGATGGAAGATCCCACCTTCAAGGAAAA |
| | CTACCGGTTTCATGCCATTAACGGCTACATAATGGACACGTTGCCAGGACTGGTCATGGCCCAGGACCAGAGAATCCG |
| | GTGGTATCTGCTCTCCATGGGCTCCAACGAAAACATTCACAGCATTCATTTTTCCGGCCATGTGTTCACCGTCCGGAA |
| | GAAGGAAGAGTACAAGATGGCTCTGTACAACCTCTACCCTGGAGTGTTCGAGACTGTGGAAATGCTGCCTAGCAAGGC |
| | CGGCATTTGGAGAGTGGAATGCCTGATCGGAGAGCATTTGCACGCCGGAATGTCCACCCTGTTTCTTGTGTACTCCAA |
| | CAAGTGCCAGACCCCGCTGGGAATGGCCTCAGGTCATATTAGGGATTTCCAGATCACTGCTTCGGGGCAGTACGGGCA |
| | GTGGGCACCTAAGTTGGCCCGGCTGCACTACTCTGGCTCCATCAATGCCTGGTCCACCAAGGAACCCTTCTCCTGGAT |
| | TAAGGTGGACCTCCTGGCCCCAATGATTATTCACGGTATTAAGACCCAGGGTGCCCGACAGAAGTTCTCCTCACTCTA |
| | CATCTCGCAATTCATCATAATGTACAGCCTGGATGGGAAGAAGTGGCAGACCTACCGGGGAAACTCCACTGGAACGCT |
| | CATGGTGTTTTTCGGCAACGTGGACTCCTCCGGCATTAAGCACAACATCTTCAACCCTCCGATCATTGCTCGGTACAT |
| | CCGGCTGCACCCAACTCACTACAGCATCCGGTCCACCCTGCGGATGGAACTGATGGGTTGTGACCTGAACTCCTGCTC |
| | CATGCCCCTTGGGATGGAATCCAAGGCCATTAGCGATGCACAGATCACCGCCTCTTCATACTTCACCAACATGTTCGC |
| | GACCTGGTCCCCGTCGAAGGCCCGCCTGCACCTCCAAGGTCGCTCCAATGCGTGGCGGCCTCAAGTGAACAACCCCAA |
| | GGAGTGGCTCCAGGTCGACTTCCAAAAGACCATGAAGGTCACCGGAGTGACCACCCAGGGCGTGAAGTCCCTGCTGAC |
| | CTCTATGTACGTTAAGGAGTTCCTCATCTCCTCAAGCCAAGACGGACATCAGTGGACCCTGTTCTTCCAAAACGGAAA |
| | AGTCAAAGTATTCCAGGGCAACCAGGACTCCTTCACCCCTGTGGTCAACAGCCTGGACCCCCCATTGCTGACCCGCTA |
| | CCTCCGCATCCACCCCCAAAGCTGGGTCCACCAGATCGCACTGCGCATGGAGGTCCTTGGATGCGAAGCCCAAGATCT |
| | GTACTAAGCGGCCGCTCATAATCAACCTCTGGATTACAAAATTTGTGAAAGATTGACTGGTATTCTTAACTATGTTGC |
| | TCCTTTTACGCTATGTGGATACGCTGCTTTAATGCCTTTGTATCATGCTATTGCTTCCCGTATGGCTTTCATTTTCTC |
| | CTCCTTGTATAAATCCTGGTTGCTGTCTCTTTATGAGGAGTTGTGGCCCGTTGTCAGGCAACGTGGCGTGGTGTGCAC |
| | TGTGTTTGCTGACGCAACCCCCACTGGTTGGGGCATTGCCACCACCTGTCAGCTCCTTTCCGGGACTTTCGCTTTCCC |
| | CCTCCCTATTGCCACGGCGGAACTCATCGCCGCCTGCCTTGCCCGCTGCTGGACAGGGGCTCGGCTGTTGGGCACTGA |
| | CAATTCCGTGGTGTTGTCGGGGAAATCATCGTCCTTTCCTTGGCTGCTCGCCTGTGTTGCCACCTGGATTCTGCGCGG |
| | GACGTCCTTCTGCTACGTCCCTTCGGCCCTCAATCCAGCGGACCTTCCTTCCCGCGGCCTGCTGCCGGCTCTGCGGCC |
| | TCTTCCGCGTCTTCGCCTTCGCCCTCAGACGAGTCGGATCTCCCTTTGGGCCGCCTCCCCGCTGCCTAGGCGACTGTG |

TABLE 1-continued

Additional Nucleotide and Amino Acid Sequences

| SEQ ID NO/ Description | Nucleotide or amino acid sequence |
|---|---|
| | CCTTCTAGTTGCCAGCCATCTGTTGTTTGCCCCTCCCCCGTGCCTTCCTTGACCCTGGAAGGTGCCACTCCCACTGTC CTTTCCTAATAAAATGAGGAAATTGCATCGCATTGTCTGAGTAGGTGTCATTCTATTCTGGGGGGTGGGGTGGGGCAG GACAGCAAGGGGGAGGATTGGGAAGACAATAGCAGGCATGCTGGGGAAGACCATGGGCGCGCCAGGCCTGTCGACGCC CGGGCGGTACCGCGATCGCTCGCGACGCATAAAG |
| SEQ ID NO: 36 human liver-specific alpha-1-antitrypsin (A1AT) promoter | ATCGATGGCCCCAGGTTAATTTTTAAAAAGCAGTCAAAAGTCCAAGTGGCCCTTGGCAGCATTTACTCTCTCTGTTTG CTCTGGTTAATAATCTCAGGAGCACAAACATTCCTGGAGGCAGGAGAAGAAATCAACATCCTGGACTTATCCTCTGGG CCTCTCCCCACCTTCGATGGCCCCAGGTTAATTTTTAAAAAGCAGTCAAAAGTCCAAGTGGCCCTTGGCAGCATTTAC TCTCTCTGTTTGCTCTGGTTAATAATCTCAGGAGCACAAACATTCCTGGAGGCAGGAGAAGAAATCAACATCCTGGAC TTATCCTCTGGGCCTCTCCCCACCTTCGAACTAGCCACTAGCCTGAGGCTGGTCAAAATTGAACCTCCTCCTGCTCTG AGCAGCCTGGGGGGCAGACTAAGCAGAGGGCTGTGCAGACCCACATAAAGAGCCTACTGTGTGCCAGGCACTTCACCC GAGGCACTTCACAAGCATGCTTGGGAATGAAACTTCCAACTCTTTGGGATGCAGGTGAAACAGTTCCTGGTTCAGAGA GGTGAAGCGGCCTGCCTGAGGCAGCACAGCTCTTCTTTACAGATGTGCTTCCCCACCTCTACCCTGTCTCACGGCCCC CCATGCCAGCCTGACGGTTGTGTCTGCCTCAGTCATGCTCCATTTTTCCATCGGGACCATCAAGAGGGTGTTTGTGTC TAAGGCTGACTGGGTAACTTTGGATGAGCGGTCTCTCCGCTCTGAGCCTGTTTCCTCATCTGTCAAATGGGCTCTAAC CCACTCTGATCTCCCAGGGCGGCAGTAAGTCTTCAGCATCAGGCATTTTGGGGTGACTCAGTAAATGGTAGATCTTGC TACCAGTGGAACAGCCACTAAGGATTCTGCAGTGAGAGCAGAGGGCCAGCTAAGTGGTACTCTCCCAGAGACTGTCTG ACTCACGCCACCCCCTCCACCTTGGACACAGGACGCTGTGGTTTCTGAGCCAGGTACAATGACTCCTTTCGGTAAGTG CAGTGGAAGCTGTACACTGCCCAGGCAAAGCGTCCGGGCAGCGTAGGCGGGCGACTCAGATCCCAGCCAGTGGACTTA GCCCCTGTTTGCTCCTCCGATAACTGGGGTGACCTTGGTTAATATTCACCAGCAGCCTCCCCCGTTGCCCCTCTGGAT CCACTGCTTAAATACGGACGAGGACAGGGCCCTGTCTCCTCAGCTTCAGGCACCACCACTGACCTGGGACAG |

What is claimed is:

1. An isolated nucleic acid molecule comprising a nucleotide sequence at least 85% identical to SEQ ID NO: 9, wherein the nucleotide sequence encodes a polypeptide with factor VIII (FVIII) activity.

2. The isolated nucleic acid molecule of claim 1, wherein the nucleotide sequence comprises a nucleotide sequence at least 90% identical to nucleotides 58-4824 of SEQ ID NO: 9.

3. The isolated nucleic acid molecule of claim 1, wherein:

a. the nucleic acid molecule further comprises a nucleotide sequence encoding a signal peptide;

b. the nucleic acid molecule further comprises a nucleotide sequence encoding a signal peptide comprising the amino acid sequence of SEQ ID NO: 11; and/or c. the nucleotide sequence is codon-optimized to contain fewer CpG motifs relative to SEQ ID NO: 32.

4. The isolated nucleic acid molecule of claim 1, further comprising:

a. an enhancer element;

b. an intronic sequence;

c. a post-transcriptional regulatory element; and/or d. a first inverted terminal repeat (ITR) and a second ITR flanking the genetic cassette.

5. The isolated nucleic acid molecule of claim 4, wherein:

a. the enhancer element is an A1MB2 enhancer element;

b. the enhancer element comprises the nucleotide sequence of SEQ ID NO: 15;

c. the intronic sequence is a chimeric intron, a hybrid intron, or a synthetic intron;

d. the intronic sequence comprises the nucleotide sequence of SEQ ID NO: 17;

e. the post-transcriptional regulatory element comprises a Woodchuck Posttranscriptional Regulatory Element (WPRE), optionally wherein the WPRE comprises the nucleotide sequence of SEQ ID NO: 18;

f. the first ITR and/or the second ITR are derived from a member of the viral family Parvoviridae, and/or g. the first ITR and/or the second ITR are derived from a human Bocavirus (HboV1), human erythrovirus (B19), Goose Parvovirus (GPV), variants thereof, or combinations thereof.

6. The isolated nucleic acid molecule of claim 5, wherein:

(a) the A1MB2 enhancer element comprises the nucleotide sequence of SEQ ID NO: 15, (b) the liver-specific modified mouse transthyretin (mTTR) promoter comprises the nucleotide sequence of SEQ ID NO: 16, (c) the chimeric intron comprises the nucleotide sequence of SEQ ID NO: 17, (d) the nucleotide sequence encoding a FVIII protein comprises a nucleic acid sequence at least 85% identical to SEQ ID NO: 9 or SEQ ID NO: 33;

(e) the Woodchuck Posttranscriptional Regulatory Element (WPRE) comprises the nucleotide sequence of SEQ ID NO: 18; and (f) the Bovine Growth Hormone Polyadenylation (bGHpA) signal comprises the nucleotide sequence of SEQ ID NO: 19.

7. A vector comprising the nucleic acid molecule of claim 1.

8. An isolated host cell comprising the nucleic acid molecule of claim 1.

9. A method of producing a polypeptide with FVIII activity, comprising: culturing the host cell of claim 8 under conditions whereby a polypeptide with FVIII activity is produced, and recovering the polypeptide with FVIII activity.

10. A pharmaceutical composition comprising the nucleic acid molecule of claim 1.

11. An isolated nucleic acid molecule comprising a nucleotide sequence at least 85% identical to SEQ ID NO: 33, wherein the nucleotide sequence encodes a polypeptide with factor VIII (FVIII) activity.

* * * * *